US009102955B2

(12) United States Patent
McBride et al.

(10) Patent No.: US 9,102,955 B2
(45) Date of Patent: *Aug. 11, 2015

(54) YEAST EXPRESSING CELLULASES FOR SIMULTANEOUS SACCHARIFICATION AND FERMENTATION USING CELLULOSE

(75) Inventors: John McBride, Lyme, NH (US); Elena Brevnova, Lebanon, NH (US); Mark Mellon, Grantham, NH (US); Allan Froehlich, Lebanon, NH (US); Kristen Deleault, Canaan, NH (US); Vineet Rajgarhia, Dublin, CA (US); Riaan Den Haan, Durbanville (ZA); Merja Penttila, Helsinki (FI); Marja Ilmen, Helsinki (FI); Matti Siika-Aho, Helsinki (FI); Jaana Uusitalo, Espoo (FI); Emily A. Stonehouse, Lebanon, NH (US); Alan Gilbert, Cambridge, MA (US); Haowen Xu, Lebanon, NH (US); Deidre Willes, Lebanon, NH (US); John Bardsley, Newport, NH (US); Anu Koivula, Helsinki (FI); Sanni Voutilainen, Siuntio (FI)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 13/130,549

(22) PCT Filed: Nov. 23, 2009

(86) PCT No.: PCT/US2009/065571

§ 371 (c)(1),
(2), (4) Date: Feb. 7, 2012

(87) PCT Pub. No.: WO2010/060056

PCT Pub. Date: May 27, 2010

(65) Prior Publication Data

US 2012/0129229 A1 May 24, 2012

Related U.S. Application Data

(60) Provisional application No. 61/116,981, filed on Nov. 21, 2008.

(51) Int. Cl.

| | |
|---|---|
| ***C12N 1/19*** | (2006.01) |
| ***C12P 7/10*** | (2006.01) |
| ***C12N 15/80*** | (2006.01) |
| ***C12P 7/14*** | (2006.01) |
| ***C12P 39/00*** | (2006.01) |
| ***C12N 9/42*** | (2006.01) |

(52) U.S. Cl.
CPC ................. *C12P 7/10* (2013.01); *C12N 9/2437* (2013.01); *C12N 9/2445* (2013.01); *C12N 15/80* (2013.01); *C12P 7/14* (2013.01); *C12P 39/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 5,811,381 | A | 9/1998 | Emalfarb et al. | |
| 6,105,707 | A | 8/2000 | Tamura et al. | |
| 7,026,152 | B2 * | 4/2006 | Ingram et al. | 435/210 |
| 7,344,876 | B2 | 3/2008 | Levine | |
| 7,449,319 | B2 | 11/2008 | Dunn-Coleman et al. | |
| 8,658,398 | B2 | 2/2014 | Brevnova et al. | |
| 2003/0157595 | A1 | 8/2003 | Emalfarb et al. | |
| 2006/0110812 | A1 | 5/2006 | O'Neal Ingram et al. | |
| 2006/0234364 | A1 * | 10/2006 | Rajgarhia et al. | 435/161 |
| 2007/0238155 | A1 | 10/2007 | Gusakov et al. | |
| 2008/0076159 | A1 | 3/2008 | Baez-Vasquez et al. | |
| 2008/0193992 | A1 | 8/2008 | Levine | |
| 2009/0280105 | A1 | 11/2009 | Gusakov et al. | |
| 2010/0075363 | A1 | 3/2010 | McBride et al. | |
| 2011/0124074 | A1 | 5/2011 | Den Haan et al. | |
| 2011/0177542 | A1 | 7/2011 | Van zyl et al. | |
| 2011/0189744 | A1 | 8/2011 | McBride et al. | |
| 2011/0312054 | A1 | 12/2011 | Brevnova et al. | |
| 2012/0003701 | A1 | 1/2012 | Brevnova et al. | |
| 2012/0040409 | A1 | 2/2012 | Hau et al. | |
| 2012/0142046 | A1 | 6/2012 | McBride et al. | |
| 2012/0295306 | A1 | 11/2012 | Currie et al. | |
| 2012/0322078 | A1 | 12/2012 | McBride et al. | |

(Continued)

FOREIGN PATENT DOCUMENTS

| | | | |
|---|---|---|---|
| WO | WO 2005/116271 | A2 | 12/2005 |
| WO | WO 2008/064314 | A2 | 5/2008 |
| WO | WO 2008/155665 | A2 | 12/2008 |

(Continued)

OTHER PUBLICATIONS

Carrard et al. Proc. Natl. Acad. Sci. USA (Sep. 12, 2000) 97 (19), 10342-10347.*
Machida et al. Appl. Environ. Microbiol. (1988) 54 (12), 3174-3155.*
Collins et al. GenBank (Mar. 20, 2002) Accession No. AY081766.*
International Search Report, mailed May 14, 2010 in Patent Cooperation Treaty Application No. PCT/US2009/065571, filed Nov. 23, 2009.
Written Opinion of the International Searching Authority, mailed on May 14, 2010, for International Application No. PCT/US09/65571, filed Nov. 23, 2009.

(Continued)

*Primary Examiner* — Nashaat Nashed
(74) *Attorney, Agent, or Firm* — Nutter McClennen & Fish LLP

(57) ABSTRACT

Host cells, comprising *Kluveryomyces* expressing heterologous cellulases produce ethanol from cellulose In addition, multiple host cells expressing different heterlogous cellulases can be co-cultured together and used to produce ethanol from cellulose The recombinant yeast strains and co-cultures of the yeast strains can be used to produce ethanol on their own, or can also be used in combination with externally added cellulases to increase the efficiency of sacchanfication and fermentation processes.

27 Claims, 42 Drawing Sheets

(56) References Cited

U.S. PATENT DOCUMENTS

| | | | |
|---|---|---|---|
| 2013/0273555 | A1 | 10/2013 | Sillers et al. |
| 2013/0323822 | A1 | 12/2013 | Brevnova et al. |

FOREIGN PATENT DOCUMENTS

| | | | |
|---|---|---|---|
| WO | WO 2009/138877 A2 | 11/2009 | |
| WO | WO 2009/139839 A1 | 11/2009 | |
| WO | WO 2010/005553 A1 | 1/2010 | |
| WO | WO 2010/075529 A2 | 7/2010 | |
| WO | WO 2010/124000 A2 | 10/2010 | |
| WO | WO 2011/022651 A1 | 2/2011 | |
| WO | WO 2014/035458 A1 | 3/2014 | |
| WO | WO 2014/151805 A2 | 9/2014 | |

OTHER PUBLICATIONS

Cho, K.M. and Young, J.Y., "Novel SSF Process for Ethanol Production from Microcrystalline Cellulose Using the δ-Integrated Recombinant Yeast, *Saccharomyces cerevisiae* L2612δGC," *J. Microbiol. Biotechnol. 9*(3):340-345, The Korean Society for Applied Microbiology, Korea, (1999).

Cho, K.M., et al., "δ-Integration of endo/exo-glucanase and β-glucosidase genes into the yeast chromosomes for direct conversion of cellulose to ethanol," *Enzyme and Microbial Technology* 23-30, Elsevier, Netherlands (1999).

Crous, J.M., et al., "Cloning and expression of an *Aspergillus kawachii* endo-1,4-β-xylanase gene in *Saccharomyces cerevisiae,*" *Curr. Gen. 28*:467-473, Springer International, United States (1995).

Den Haan, R., et al., "Hydrolysis and fermentation of amorphous cellulose by recombinant *Saccharomyces cerevisiae,*" *Metabolic Engineering 9*:87-94, Elsevier, Belgium (2007).

Fujita, Y., et al., "Direct and Efficient Production of Ethanol from Cellulosic Material with a Yeast Strain Displaying Cellulolytic Enzymes," *App. Env. Microbiol. 68*(10):5136-5141, American Society for Microbiology, United States (2002).

Fujita, Y., et al., "Synergistic Saccharification, and Direct Fermentation to Ethanol, of Amorphous Cellulose by Use of an Engineered Yeast Strain Codisplaying Three Types of Cellulolytic Enzyme," *App. Env. Microbiol. 70*(2):1207-1212, American Society for Microbiology, United States (2004).

Hong, J., et al., "Cloning of a Gene Encoding a Highly Stable Endo-β-1,4-Glucanase from *Aspergillus niger* and its Expression in Yeast," *J. Biosci. Bioeng. 92*(5):434-441, Society for Bioscience and Bioengineering, Japan (2001).

Hong, J., et al., "Cloning of a gene encoding thermostable cellobiohydrolase from *Thermoascus aurantiacus* and its expression in yeast," *Appl. Microbiol. Biotechnol. 63*:42-50, Springer International, Germany (2003).

Hong, J., et al., "Construction of thermotolerant yeast expressing thermostable cellulase genes," *J. Biotechnol. 130*:114-123, Elsevier, Netherlands (2007).

Hong, J., et al., "Cloning and functional expression of thermostable β-glucosidase gene from *Thermoascus aurantiacus,*" *Appl. Microbiol. Biotechnol. 73*(6):1331-1339, Springer International, Germany (2007).

Jung, H., et al., "Binding and Reversibility of *Thermobifida fusca* Cel5A, Cel6B, and Cel48A and Their Respective Catalytic Domains to Bacterial Microcrystalline Cellulose," *Biotechnol. Bioeng. 84*(2):151-159, Wiley Interscience, United States (2003).

Kuyper, M., et al., "Minimal metabolic engineering of *Saccharomyces cerevisiae* for efficient anaerobic xylose fermentation: a proof of principle," *FEMS Yeast Res. 4*:655-664, Elsevier, England (2004).

Kuyper, M., et al., "Metabolic engineering of a xylose-isomerase-expressing *Saccharomyces cerevisiae* strain for rapid anaerobix xylose fermentation," *FEMS Yeast Res. 5*:399-409, Elsevier, England (2005).

Kuyper, M., et al., "Evolutionary engineering of mixed-sugar utilization by a xylose-fermenting *Saccharomyces cerevisiae* strain," *FEMS Yeast Res. 5*:925-934, Elsevier, England (2005).

McBride, J.E., et al., "Utilization of cellobiose by recombinant β-glucosidase-expressing strains of *Saccharomyces cerevisiae*: characterization and evaluation of the sufficiency of expression," *Enzyme and Microbial Technology 37*:93-101, Elsevier, Netherlands (2005).

Saloheimo, A., et al., "A novel, small endoglucanase gene, *egl5*, from *Trichoderma reesei* isolated by expression in yeast," *Mol. Microbiol. 13*(2):219-228, Blackwell Scientific, England (1994).

Teeri, T., et al., "Homologous domains in *Trichoderma reesei* cellulolytic enzymes: gene sequence and expression of cellobiohydrolase II," *Gene 51*:43-52, Elsevier, Netherlands (1987).

van Rensburg, P., et al., "Engineering Yeast for Efficient Cellulose Degradation," *Yeast 14*:67-76, Wiley, England (1998).

van Rooyen, R., et al., "Construction of cellobiose-growing and fermenting *Saccharomyces cerevisiae* strains," *J. Biotechnol. 120*:284-295, Elsevier, Netherlands (2005).

Wu, G., et al., "The Synthetic Gene Designer: A flexible web platform to explore sequence manipulation for heterologous expression," *Protein Expression & Purification 47*:441-445, Academic Press, United States (2006).

Zhang, Y.H., et al., "A Transition from Cellulose Swelling to Cellulose Dissolution by *o*-Phosphoric Acid: Evidence from Enzymatic Hydrolysis and Supramolecular Structure," *Biomacromolecules 7*:644-648, American Chemical Society, United States (2006).

International Preliminary Report on Patentability, mailed on May 24, 2011, for International Application No. PCT/US2009/065571, filed Nov. 23, 2011.

Office Action mailed Aug. 9, 2013, in U.S. Appl. No. 12/992,001, McBride et al., filed Apr. 14, 2011.

Office Action mailed Oct. 7, 2013, in U.S. Appl. No. 12/516,175, McBride et al., filed Jun. 26, 2009.

Office Action mailed Feb. 9, 2012 in U.S. Appl. No. 12/516,175, McBride et al., filed Jun. 26, 2009.

Office Action mailed Aug. 2, 2011, in U.S. Appl. No. 12/516,175, McBride et al., filed Jun. 26, 2009.

Den Haan, R., et al., "Functional expression of cellobiohydrolases in *Saccharomyces cerevisiae* towards one-step conversion of cellulose to ethanol," *Enzyme and Microbial Technology 40*:1291-99, Elsevier Inc., United States (Apr. 2007).

Fan, Z., et al., "Theoretical Analysis of Selection-Based Strain Improvement for Microorganisms With Growth Dependent Upon Extracytoplasmic Enzymes," *Biotechnol. Bioeng. 92*(1):35-44, Wiley Periodicals, United States (2005).

Greene, N., et al, "Growing Energy: How Biofuels Can Help End America's Oil Dependence," NRDC Report, Dec. 2004, 86 pages.

Ilmén, M., et al., "High level secretion of cellobiohydrolases by *Saccharomyces cerevisiae,*" *Biotechnol. Biofuels 4*:30, 15 pages, BioMed Central Ltd., United States (2011).

Lynd, L.R., et al., "Consolidated bioprocessing of cellulosic biomass: an update," *Curr. Curr. Opin. Biotechnol. 16*:577-83, Elsevier Inc., United States (2005).

Lynd, L.R., et al., "Chapter 4: Energy Myth Three—High Land Requirements and an Unfavorable Energy Balance Preclude Biomass Ethanol from Playing a Large Role in Providing Energy Services," in *Energy and American Society—Thirteen Myths*, Sovacool B.K., and Brown, M.A., eds., pp. 75-101, Springer, Germany (Jan. 2007).

Olson, D.G., et al., "Recent progress in consolidated bioprocessing," *Curr. Opin. Biotechnol. 23*:396-405, Elsevier, United States (2012).

Stewart, E.J., et al., "Disulfide bond formation in the *Escherichia coli* cytoplasm: an in vivo role reversal for the thioredoxins," *EMBO J. 17*(19):5543-50, Oxford University Press, England (1998).

Van Zyl, W.H., et al., "Consolidated Bioprocessing for Bioethanol Production Using *Saccharomyces cerevisiae,*" *Adv. Biochem. Engin./Biotechnol. 108*:205-35, Springer-Verlag Berlin Heidelberg, Germany (Apr. 2007).

Office Action mailed May 19, 2014, in U.S. Appl. No. 12/992,001, McBride et al., filed Apr. 14, 2011.

* cited by examiner

A:

B:

Figure 39
• Genes Modified in M0509.

| Gene | Enzyme | EC number | Organism | Modification | Promoter | Terminator |
|---|---|---|---|---|---|---|
| XylA | xylose isomerase | 5.3.1.5 | Piromyces sp. E2 | multi-copy integration | TPI | CYC1 |
| XKS1 | xylulokinase | 2.7.1.17 | S. cerevisiae | multi-copy integration | ADH1 | CYC1 |
| TAL1 | transaldolase | 2.2.1.2 | S. cerevisiae | increased expression | TPI | --- |
| TKL1 | transketolase | 2.2.1.1 | S. cerevisiae | increased expression | TPI | --- |
| RPE1 | ribulose-5-phosphate epimerase | 5.1.3.1 | S. cerevisiae | increased expression | TPI | --- |
| RKI1 | ribulose-5-phosphate isomerase | 5.3.1.6 | S. cerevisiae | increased expression | TPI | --- |
| GRE3 | aldose reductase | 1.1.1.21 | S. cerevisiae | deleted | --- | --- |

ADH1 = S. cerevisiae alcohol dehydrogenase1, TPI = S. cerevisiae triose phosphate isomerase, CYC1 = S. cerevisiae cytochrome c, isoform 1

Figure 40
• Strains used to construct M0509 and relevant genetic modifications

| Strain | Genetic Loci | | | | | |
|---|---|---|---|---|---|---|
| | GRE3 | RKI1 | RPE1 | TAL1 | TKL1 | XylA & XKS1 |
| M0086 | +/+ | +/+ | +/+ | +/+ | +/+ | |
| M0150 | GRE3+/gre3::loxP-kan | | | | | |
| M0207 | gre3::loxP-dsdA/gre3::loxP-kan | | | | | |
| M0222 | gre3::loxP/gre3::loxP | | | | | |
| M0227 | gre3::loxP/gre3::loxP | RKI1+/loxP-kan-P$_{TPI}$-RKI1 | | | | |
| M0237 | gre3::loxP/gre3::loxP | RKI1+/loxP-kan-P$_{TPI}$-RKI1 | RPE1+/loxP-nat-P$_{TPI}$-RPE1 | | | |
| M0252 | gre3::loxP/gre3::loxP | RKI1+/loxP-P$_{TPI}$-RKI1 | RPE1+/loxP-P$_{TPI}$-RPE1 | | | |
| M0267 | gre3::loxP/gre3::loxP | RKI1+/loxP-P$_{TPI}$-RKI1 | RPE1+/loxP-P$_{TPI}$-RPE1 | TAL1+/loxP-kan-P$_{TPI}$-TAL1 | | |
| M0277 | gre3::loxP/gre3::loxP | RKI1+/loxP-P$_{TPI}$-RKI1 | RPE1+/loxP-P$_{TPI}$-RPE1 | TAL1+/loxP-kan-P$_{TPI}$-TAL1 | TKL+/loxP-nat-P$_{TPI}$-TKL | |
| M0280 | gre3::loxP/gre3::loxP | RKI1+/loxP-P$_{TPI}$-RKI1 | RPE1+/loxP-P$_{TPI}$-RPE1 | TAL1+/loxP-P$_{TPI}$-TAL1 | TKL+/loxP-P$_{TPI}$-TKL | |
| M0407 | gre3::loxP/gre3::loxP | RKI1+/loxP-P$_{TPI}$-RKI1 | RPE1+/loxP-P$_{TPI}$-RPE1 | TAL1+/loxP-P$_{TPI}$-TAL1 | TKL+/loxP-P$_{TPI}$-TKL | delta::P$_{ADH1}$-XKS P$_{TPI}$-xylA ~10 copies |
| M0509 | gre3::loxP/gre3::loxP | RKI1+/loxP-P$_{TPI}$-RKI1 | RPE1+/loxP-P$_{TPI}$-RPE1 | TAL1+/loxP-P$_{TPI}$-TAL1 | TKL+/loxP-P$_{TPI}$-TKL | delta::P$_{ADH1}$-XKS P$_{TPI}$-xylA ~20 copies |

Figure 41

Strain M1105 Genealogy

| Strain | Selection | Parent | Genotype |
|---|---|---|---|
| M0509 | | | *gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS* |
| M1017 | YPX, 41°C | M0509 | genotype not confirmed following cytostat evolution |
| M1046 | YMX, 41°C | M1017 | genotype not confirmed following cytostat evolution |
| M1080 | YMX, 40°C | M1046 | genotype not confirmed following cytostat evolution |
| M1105 | YPDX+acetate, 39°C | M1080 | genotype not confirmed following cytostat evolution |

Figure 42

Strain 1254 Genealogy

| Strain | Selection | Parent | Genotype |
|---|---|---|---|
| M0509 | | | *gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS* |
| M1017 | YPX, 41°C | M0509 | genotype not confirmed following cytostat evolution |
| M1046 | YMX, 41°C | M1017 | genotype not confirmed following cytostat evolution |
| M1080 | YMX, 40°C | M1046 | genotype not confirmed following cytostat evolution |
| M1105 | YPDX+acetate, 39°C | M1080 | genotype not confirmed following cytostat evolution |
| M1155 | Xylose minimal + 8 g/L acetate, pH 5.5, 40° | M1105 | genotype not confirmed following cytostat evolution |
| M1202 | Complex glucose + 12 g/L acetate, pH 5.4, 41°C | M1155 | genotype not confirmed following cytostat evolution |
| M1254 | 5% solids equivalent MS419 hydrolysate + yeast nitrogen base w/o amino acids, pH 4.8, 39°C | M1202+ M1155 | genotype not confirmed following cytostat evolution |

SEQUENCE LISTING

```
<160> NUMBER OF SEQ ID NOS: 74

<210> SEQ ID NO 1
<211> LENGTH: 1590
<212> TYPE: DNA
<213> ORGANISM: Humicola grisea

<400> SEQUENCE: 1

gaattcatga gaaccgctaa gttcgctacc ttggctgcct tggttgcctc tgctgctgct      60

caacaagcct gttccttgac tactgaacgt cacccatctt tgtcttggaa caagtgtact     120

gctggtggtc aatgtcaaac tgtccaagcc tccatcactt tggactctaa ttggagatgg     180

acccaccaag tctctggtag tactaactgt tacaccggta ataagtggga cacttctatt     240

tgtactgacg ctaagtcttg tgctcaaaat tgttgtgttg atggtgctga ttacacctcc     300

acttatggta ttaccaccaa cggtgactct ttgtccttga agttcgttac taaaggtcaa     360

cattccacca acgtcggttc tagaacctac ttaatggacg gtgaagacaa gtaccaaacc     420

ttcgaattgt tgggtaatga atttaccttc gatgtcgatg tgtctaacat cggttgtggt     480

ttgaacggtg ctttatactt cgtttctatg gacgccgacg gtggtttgtc tcgttaccca     540

ggtaataagg ctggtgccaa gtatggtacc ggttactgtg atgctcaatg cccaagagac     600

attaagttca tcaacggtga agctaacatt gaaggttgga ctggttctac caacgaccca     660

aacgctggcg ccggtagata cggtacctgt tgttccgaaa tggacatttg ggaagccaac     720

aacatggcta ctgcttttac tccacaccca tgtaccatca ttggtcaatc cagatgtgaa     780

ggtgactcct gtggcggtac ctactccaac gaaagatacg ctggtgtttg tgatccagac     840

ggttgtgact tcaactccta cagacaaggt aacaagactt tctatggtaa gggtatgact     900

gtcgatacca ccaagaagat caccgtcgtc acccaattct tgaaggacgc taacggtgat     960

ttaggtgaaa ttaaaagatt ctacgtccaa gatggtaaga tcatcccaaa ctctgaatct    1020

accattccag gtgttgaagg taattccatc actcaagact ggtgtgacag acaaaaggtt    1080

gccttcggtg atattgacga cttcaacaga aagggtggta tgaagcaaat gggtaaggct    1140

ttggccggtc caatggtctt ggttatgtct atttgggacg atcacgcttc caacatgttg    1200

tggttggact ccaccttccc agttgatgct gctggtaagc caggtgccga aagaggtgct    1260

tgtccaacta cttccggtgt cccagctgaa gttgaagccg aagctccaaa ttctaacgtt    1320

gtcttctcta acatcagatt cggtccaatc ggttccacag tcgctggttt gccaggtgct    1380

ggtaatggtg gtaataacgg tggtaaccca ccaccaccaa ccactaccac ttcttctgcc    1440

ccagctacta ccaccaccgc ttctgctggt ccaaaggctg gtagatggca acaatgtggt    1500

ggtattggtt tcaccggtcc aacccaatgt gaagaaccat acatctgtac caagttgaac    1560

gactggtact ctcaatgttt ataactcgag                                     1590


<210> SEQ ID NO 2
<211> LENGTH: 1383
<212> TYPE: DNA
<213> ORGANISM: Thermoascus aurantiacus

<400> SEQUENCE: 2

gaattcatgt accaaagagc tctattgttc tccttcttct tggccgccgc tagagctcat      60
```

-continued gaagccggta ctgtcaccgc cgaaaaccac ccatccttga cttggcaaca atgttcctct 120
ggtggttctt gtactactca aaacgggaag gttgttattg acgctaactg gagatgggtt 180
cacactacct ccggttacac caactgttac actggtaaca cttgggatac ttccatctgt 240
ccagacgacg ttacctgtgc tcaaaactgt gctttggacg gtgctgacta ctccggtact 300
tacggtgtca ctacctctgg caacgcgttg agattgaact tcgtcaccca atcttctggt 360
aagaacatcg gttctagatt gtacttgttg caagacgata ctacttacca aatcttcaag 420
ttgttgggtc aagagttcac tttcgacgtt gatgtttcca acttgccttg tggtttgaac 480
ggtgctttgt acttcgttgc tatggacgcc gacggtaact tatccaagta cccaggtaac 540
aaggccggtg ccaagtacgg taccggttac tgtgattctc aatgtccaag agacctaaaa 600
ttcattaacg gtcaagctaa cgtcgaaggt tggcaaccat ctgctaacga tccaaacgcc 660
ggtgtcggta atcacggttc ctcctgtgct gaaatggacg tttgggaagc taactctatc 720
tccaccgccg tcactccaca tccatgtgat accccaggtc aaaccatgtg tcaaggtgat 780
gattgtggtg gtacctactc ttccactaga tacgctggta cctgtgacac cgacggttgt 840
gatttcaacc cataccaacc aggtaaccac tctttctacg gtccaggtaa gattgtcgat 900
acttcttcta agttcactgt tgtcactcaa ttcattaccg acgatggtac cccatctggt 960
accctaactg aaattaagag attctacgtc caaaacggta aagtcattcc acaatccgaa 1020
agcaccattt ccggtgttac cggtaactcc atcaccactg aatactgtac cgctcaaaag 1080
gccgcctttg acaacaccgg tttcttcacc catggtggtt tgcaaaagat ttctcaagcc 1140
ttggctcaag gtatggtttt ggtcatgtcc ttgtgggatg accacgctgc taacatgttg 1200
tggttggatt ctacttaccc aactgacgct gatccagaca ccccaggtgt tgctagaggt 1260
acttgtccaa ccacttctgg tgttccagct gacgtcgaat ctcaaaaccc taactcttac 1320
gttatctact ctaacatcaa ggtgggtcca attaactcca ccttcactgc taactaactc 1380
gag 1383

<210> SEQ ID NO 3
<211> LENGTH: 1380
<212> TYPE: DNA
<213> ORGANISM: Talaromyces emersonii

<400> SEQUENCE: 3
gaattcatgc taagaagagc tttactattg agctcttctg ctatcttggc cgttaaggct 60
caacaagccg gtaccgctac tgctgaaaac caccctccat tgacctggca agaatgtacc 120
gctccaggtt cttgtaccac ccaaaacggt gctgtcgtct tggacgctaa ctggagatgg 180
gtccacgacg tcaacggtta cactaactgt tacaccggta acacctggga cccaacttac 240
tgtccagacg acgaaacttg cgctcaaaac tgtgccttgg acggtgctga ctacgaaggt 300
acttacggtg ttacctcctc tggttcttcc ttgaagttga acttcgtcac tggttctaac 360
gtcggttcca gattgtattt gttgcaagat gactccactt accaaatctt caagttgttg 420
aacagagaat ttctttcga cgtcgatgtg tccaacttgc cttgtggttt gaacggtgct 480
ctatacttcg ttgctatgga cgctgatggt ggtgtttcca agtacccaaa caacaaggct 540
ggtgccaaat acggtactgg ttactgtgac tctcaatgtc cacgtgactt gaagtttatt 600
gatggtgaag ctaatgtcga aggttggcaa ccatcttcta acaacgctaa cactggcatc 660
ggtgaccacg gttcttgctg tgccgaaatg gacgtttggg aagccaactc catttccaac 720

-continued gccgtcactc cacacccatg tgacactcca ggtcaaacta tgtgttccgg cgatgactgt 780
ggtggtactt actctaacga tagatacgct ggtacctgtg atccagacgg ttgcgacttc 840
aatccataca gaatgggtaa cacttccttt tacggtccag gcaagatcat cgacactact 900
aagccattca ctgttgtcac ccaattcttg accgacgatg gtactgatac cggtactttg 960
tccgaaatca agagattcta catccaaaac tctaacgtca tcccacaacc aaattccgac 1020
atctctggtg tcactggtaa ctccattacc accgaatttt gtaccgccca aaagcaagct 1080
ttcggtgaca ccgacgactt ctctcaacac ggtggtttgg ctaagatggg tgctgctatg 1140
caacaaggta tggttttggt catgtctttg tgggacgact acgctgctca aatgttgtgg 1200
ttggactccg attacccaac cgatgccgac ccaaccaccc ctggtatcgc tagaggtacc 1260
tgtccaactg actctggtgt tccatctgac gtcgaatccc aatctccaaa ctcctacgtc 1320
acttactcca acattaaatt cggtccaatc aactccactt tcactgcttc ttaactcgag 1380

<210> SEQ ID NO 4
<211> LENGTH: 1392
<212> TYPE: DNA
<213> ORGANISM: Talaromyces emersonii

<400> SEQUENCE: 4
gaattcatgc gtaacttgtt ggccttggct ccagccgctt tgttggttgg tgctgccgaa 60
gctcaacaat ccttgtgggg tcaatgcggt ggttcctcct ggactggtgc aacttcctgt 120
gccgctggtg ccacctgttc caccattaac ccatactacg ctcaatgtgt tccagccact 180
gccactccaa ctaccttgac taccaccact aagccaacct ccaccggtgg tgctgctcca 240
accactccac caccaactac taccggtact accacctctc cagtcgtcac cagacctgcc 300
tccgcctccg gtaatccatt cgaaggttat caattgtacg ctaaccctta ctacgcttct 360
gaagtcattt ccttggctat cccatctttg agctccgagt tggtcccaaa ggcctccgaa 420
gttgctaagg tcccttcatt tgtctggtta gatcaagctg ccaaggttcc atctatgggt 480
gattacttga aggatattca atctcaaaac gctgctggtg ctgatccacc aatcgccggt 540
attttcgttg tttacgattt gccagataga gactgtgccg ccgctgcttc taacggtgaa 600
ttttctatcg ccaacaacgg tgtcgcttta tacaaacaat atatcgattc cattagagaa 660
caattaacca cttactccga cgtccatacc atcttggtta tcgaaccaga ctctttggct 720
aacgttgtca ctaacttgaa cgttccaaaa tgtgctaacg ctcaagatgc ttacttggaa 780
tgtatcaact acgctattac ccaattggac ttgccaaacg ttgctatgta cttggacgct 840
ggtcacgccg gttggttggg ttggcaagcc aacttggccc cagctgctca attattcgct 900
tctgtttaca agaacgcctc ttccccagcc tctgttagag gtttggctac caacgtggct 960
aactacaacg cctggtccat ttctagatgt ccatcctaca ctcaaggtga cgctaactgt 1020
gatgaagaag attacgttaa cgctttgggt ccattgttcc aagaacaagg tttcccagct 1080
tacttcatca tcgacacttc ccgtaacggt gtcagaccaa ctaagcaatc tcaatggggt 1140
gactggtgta acgttattgg taccggtttc ggtgttagac caaccaccga cactggtaac 1200
ccattggaag acgctttcgt ttgggtcaag ccaggtggtg aatccgacgg tacctccaac 1260
actactagcc cacgttacga ttaccactgt ggtttgtctg acgctttgca accagctcca 1320
gaagctggta cctggttcca agcctacttc gaacaattgt tgactaacgc caacccattg 1380
ttctaactcg ag 1392

<210> SEQ ID NO 5
<211> LENGTH: 1449
<212> TYPE: DNA
<213> ORGANISM: Chrysosporium lucknowense

<400> SEQUENCE: 5

```
atggccaaga agttgttcat taccgctgcc ttagctgccg cagtgcttgc tgcaccagtg     60

atcgaagaga gacaaaattg cggagccgtc tggacacagt gcggaggcaa cggctggcaa    120

ggcccaacat gttgtgcttc tggctcaacg tgcgtggcac agaacgagtg gtattcccag    180

tgccttccaa actcccaggt gacttcttca acaaccccca gctcaacgtc tacttcacag    240

agatccacaa gtacctcttc tagcacaacc agaagtggct catcctcatc tagcagtacg    300

acccctccac ccgtatcaag tcctgtcacg agtatccctg gcggagcaac ctcaacagcc    360

agttattccg gcaatccttt ctctggagtg agattatttg caaacgacta ttatagatca    420

gaggttcaca accttgcaat tccttctatg acgggaaccc tagccgcaaa ggcttccgcc    480

gtagcagaag tccctagttt ccaatggctt gacagaaacg ttacaataga tacacttatg    540

gtacagactt tatctcaggt tagagctttg aataaggccg gtgccaaccc accttatgct    600

gcccaattag tagtctatga cttgccagat agagactgtg ctgccgcagc ttctaatggt    660

gaattttcca tcgcaaatgg cggagctgca aactatagat catacattga tgcaataaga    720

aaacacatca ttgagtattc tgatattaga ataatccttg tgattgaacc agactccatg    780

gctaatatgg ttaccaacat gaatgtagcc aagtgttcta acgcagcttc cacataccat    840

gagctaaccg tatatgcatt aaaacaactg aatctaccta acgttgctat gtacttagat    900

gccggtcatg ccggatggtt gggctggcct gcaaatatcc aacccgcagc tgaattgttc    960

gctggaatct acaacgacgc cggaaagccc gctgccgtta gaggcttagc cacaaatgtt   1020

gcaaattaca acgcttggtc aattgctagt gccccttctt atacctcacc aaatcctaac   1080

tacgatgaga aacattacat agaagcattt tccccattgt taaactccgc tggattccct   1140

gccagattca tcgtggatac cggtagaaac ggcaaacaac caactggaca acaacaatgg   1200

ggagattggt gtaacgtcaa gggaaccggc ttcggcgtca ggcctacggc aaacaccgga   1260

cacgagctag tcgacgcttt tgtatgggtt aagccaggtg gcgaaagtga cggaacaagt   1320

gacacgagtg ctgcaagata cgattaccac tgtggtctgt ccgacgcttt acagcccgcc   1380

cccgaggctg gacaatggtt ccaggcttat tttgaacaat tgttaacgaa cgcaaatcca   1440

ccattctaa                                                           1449
```

<210> SEQ ID NO 6
<211> LENGTH: 1551
<212> TYPE: DNA
<213> ORGANISM: Artificial Sequence
<220> FEATURE:
<223> OTHER INFORMATION: T.emersonni cbh1 with CBD

<400> SEQUENCE: 6

```
atgctaagaa gagctttact attgagctct tctgctatct tggccgttaa ggctcaacaa     60

gccggtaccg ctactgctga aaaccaccct ccattgacct ggcaagaatg taccgctcca    120

ggttcttgta ccacccaaaa cggtgctgtc gtcttggacg ctaactggag atgggtccac    180

gacgtcaacg gttacactaa ctgttacacc ggtaacacct gggacccaac ttactgtcca    240

gacgacgaaa cttgcgctca aaactgtgcc ttggacggtg ctgactacga aggtacttac    300

ggtgttacct cctctggttc ttccttgaag ttgaacttcg tcactggttc taacgtcggt    360
```

-continued tccagattgt atttgttgca agatgactcc acttaccaaa tcttcaagtt gttgaacaga 420
gaattttctt tcgacgtcga tgtgtccaac ttgccttgtg gtttgaacgg tgctctatac 480
ttcgttgcta tggacgctga tggtggtgtt tccaagtacc caaacaacaa ggctggtgcc 540
aaatacggta ctggttactg tgactctcaa tgtccacgtg acttgaagtt tattgatggt 600
gaagctaatg tcgaaggttg gcaaccatct tctaacaacg ctaacactgg catcggtgac 660
cacggttctt gctgtgccga aatggacgtt tgggaagcca actccatttc caacgccgtc 720
actccacacc catgtgacac tccaggtcaa actatgtgtt ccggcgatga ctgtggtggt 780
acttactcta acgatagata cgctggtacc tgtgatccag acggttgcga cttcaatcca 840
tacagaatgg gtaacacttc cttttacggt ccaggcaaga tcatcgacac tactaagcca 900
ttcactgttg tcacccaatt cttgaccgac gatggtactg ataccggtac tttgtccgaa 960
atcaagagat tctacatcca aaactctaac gtcatcccac aaccaaattc cgacatctct 1020
ggtgtcactg gtaactccat taccaccgaa ttttgtaccg cccaaaagca agctttcggt 1080
gacaccgacg acttctctca acacggtggt ttggctaaga tgggtgctgc tatgcaacaa 1140
ggtatggttt tggtcatgtc tttgtgggac gactacgctg ctcaaatgtt gtggttggac 1200
tccgattacc caaccgatgc cgacccaacc acccctggta tcgctagagg tacctgtcca 1260
actgactctg gtgttccatc tgacgtcgaa tcccaatctc caaactccta cgtcacttac 1320
tccaacatta aattcggtcc aatcaactcc actttcactg cttctaaccc tccaggtggt 1380
aacagaggta ctaccactac tcgtaggcca gctactacaa ctggttcttc cccaggccca 1440
acccaatccc actacggtca atgtggtggt atcggttact ctggtccaac cgtctgtgct 1500
tctggtacta cctgtcaagt tttaaaccca tactactctc aatgtttgta g 1551

<210> SEQ ID NO 7
<211> LENGTH: 1608
<212> TYPE: DNA
<213> ORGANISM: Trichoderma reesei

<400> SEQUENCE: 7
atggtctcct tcacctccct gctggccggc gttgccgcta tctctggtgt cctagcagcc 60
cctgccgcag aagttgaacc tgtcgcagtt gagaaacgtg aggccgaagc agaagctcaa 120
tccgcttgta ccctacaatc cgaaactcac ccaccattga cctggcaaaa gtgttctagc 180
ggtggaactt gtactcaaca aactggttct gttgttatcg acgctaactg gagatggaca 240
cacgccacta actcttctac caactgttac gacggtaaca cttggtcttc cactttatgt 300
ccagataacg aaacttgtgc taagaattgc tgtttggacg gtgccgccta cgcttctacc 360
tacggtgtta ccacctccgg taactccttg tctattggtt tcgtcactca atccgctcaa 420
aagaacgttg gtgctagatt gtacttgatg gcttctgaca ctacttatca agaatttact 480
ttgttgggta acgaattttc tttcgatgtt gacgtttccc aattgccatg tggcttgaac 540
ggtgctttgt actttgtctc tatggatgct gacggtggtg tttctaagta cccaactaac 600
actgccggtg ctaagtacgg tactggttac tgtgattctc aatgtccacg tgacttgaag 660
ttcattaacg gtcaagccaa cgtcgaaggt tgggaaccat cctccaacaa cgctaacacc 720
ggtatcggtg gtcacggttc ctgttgttcc gaaatggaca tctgggaagc taacagtatt 780
tctgaagctt tgacaccaca cccatgcacc actgtcggtc aagaaatttg tgaaggtgat 840
ggatgtggtg gaacctactc tgataacaga tacggtggta cttgtgaccc agacggttgt 900
gactggaacc catacagatt gggtaacact tctttctatg gtccaggttc ttctttcacc 960

-continued

```
ttggatacca ccaagaagtt gactgttgtt acccaattcg aaacttctgg tgctatcaac   1020

agatactacg ttcaaaacgg tgtcaccttc caacaaccaa acgctgaatt gggttcttac   1080

tctggtaatg aattgaacga cgactactgt accgctgaag aagctgaatt tggtggttcc   1140

tctttctccg acaagggtgg tttgacccaa ttcaagaagg ctacctccgg tggtatggtt   1200

ttggttatgt ccttgtggga tgattactac gcaaacatgt tatggttaga cagtacttac   1260

ccaactaacg aaacctcctc tactccaggt gctgtcagag gttcctgttc tacctcttct   1320

ggtgttccag ctcaagttga atctcaatct ccaaacgcta aggtcacttt ctccaacatc   1380

aagttcggtc caatcggttc cactggtaat ccatctggtg gaaaccctcc aggtggtaac   1440

agaggtacta ccactactcg taggccagct actacaactg gttcttcccc aggcccaacc   1500

caatcccact acggtcaatg tggtggtatc ggttactctg gtccaaccgt ctgtgcttct   1560

ggtactacct gtcaagtttt aaacccatac tactctcaat gtttgtaa                1608
```

<210> SEQ ID NO 8
<211> LENGTH: 1479
<212> TYPE: DNA
<213> ORGANISM: Trichoderma reesei

<400> SEQUENCE: 8

```
atggtctcct tcacctccct gctggccggc gttgccgcta tctctggtgt cctagcagcc     60

cctgccgcag aagttgaacc tgtcgcagtt gagaaacgtg aggccgaagc agaagctgtc    120

ccattagaag aaagacaagc ctgctcctct gtttggggtc aatgtggtgg tcaaaactgg    180

tctggtccaa cttgttgtgc ttccggttct acctgtgttt actccaacga ctactattcc    240

caatgtttgc caggtgctgc ttcctcttcc tcttcaacta gagctgcttc tacaacttct    300

agggtctccc caaccacttc cagatcctct tctgctactc caccaccagg ttctactacc    360

actagagttc caccagtcgg ttccggtact gctacttact ctggtaaccc tttcgtcggt    420

gttactccat gggctaacgc ttactacgct tctgaagttt cttctttggc tatcccatct    480

ttgactggtg ctatggctac cgctgctgct gctgtcgcca aagttccatc cttcatgtgg    540

ttggacacct tggacaaaac tccattaatg gaacaaacct tggcagacat aaggactgct    600

aacaagaacg gcggtaacta cgctggtcaa tttgttgtgt acgacttgcc agacagagac    660

tgtgctgctt tggcttccaa cggtgaatac tccatcgctg acggtggtgt cgccaagtac    720

aagaactaca ttgataccat tagacaaatc gttgtcgaat actctgacat cagaaccttg    780

ttagtcatcg aaccagattc tttagccaat ttagtcacca acttgggtac tccaaagtgt    840

gctaacgctc aatctgccta cttagaatgt atcaattatg cagttaccca attgaacttg    900

ccaaacgttg ctatgtactt ggacgctggt cacgccggtt ggttgggttg gccagctaac    960

caagacccag ccgctcaatt attcgccaac gtttacaaga atgcctcttc tcctagagcc   1020

ttgcgtggtt tggctactaa cgtcgctaac tacaacggtt ggaacatcac ttctccacca   1080

tcttacaccc aaggtaacgc tgtttacaac gaaaagttgt acattcacgc tatcggtcca   1140

ttattggcta accatggttg gtctaacgcc ttcttcatca ccgaccaagg tagatccggt   1200

aaacaaccaa ctggtcaaca acaatggggt gattggtgta acgtcatcgg tactggtttc   1260

ggtatcagac catccgctaa cactggtgat tccttgttgg attccttcgt ctgggttaag   1320

ccaggtggtg aatgtgatgg cacctctgat tcctctgctc caagattcga ttcccactgc   1380

gccttgccag acgctttgca accagcccca caagctggtg catggttcca agcttacttt   1440
```

-continued gtccaattgt tgaccaacgc taacccatct ttcttgtaa 1479

<210> SEQ ID NO 9
<211> LENGTH: 1618
<212> TYPE: DNA
<213> ORGANISM: Chaetomium thermophilum

<400> SEQUENCE: 9
ttaattaaac aatgatgtac aagaaatttg cagccctagc tgctttagtt gcaggagctt 60
ccgctcaaca ggcatgttca ttgactgccg aaaatcatcc atccttaacg tggaagagat 120
gcacgtcagg aggttcatgc tccactgtaa acggagctgt cacaatagat gcaaattgga 180
gatggaccca cactgtgtcc ggtagtacaa actgctacac cggtaatcaa tgggatacgt 240
ctttgtgtac agatggaaag tcatgcgctc agacctgttg cgtggatgga gcagactact 300
cttctactta cggaatcacg acatcaggtg acagtcttaa tttgaaattc gtaaccaagc 360
accagtacgg aacaaatgta ggctccagag tgtacttaat ggagaacgat accaaatatc 420
aaatgttcga gttattaggc aatgagttta cctttgacgt agacgttagc aatttgggtt 480
gcggattaaa cggcgccctt tacttcgtgt ctatggatgc tgacggaggt atgtcaaagt 540
attctggtaa caaagccgga gcaaagtacg gtacaggtta ttgtgacgct cagtgcccta 600
gagatttgaa gtttatcaac ggagaagcca acgttggtaa ctggacgcca agtactaacg 660
acgcaaacgc tggattcggc agatacggta gttgttgctc agaaatggac gtgtgggagg 720
ccaataacat ggcaaccgct tttactcctc acccatgtac aactgttgga caatctagat 780
gtgaagccga cacgtgcggt ggcacctaca gtagcgatag gtatgcagga gtatgtgatc 840
ctgacggttg cgatttcaat gcttatagac aaggagacaa aacgttttat ggtaaaggta 900
tgaccgtcga tactaacaag aagatgactg tggttaccca gttccacaag aactcagctg 960
gagtattgtc tgaaattaaa agattctacg tccaggatgg aaagattatt gctaatgccg 1020
agagtaagat accaggtaac cctggaaata gtatcacaca ggaatactgt gacgctcaga 1080
aggtagcttt tagcaacacc gatgacttca atagaaaggg tggaatggct caaatgagta 1140
aggctttagc cggtccaatg gtgttggtga tgtctgtttg ggatgatcac tatgcaaaca 1200
tgctttggct tgacagcacc tatcctatcg accaagccgg agccccaggt gctgaaaggg 1260
gtgcatgtcc aaccacgagt ggtgtgcccg ccgagattga agctcaagtg cctaatagta 1320
acgttatctt ttccaatata agattcggac caatcggatc cactgttcca ggtttggatg 1380
gatctaatcc tggcaaccca acaaccacgg tagtccctcc agcttcaact tccacaagta 1440
gaccaacaag ttcaacgtcc agtccagtgt ctactcctac cggacaacca ggaggctgta 1500
ccactcagaa atggggtcaa tgcggtggaa ttggctatac aggttgtacg aattgcgttg 1560
caggaaccac ttgtacacag ttaaaccctt ggtactcaca atgcctataa ggcgcgcc 1618

<210> SEQ ID NO 10
<211> LENGTH: 969
<212> TYPE: DNA
<213> ORGANISM: Coptotermes lacteus

<400> SEQUENCE: 10
atgagatttc cttccatatt caccgctgtt ttgttcgcag cctcaagtgc tttagcagaa 60
tgtactaagg gtggatgtac taacaagaat ggatacatag ttcatgataa gcacgtcggt 120
gacatccaga atagagacac tttggaccct ccagacttag attatgaaaa ggacgtggga 180
gtaaccgtgt ccggtggaac ccttagtcaa agattagtct caacttggaa cggtaagaaa 240

```
gtcgtgggaa gtagattgta tattgtggac gaagccgacg agaaatatca attattcaca    300

tttgtcggta aggagttcac ctataccgtt gatatgtccc agatccaatg tggaatcaat    360

gccgcattat acacagtgga aatgcctgcc gctggaaaga cccctggagg tgttaagtat    420

ggatatggat attgtgatgc caactgcgtg gatggagatt gttgtatgga gttcgatatc    480

caagaagctt ctaacaaggc aatcgtttac accacccatt cctgtcaaag tcaaacttca    540

ggttgcgata cctcaggatg cggttacaac ccttacagag acagtggtga caaggcattc    600

tggggaacaa ctataaacgt aaaccagcct gtgacaattg taacacagtt tatcggttct    660

ggtagttcct taactgaagt caaaagattg tgcgtgcaag gtggaaagac cttccctcca    720

gccaaatcat taaccgacag ttattgtaat gccaacgact atagaagttt gagaactatg    780

ggtgcatcca tggctagagg acacgttgtt gtgttttctt tgtgggattc taatggtatg    840

agttggatgg atggaggtaa cgccggtcct tgtacctcat ataatattga atctttggaa    900

tccagtcagc caaacttaaa ggtcacatgg tcaaacgtga aatacggaga gatcgattct    960

ccttattaa                                                            969
```

<210> SEQ ID NO 11
<211> LENGTH: 1356
<212> TYPE: DNA
<213> ORGANISM: Coptotermes formosanus

<400> SEQUENCE: 11

```
atgagattcc cttccatttt cactgctgtt ttgttcgcag cctcaagtgc tttagcagcc     60

tatgactaca agacagtatt gaagaactcc ttgttgttct acgaagctca aagaagtgga    120

aaattgcctg cagaccagaa ggtgacctgg agaaaagatt ccgcattaaa cgacaaggga    180

cagaagggag aggacttaac tggaggttat tacgacgccg gagactttgt gaagttcggt    240

tttccaatgg catacacagt taccgtgttg gcctggggtt tagtcgatta tgaatctgct    300

tacagtactg cgggtgcctt ggatgatggt agaaaggcct tgaaatgggg tacagattat    360

ttcttgaaag cacataccgc tgccaatgag ttttacggac aggtgggtca gggagatgtg    420

gatcatgctt actggggacg tcctgaggac atgactatgt ctagaccagc ttacaagatc    480

gatacatcaa aacctggtag tgacttagct gcagaaacag cagccgcttt agcagcaacc    540

gcaatagctt acaagtcagc cgattctacc tacagtaaca acttaattac tcatgcaaag    600

cagttgttcg attttgcaaa caattataga ggaaagtact ctgatagtat taccgatgcc    660

aagaatttct atgcatccgg tgattataag gacgaattag tatgggctgc agcctggttg    720

tatagagcta caaatgataa cacttactta accaaagccg aatcattgta taatgaattt    780

ggtttaggat cttggaacgg tgcattcaat tgggataaca agatatccgg agttcaggtc    840

ttattagcca aattgacatc caaacaagca tacaaagata aagttcaggg ttatgttgat    900

tacttagtct cctctcaaaa gaaaactcca aagggattgg tctatattga ccaatgggga    960

accttaagac acgcagctaa tagtgccttg atcgctttac aggccgctga tttgggtata   1020

aacgctgcta gttatagaca atacgcaaag aagcaaattg attatgcctt aggtgacgga   1080

ggtcgttctt acgtggtcgg attcggaact aaccctccag taagacctca tcatagatcc   1140

agttcctgtc ctgacgcacc agccgcttgc gactggaata cttacaactc tgccggacca   1200

aatgcccacg tcttgaccgg agccttagta ggtggaccag attccaacga tagttacaca   1260

gattcacgtt ctgattatat cagtaacgaa gtcgctactg attacaatgc cggtttccaa   1320
```

-continued

```
tctgcagttg ctggtttgtt gaaagccgga gtataa                            1356


<210> SEQ ID NO 12
<211> LENGTH: 1356
<212> TYPE: DNA
<213> ORGANISM: Nasutitermes takasagoensis

<400> SEQUENCE: 12

atgagatttc catctatttt cactgccgtc ttatttgcag cctccagtgc attagcagcc     60

tatgattata aacaagtttt gagagattcc ttattgttct acgaagctca gagaagcggt    120

agattaccag cagaccagaa ggtcacttgg agaaaagatt cagccttgaa tgatcaggga    180

gatcaaggtc aagacttaac cggaggttat tttgacgccg gtgattttgt gaaatttggt    240

ttcccaatgg catatactgc taccgtcttg gcctggggtt taatcgattt tgaggcagga    300

tacagttccg ctggtgcctt ggatgacggt agaaaagcag taaagtgggc aactgattac    360

tttataaagg cccacacttc acagaatgag ttttacggac aagtcggtca gggtgacgct    420

gatcacgctt tctggggacg tcctgaagat atgaccatgg ctagaccagc ctacaagatt    480

gacaccagca gaccaggtag tgacttagcg ggtgaaaccg cagcggcatt ggcagctgcc    540

agtatcgtgt ttagaaatgt tgatggtaca tactctaaca acttacttac tcatgccaga    600

caattatttg actttgcaaa taactacaga ggaaaatact cagattccat aaccgacgct    660

agaaactttt acgccagtgc agattaccgt gacgaattgg tttgggctgc cgcatggttg    720

tacagagcta caaatgacaa cacttacttg aataccgcag aatccttgta tgatgaattt    780

ggattgcaga actggggtgg agggttaaac tgggattcaa aggtgtctgg tgtccaggtc    840

ttgttagcaa aattgaccaa caaacaggct tacaaagata ctgtgcagtc ttacgtgaat    900

tacctgatta ataaccagca aaagacccca aaaggattgt tatacattga tatgtggggt    960

acattgagac acgccgcaaa tgctgcattc atcatgttgg aagctgccga gttgggttta   1020

tccgcatcat cttacagaca gtttgctcaa actcagatcg actacgcttt gggtgacggt   1080

ggaagaagtt tcgtctgtgg ttttggttca aaccctccta caagaccaca tcatcgttct   1140

tccagttgcc cgcctgcccc agcaacttgt gactggaata cattcaactc acctgaccca   1200

aattaccacg tgttatctgg agctttggta ggaggaccag atcaaaacga taattatgtg   1260

gatgatagat ccgactacgt ccataacgaa gtggcaaccg actacaacgc cggatttcag   1320

agtgctttgg cagccttagt tgctttgggt tattaa                            1356


<210> SEQ ID NO 13
<211> LENGTH: 1356
<212> TYPE: DNA
<213> ORGANISM: Coptotermes acinaciformis

<400> SEQUENCE: 13

atgagattcc ctagtatttt cactgccgtc ttatttgcag ccagttctgc tttagccgca     60

tatgattata ccacagtttt gaaaagttcc ttattgttct acgaagctca aagatccggt    120

aagttgccag ccgaccagaa ggtcacttgg agaaaagatt cagcattaga cgataaagga    180

aataatggag aggacttaac aggaggttat tatgacgctg gtgattttgt gaagtttggt    240

tttcctttag catacaccgc tactgtttta gcctggggtt tggtggacta tgaagcgggt    300

tactcatccg ctggagccac agatgacggt agaaaggcag tgaaatgggc aaccgactat    360

ttgttgaagg cacatactgc cgctaccgag ttatacggac aggtcgggga cggtgacgcc    420

gatcacgcat attggggacg tcctgaagat atgactatgg ctagaccagc atacaagatc    480
```

-continued gacgctagca gaccaggatc tgacttagcg ggtgaaaccg ctgccgcttt agccgctgca 540
tccatagttt tcaaaggtgt agattcttca tattctgaca acttgttagc tcacgctaaa 600
cagttatttg atttcgctga caattataga ggaaaataca gtgattccat aacacaagct 660
tcaaactttt acgcctccgg agattacaaa gacgagttag tctgggctgc cacttggttg 720
tacagagcaa ccaacgataa tacatatttg accaaagcag aatccttgta caacgagttc 780
ggattaggaa actggaacgg agcctttaat tgggacaaca aggtgtccgg tgttcaggtg 840
ttgttagcca aattgacctc caagcaggct tataaagaca ccgttcaagg atacgtcgat 900
tatttgatta acaatcagca aaagacccca aagggtttgt tatacataga ccaatggggg 960
accttgagac acgcagctaa tgctgcctta ataatcttac aggctgctga tttgggtatt 1020
tctgccgaca gttatagaca attcgcaaag aagcaaatag attacgcttt aggtgacgga 1080
ggtagatcat atgtagttgg ttttggagac aatcctccaa cacatcctca tcaccgttct 1140
tcctcatgcc ctgacgcccc agcagtatgc gattggaata ctttcaattc acctgatcca 1200
aactttcatg tcttaaccgg agctttagtg ggaggtcctg atcagaacga taactacgtt 1260
gatgatcgtt ctgactacgt gtccaacgag gttgcaaccg actataatgc aggattccaa 1320
agtgctgtgg ccgctttagt tactttagga gtttaa 1356

<210> SEQ ID NO 14
<211> LENGTH: 1356
<212> TYPE: DNA
<213> ORGANISM: Mastotermes darwinensis

<400> SEQUENCE: 14
atgagattcc caagtatatt tactgctgtt ttgttcgcag ccagttctgc tttagcagcc 60
tatgattaca atgacgtatt aaccaaaagt ttgttgttct acgaagctca aagatccggt 120
aagttacctt ctgatcagaa agtcacctgg agaaaagatt cagcattaaa cgataaggga 180
caaaatggtg aggacttaac tggtggatat tatgacgccg gtgattacgt gaagtttggt 240
tttccaatgg catatactgc taccgttttg gcttggggtt tagtggacca tcctgccgga 300
tacagttctg cgggtgtctt ggatgatggt agaaaagctg tgaagtgggt taccgattac 360
ttaatcaaag cccacgtatc aaagaacgaa ttatacggac aggtcggtga cggtgacgca 420
gatcacgctt attggggacg tccagaggat atgacaatgg caagaccagc atacaaaata 480
gacacttcaa gaccaggttc cgacttagcg ggtgaaaccg cagcggcatt ggctgctgca 540
tctattgtgt ttaagtcaac agattctaat tacgccaaca ccttattgac ccacgcaaaa 600
caattattcg actttgccaa taactataga ggtaagtata gtgattccat aacacaggca 660
tctaatttct acagtagttc cgactataaa gatgaattgg tttgggcagc tgtatggttg 720
tacagagcca ctaacgatca gacctatttg acaactgcag agaagttata ctcagacttg 780
ggattacagt cctggaacgg aggtttcaca tgggacacca aaattagtgg agtagaagtg 840
ttattggcta agattactgg taaacaggca tataaggaca aagtaaaggg atattgtgat 900
tatatctcag gatctcagca gaaaacacct aaaggattag tttacataga taagtggggt 960
tccttaagaa tggccgcaaa cgccgcatat atttgcgctg tagccgcaga cgtcggaatc 1020
agttcaacag cttacagaca gttcgccaaa acacagatta attacatatt gggtgatgcc 1080
ggacgttctt ttgtggttgg ttacggaaac aacccaccta cacacccaca tcacagatcc 1140
agttcatgtc ctgacgcccc agcaacatgc gattggaata actacaacag tgctaaccct 1200
aatccacatg ttttatacgg tgcattagtt ggtggaccag attccaacga taattatcaa 1260
gacttaagat cagattatgt cgccaacgaa gtggcaacag actacaatgc agccttccag 1320
tcattgttag cattaatcgt ggacttaggt ttgtaa 1356

<210> SEQ ID NO 15
<211> LENGTH: 1356
<212> TYPE: DNA
<213> ORGANISM: Nasutitermes walkeri

<400> SEQUENCE: 15
atgagatttc catctatttt cactgccgtc ttatttgcag cctcaagtgc tttagcagcc 60
tatgattaca aacaagtatt gagagattcc ttattgttct acgaagctca gagaagcggt 120
agattaccag cagaccagaa ggtcacctgg agaaaagatt ccgccttgaa tgatcaggga 180
gagcaaggtc aagacttaac cggaggttat tttgacgccg gtgattttgt gaagtttgga 240
ttcccaatgg cttatacagc aaccgttttg gcctggggtt taatcgactt tgaagccggt 300
tactcttctg ctggtgcctt ggacgatggt agaaaagcag taaagtgggc tactgattac 360
tttataaaag cccatacttc tcaaaacgag ttttacggac aagtcggtca gggtgacgta 420
gatcacgcat attggggacg tcctgaagat atgacaatgg ctagaccagc ctacaagatt 480
gataccagca gaccaggtag tgacttagca ggagaaactg ctgcagcttt ggctgccgca 540
tccatcgttt tcaagaatgt agatggtaca tattccaaca acttacttac tcatgctaga 600
cagttgtttg atttcgccaa caattacaga ggaaaatact ctgatagtat taccgatgca 660
agaaactttt acgctagtgc cgactataga gatgagttag tctgggcagc tgcctggttg 720
tacagagcaa ccaacgacaa ttcttacttg aacactgctg aatcattata caacgagttt 780
ggattgcaaa attggggtgg agggttaaac tgggattcta aagtgagtgg tgttcaagtt 840
ttgttagcca agttgaccaa caaacaagag tataaggaca ctattcaatc atacgtgaat 900
tacttaatca ataaccaaca gaaaactcca aagggattgt tatacattga catgtggggg 960
accttgagac acgcagctaa cgcagccttt ataatgttag aagctgccga cttaggttta 1020
tccgcttcat cttatagaca gttcgcccaa acacaaatag actacgcatt gggggacggt 1080
ggacgttctt ttgtctgtgg tttcggttct aatcctccaa ctagacctca tcatagatcc 1140
agttcatgcc cgcctgctcc agctacctgt gattggaata cattcaattc tcctgaccca 1200
aactacaatg ttttatccgg tgccttggtt ggtggtcctg accagaatga taactacgtg 1260
gacgatagaa gtgattatgt ccataatgag gtagcaactg actacaatgc cggtttccaa 1320
tcagccttag ccgctttagt cgccttaggt tactaa 1356

<210> SEQ ID NO 16
<211> LENGTH: 1356
<212> TYPE: DNA
<213> ORGANISM: Reticulitermes speratus

<400> SEQUENCE: 16
atgagattcc caagtatatt tactgccgtc ttatttgcag cctccagtgc attagccgct 60
tatgactaca aaacagtatt gtccaattcc ttgttgttct acgaagctca aagatccggt 120
aagttacctt ctgaccagaa agtgacctgg agaaaggatt cagcattaaa cgacaaagga 180
caaaagggtg aggacttaac cggtggatat tacgacgccg gagactttgt gaaatttggt 240
tttccaatgg cttacacagt taccgtattg gcatggggtg ttattgatta cgaatccgcc 300
tactctgccg caggagcttt agattcaggt agaaaggcct tgaaatatgg gaccgactat 360

-continued ttcttaaagg cacatacagc agctaacgag ttttacggac aggtgggtca aggtgacgtt 420
gaccacgcat actggggacg tcctgaagat atgaccatga gcagaccagc atacaaaata 480
gacacttcta agcctggttc cgacttagct gcagagactg cagctgcatt agcagccaca 540
gctattgcat acaaatctgc cgatgcaaca tattccaaca atttgataac acatgcaaaa 600
caattattcg actttgccaa caattacaga ggaaaatatt ccgatagtat taccgatgcc 660
aagaactttt atgcttctgg tgattacaaa gacgaattgg tatgggccgc tgcatggttg 720
tacagagcaa ccaatgacaa cacatatttg actaaggcag aatccttata caatgaattt 780
ggtttgggaa acttcaatgg tgccttcaat tgggataaca aagtctccgg agtccaggtg 840
ttattggcca agttaacctc aaaacaagtg tataaggata aggtacagtc ttacgtggac 900
tatttgatct cctcacaaaa aaagacacca aaaggtttag tgtacatcga tcaatggggt 960
actttaagac acgcagctaa ttctgctttg atcgctttgc aggcagctga cttaggaatt 1020
aacgctgcta cttacagagc ctacgcaaag aagcaaatcg actatgcttt gggtgatggt 1080
ggaagatcct atgttattgg atttgggacc aaccctccag taagaccaca tcacagaagt 1140
tcatcttgcc cagatgcacc agctgtctgc gattggaaca cctataactc cgctggtcca 1200
aacgcccacg tgttaaccgg tgcattggtt ggaggacctg atagtaatga tagttatacc 1260
gatgctcgtt ctgactacat atccaacgaa gtggcaactg attacaatgc gggtttccaa 1320
tccgctgtcg ctggattatt gaaggcgggt gtctaa 1356

<210> SEQ ID NO 17
<211> LENGTH: 1227
<212> TYPE: DNA
<213> ORGANISM: Neosartorya fischeri

<400> SEQUENCE: 17
atgagatttc catctatttt cactgcagtt ttgttcgcag ccagttccgc tttggcccaa 60
cagatcgggt ccatcgccga aaatcatcct gagttgacaa cctatagatg ctcctctcaa 120
gctggatgcg tagcacagag tacttccgtc gtgttagata ttaacgctca ttggattcat 180
caaaacggtg cccaaacaag ttgcactacc tcaagtggat tggacccttc attgtgccct 240
gataaagtca cctgttctca gaactgcgta gtcgaaggaa taaccgacta ctcatctttt 300
ggtgtgcaaa actccggaga tgcaatgaca ttaagacagt atcaagttca aaatggacag 360
atcaaaacat tgcgtcctag agtgtacttg ttagctgagg atggaatcaa ttactccaaa 420
ttgcagttgt tgaaccaaga gtttactttc gatgtggacg cttccaaatt gccttgtggt 480
atgaatggag ctttatattt gtcagaaatg gatgcttctg gtggacgttc tgccttgaac 540
ccagcgggtg ccacatatgg aacaggttac tgtgatgccc agtgcttcaa cccaggtcca 600
tggataaatg gagaagcaaa tactgctgga gccggtgcat gttgccaaga gatggactta 660
tgggaagcca actcccgttc taccattttc agtcctcacc catgtacaac tgcgggtttg 720
tatgcctgta ctggagctga gtgctactca atctgtgacg gttatggttg cacttacaac 780
ccttatgaat taggagccaa agattactat ggttacggtt tgactattga caccgcaaag 840
ccaataacag tggttactca gtttatgacc gctgataata cagcaaccgg tacattagca 900
gagatcagaa gattatatgt tcaagatggt aaagtaatcg gaaatacagc cgtggccatg 960
accgaggcat tttgtagttc tagtagaaca tttgaagagt taggtggttt gcaaagaatg 1020
ggagaagctt taggtagagg aatggtgcca gttttctcaa tatgggacga tcctggtttg 1080

```
tggatgcatt ggttagattc tgacggtgca ggaccttgtg gtaatactga aggtgatcct   1140

gccttcattc aggctaacta cccaaatacc gccgtaacat tctccaaggt gagatgggga   1200

gatatcggtt ctacctatag ttcttaa                                        1227
```

<210> SEQ ID NO 18
<211> LENGTH: 915
<212> TYPE: DNA
<213> ORGANISM: Reticulitermes flavipes

<400> SEQUENCE: 18

```
atgagatttc catctatttt cactgctgtt ttgttcgcag cctcaagtgc tttagcacaa     60

tggatgcaga tcggtggtaa gcagaaatat cctgccttta agccaggtgc taagtacgga    120

agaggttatt gtgacggaca gtgccctcac gacatgaagg tgtctagtgg aagagcaaac    180

gttgacggat ggaagccaca agacaacgac gaaaatagtg gaaatggaaa attgggtaca    240

tgttgctggg agatggatat atgggaagga aacttagtgt cccaagccta caccgttcac    300

gctggttcca agtccggaca atatgagtgt actggaacac aatgcggtga caccgacagt    360

ggtgaaagat tcaagggaac atgcgataaa gatggttgtg atttcgcaag ttacagatgg    420

ggagctacag actattacgg tcctggaaag accgtggaca ccaaacagcc aatgacagtc    480

gtgacccagt tcattggtga ccctttgact gagataaaga gagtttatgt acaaggagga    540

aaagtcataa acaattccaa aacatctaac ttaggttcag tgtacgattc tttgactgag    600

gccttctgcg atgacaccaa acaggttaca ggtgatacaa atgactttaa ggctaaagga    660

ggtatgtctg gattctccaa gaacttagac accccacaag ttttggtgat gtctttatgg    720

gatgaccata cagctaatat gttatggtta gattctactt atcctaccga tagtacaaag    780

ccaggtgccg caagaggtac ttgtgccgtc acctccgggg accctaaaga tgtggaatcc    840

aagcaagcca actctcaggt agtttacagt gacattaagt ttggtcctat taattcaaca    900

tacaaagcaa attaa                                                     915
```

<210> SEQ ID NO 19
<211> LENGTH: 1428
<212> TYPE: DNA
<213> ORGANISM: Trichoderma reesei

<400> SEQUENCE: 19

```
atggtctcct tcacctccct gctggccggc gttgccgcta tctctggtgt cctagcagcc     60

cctgccgcag aagttgaacc tgtcgcagtt gagaaacgtg aggccgaagc agaagctcaa    120

caaccaggaa catcaacacc agaagtccat ccaaagttaa caacctataa atgtactaag    180

agtggagggt gtgtagcgca ggacacaagt gtggtcttag actggaatta tcgttggatg    240

catgatgcca attataattc ctgtactgtt aacggcggtg ttaacactac gttatgcccc    300

gatgaagcga cttgtggtaa gaattgtttt attgaagggg ttgactacgc cgctagtggt    360

gttacgacga gtgggtcatc cttgacgatg aatcaataca tgccttcttc tagtggtggg    420

tattcctctg tgtctccaag gctgtattta ttggattccg atggggaata tgttatgtta    480

aaattaaatg ggcaagaact gagttttgat gtggatctat ctgcattacc ttgtggagaa    540

aatggtagtc tttatttatc acaaatggac gaaaacggcg gagccaatca gtacaataca    600

gctggtgcta attatggttc aggctattgt gatgctcaat gtccagtgca gacttggagg    660

aatggcacct taaacacatc acatcaagga ttttgctgta acgaaatgga catattagaa    720

ggtaattcaa gagctaatgc actaactccg cactcttgta ctgcgaccgc atgtgattct    780
```

gccggttgtg gtttcaaccc ttatggttct ggttataaga gttactacgg tccgggagac 840
accgtggata cgtcaaagac cttcactata atcactcagt ttaacacaga taacggatct 900
ccgagtggta atttggtgag tattactagg aaatatcagc agaacggtgt tgatattccg 960
tccgcgcagc caggcggtga cactatatct agctgtcctt ccgccagtgc ctatggcgga 1020
cttgctacaa tgggtaaggc attgtcctca ggtatggtcc tagtattttc tatttggaat 1080
gataattcac aatacatgaa ttggctggat tctggtaatg caggcccttg ctcctctaca 1140
gaaggtaacc caagcaatat actagctaat aacccaaata ctcatgttgt ctttagtaat 1200
attagatggg gcgatatagg tagcactacg aacagtaccg cacctcctcc tccacctgct 1260
agctccacga cattttccac tactagaagg tccagcacta ccagctcatc accatcttgt 1320
actcaaaccc attggggaca gtgtggtggt ataggttaca gcggttgcaa aacttgcaca 1380
tctggtacta catgccaata cagtaatgac tattactcac aatgttaa 1428

<210> SEQ ID NO 20
<211> LENGTH: 2688
<212> TYPE: DNA
<213> ORGANISM: Saccharomycopsis fibuligera

<400> SEQUENCE: 20
atggtctcct tcacctccct cctcgccggc gtcgccgcca tctcgggcgt cttggccgct 60
cccgccgccg aggtcgaatc cgtggctgtg gagaagcgct cggactcgcg agtcccaatt 120
caaaactata cccagtctcc atcccagaga gatgagagct cccaatgggt gagcccgcat 180
tattatccaa ctccacaagg tggtaggctc caagacgtct ggcaagaagc atatgctaga 240
gcaaaagcca tcgttggcca gatgactatt gttgaaaagg tcaatttgac cactggtacc 300
ggttggcaat tagatccatg tgttggtaat accggttctg ttccaagatt cggcatccca 360
aacctttgcc tacaagatgg gccattgggt gttcgattcg ctgactttgt tactggctat 420
ccatccggtc ttgctactgg tgcaacgttc aataaggatt tgtttcttca aagaggtcaa 480
gctctcggtc atgagttcaa cagcaaaggt gtacatattg cgttgggccc tgctgttggc 540
ccacttggtg tcaaagccag aggtggcaga aatttcgaag cctttggttc cgacccatat 600
ctccaaggta ctgctgctgc tgcaaccatc aaaggtctcc aagagaataa tgttatggct 660
tgtgtcaagc actttattgg taacgaacaa gaaaagtaca gacagccaga tgacataaac 720
cctgccacca accaaactac taaagaagct attagtgcca acattccaga cagagccatg 780
catgagttgt acttgtggcc atttgccgat tcggttcgag caggtgttgg ttctgttatg 840
tgctcttata acagagtcaa caacacttac gcttgcgaaa actcttacat gatgaaccac 900
ttgcttaaag aagagttggg ttttcaaggc tttgttgttt cggactgggg tgcacaatta 960
agtggggttt atagcgctat ctcgggctta gatatgtcta tgcctggtga agtgtatggg 1020
ggatggaaca ccggcacgtc tttctggggt caaaacttga cgaaagctat ttacaatgag 1080
actgttccga ttgaaagatt agatgatatg gcaaccagga tcttggctgc tttgtatgct 1140
accaatagtt tcccaacaga agatcacctt ccaaattttt cttcatggac aacgaaagaa 1200
tatggcaata aatattatgc tgacaacact accgagattg tcaaagtcaa ctaccatgtg 1260
gacccatcaa atgactttac ggaggacaca gctttgaagg ttgctgagga atctattgtg 1320
cttttaaaaa atgaaaacaa cactttgcca atttctcccg aaaaggctaa aagattacta 1380
ttgtcgggta ttgctgcagg ccctgatccg ataggttatc agtgtgaaga tcaatcttgc 1440

-continued

```
acaaatggcg ctttgtttca aggttggggt tctggcagtg ttggttctcc aaaatatcaa   1500

gtcactccat ttgaggaaat ttcttatctt gcaagaaaaa acaagatgca atttgattat   1560

attcgggagt cttacgactt agctcaagtt actaaagtag cttccgatgc tcatttgtct   1620

atagttgttg tctctgctgc aagcggtgag ggttatataa ccgttgacgg taaccaaggt   1680

gacagaagaa atctcacttt gtggaacaac ggtgataaat tgattgaaac agttgctgaa   1740

aactgtgcca atactgttgt tgttgttact tctactggtc aaattaattt tgaaggcttt   1800

gctgatcacc caaatgttac cgcaattgtc tgggccggcc cattaggtga cagatccggg   1860

actgctatcg ccaatattct tttggtaaa gcgaacccat caggtcatct tccattcact    1920

attgctaaga ctgacgatga ttacattcca attgaaacct acagtccatc gagtggtgaa   1980

cctgaagaca accacttggt tgaaaatgac ttgcttgttg actatagata ttttgaagag   2040

aagaatattg agccaagata cgcatttggt tatggcttgt cttacaatga gtatgaagtt   2100

agcaatgcaa aggtctcggc agccaaaaaa gttgatgagg agttgcctga accagctacc   2160

tacttatcgg agtttagcta tcaaaatgca aaagacagca aaaatccaag tgatgctttt   2220

gctccaacag atttaaacag agttaatgag tacctttatc catatttaga tagcaatgtt   2280

accttaaaag acggaaacta tgagtatccc gatggctaca gcactgagca aagaacaaca   2340

cctatccaac ctgggggcgg cttgggaggc aacgatgctt tgtgggaggt cgcttataaa   2400

gttgaagtgg acgttcaaaa cttgggtaac tccactgata agtttgttcc acagttgtat   2460

ttgaaacacc ctgaggatgg caagtttgaa acccctattc aattgagagg gtttgaaaag   2520

gttgagttgt ccccgggtga gaagaagaca gttgagtttg agcttttgag aagagatctt   2580

agtgtgtggg ataccaccag acagtcttgg atcgttgaat ctggtactta tgaggcctta   2640

attggtgttg ctgttaatga tatcaagaca tctgtcctgt ttactatt               2688


<210> SEQ ID NO 21
<211> LENGTH: 525
<212> TYPE: PRT
<213> ORGANISM: Humicola grisea

<400> SEQUENCE: 21

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160
```

```
Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Pro Thr Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525


<210> SEQ ID NO 22
<211> LENGTH: 456
<212> TYPE: PRT
<213> ORGANISM: Thermoascus aurantiacus

<400> SEQUENCE: 22

Met Tyr Gln Arg Ala Leu Leu Phe Ser Phe Phe Leu Ala Ala Ala Arg
```

-continued

```
1               5                   10                  15

Ala His Glu Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Asn Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Ser Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Thr Asp Gly Cys Asp Phe Asn Pro Tyr Gln Pro Gly Asn His
        275                 280                 285

Ser Phe Tyr Gly Pro Gly Lys Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Asp Asn Thr Gly Phe Phe Thr
        355                 360                 365

His Gly Gly Leu Gln Lys Ile Ser Gln Ala Leu Ala Gln Gly Met Val
    370                 375                 380

Leu Val Met Ser Leu Trp Asp Asp His Ala Ala Asn Met Leu Trp Leu
385                 390                 395                 400

Asp Ser Thr Tyr Pro Thr Asp Ala Asp Pro Asp Thr Pro Gly Val Ala
                405                 410                 415

Arg Gly Thr Cys Pro Thr Thr Ser Gly Val Pro Ala Asp Val Glu Ser
            420                 425                 430
```

Gln Asn Pro Asn Ser Tyr Val Ile Tyr Ser Asn Ile Lys Val Gly Pro
435 440 445

Ile Asn Ser Thr Phe Thr Ala Asn
450 455

<210> SEQ ID NO 23
<211> LENGTH: 455
<212> TYPE: PRT
<213> ORGANISM: Talaromyces emersonii

<400> SEQUENCE: 23

Met Leu Arg Arg Ala Leu Leu Leu Ser Ser Ser Ala Ile Leu Ala Val
1 5 10 15

Lys Ala Gln Gln Ala Gly Thr Ala Thr Ala Glu Asn His Pro Pro Leu
20 25 30

Thr Trp Gln Glu Cys Thr Ala Pro Gly Ser Cys Thr Thr Gln Asn Gly
35 40 45

Ala Val Val Leu Asp Ala Asn Trp Arg Trp Val His Asp Val Asn Gly
50 55 60

Tyr Thr Asn Cys Tyr Thr Gly Asn Thr Trp Asp Pro Thr Tyr Cys Pro
65 70 75 80

Asp Asp Glu Thr Cys Ala Gln Asn Cys Ala Leu Asp Gly Ala Asp Tyr
85 90 95

Glu Gly Thr Tyr Gly Val Thr Ser Ser Gly Ser Ser Leu Lys Leu Asn
100 105 110

Phe Val Thr Gly Ser Asn Val Gly Ser Arg Leu Tyr Leu Leu Gln Asp
115 120 125

Asp Ser Thr Tyr Gln Ile Phe Lys Leu Leu Asn Arg Glu Phe Ser Phe
130 135 140

Asp Val Asp Val Ser Asn Leu Pro Cys Gly Leu Asn Gly Ala Leu Tyr
145 150 155 160

Phe Val Ala Met Asp Ala Asp Gly Gly Val Ser Lys Tyr Pro Asn Asn
165 170 175

Lys Ala Gly Ala Lys Tyr Gly Thr Gly Tyr Cys Asp Ser Gln Cys Pro
180 185 190

Arg Asp Leu Lys Phe Ile Asp Gly Glu Ala Asn Val Glu Gly Trp Gln
195 200 205

Pro Ser Ser Asn Asn Ala Asn Thr Gly Ile Gly Asp His Gly Ser Cys
210 215 220

Cys Ala Glu Met Asp Val Trp Glu Ala Asn Ser Ile Ser Asn Ala Val
225 230 235 240

Thr Pro His Pro Cys Asp Thr Pro Gly Gln Thr Met Cys Ser Gly Asp
245 250 255

Asp Cys Gly Gly Thr Tyr Ser Asn Asp Arg Tyr Ala Gly Thr Cys Asp
260 265 270

Pro Asp Gly Cys Asp Phe Asn Pro Tyr Arg Met Gly Asn Thr Ser Phe
275 280 285

Tyr Gly Pro Gly Lys Ile Ile Asp Thr Thr Lys Pro Phe Thr Val Val
290 295 300

Thr Gln Phe Leu Thr Asp Asp Gly Thr Asp Thr Gly Thr Leu Ser Glu
305 310 315 320

Ile Lys Arg Phe Tyr Ile Gln Asn Ser Asn Val Ile Pro Gln Pro Asn
325 330 335

Ser Asp Ile Ser Gly Val Thr Gly Asn Ser Ile Thr Thr Glu Phe Cys

```
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser
    450                 455


<210> SEQ ID NO 24
<211> LENGTH: 459
<212> TYPE: PRT
<213> ORGANISM: Talaromyces emersonii

<400> SEQUENCE: 24

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
        35                  40                  45

Pro Tyr Tyr Ala Gln Cys Val Pro Ala Thr Ala Thr Pro Thr Thr Leu
    50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                245                 250                 255
```

-continued

```
Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala
    290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
                325                 330                 335

Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
        355                 360                 365

Val Arg Pro Thr Lys Gln Ser Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Leu Phe
    450                 455


<210> SEQ ID NO 25
<211> LENGTH: 482
<212> TYPE: PRT
<213> ORGANISM: Chrysosporium lucknowense

<400> SEQUENCE: 25

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175
```

Asp Thr Leu Met Val Gln Thr Leu Ser Gln Val Arg Ala Leu Asn Lys
180 185 190

Ala Gly Ala Asn Pro Pro Tyr Ala Ala Gln Leu Val Val Tyr Asp Leu
195 200 205

Pro Asp Arg Asp Cys Ala Ala Ala Ala Ser Asn Gly Glu Phe Ser Ile
210 215 220

Ala Asn Gly Gly Ala Ala Asn Tyr Arg Ser Tyr Ile Asp Ala Ile Arg
225 230 235 240

Lys His Ile Ile Glu Tyr Ser Asp Ile Arg Ile Ile Leu Val Ile Glu
245 250 255

Pro Asp Ser Met Ala Asn Met Val Thr Asn Met Asn Val Ala Lys Cys
260 265 270

Ser Asn Ala Ala Ser Thr Tyr His Glu Leu Thr Val Tyr Ala Leu Lys
275 280 285

Gln Leu Asn Leu Pro Asn Val Ala Met Tyr Leu Asp Ala Gly His Ala
290 295 300

Gly Trp Leu Gly Trp Pro Ala Asn Ile Gln Pro Ala Ala Glu Leu Phe
305 310 315 320

Ala Gly Ile Tyr Asn Asp Ala Gly Lys Pro Ala Ala Val Arg Gly Leu
325 330 335

Ala Thr Asn Val Ala Asn Tyr Asn Ala Trp Ser Ile Ala Ser Ala Pro
340 345 350

Ser Tyr Thr Ser Pro Asn Pro Asn Tyr Asp Glu Lys His Tyr Ile Glu
355 360 365

Ala Phe Ser Pro Leu Leu Asn Ser Ala Gly Phe Pro Ala Arg Phe Ile
370 375 380

Val Asp Thr Gly Arg Asn Gly Lys Gln Pro Thr Gly Gln Gln Gln Trp
385 390 395 400

Gly Asp Trp Cys Asn Val Lys Gly Thr Gly Phe Gly Val Arg Pro Thr
405 410 415

Ala Asn Thr Gly His Glu Leu Val Asp Ala Phe Val Trp Val Lys Pro
420 425 430

Gly Gly Glu Ser Asp Gly Thr Ser Asp Thr Ser Ala Ala Arg Tyr Asp
435 440 445

Tyr His Cys Gly Leu Ser Asp Ala Leu Gln Pro Ala Pro Glu Ala Gly
450 455 460

Gln Trp Phe Gln Ala Tyr Phe Glu Gln Leu Leu Thr Asn Ala Asn Pro
465 470 475 480

Pro Phe

<210> SEQ ID NO 26
<211> LENGTH: 516
<212> TYPE: PRT
<213> ORGANISM: Artificial Sequence
<220> FEATURE:
<223> OTHER INFORMATION: T.emersonni cbh1 with CBD

<400> SEQUENCE: 26

Met Leu Arg Arg Ala Leu Leu Leu Ser Ser Ser Ala Ile Leu Ala Val
1 5 10 15

Lys Ala Gln Gln Ala Gly Thr Ala Thr Ala Glu Asn His Pro Pro Leu
20 25 30

Thr Trp Gln Glu Cys Thr Ala Pro Gly Ser Cys Thr Thr Gln Asn Gly
35 40 45

-continued

```
Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Asn Pro Pro Gly Gly Asn Arg Gly Thr
    450                 455                 460

Thr Thr Thr Arg Arg Pro Ala Thr Thr Thr Gly Ser Ser Pro Gly Pro
```

465 470 475 480

Thr Gln Ser His Tyr Gly Gln Cys Gly Gly Ile Gly Tyr Ser Gly Pro
485 490 495

Thr Val Cys Ala Ser Gly Thr Thr Cys Gln Val Leu Asn Pro Tyr Tyr
500 505 510

Ser Gln Cys Leu
515

<210> SEQ ID NO 27
<211> LENGTH: 535
<212> TYPE: PRT
<213> ORGANISM: Trichoderma reesei

<400> SEQUENCE: 27

Met Val Ser Phe Thr Ser Leu Leu Ala Gly Val Ala Ala Ile Ser Gly
1 5 10 15

Val Leu Ala Ala Pro Ala Ala Glu Val Glu Pro Val Ala Val Glu Lys
20 25 30

Arg Glu Ala Glu Ala Glu Ala Gln Ser Ala Cys Thr Leu Gln Ser Glu
35 40 45

Thr His Pro Pro Leu Thr Trp Gln Lys Cys Ser Ser Gly Gly Thr Cys
50 55 60

Thr Gln Gln Thr Gly Ser Val Val Ile Asp Ala Asn Trp Arg Trp Thr
65 70 75 80

His Ala Thr Asn Ser Ser Thr Asn Cys Tyr Asp Gly Asn Thr Trp Ser
85 90 95

Ser Thr Leu Cys Pro Asp Asn Glu Thr Cys Ala Lys Asn Cys Cys Leu
100 105 110

Asp Gly Ala Ala Tyr Ala Ser Thr Tyr Gly Val Thr Thr Ser Gly Asn
115 120 125

Ser Leu Ser Ile Gly Phe Val Thr Gln Ser Ala Gln Lys Asn Val Gly
130 135 140

Ala Arg Leu Tyr Leu Met Ala Ser Asp Thr Thr Tyr Gln Glu Phe Thr
145 150 155 160

Leu Leu Gly Asn Glu Phe Ser Phe Asp Val Asp Val Ser Gln Leu Pro
165 170 175

Cys Gly Leu Asn Gly Ala Leu Tyr Phe Val Ser Met Asp Ala Asp Gly
180 185 190

Gly Val Ser Lys Tyr Pro Thr Asn Thr Ala Gly Ala Lys Tyr Gly Thr
195 200 205

Gly Tyr Cys Asp Ser Gln Cys Pro Arg Asp Leu Lys Phe Ile Asn Gly
210 215 220

Gln Ala Asn Val Glu Gly Trp Glu Pro Ser Ser Asn Asn Ala Asn Thr
225 230 235 240

Gly Ile Gly Gly His Gly Ser Cys Cys Ser Glu Met Asp Ile Trp Glu
245 250 255

Ala Asn Ser Ile Ser Glu Ala Leu Thr Pro His Pro Cys Thr Thr Val
260 265 270

Gly Gln Glu Ile Cys Glu Gly Asp Gly Cys Gly Gly Thr Tyr Ser Asp
275 280 285

Asn Arg Tyr Gly Gly Thr Cys Asp Pro Asp Gly Cys Asp Trp Asn Pro
290 295 300

Tyr Arg Leu Gly Asn Thr Ser Phe Tyr Gly Pro Gly Ser Ser Phe Thr
305 310 315 320

-continued

```
Leu Asp Thr Thr Lys Lys Leu Thr Val Val Thr Gln Phe Glu Thr Ser
                325                 330                 335

Gly Ala Ile Asn Arg Tyr Tyr Val Gln Asn Gly Val Thr Phe Gln Gln
            340                 345                 350

Pro Asn Ala Glu Leu Gly Ser Tyr Ser Gly Asn Glu Leu Asn Asp Asp
        355                 360                 365

Tyr Cys Thr Ala Glu Glu Ala Glu Phe Gly Gly Ser Ser Phe Ser Asp
    370                 375                 380

Lys Gly Gly Leu Thr Gln Phe Lys Lys Ala Thr Ser Gly Gly Met Val
385                 390                 395                 400

Leu Val Met Ser Leu Trp Asp Asp Tyr Tyr Ala Asn Met Leu Trp Leu
                405                 410                 415

Asp Ser Thr Tyr Pro Thr Asn Glu Thr Ser Ser Thr Pro Gly Ala Val
            420                 425                 430

Arg Gly Ser Cys Ser Thr Ser Ser Gly Val Pro Ala Gln Val Glu Ser
        435                 440                 445

Gln Ser Pro Asn Ala Lys Val Thr Phe Ser Asn Ile Lys Phe Gly Pro
    450                 455                 460

Ile Gly Ser Thr Gly Asn Pro Ser Gly Gly Asn Pro Pro Gly Gly Asn
465                 470                 475                 480

Arg Gly Thr Thr Thr Thr Arg Arg Pro Ala Thr Thr Thr Gly Ser Ser
                485                 490                 495

Pro Gly Pro Thr Gln Ser His Tyr Gly Gln Cys Gly Gly Ile Gly Tyr
            500                 505                 510

Ser Gly Pro Thr Val Cys Ala Ser Gly Thr Thr Cys Gln Val Leu Asn
        515                 520                 525

Pro Tyr Tyr Ser Gln Cys Leu
    530                 535


<210> SEQ ID NO 28
<211> LENGTH: 471
<212> TYPE: PRT
<213> ORGANISM: Trichoderma reesei

<400> SEQUENCE: 28

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160
```

-continued

Asp Thr Leu Asp Lys Thr Pro Leu Met Glu Gln Thr Leu Ala Asp Ile
165 170 175

Arg Thr Ala Asn Lys Asn Gly Gly Asn Tyr Ala Gly Gln Phe Val Val
180 185 190

Tyr Asp Leu Pro Asp Arg Asp Cys Ala Ala Leu Ala Ser Asn Gly Glu
195 200 205

Tyr Ser Ile Ala Asp Gly Gly Val Ala Lys Tyr Lys Asn Tyr Ile Asp
210 215 220

Thr Ile Arg Gln Ile Val Val Glu Tyr Ser Asp Ile Arg Thr Leu Leu
225 230 235 240

Val Ile Glu Pro Asp Ser Leu Ala Asn Leu Val Thr Asn Leu Gly Thr
245 250 255

Pro Lys Cys Ala Asn Ala Gln Ser Ala Tyr Leu Glu Cys Ile Asn Tyr
260 265 270

Ala Val Thr Gln Leu Asn Leu Pro Asn Val Ala Met Tyr Leu Asp Ala
275 280 285

Gly His Ala Gly Trp Leu Gly Trp Pro Ala Asn Gln Asp Pro Ala Ala
290 295 300

Gln Leu Phe Ala Asn Val Tyr Lys Asn Ala Ser Ser Pro Arg Ala Leu
305 310 315 320

Arg Gly Leu Ala Thr Asn Val Ala Asn Tyr Asn Gly Trp Asn Ile Thr
325 330 335

Ser Pro Pro Ser Tyr Thr Gln Gly Asn Ala Val Tyr Asn Glu Lys Leu
340 345 350

Tyr Ile His Ala Ile Gly Arg Leu Leu Ala Asn His Gly Trp Ser Asn
355 360 365

Ala Phe Phe Ile Thr Asp Gln Gly Arg Ser Gly Lys Gln Pro Thr Gly
370 375 380

Gln Gln Gln Trp Gly Asp Trp Cys Asn Val Ile Gly Thr Gly Phe Gly
385 390 395 400

Ile Arg Pro Ser Ala Asn Thr Gly Asp Ser Leu Leu Asp Ser Phe Val
405 410 415

Trp Val Lys Pro Gly Gly Glu Cys Asp Gly Thr Ser Asp Ser Ser Ala
420 425 430

Pro Arg Phe Asp Ser His Cys Ala Leu Pro Asp Ala Leu Gln Pro Ala
435 440 445

Ala Gln Ala Gly Ala Trp Phe Gln Ala Tyr Phe Val Gln Leu Leu Thr
450 455 460

Asn Ala Asn Pro Ser Phe Leu
465 470

<210> SEQ ID NO 29
<211> LENGTH: 532
<212> TYPE: PRT
<213> ORGANISM: Chaetomium thermophilum

<400> SEQUENCE: 29

Met Met Tyr Lys Lys Phe Ala Ala Leu Ala Ala Leu Val Ala Gly Ala
1 5 10 15

Ser Ala Gln Gln Ala Cys Ser Leu Thr Ala Glu Asn His Pro Ser Leu
20 25 30

Thr Trp Lys Arg Cys Thr Ser Gly Gly Ser Cys Ser Thr Val Asn Gly
35 40 45

Ala Val Thr Ile Asp Ala Asn Trp Arg Trp Thr His Thr Val Ser Gly

-continued

```
    50                  55                  60

Ser Thr Asn Cys Tyr Thr Gly Asn Gln Trp Asp Thr Ser Leu Cys Thr
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln Tyr Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Val
        195                 200                 205

Gly Asn Trp Thr Pro Ser Thr Asn Asp Ala Asn Ala Gly Phe Gly Arg
    210                 215                 220

Tyr Gly Ser Cys Cys Ser Glu Met Asp Val Trp Glu Ala Asn Asn Met
225                 230                 235                 240

Ala Thr Ala Phe Thr Pro His Pro Cys Thr Thr Val Gly Gln Ser Arg
                245                 250                 255

Cys Glu Ala Asp Thr Cys Gly Gly Thr Tyr Ser Ser Asp Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Asn Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Tyr
            340                 345                 350

Cys Asp Ala Gln Lys Val Ala Phe Ser Asn Thr Asp Asp Phe Asn Arg
        355                 360                 365

Lys Gly Gly Met Ala Gln Met Ser Lys Ala Leu Ala Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Gln Ala Gly Ala Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Asn Pro Gly Asn Pro Thr
    450                 455                 460

Thr Thr Val Val Pro Pro Ala Ser Thr Ser Thr Ser Arg Pro Thr Ser
465                 470                 475                 480
```

Ser Thr Ser Ser Pro Val Ser Thr Pro Thr Gly Gln Pro Gly Gly Cys
485 490 495

Thr Thr Gln Lys Trp Gly Gln Cys Gly Gly Ile Gly Tyr Thr Gly Cys
500 505 510

Thr Asn Cys Val Ala Gly Thr Thr Cys Thr Gln Leu Asn Pro Trp Tyr
515 520 525

Ser Gln Cys Leu
530

<210> SEQ ID NO 30
<211> LENGTH: 322
<212> TYPE: PRT
<213> ORGANISM: Coptotermes lacteus

<400> SEQUENCE: 30

Met Arg Phe Pro Ser Ile Phe Thr Ala Val Leu Phe Ala Ala Ser Ser
1 5 10 15

Ala Leu Ala Glu Cys Thr Lys Gly Gly Cys Thr Asn Lys Asn Gly Tyr
20 25 30

Ile Val His Asp Lys His Val Gly Asp Ile Gln Asn Arg Asp Thr Leu
35 40 45

Asp Pro Pro Asp Leu Asp Tyr Glu Lys Asp Val Gly Val Thr Val Ser
50 55 60

Gly Gly Thr Leu Ser Gln Arg Leu Val Ser Thr Trp Asn Gly Lys Lys
65 70 75 80

Val Val Gly Ser Arg Leu Tyr Ile Val Asp Glu Ala Asp Glu Lys Tyr
85 90 95

Gln Leu Phe Thr Phe Val Gly Lys Glu Phe Thr Tyr Thr Val Asp Met
100 105 110

Ser Gln Ile Gln Cys Gly Ile Asn Ala Ala Leu Tyr Thr Val Glu Met
115 120 125

Pro Ala Ala Gly Lys Thr Pro Gly Gly Val Lys Tyr Gly Tyr Gly Tyr
130 135 140

Cys Asp Ala Asn Cys Val Asp Gly Asp Cys Cys Met Glu Phe Asp Ile
145 150 155 160

Gln Glu Ala Ser Asn Lys Ala Ile Val Tyr Thr Thr His Ser Cys Gln
165 170 175

Ser Gln Thr Ser Gly Cys Asp Thr Ser Gly Cys Gly Tyr Asn Pro Tyr
180 185 190

Arg Asp Ser Gly Asp Lys Ala Phe Trp Gly Thr Thr Ile Asn Val Asn
195 200 205

Gln Pro Val Thr Ile Val Thr Gln Phe Ile Gly Ser Gly Ser Ser Leu
210 215 220

Thr Glu Val Lys Arg Leu Cys Val Gln Gly Gly Lys Thr Phe Pro Pro
225 230 235 240

Ala Lys Ser Leu Thr Asp Ser Tyr Cys Asn Ala Asn Asp Tyr Arg Ser
245 250 255

Leu Arg Thr Met Gly Ala Ser Met Ala Arg Gly His Val Val Val Phe
260 265 270

Ser Leu Trp Asp Ser Asn Gly Met Ser Trp Met Asp Gly Gly Asn Ala
275 280 285

Gly Pro Cys Thr Ser Tyr Asn Ile Glu Ser Leu Glu Ser Ser Gln Pro
290 295 300

Asn Leu Lys Val Thr Trp Ser Asn Val Lys Tyr Gly Glu Ile Asp Ser 305 310 315 320

Pro Tyr

<210> SEQ ID NO 31
<211> LENGTH: 451
<212> TYPE: PRT
<213> ORGANISM: Coptotermes formosanus

<400> SEQUENCE: 31

Met Arg Phe Pro Ser Ile Phe Thr Ala Val Leu Phe Ala Ala Ser Ser
1 5 10 15

Ala Leu Ala Ala Tyr Asp Tyr Lys Thr Val Leu Lys Asn Ser Leu Leu
20 25 30

Phe Tyr Glu Ala Gln Arg Ser Gly Lys Leu Pro Ala Asp Gln Lys Val
35 40 45

Thr Trp Arg Lys Asp Ser Ala Leu Asn Asp Lys Gly Gln Lys Gly Glu
50 55 60

Asp Leu Thr Gly Gly Tyr Tyr Asp Ala Gly Asp Phe Val Lys Phe Gly
65 70 75 80

Phe Pro Met Ala Tyr Thr Val Thr Val Leu Ala Trp Gly Leu Val Asp
85 90 95

Tyr Glu Ser Ala Tyr Ser Thr Ala Gly Ala Leu Asp Asp Gly Arg Lys
100 105 110

Ala Leu Lys Trp Gly Thr Asp Tyr Phe Leu Lys Ala His Thr Ala Ala
115 120 125

Asn Glu Phe Tyr Gly Gln Val Gly Gln Gly Asp Val Asp His Ala Tyr
130 135 140

Trp Gly Arg Pro Glu Asp Met Thr Met Ser Arg Pro Ala Tyr Lys Ile
145 150 155 160

Asp Thr Ser Lys Pro Gly Ser Asp Leu Ala Ala Glu Thr Ala Ala Ala
165 170 175

Leu Ala Ala Thr Ala Ile Ala Tyr Lys Ser Ala Asp Ser Thr Tyr Ser
180 185 190

Asn Asn Leu Ile Thr His Ala Lys Gln Leu Phe Asp Phe Ala Asn Asn
195 200 205

Tyr Arg Gly Lys Tyr Ser Asp Ser Ile Thr Asp Ala Lys Asn Phe Tyr
210 215 220

Ala Ser Gly Asp Tyr Lys Asp Glu Leu Val Trp Ala Ala Ala Trp Leu
225 230 235 240

Tyr Arg Ala Thr Asn Asp Asn Thr Tyr Leu Thr Lys Ala Glu Ser Leu
245 250 255

Tyr Asn Glu Phe Gly Leu Gly Ser Trp Asn Gly Ala Phe Asn Trp Asp
260 265 270

Asn Lys Ile Ser Gly Val Gln Val Leu Leu Ala Lys Leu Thr Ser Lys
275 280 285

Gln Ala Tyr Lys Asp Lys Val Gln Gly Tyr Val Asp Tyr Leu Val Ser
290 295 300

Ser Gln Lys Lys Thr Pro Lys Gly Leu Val Tyr Ile Asp Gln Trp Gly
305 310 315 320

Thr Leu Arg His Ala Ala Asn Ser Ala Leu Ile Ala Leu Gln Ala Ala
325 330 335

Asp Leu Gly Ile Asn Ala Ala Ser Tyr Arg Gln Tyr Ala Lys Lys Gln
340 345 350

Ile Asp Tyr Ala Leu Gly Asp Gly Gly Arg Ser Tyr Val Val Gly Phe

```
        355                 360                 365

Gly Thr Asn Pro Pro Val Arg Pro His His Arg Ser Ser Ser Cys Pro
    370                 375                 380

Asp Ala Pro Ala Ala Cys Asp Trp Asn Thr Tyr Asn Ser Ala Gly Pro
385                 390                 395                 400

Asn Ala His Val Leu Thr Gly Ala Leu Val Gly Gly Pro Asp Ser Asn
                405                 410                 415

Asp Ser Tyr Thr Asp Ser Arg Ser Asp Tyr Ile Ser Asn Glu Val Ala
            420                 425                 430

Thr Asp Tyr Asn Ala Gly Phe Gln Ser Ala Val Ala Gly Leu Leu Lys
        435                 440                 445

Ala Gly Val
    450


<210> SEQ ID NO 32
<211> LENGTH: 451
<212> TYPE: PRT
<213> ORGANISM: Nasutitermes takasagoensis

<400> SEQUENCE: 32

Met Arg Phe Pro Ser Ile Phe Thr Ala Val Leu Phe Ala Ala Ser Ser
1               5                   10                  15

Ala Leu Ala Ala Tyr Asp Tyr Lys Gln Val Leu Arg Asp Ser Leu Leu
            20                  25                  30

Phe Tyr Glu Ala Gln Arg Ser Gly Arg Leu Pro Ala Asp Gln Lys Val
        35                  40                  45

Thr Trp Arg Lys Asp Ser Ala Leu Asn Asp Gln Gly Asp Gln Gly Gln
    50                  55                  60

Asp Leu Thr Gly Gly Tyr Phe Asp Ala Gly Asp Phe Val Lys Phe Gly
65                  70                  75                  80

Phe Pro Met Ala Tyr Thr Ala Thr Val Leu Ala Trp Gly Leu Ile Asp
                85                  90                  95

Phe Glu Ala Gly Tyr Ser Ser Ala Gly Ala Leu Asp Asp Gly Arg Lys
            100                 105                 110

Ala Val Lys Trp Ala Thr Asp Tyr Phe Ile Lys Ala His Thr Ser Gln
        115                 120                 125

Asn Glu Phe Tyr Gly Gln Val Gly Gln Gly Asp Ala Asp His Ala Phe
    130                 135                 140

Trp Gly Arg Pro Glu Asp Met Thr Met Ala Arg Pro Ala Tyr Lys Ile
145                 150                 155                 160

Asp Thr Ser Arg Pro Gly Ser Asp Leu Ala Gly Glu Thr Ala Ala Ala
                165                 170                 175

Leu Ala Ala Ala Ser Ile Val Phe Arg Asn Val Asp Gly Thr Tyr Ser
            180                 185                 190

Asn Asn Leu Leu Thr His Ala Arg Gln Leu Phe Asp Phe Ala Asn Asn
        195                 200                 205

Tyr Arg Gly Lys Tyr Ser Asp Ser Ile Thr Asp Ala Arg Asn Phe Tyr
    210                 215                 220

Ala Ser Ala Asp Tyr Arg Asp Glu Leu Val Trp Ala Ala Ala Trp Leu
225                 230                 235                 240

Tyr Arg Ala Thr Asn Asp Asn Thr Tyr Leu Asn Thr Ala Glu Ser Leu
                245                 250                 255

Tyr Asp Glu Phe Gly Leu Gln Asn Trp Gly Gly Gly Leu Asn Trp Asp
            260                 265                 270
```

-continued

```
Ser Lys Val Ser Gly Val Gln Val Leu Leu Ala Lys Leu Thr Asn Lys
        275                 280                 285

Gln Ala Tyr Lys Asp Thr Val Gln Ser Tyr Val Asn Tyr Leu Ile Asn
    290                 295                 300

Asn Gln Gln Lys Thr Pro Lys Gly Leu Leu Tyr Ile Asp Met Trp Gly
305                 310                 315                 320

Thr Leu Arg His Ala Ala Asn Ala Ala Phe Ile Met Leu Glu Ala Ala
                325                 330                 335

Glu Leu Gly Leu Ser Ala Ser Ser Tyr Arg Gln Phe Ala Gln Thr Gln
            340                 345                 350

Ile Asp Tyr Ala Leu Gly Asp Gly Gly Arg Ser Phe Val Cys Gly Phe
        355                 360                 365

Gly Ser Asn Pro Pro Thr Arg Pro His His Arg Ser Ser Ser Cys Pro
    370                 375                 380

Pro Ala Pro Ala Thr Cys Asp Trp Asn Thr Phe Asn Ser Pro Asp Pro
385                 390                 395                 400

Asn Tyr His Val Leu Ser Gly Ala Leu Val Gly Gly Pro Asp Gln Asn
                405                 410                 415

Asp Asn Tyr Val Asp Asp Arg Ser Asp Tyr Val His Asn Glu Val Ala
            420                 425                 430

Thr Asp Tyr Asn Ala Gly Phe Gln Ser Ala Leu Ala Ala Leu Val Ala
        435                 440                 445

Leu Gly Tyr
    450


<210> SEQ ID NO 33
<211> LENGTH: 451
<212> TYPE: PRT
<213> ORGANISM: Coptotermes acinaciformis

<400> SEQUENCE: 33

Met Arg Phe Pro Ser Ile Phe Thr Ala Val Leu Phe Ala Ala Ser Ser
1               5                   10                  15

Ala Leu Ala Ala Tyr Asp Tyr Thr Thr Val Leu Lys Ser Ser Leu Leu
            20                  25                  30

Phe Tyr Glu Ala Gln Arg Ser Gly Lys Leu Pro Ala Asp Gln Lys Val
        35                  40                  45

Thr Trp Arg Lys Asp Ser Ala Leu Asp Asp Lys Gly Asn Asn Gly Glu
    50                  55                  60

Asp Leu Thr Gly Gly Tyr Tyr Asp Ala Gly Asp Phe Val Lys Phe Gly
65                  70                  75                  80

Phe Pro Leu Ala Tyr Thr Ala Thr Val Leu Ala Trp Gly Leu Val Asp
                85                  90                  95

Tyr Glu Ala Gly Tyr Ser Ser Ala Gly Ala Thr Asp Asp Gly Arg Lys
            100                 105                 110

Ala Val Lys Trp Ala Thr Asp Tyr Leu Leu Lys Ala His Thr Ala Ala
        115                 120                 125

Thr Glu Leu Tyr Gly Gln Val Gly Asp Gly Asp Ala Asp His Ala Tyr
    130                 135                 140

Trp Gly Arg Pro Glu Asp Met Thr Met Ala Arg Pro Ala Tyr Lys Ile
145                 150                 155                 160

Asp Ala Ser Arg Pro Gly Ser Asp Leu Ala Gly Glu Thr Ala Ala Ala
                165                 170                 175

Leu Ala Ala Ala Ser Ile Val Phe Lys Gly Val Asp Ser Ser Tyr Ser
            180                 185                 190
```

```
Asp Asn Leu Leu Ala His Ala Lys Gln Leu Phe Asp Phe Ala Asp Asn
        195                 200                 205

Tyr Arg Gly Lys Tyr Ser Asp Ser Ile Thr Gln Ala Ser Asn Phe Tyr
    210                 215                 220

Ala Ser Gly Asp Tyr Lys Asp Glu Leu Val Trp Ala Ala Thr Trp Leu
225                 230                 235                 240

Tyr Arg Ala Thr Asn Asp Asn Thr Tyr Leu Thr Lys Ala Glu Ser Leu
                245                 250                 255

Tyr Asn Glu Phe Gly Leu Gly Asn Trp Asn Gly Ala Phe Asn Trp Asp
            260                 265                 270

Asn Lys Val Ser Gly Val Gln Val Leu Leu Ala Lys Leu Thr Ser Lys
        275                 280                 285

Gln Ala Tyr Lys Asp Thr Val Gln Gly Tyr Val Asp Tyr Leu Ile Asn
    290                 295                 300

Asn Gln Gln Lys Thr Pro Lys Gly Leu Leu Tyr Ile Asp Gln Trp Gly
305                 310                 315                 320

Thr Leu Arg His Ala Ala Asn Ala Ala Leu Ile Ile Leu Gln Ala Ala
                325                 330                 335

Asp Leu Gly Ile Ser Ala Asp Ser Tyr Arg Gln Phe Ala Lys Lys Gln
            340                 345                 350

Ile Asp Tyr Ala Leu Gly Asp Gly Gly Arg Ser Tyr Val Val Gly Phe
        355                 360                 365

Gly Asp Asn Pro Pro Thr His Pro His His Arg Ser Ser Ser Cys Pro
    370                 375                 380

Asp Ala Pro Ala Val Cys Asp Trp Asn Thr Phe Asn Ser Pro Asp Pro
385                 390                 395                 400

Asn Phe His Val Leu Thr Gly Ala Leu Val Gly Gly Pro Asp Gln Asn
                405                 410                 415

Asp Asn Tyr Val Asp Asp Arg Ser Asp Tyr Val Ser Asn Glu Val Ala
            420                 425                 430

Thr Asp Tyr Asn Ala Gly Phe Gln Ser Ala Val Ala Ala Leu Val Thr
        435                 440                 445

Leu Gly Val
    450


<210> SEQ ID NO 34
<211> LENGTH: 451
<212> TYPE: PRT
<213> ORGANISM: Mastotermes darwinensis

<400> SEQUENCE: 34

Met Arg Phe Pro Ser Ile Phe Thr Ala Val Leu Phe Ala Ala Ser Ser
1               5                   10                  15

Ala Leu Ala Ala Tyr Asp Tyr Asn Asp Val Leu Thr Lys Ser Leu Leu
            20                  25                  30

Phe Tyr Glu Ala Gln Arg Ser Gly Lys Leu Pro Ser Asp Gln Lys Val
        35                  40                  45

Thr Trp Arg Lys Asp Ser Ala Leu Asn Asp Lys Gly Gln Asn Gly Glu
    50                  55                  60

Asp Leu Thr Gly Gly Tyr Tyr Asp Ala Gly Asp Tyr Val Lys Phe Gly
65                  70                  75                  80

Phe Pro Met Ala Tyr Thr Ala Thr Val Leu Ala Trp Gly Leu Val Asp
                85                  90                  95

His Pro Ala Gly Tyr Ser Ser Ala Gly Val Leu Asp Asp Gly Arg Lys
```

```
            100                 105                 110

Ala Val Lys Trp Val Thr Asp Tyr Leu Ile Lys Ala His Val Ser Lys
        115                 120                 125

Asn Glu Leu Tyr Gly Gln Val Gly Asp Gly Asp Ala Asp His Ala Tyr
    130                 135                 140

Trp Gly Arg Pro Glu Asp Met Thr Met Ala Arg Pro Ala Tyr Lys Ile
145                 150                 155                 160

Asp Thr Ser Arg Pro Gly Ser Asp Leu Ala Gly Glu Thr Ala Ala Ala
                165                 170                 175

Leu Ala Ala Ala Ser Ile Val Phe Lys Ser Thr Asp Ser Asn Tyr Ala
            180                 185                 190

Asn Thr Leu Leu Thr His Ala Lys Gln Leu Phe Asp Phe Ala Asn Asn
        195                 200                 205

Tyr Arg Gly Lys Tyr Ser Asp Ser Ile Thr Gln Ala Ser Asn Phe Tyr
    210                 215                 220

Ser Ser Ser Asp Tyr Lys Asp Glu Leu Val Trp Ala Ala Val Trp Leu
225                 230                 235                 240

Tyr Arg Ala Thr Asn Asp Gln Thr Tyr Leu Thr Thr Ala Glu Lys Leu
                245                 250                 255

Tyr Ser Asp Leu Gly Leu Gln Ser Trp Asn Gly Gly Phe Thr Trp Asp
            260                 265                 270

Thr Lys Ile Ser Gly Val Glu Val Leu Leu Ala Lys Ile Thr Gly Lys
        275                 280                 285

Gln Ala Tyr Lys Asp Lys Val Lys Gly Tyr Cys Asp Tyr Ile Ser Gly
    290                 295                 300

Ser Gln Gln Lys Thr Pro Lys Gly Leu Val Tyr Ile Asp Lys Trp Gly
305                 310                 315                 320

Ser Leu Arg Met Ala Ala Asn Ala Ala Tyr Ile Cys Ala Val Ala Ala
                325                 330                 335

Asp Val Gly Ile Ser Ser Thr Ala Tyr Arg Gln Phe Ala Lys Thr Gln
            340                 345                 350

Ile Asn Tyr Ile Leu Gly Asp Ala Gly Arg Ser Phe Val Val Gly Tyr
        355                 360                 365

Gly Asn Asn Pro Pro Thr His Pro His His Arg Ser Ser Ser Cys Pro
    370                 375                 380

Asp Ala Pro Ala Thr Cys Asp Trp Asn Asn Tyr Asn Ser Ala Asn Pro
385                 390                 395                 400

Asn Pro His Val Leu Tyr Gly Ala Leu Val Gly Gly Pro Asp Ser Asn
                405                 410                 415

Asp Asn Tyr Gln Asp Leu Arg Ser Asp Tyr Val Ala Asn Glu Val Ala
            420                 425                 430

Thr Asp Tyr Asn Ala Ala Phe Gln Ser Leu Leu Ala Leu Ile Val Asp
        435                 440                 445

Leu Gly Leu
    450


<210> SEQ ID NO 35
<211> LENGTH: 451
<212> TYPE: PRT
<213> ORGANISM: Nasutitermes walkeri

<400> SEQUENCE: 35

Met Arg Phe Pro Ser Ile Phe Thr Ala Val Leu Phe Ala Ala Ser Ser
1               5                   10                  15
```

-continued

```
Ala Leu Ala Ala Tyr Asp Tyr Lys Gln Val Leu Arg Asp Ser Leu Leu
            20                  25                  30

Phe Tyr Glu Ala Gln Arg Ser Gly Arg Leu Pro Ala Asp Gln Lys Val
        35                  40                  45

Thr Trp Arg Lys Asp Ser Ala Leu Asn Asp Gln Gly Glu Gln Gly Gln
    50                  55                  60

Asp Leu Thr Gly Gly Tyr Phe Asp Ala Gly Asp Phe Val Lys Phe Gly
65                  70                  75                  80

Phe Pro Met Ala Tyr Thr Ala Thr Val Leu Ala Trp Gly Leu Ile Asp
                85                  90                  95

Phe Glu Ala Gly Tyr Ser Ser Ala Gly Ala Leu Asp Asp Gly Arg Lys
            100                 105                 110

Ala Val Lys Trp Ala Thr Asp Tyr Phe Ile Lys Ala His Thr Ser Gln
        115                 120                 125

Asn Glu Phe Tyr Gly Gln Val Gly Gln Gly Asp Val Asp His Ala Tyr
    130                 135                 140

Trp Gly Arg Pro Glu Asp Met Thr Met Ala Arg Pro Ala Tyr Lys Ile
145                 150                 155                 160

Asp Thr Ser Arg Pro Gly Ser Asp Leu Ala Gly Glu Thr Ala Ala Ala
                165                 170                 175

Leu Ala Ala Ala Ser Ile Val Phe Lys Asn Val Asp Gly Thr Tyr Ser
            180                 185                 190

Asn Asn Leu Leu Thr His Ala Arg Gln Leu Phe Asp Phe Ala Asn Asn
        195                 200                 205

Tyr Arg Gly Lys Tyr Ser Asp Ser Ile Thr Asp Ala Arg Asn Phe Tyr
    210                 215                 220

Ala Ser Ala Asp Tyr Arg Asp Glu Leu Val Trp Ala Ala Ala Trp Leu
225                 230                 235                 240

Tyr Arg Ala Thr Asn Asp Asn Ser Tyr Leu Asn Thr Ala Glu Ser Leu
                245                 250                 255

Tyr Asn Glu Phe Gly Leu Gln Asn Trp Gly Gly Gly Leu Asn Trp Asp
            260                 265                 270

Ser Lys Val Ser Gly Val Gln Val Leu Leu Ala Lys Leu Thr Asn Lys
        275                 280                 285

Gln Glu Tyr Lys Asp Thr Ile Gln Ser Tyr Val Asn Tyr Leu Ile Asn
    290                 295                 300

Asn Gln Gln Lys Thr Pro Lys Gly Leu Leu Tyr Ile Asp Met Trp Gly
305                 310                 315                 320

Thr Leu Arg His Ala Ala Asn Ala Ala Phe Ile Met Leu Glu Ala Ala
                325                 330                 335

Asp Leu Gly Leu Ser Ala Ser Ser Tyr Arg Gln Phe Ala Gln Thr Gln
            340                 345                 350

Ile Asp Tyr Ala Leu Gly Asp Gly Gly Arg Ser Phe Val Cys Gly Phe
        355                 360                 365

Gly Ser Asn Pro Pro Thr Arg Pro His His Arg Ser Ser Ser Cys Pro
    370                 375                 380

Pro Ala Pro Ala Thr Cys Asp Trp Asn Thr Phe Asn Ser Pro Asp Pro
385                 390                 395                 400

Asn Tyr Asn Val Leu Ser Gly Ala Leu Val Gly Gly Pro Asp Gln Asn
                405                 410                 415

Asp Asn Tyr Val Asp Asp Arg Ser Asp Tyr Val His Asn Glu Val Ala
            420                 425                 430

Thr Asp Tyr Asn Ala Gly Phe Gln Ser Ala Leu Ala Ala Leu Val Ala
```

```
        435                 440                 445

Leu Gly Tyr
    450


<210> SEQ ID NO 36
<211> LENGTH: 451
<212> TYPE: PRT
<213> ORGANISM: Reticulitermes speratus

<400> SEQUENCE: 36

Met Arg Phe Pro Ser Ile Phe Thr Ala Val Leu Phe Ala Ala Ser Ser
1               5                   10                  15

Ala Leu Ala Ala Tyr Asp Tyr Lys Thr Val Leu Ser Asn Ser Leu Leu
            20                  25                  30

Phe Tyr Glu Ala Gln Arg Ser Gly Lys Leu Pro Ser Asp Gln Lys Val
        35                  40                  45

Thr Trp Arg Lys Asp Ser Ala Leu Asn Asp Lys Gly Gln Lys Gly Glu
    50                  55                  60

Asp Leu Thr Gly Gly Tyr Tyr Asp Ala Gly Asp Phe Val Lys Phe Gly
65                  70                  75                  80

Phe Pro Met Ala Tyr Thr Val Thr Val Leu Ala Trp Gly Val Ile Asp
                85                  90                  95

Tyr Glu Ser Ala Tyr Ser Ala Ala Gly Ala Leu Asp Ser Gly Arg Lys
            100                 105                 110

Ala Leu Lys Tyr Gly Thr Asp Tyr Phe Leu Lys Ala His Thr Ala Ala
        115                 120                 125

Asn Glu Phe Tyr Gly Gln Val Gly Gln Gly Asp Val Asp His Ala Tyr
    130                 135                 140

Trp Gly Arg Pro Glu Asp Met Thr Met Ser Arg Pro Ala Tyr Lys Ile
145                 150                 155                 160

Asp Thr Ser Lys Pro Gly Ser Asp Leu Ala Ala Glu Thr Ala Ala Ala
                165                 170                 175

Leu Ala Ala Thr Ala Ile Ala Tyr Lys Ser Ala Asp Ala Thr Tyr Ser
            180                 185                 190

Asn Asn Leu Ile Thr His Ala Lys Gln Leu Phe Asp Phe Ala Asn Asn
        195                 200                 205

Tyr Arg Gly Lys Tyr Ser Asp Ser Ile Thr Asp Ala Lys Asn Phe Tyr
    210                 215                 220

Ala Ser Gly Asp Tyr Lys Asp Glu Leu Val Trp Ala Ala Ala Trp Leu
225                 230                 235                 240

Tyr Arg Ala Thr Asn Asp Asn Thr Tyr Leu Thr Lys Ala Glu Ser Leu
                245                 250                 255

Tyr Asn Glu Phe Gly Leu Gly Asn Phe Asn Gly Ala Phe Asn Trp Asp
            260                 265                 270

Asn Lys Val Ser Gly Val Gln Val Leu Leu Ala Lys Leu Thr Ser Lys
        275                 280                 285

Gln Val Tyr Lys Asp Lys Val Gln Ser Tyr Val Asp Tyr Leu Ile Ser
    290                 295                 300

Ser Gln Lys Lys Thr Pro Lys Gly Leu Val Tyr Ile Asp Gln Trp Gly
305                 310                 315                 320

Thr Leu Arg His Ala Ala Asn Ser Ala Leu Ile Ala Leu Gln Ala Ala
                325                 330                 335

Asp Leu Gly Ile Asn Ala Ala Thr Tyr Arg Ala Tyr Ala Lys Lys Gln
            340                 345                 350
```

Ile Asp Tyr Ala Leu Gly Asp Gly Gly Arg Ser Tyr Val Ile Gly Phe
355 360 365

Gly Thr Asn Pro Pro Val Arg Pro His His Arg Ser Ser Ser Cys Pro
370 375 380

Asp Ala Pro Ala Val Cys Asp Trp Asn Thr Tyr Asn Ser Ala Gly Pro
385 390 395 400

Asn Ala His Val Leu Thr Gly Ala Leu Val Gly Gly Pro Asp Ser Asn
405 410 415

Asp Ser Tyr Thr Asp Ala Arg Ser Asp Tyr Ile Ser Asn Glu Val Ala
420 425 430

Thr Asp Tyr Asn Ala Gly Phe Gln Ser Ala Val Ala Gly Leu Leu Lys
435 440 445

Ala Gly Val
450

<210> SEQ ID NO 37
<211> LENGTH: 408
<212> TYPE: PRT
<213> ORGANISM: Neosartorya fischeri

<400> SEQUENCE: 37

Met Arg Phe Pro Ser Ile Phe Thr Ala Val Leu Phe Ala Ala Ser Ser
1 5 10 15

Ala Leu Ala Gln Gln Ile Gly Ser Ile Ala Glu Asn His Pro Glu Leu
20 25 30

Thr Thr Tyr Arg Cys Ser Ser Gln Ala Gly Cys Val Ala Gln Ser Thr
35 40 45

Ser Val Val Leu Asp Ile Asn Ala His Trp Ile His Gln Asn Gly Ala
50 55 60

Gln Thr Ser Cys Thr Thr Ser Ser Gly Leu Asp Pro Ser Leu Cys Pro
65 70 75 80

Asp Lys Val Thr Cys Ser Gln Asn Cys Val Val Glu Gly Ile Thr Asp
85 90 95

Tyr Ser Ser Phe Gly Val Gln Asn Ser Gly Asp Ala Met Thr Leu Arg
100 105 110

Gln Tyr Gln Val Gln Asn Gly Gln Ile Lys Thr Leu Arg Pro Arg Val
115 120 125

Tyr Leu Leu Ala Glu Asp Gly Ile Asn Tyr Ser Lys Leu Gln Leu Leu
130 135 140

Asn Gln Glu Phe Thr Phe Asp Val Asp Ala Ser Lys Leu Pro Cys Gly
145 150 155 160

Met Asn Gly Ala Leu Tyr Leu Ser Glu Met Asp Ala Ser Gly Gly Arg
165 170 175

Ser Ala Leu Asn Pro Ala Gly Ala Thr Tyr Gly Thr Gly Tyr Cys Asp
180 185 190

Ala Gln Cys Phe Asn Pro Gly Pro Trp Ile Asn Gly Glu Ala Asn Thr
195 200 205

Ala Gly Ala Gly Ala Cys Cys Gln Glu Met Asp Leu Trp Glu Ala Asn
210 215 220

Ser Arg Ser Thr Ile Phe Ser Pro His Pro Cys Thr Thr Ala Gly Leu
225 230 235 240

Tyr Ala Cys Thr Gly Ala Glu Cys Tyr Ser Ile Cys Asp Gly Tyr Gly
245 250 255

Cys Thr Tyr Asn Pro Tyr Glu Leu Gly Ala Lys Asp Tyr Tyr Gly Tyr
260 265 270

```
Gly Leu Thr Ile Asp Thr Ala Lys Pro Ile Thr Val Val Thr Gln Phe
        275                 280                 285

Met Thr Ala Asp Asn Thr Ala Thr Gly Thr Leu Ala Glu Ile Arg Arg
    290                 295                 300

Leu Tyr Val Gln Asp Gly Lys Val Ile Gly Asn Thr Ala Val Ala Met
305                 310                 315                 320

Thr Glu Ala Phe Cys Ser Ser Ser Arg Thr Phe Glu Glu Leu Gly Gly
                325                 330                 335

Leu Gln Arg Met Gly Glu Ala Leu Gly Arg Gly Met Val Pro Val Phe
            340                 345                 350

Ser Ile Trp Asp Asp Pro Gly Leu Trp Met His Trp Leu Asp Ser Asp
        355                 360                 365

Gly Ala Gly Pro Cys Gly Asn Thr Glu Gly Asp Pro Ala Phe Ile Gln
    370                 375                 380

Ala Asn Tyr Pro Asn Thr Ala Val Thr Phe Ser Lys Val Arg Trp Gly
385                 390                 395                 400

Asp Ile Gly Ser Thr Tyr Ser Ser
                405


<210> SEQ ID NO 38
<211> LENGTH: 304
<212> TYPE: PRT
<213> ORGANISM: Reticulitermes flavipes

<400> SEQUENCE: 38

Met Arg Phe Pro Ser Ile Phe Thr Ala Val Leu Phe Ala Ala Ser Ser
1               5                   10                  15

Ala Leu Ala Gln Trp Met Gln Ile Gly Gly Lys Gln Lys Tyr Pro Ala
            20                  25                  30

Phe Lys Pro Gly Ala Lys Tyr Gly Arg Gly Tyr Cys Asp Gly Gln Cys
        35                  40                  45

Pro His Asp Met Lys Val Ser Ser Gly Arg Ala Asn Val Asp Gly Trp
    50                  55                  60

Lys Pro Gln Asp Asn Asp Glu Asn Ser Gly Asn Gly Lys Leu Gly Thr
65                  70                  75                  80

Cys Cys Trp Glu Met Asp Ile Trp Glu Gly Asn Leu Val Ser Gln Ala
                85                  90                  95

Tyr Thr Val His Ala Gly Ser Lys Ser Gly Gln Tyr Glu Cys Thr Gly
            100                 105                 110

Thr Gln Cys Gly Asp Thr Asp Ser Gly Glu Arg Phe Lys Gly Thr Cys
        115                 120                 125

Asp Lys Asp Gly Cys Asp Phe Ala Ser Tyr Arg Trp Gly Ala Thr Asp
    130                 135                 140

Tyr Tyr Gly Pro Gly Lys Thr Val Asp Thr Lys Gln Pro Met Thr Val
145                 150                 155                 160

Val Thr Gln Phe Ile Gly Asp Pro Leu Thr Glu Ile Lys Arg Val Tyr
                165                 170                 175

Val Gln Gly Gly Lys Val Ile Asn Asn Ser Lys Thr Ser Asn Leu Gly
            180                 185                 190

Ser Val Tyr Asp Ser Leu Thr Glu Ala Phe Cys Asp Asp Thr Lys Gln
        195                 200                 205

Val Thr Gly Asp Thr Asn Asp Phe Lys Ala Lys Gly Gly Met Ser Gly
    210                 215                 220

Phe Ser Lys Asn Leu Asp Thr Pro Gln Val Leu Val Met Ser Leu Trp
```

-continued 225 230 235 240

Asp Asp His Thr Ala Asn Met Leu Trp Leu Asp Ser Thr Tyr Pro Thr
245 250 255

Asp Ser Thr Lys Pro Gly Ala Ala Arg Gly Thr Cys Ala Val Thr Ser
260 265 270

Gly Asp Pro Lys Asp Val Glu Ser Lys Gln Ala Asn Ser Gln Val Val
275 280 285

Tyr Ser Asp Ile Lys Phe Gly Pro Ile Asn Ser Thr Tyr Lys Ala Asn
290 295 300

<210> SEQ ID NO 39
<211> LENGTH: 475
<212> TYPE: PRT
<213> ORGANISM: Trichoderma reesei

<400> SEQUENCE: 39

Met Val Ser Phe Thr Ser Leu Leu Ala Gly Val Ala Ala Ile Ser Gly
1 5 10 15

Val Leu Ala Ala Pro Ala Ala Glu Val Glu Pro Val Ala Val Glu Lys
20 25 30

Arg Glu Ala Glu Ala Glu Ala Gln Gln Pro Gly Thr Ser Thr Pro Glu
35 40 45

Val His Pro Lys Leu Thr Thr Tyr Lys Cys Thr Lys Ser Gly Gly Cys
50 55 60

Val Ala Gln Asp Thr Ser Val Val Leu Asp Trp Asn Tyr Arg Trp Met
65 70 75 80

His Asp Ala Asn Tyr Asn Ser Cys Thr Val Asn Gly Gly Val Asn Thr
85 90 95

Thr Leu Cys Pro Asp Glu Ala Thr Cys Gly Lys Asn Cys Phe Ile Glu
100 105 110

Gly Val Asp Tyr Ala Ala Ser Gly Val Thr Thr Ser Gly Ser Ser Leu
115 120 125

Thr Met Asn Gln Tyr Met Pro Ser Ser Ser Gly Gly Tyr Ser Ser Val
130 135 140

Ser Pro Arg Leu Tyr Leu Leu Asp Ser Asp Gly Glu Tyr Val Met Leu
145 150 155 160

Lys Leu Asn Gly Gln Glu Leu Ser Phe Asp Val Asp Leu Ser Ala Leu
165 170 175

Pro Cys Gly Glu Asn Gly Ser Leu Tyr Leu Ser Gln Met Asp Glu Asn
180 185 190

Gly Gly Ala Asn Gln Tyr Asn Thr Ala Gly Ala Asn Tyr Gly Ser Gly
195 200 205

Tyr Cys Asp Ala Gln Cys Pro Val Gln Thr Trp Arg Asn Gly Thr Leu
210 215 220

Asn Thr Ser His Gln Gly Phe Cys Cys Asn Glu Met Asp Ile Leu Glu
225 230 235 240

Gly Asn Ser Arg Ala Asn Ala Leu Thr Pro His Ser Cys Thr Ala Thr
245 250 255

Ala Cys Asp Ser Ala Gly Cys Gly Phe Asn Pro Tyr Gly Ser Gly Tyr
260 265 270

Lys Ser Tyr Tyr Gly Pro Gly Asp Thr Val Asp Thr Ser Lys Thr Phe
275 280 285

Thr Ile Ile Thr Gln Phe Asn Thr Asp Asn Gly Ser Pro Ser Gly Asn
290 295 300

```
Leu Val Ser Ile Thr Arg Lys Tyr Gln Gln Asn Gly Val Asp Ile Pro
305                 310                 315                 320

Ser Ala Gln Pro Gly Gly Asp Thr Ile Ser Ser Cys Pro Ser Ala Ser
                325                 330                 335

Ala Tyr Gly Gly Leu Ala Thr Met Gly Lys Ala Leu Ser Ser Gly Met
            340                 345                 350

Val Leu Val Phe Ser Ile Trp Asn Asp Asn Ser Gln Tyr Met Asn Trp
        355                 360                 365

Leu Asp Ser Gly Asn Ala Gly Pro Cys Ser Ser Thr Glu Gly Asn Pro
    370                 375                 380

Ser Asn Ile Leu Ala Asn Asn Pro Asn Thr His Val Val Phe Ser Asn
385                 390                 395                 400

Ile Arg Trp Gly Asp Ile Gly Ser Thr Thr Asn Ser Thr Ala Pro Pro
                405                 410                 415

Pro Pro Pro Ala Ser Ser Thr Thr Phe Ser Thr Thr Arg Arg Ser Ser
            420                 425                 430

Thr Thr Ser Ser Ser Pro Ser Cys Thr Gln Thr His Trp Gly Gln Cys
        435                 440                 445

Gly Gly Ile Gly Tyr Ser Gly Cys Lys Thr Cys Thr Ser Gly Thr Thr
    450                 455                 460

Cys Gln Tyr Ser Asn Asp Tyr Tyr Ser Gln Cys
465                 470                 475


<210> SEQ ID NO 40
<211> LENGTH: 896
<212> TYPE: PRT
<213> ORGANISM: Saccharomycopsis fibuligera

<400> SEQUENCE: 40

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Ser Asp Ser Arg Val Pro Ile Gln Asn Tyr Thr Gln Ser Pro Ser
        35                  40                  45

Gln Arg Asp Glu Ser Ser Gln Trp Val Ser Pro His Tyr Tyr Pro Thr
    50                  55                  60

Pro Gln Gly Gly Arg Leu Gln Asp Val Trp Gln Glu Ala Tyr Ala Arg
65                  70                  75                  80

Ala Lys Ala Ile Val Gly Gln Met Thr Ile Val Glu Lys Val Asn Leu
                85                  90                  95

Thr Thr Gly Thr Gly Trp Gln Leu Asp Pro Cys Val Gly Asn Thr Gly
            100                 105                 110

Ser Val Pro Arg Phe Gly Ile Pro Asn Leu Cys Leu Gln Asp Gly Pro
        115                 120                 125

Leu Gly Val Arg Phe Ala Asp Phe Val Thr Gly Tyr Pro Ser Gly Leu
    130                 135                 140

Ala Thr Gly Ala Thr Phe Asn Lys Asp Leu Phe Leu Gln Arg Gly Gln
145                 150                 155                 160

Ala Leu Gly His Glu Phe Asn Ser Lys Gly Val His Ile Ala Leu Gly
                165                 170                 175

Pro Ala Val Gly Pro Leu Gly Val Lys Ala Arg Gly Gly Arg Asn Phe
            180                 185                 190

Glu Ala Phe Gly Ser Asp Pro Tyr Leu Gln Gly Thr Ala Ala Ala Ala
        195                 200                 205
```

```
Thr Ile Lys Gly Leu Gln Glu Asn Asn Val Met Ala Cys Val Lys His
    210                 215                 220

Phe Ile Gly Asn Glu Gln Glu Lys Tyr Arg Gln Pro Asp Asp Ile Asn
225                 230                 235                 240

Pro Ala Thr Asn Gln Thr Thr Lys Glu Ala Ile Ser Ala Asn Ile Pro
                245                 250                 255

Asp Arg Ala Met His Glu Leu Tyr Leu Trp Pro Phe Ala Asp Ser Val
            260                 265                 270

Arg Ala Gly Val Gly Ser Val Met Cys Ser Tyr Asn Arg Val Asn Asn
        275                 280                 285

Thr Tyr Ala Cys Glu Asn Ser Tyr Met Met Asn His Leu Leu Lys Glu
    290                 295                 300

Glu Leu Gly Phe Gln Gly Phe Val Val Ser Asp Trp Gly Ala Gln Leu
305                 310                 315                 320

Ser Gly Val Tyr Ser Ala Ile Ser Gly Leu Asp Met Ser Met Pro Gly
                325                 330                 335

Glu Val Tyr Gly Gly Trp Asn Thr Gly Thr Ser Phe Trp Gly Gln Asn
            340                 345                 350

Leu Thr Lys Ala Ile Tyr Asn Glu Thr Val Pro Ile Glu Arg Leu Asp
        355                 360                 365

Asp Met Ala Thr Arg Ile Leu Ala Ala Leu Tyr Ala Thr Asn Ser Phe
    370                 375                 380

Pro Thr Glu Asp His Leu Pro Asn Phe Ser Ser Trp Thr Thr Lys Glu
385                 390                 395                 400

Tyr Gly Asn Lys Tyr Tyr Ala Asp Asn Thr Thr Glu Ile Val Lys Val
                405                 410                 415

Asn Tyr His Val Asp Pro Ser Asn Asp Phe Thr Glu Asp Thr Ala Leu
            420                 425                 430

Lys Val Ala Glu Glu Ser Ile Val Leu Leu Lys Asn Glu Asn Asn Thr
        435                 440                 445

Leu Pro Ile Ser Pro Glu Lys Ala Lys Arg Leu Leu Leu Ser Gly Ile
    450                 455                 460

Ala Ala Gly Pro Asp Pro Ile Gly Tyr Gln Cys Glu Asp Gln Ser Cys
465                 470                 475                 480

Thr Asn Gly Ala Leu Phe Gln Gly Trp Gly Ser Gly Ser Val Gly Ser
                485                 490                 495

Pro Lys Tyr Gln Val Thr Pro Phe Glu Glu Ile Ser Tyr Leu Ala Arg
            500                 505                 510

Lys Asn Lys Met Gln Phe Asp Tyr Ile Arg Glu Ser Tyr Asp Leu Ala
        515                 520                 525

Gln Val Thr Lys Val Ala Ser Asp Ala His Leu Ser Ile Val Val Val
    530                 535                 540

Ser Ala Ala Ser Gly Glu Gly Tyr Ile Thr Val Asp Gly Asn Gln Gly
545                 550                 555                 560

Asp Arg Arg Asn Leu Thr Leu Trp Asn Asn Gly Asp Lys Leu Ile Glu
                565                 570                 575

Thr Val Ala Glu Asn Cys Ala Asn Thr Val Val Val Val Thr Ser Thr
            580                 585                 590

Gly Gln Ile Asn Phe Glu Gly Phe Ala Asp His Pro Asn Val Thr Ala
        595                 600                 605

Ile Val Trp Ala Gly Pro Leu Gly Asp Arg Ser Gly Thr Ala Ile Ala
    610                 615                 620
```

Asn Ile Leu Phe Gly Lys Ala Asn Pro Ser Gly His Leu Pro Phe Thr
625 630 635 640

Ile Ala Lys Thr Asp Asp Asp Tyr Ile Pro Ile Glu Thr Tyr Ser Pro
645 650 655

Ser Ser Gly Glu Pro Glu Asp Asn His Leu Val Glu Asn Asp Leu Leu
660 665 670

Val Asp Tyr Arg Tyr Phe Glu Glu Lys Asn Ile Glu Pro Arg Tyr Ala
675 680 685

Phe Gly Tyr Gly Leu Ser Tyr Asn Glu Tyr Glu Val Ser Asn Ala Lys
690 695 700

Val Ser Ala Ala Lys Lys Val Asp Glu Glu Leu Pro Glu Pro Ala Thr
705 710 715 720

Tyr Leu Ser Glu Phe Ser Tyr Gln Asn Ala Lys Asp Ser Lys Asn Pro
725 730 735

Ser Asp Ala Phe Ala Pro Thr Asp Leu Asn Arg Val Asn Glu Tyr Leu
740 745 750

Tyr Pro Tyr Leu Asp Ser Asn Val Thr Leu Lys Asp Gly Asn Tyr Glu
755 760 765

Tyr Pro Asp Gly Tyr Ser Thr Glu Gln Arg Thr Thr Pro Ile Gln Pro
770 775 780

Gly Gly Gly Leu Gly Gly Asn Asp Ala Leu Trp Glu Val Ala Tyr Lys
785 790 795 800

Val Glu Val Asp Val Gln Asn Leu Gly Asn Ser Thr Asp Lys Phe Val
805 810 815

Pro Gln Leu Tyr Leu Lys His Pro Glu Asp Gly Lys Phe Glu Thr Pro
820 825 830

Ile Gln Leu Arg Gly Phe Glu Lys Val Glu Leu Ser Pro Gly Glu Lys
835 840 845

Lys Thr Val Glu Phe Glu Leu Leu Arg Arg Asp Leu Ser Val Trp Asp
850 855 860

Thr Thr Arg Gln Ser Trp Ile Val Glu Ser Gly Thr Tyr Glu Ala Leu
865 870 875 880

Ile Gly Val Ala Val Asn Asp Ile Lys Thr Ser Val Leu Phe Thr Ile
885 890 895

<210> SEQ ID NO 41
<211> LENGTH: 144
<212> TYPE: DNA
<213> ORGANISM: Artificial Sequence
<220> FEATURE:
<223> OTHER INFORMATION: flexible linker fusion

<400> SEQUENCE: 41
ggaggaggtg gttcaggagg tggtgggtct gcttggcatc cacaatttgg aggaggcggt 60
ggtgaaaatc tgtatttcca gggaggcgga ggtgattaca aggatgacga caaaggaggt 120
ggtggatcag gaggtggtgg ctcc 144

<210> SEQ ID NO 42
<211> LENGTH: 117
<212> TYPE: DNA
<213> ORGANISM: Artificial Sequence
<220> FEATURE:
<223> OTHER INFORMATION: flexible linker fusion

<400> SEQUENCE: 42
ggtggcggtg gatctggagg aggcggttct tggtctcacc cacaatttga aaagggtgga 60

-continued gaaaacttgt actttcaagg cggtggtgga ggttctggcg gaggtggctc cggctca 117

<210> SEQ ID NO 43
<211> LENGTH: 455
<212> TYPE: PRT
<213> ORGANISM: Artificial Sequence
<220> FEATURE:
<223> OTHER INFORMATION: CBH1 consensus sequence

<400> SEQUENCE: 43

```
Met Arg Phe Pro Ser Ile Phe Thr Ala Val Leu Phe Ala Ala Ser Ser
1               5                   10                  15

Ala Leu Ala Gln Gln Ala Gly Thr Leu Thr Ala Glu Thr His Pro Ser
            20                  25                  30

Leu Thr Trp Gln Lys Cys Thr Ser Gly Gly Ser Cys Thr Thr Val Asn
        35                  40                  45

Gly Ser Val Val Ile Asp Ala Asn Trp Arg Trp Val His Ala Thr Ser
    50                  55                  60

Gly Ser Thr Asn Cys Tyr Thr Gly Asn Thr Trp Asp Thr Thr Leu Cys
65                  70                  75                  80

Pro Asp Asp Val Thr Cys Ala Gln Asn Cys Ala Leu Asp Gly Ala Asp
                85                  90                  95

Tyr Ser Ser Thr Tyr Gly Val Thr Thr Ser Gly Asn Ser Leu Arg Leu
            100                 105                 110

Asn Phe Val Thr Gln Gly Ser Gln Lys Asn Val Gly Ser Arg Leu Tyr
        115                 120                 125

Leu Met Glu Asp Asp Thr Thr Tyr Gln Met Phe Lys Leu Leu Gly Gln
    130                 135                 140

Glu Phe Thr Phe Asp Val Asp Val Ser Asn Leu Pro Cys Gly Leu Asn
145                 150                 155                 160

Gly Ala Leu Tyr Phe Val Ala Met Asp Ala Asp Gly Gly Met Ser Lys
                165                 170                 175

Tyr Pro Gly Asn Lys Ala Gly Ala Lys Tyr Gly Thr Gly Tyr Cys Asp
            180                 185                 190

Ser Gln Cys Pro Arg Asp Leu Lys Phe Ile Asn Gly Gln Ala Asn Val
        195                 200                 205

Glu Gly Trp Glu Pro Ser Ser Asn Asp Ala Asn Ala Gly Ile Gly Asn
    210                 215                 220

His Gly Ser Cys Cys Ala Glu Met Asp Ile Trp Glu Ala Asn Ser Ile
225                 230                 235                 240

Ser Thr Ala Phe Thr Pro His Pro Cys Asp Thr Ile Gly Gln Thr Met
                245                 250                 255

Cys Glu Gly Asp Ser Cys Gly Gly Thr Tyr Ser Ser Asp Arg Tyr Gly
            260                 265                 270

Gly Thr Cys Asp Pro Asp Gly Cys Asp Phe Asn Pro Tyr Arg Met Gly
        275                 280                 285

Asn Lys Thr Phe Tyr Gly Pro Gly Lys Thr Val Asp Thr Thr Lys Lys
    290                 295                 300

Val Thr Val Val Thr Gln Phe Ile Thr Gly Ser Ser Gly Thr Leu Ser
305                 310                 315                 320

Glu Ile Lys Arg Phe Tyr Val Gln Asn Gly Lys Val Ile Pro Asn Ser
                325                 330                 335

Glu Ser Thr Ile Ser Gly Val Ser Gly Asn Ser Ile Thr Thr Asp Phe
            340                 345                 350

Cys Thr Ala Gln Lys Thr Ala Phe Gly Asp Thr Asp Asp Phe Ala Lys
```

-continued

```
        355                 360                 365

Lys Gly Gly Leu Glu Gly Met Gly Lys Ala Leu Ala Gln Gly Met Val
    370                 375                 380

Leu Val Met Ser Leu Trp Asp Asp His Ala Ala Asn Met Leu Trp Leu
385                 390                 395                 400

Asp Ser Thr Tyr Pro Thr Asp Ala Thr Ser Ser Thr Pro Gly Ala Ala
                405                 410                 415

Arg Gly Ser Cys Asp Thr Ser Ser Gly Val Pro Ala Asp Val Glu Ala
            420                 425                 430

Asn Ser Pro Asn Ser Tyr Val Thr Phe Ser Asn Ile Lys Phe Gly Pro
        435                 440                 445

Ile Gly Ser Thr Phe Thr Gly
    450                 455
```

<210> SEQ ID NO 44
<211> LENGTH: 1368
<212> TYPE: DNA
<213> ORGANISM: Artificial Sequence
<220> FEATURE:
<223> OTHER INFORMATION: codon optimized CBH1 consensus sequence

<400> SEQUENCE: 44

```
atgagatttc cttcaatctt cactgctgtt ttgttcgcag cctcaagtgc tttagcacaa     60

caggccggaa cattgacagc agaaactcat ccttccttaa cctggcaaaa gtgcacttct    120

ggaggttcat gcactacagt gaatggatct gtcgtgatcg atgcaaactg gagatgggtt    180

cacgcaactt caggttctac caactgttat accggaaaca cttgggacac cacattgtgc    240

ccagatgacg tcacgtgcgc tcagaactgt gctttggatg gagctgatta cagttcaacc    300

tatggtgtaa ctacatccgg aaactctttg agattaaact tcgttactca aggaagtcaa    360

aagaacgttg gttctagatt gtacttaatg gaggacgata caacctatca aatgttcaaa    420

ttgttaggtc aggagttcac ctttgacgta gatgtcagta acttgccatg tgggttaaac    480

ggagctttat actttgtggc aatggatgct gacggtggaa tgtccaagta tccaggaaac    540

aaagccggtg caaagtacgg tacaggatat tgtgattcac agtgccctag agatttgaag    600

ttcattaacg gtcaagcaaa tgtggagggt tgggaaccat ctagtaacga tgccaatgcg    660

ggtattggta atcatgggtc ctgttgcgct gagatggata tctgggaggc caactcaata    720

tctactgcct ttacccctca cccatgcgat acaattggtc aaactatgtg cgagggtgat    780

tcatgtggtg gaacctactc ctctgataga tacggaggta catgcgatcc agatggttgc    840

gactttaatc catacagaat gggaaacaaa accttttacg gtcctggaaa gacagttgat    900

actaccaaga aagtaacagt cgtgacccag tttatcaccg gtagttctgg aaccttatcc    960

gaaatcaaaa gattctacgt tcagaacggt aaagtaattc caaacagtga atctacaatt   1020

tcaggagtga gtggtaattc tattactacc gacttttgta cagctcagaa aacagcattt   1080

ggtgacaccg atgactttgc taagaagggt ggattagaag gtatgggtaa agctttggcc   1140

cagggaatgg tgttagttat gtctttatgg gatgatcacg ccgcaaatat gttatggttg   1200

gattcaacat atccaactga tgccacaagt agtacacctg gagctgccag aggttcttgt   1260

gatacatctt ccggtgttcc agccgatgta gaagcaaatt ctcctaactc ctatgttacc   1320

ttctccaata taaagtttgg tccaatcggt tcaacattca ctggttaa                1368
```

<210> SEQ ID NO 45
<211> LENGTH: 1572

<212> TYPE: DNA
<213> ORGANISM: Acremonium thermophilum

<400> SEQUENCE: 45
atgtatacca aatttgctgc attggccgct ttagttgcaa cagtaagagg tcaagccgct 60
tgttctctaa ccgcagaaac tcacccatct ctacaatggc agaaatgcac agcccctgga 120
tcttgtacaa ctgtctccgg ccaagtcacc attgacgcta attggagatg gcttcaccaa 180
actaactctt caacgaattg ttataccggt aacgaatggg atacttccat atgttcatcc 240
gatacagact gcgcaacgaa atgttgttta gatggagcag actatacggg aacttatggt 300
gttacagcct caggtaattc cctaaacctt aagttcgtaa ctcaaggacc atatagtaag 360
aatatcggct ctagaatgta cttgatggaa agtgagagca aatatcaggg ttttacgtta 420
ttgggacaag agtttacatt tgatgttgat gtgagtaact taggttgcgg cctaaacggc 480
gccttgtact tcgtttctat ggatcttgat ggaggtgtat caaaatacac gaccaacaag 540
gctggagcca aatatggtac gggatattgt gacagccaat gccctagaga cttaaagttc 600
attaacggtc aggcaaatat tgacggctgg caaccaagca gtaacgacgc taatgccgga 660
ctaggtaacc atggctcatg ttgttccgaa atggatatct gggaagccaa taaggtgtcc 720
gctgcctaca ccccccatcc atgcacgaca atcggtcaga caatgtgtac cggtgatgac 780
tgtggaggca catactcaag tgataggtac gccggtatat gtgatcctga cggttgcgat 840
ttcaactctt atagaatggg agatacatcc ttttacggcc ccggtaaaac agttgatacg 900
ggtagtaagt tcactgttgt tactcagttc ttaacaggtt cagacggcaa tcttagtgaa 960
atcaaaagat tctacgttca gaatggaaaa gtcattccta attccgagag taagattgct 1020
ggtgtgtctg gtaacagtat cacgaccgac ttctgtaccg cccaaaagac tgcctttgga 1080
gatacgaatg ttttcgagga aaggggcggt cttgctcaaa tggcaaggc tttggccgaa 1140 ccaatggtat tagtcctatc cgtttgggat gatcatgcag tgaatatgct ttggcttgat 1200
agcacctacc ctactgacag caccaagcca ggagctgcca gaggtgactg tcctatcaca 1260
agtggcgttc cagcagatgt agagagccaa gctccaaact ccaatgtgat ctattctaac 1320
atcagatttg gccccattaa tagtacctat acaggaacgc cctctggtgg taaccctcca 1380
ggcggaggca ccacaactac cacgaccaca acgacttcaa agccttctgg ccctacgaca 1440
actaccaatc cttccggacc acagcaaact cactggggtc agtgtggagg ccaaggatgg 1500
acgggtccta ccgtgtgtca atcaccttac acatgcaaat acagtaatga ctggtactct 1560
cagtgtttat aa 1572

<210> SEQ ID NO 46
<211> LENGTH: 523
<212> TYPE: PRT
<213> ORGANISM: Acremonium thermophilum

<400> SEQUENCE: 46

Met Tyr Thr Lys Phe Ala Ala Leu Ala Ala Leu Val Ala Thr Val Arg
1               5                   10                  15

Gly Gln Ala Ala Cys Ser Leu Thr Ala Glu Thr His Pro Ser Leu Gln
            20                  25                  30

Trp Gln Lys Cys Thr Ala Pro Gly Ser Cys Thr Thr Val Ser Gly Gln
        35                  40                  45

Val Thr Ile Asp Ala Asn Trp Arg Trp Leu His Gln Thr Asn Ser Ser
    50                  55                  60

-continued

```
Thr Asn Cys Tyr Thr Gly Asn Glu Trp Asp Thr Ser Ile Cys Ser Ser
65                  70                  75                  80

Asp Thr Asp Cys Ala Thr Lys Cys Cys Leu Asp Gly Ala Asp Tyr Thr
                85                  90                  95

Gly Thr Tyr Gly Val Thr Ala Ser Gly Asn Ser Leu Asn Leu Lys Phe
            100                 105                 110

Val Thr Gln Gly Pro Tyr Ser Lys Asn Ile Gly Ser Arg Met Tyr Leu
        115                 120                 125

Met Glu Ser Glu Ser Lys Tyr Gln Gly Phe Thr Leu Leu Gly Gln Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Leu Asp Gly Gly Val Ser Lys Tyr
                165                 170                 175

Thr Thr Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Ile Asp
        195                 200                 205

Gly Trp Gln Pro Ser Ser Asn Asp Ala Asn Ala Gly Leu Gly Asn His
    210                 215                 220

Gly Ser Cys Cys Ser Glu Met Asp Ile Trp Glu Ala Asn Lys Val Ser
225                 230                 235                 240

Ala Ala Tyr Thr Pro His Pro Cys Thr Thr Ile Gly Gln Thr Met Cys
                245                 250                 255

Thr Gly Asp Asp Cys Gly Gly Thr Tyr Ser Ser Asp Arg Tyr Ala Gly
            260                 265                 270

Ile Cys Asp Pro Asp Gly Cys Asp Phe Asn Ser Tyr Arg Met Gly Asp
        275                 280                 285

Thr Ser Phe Tyr Gly Pro Gly Lys Thr Val Asp Thr Gly Ser Lys Phe
    290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Glu
                325                 330                 335

Ser Lys Ile Ala Gly Val Ser Gly Asn Ser Ile Thr Thr Asp Phe Cys
            340                 345                 350

Thr Ala Gln Lys Thr Ala Phe Gly Asp Thr Asn Val Phe Glu Glu Arg
        355                 360                 365

Gly Gly Leu Ala Gln Met Gly Lys Ala Leu Ala Glu Pro Met Val Leu
    370                 375                 380

Val Leu Ser Val Trp Asp Asp His Ala Val Asn Met Leu Trp Leu Asp
385                 390                 395                 400

Ser Thr Tyr Pro Thr Asp Ser Thr Lys Pro Gly Ala Ala Arg Gly Asp
                405                 410                 415

Cys Pro Ile Thr Ser Gly Val Pro Ala Asp Val Glu Ser Gln Ala Pro
            420                 425                 430

Asn Ser Asn Val Ile Tyr Ser Asn Ile Arg Phe Gly Pro Ile Asn Ser
        435                 440                 445

Thr Tyr Thr Gly Thr Pro Ser Gly Gly Asn Pro Pro Gly Gly Gly Thr
    450                 455                 460

Thr Thr Thr Thr Thr Thr Thr Thr Ser Lys Pro Ser Gly Pro Thr Thr
465                 470                 475                 480

Thr Thr Asn Pro Ser Gly Pro Gln Gln Thr His Trp Gly Gln Cys Gly
```

-continued

```
                485                 490                 495

Gly Gln Gly Trp Thr Gly Pro Thr Val Cys Gln Ser Pro Tyr Thr Cys
            500                 505                 510

Lys Tyr Ser Asn Asp Trp Tyr Ser Gln Cys Leu
        515                 520
```

<210> SEQ ID NO 47
<211> LENGTH: 1586
<212> TYPE: DNA
<213> ORGANISM: Aspergillus kawachii

<400> SEQUENCE: 47

```
ttaattaaaa tgagaatttc taacttgatt gttgctgctt ctgctgctac tatggtttct     60

gctttgccat ctagacaaat gaaaaagagg gattctggtt ttaaatgggt tggtacttct    120

gaatctggtg ctgaatttgg ttctgcttta ccaggtactt tgggtactga ttatacttgg    180

ccagaaactt ctaaaattca agttttgaga aacaagggta tgaacatttt tagaatacca    240

ttcttgatgg aaagattaac tccagatggt ttgactggtt cttttgcttc tacttacttg    300

tctgatttga agtcaactgt tgaatttgtt actaattctg gtgcttatgc tgttttagat    360

ccacataatt acggtagatt cgatggttct attattgaat ctacttctga ttttaagact    420

tggtggaaaa atgttgctac tgaatttgct gataacgata aggttatttt cgatacaaac    480

aacgaatatc atgatatgga acaatctttg gttttgaatt tgaaccaagc tgctattaat    540

ggtattagag ctgctggtgc tactactcaa tacattttcg ttgaaggtaa tgcttatact    600

ggtgcttggg attggactac ttacaatgat gatttgtctg gtttaactga ttctgaagat    660

aagataatat acgaaatgca tcaatacttg gattctgatt cttctggtac atctgaaact    720

tgtgtttctt ctactattgg taaagaaaga attgaaaagg ctactgaatg gttgaaaact    780

aacaacaagc aaggtattat tggtgaattt gcaggtggtg ttaattctgt ttgtgaagag    840

gctgttgaag gaatgttggc ttatatgtct gaaaattctg atgtttgggt tggtgcttct    900

tggtggtctg ctggtccatg gtggggtact tacatgtatt ctttggaacc aactgatggt    960

actgcttatt ctacttattt gccaattttg gaaaaatact tcccatctgg tgatgcttca   1020

tcatcttcat ctgcttcagc ttcagttgca gccgctactt ctgctgtttc tactactact   1080

acagctgcat ttgaacaaac tactactcca gctactcaag ttgaaattgc ttcttcttca   1140

tcttcatcat cagctgttgc tgcttcacaa actactttgt ctaaggttaa gtctaaatct   1200

aaatctccat gtaaattgtc atctgctact tcatctgctg tttcatcagc tgctgcagtt   1260

actacacctg cagttgcagc tacaactcca gctgctgctc caacttcttc ttctgttgct   1320

tttgctacta cttctgttta cgttccaact actactgctg ctgcaccatc tcaagtttca   1380

tcttcagctg cagcttcatc ttcaggtgtt gttggtgttt ctgatccaca aggtccatct   1440

gctactaatt ctgctggtga agttaatcaa tattaccaat gtggtggtat taattggact   1500

ggtccaactg tttgtgcttc tccatatact tgtaaggttc aaaacgatta ctactatcaa   1560

tgtgttgctg aattataagg cgcgcc                                          1586
```

<210> SEQ ID NO 48
<211> LENGTH: 1280
<212> TYPE: DNA
<213> ORGANISM: Heterodera schachtii

<400> SEQUENCE: 48

```
ttaattaaaa tgcattgggc tgatgttgct tgttctagac caccatggcc aagagattct     60
```

gttaaagctt tgaagtgtaa ttggaacgct aatgttatta gaggtgctat gggtgttgat 120
gaaggtggtt atttgtctga tgctaatact gcttacaatt tgatggttgc tgttattgaa 180
gctgctattt ctaatggtat ctacgttatt gttgattggc atgctcataa tgctcatcca 240
gatgaagctg ttaaattctt tactagaatt gctcaagctt atggttctta cttgcatatt 300
ttgtacgaag atttcaatga accattggat gtttcttgga ctgatgtttt ggttccatac 360
cataaaaaag ttattgctgc cattagagct attgataaga agaacgttat tatcttgggt 420
actccaaaat ggtcacaaga tgttgatgtt gcttctcaaa atccaattaa ggattaccaa 480
aacttgatgt acactttgca tttttacgct tcatctcatt ttacatctga tttgggtgct 540
aaattgaaaa ctgctgttaa caatggtttg ccagtttttg ttactgaata tggtacttgt 600
gaagcttctg gtaatggtaa tttgaatact gattctatgt catcttggtg gactttgttg 660
gattctttga aaatttctta cgctaattgg gctatttctg ataaatctga agcttgttct 720
gctttgtctc caggtactac tgctgttaat gttggtgttt cttctagatg gacttcttct 780
ggtaatatgg ttgcttctta ctacaaaaaa aagtccactg gtatttcttg ttctggtagt 840
tcttcaggtt cttcaagtgg ttcatctagt ggttcttccg gtacatcttc tggttctagt 900
ggttcatcta gtggtagttc ttccggtagt tctagtggta gttctggttc aagttctggt 960
tcctcctctg gttctggttc tgcatctatt tctgttgttc catctaatac ttggaatggt 1020
ggtggtagag ttaattttga aattaagaac actggttctg ttccattgtg tggtgttgtt 1080
ttttctgttt ctttgccatc tggtactact ttgggtggtt cttggaatat ggaatctgct 1140
ggttctggtc aatattcttt accatcttgg gttagaattg aagctggtaa atcttctaaa 1200
gatgctggtt tgactttttaa tggtaaagat aagccaactg ctaaaattgt taccaccaag 1260
aagtgcttat aaggcgcgcc 1280

<210> SEQ ID NO 49
<211> LENGTH: 1277
<212> TYPE: DNA
<213> ORGANISM: Hypocrea jecorina

<400> SEQUENCE: 49
ttaattaaaa tgaacaagtc tgttgctcca ttgttgttgg ctgcttctat tttgtatggt 60
ggtgctgttg ctcaacaaac tgtttggggt caatgtggtg gtattggttg gtctggtcca 120
actaattgtg ctccaggttc tgcttgttct actttgaatc catattatgc tcaatgtatt 180
ccaggtgcta ctactattac tacttctact agaccaccat ctggtccaac aactactact 240
agagctactt ctacatcttc ttctactcca ccaacttcat ctggtgttag atttgctggt 300
gttaacattg ctggttttga ttttggttgt actactgatg gtacttgtgt tacttctaaa 360
gtttacccac cattgaaaaa tttcactggt tctaacaatt atccagatgg tattggtcaa 420
atgcaacatt ttgttaacga agatggtatg actattttta gattgccagt tggttggcaa 480
tatttggtta acaacaattt gggtggtaat ttggattcta cttctatttc taagtacgat 540
caattggttc aaggttgttt gtctttgggt gcttactgta ttgttgatat tcataattat 600
gctagatgga atggtggtat tattggtcaa ggtggtccaa caaatgctca atttacttct 660
ttgtggtcac aattggcttc aaaatatgct tctcaatcta gagtttggtt tggtattatg 720
aatgaaccac atgatgttaa cattaatact tgggctgcta ctgttcaaga agttgttact 780
gctattagaa atgctggtgc tacttctcaa ttcatttctt tgccaggtaa tgattggcaa 840
tctgctggtg cttttatttc tgatggttct gctgctgctt tgtctcaagt tactaatcca 900
gatggttcta ctactaattt gatcttcgat gttcataagt acttggattc tgataattct 960
ggtactcatg ctgaatgtac tacaaacaat attgatggtg ctttttctcc attggctact 1020
tggttgagac aaaacaatag acaagctatt ttgactgaaa ctggtggtgg taatgttcaa 1080
tcttgtatcc aagatatgtg ccaacaaatt caatacttga accaaaattc tgatgtttat 1140
ttgggttacg ttggttgggg tgctggttct tttgattcta cttacgtttt aactgaaact 1200
ccaacttctt ctggtaattc ttggactgat acttctttgg tttcttcatg tttggctaga 1260
aagttataag gcgcgcc 1277

<210> SEQ ID NO 50
<211> LENGTH: 1436
<212> TYPE: DNA
<213> ORGANISM: Orpinomyces sp.

<400> SEQUENCE: 50
ttaattaaaa tgaagttctt gaactctttg tctttgttgg gtttggttat tgctggttgt 60
gaagctatga gaaacatttc ttctaaagaa ttggttaaag aattgactat tggttggtct 120
ttgggtaata ctttggatgc ttcttgtgtt gaaactttga actactctaa agatcaaact 180
gcttctgaaa cttgttgggg taatgttaaa actactcaag aattgtacta caaattgtct 240
gatttgggtt tcaatacttt cagaatacca actacttggt ctggtcattt tggtgatgct 300
ccagattaca aaatttctga tgtttggatg aaaagagttc acgaagttgt tgattatgct 360
ttgaatactg gtggttacgc tattttgaac attcatcatg aaacttggaa ttacgctttt 420
caaaagaatt tggaatctgc taaaaagatt ttggttgcta tttggaaaca aattgctgct 480
gaatttggtg attacgatga acatttgatt tttgaaggta tgaatgaacc aagaaaagtt 540
ggtgatccag ctgaatggac tggtggtgat caagaaggtt ggaattttgt taatgaaatg 600
aacgctttgt tcgttaaaac tattagagct actggtggta acaatgctaa tagacatttg 660
atgattccaa cttatgctgc ttctgttaat gatggttcta ttaacaattt taagtaccca 720
aatggtgatg ataaagttat tgtttctttg cattcttact ctccatacaa ttttgctttg 780
aacaatggtc caggtgctat ttctaatttc tacgatggta acgaaattga ttgggttatg 840
aacactatta actcttcatt catttctaag ggtattccag ttattattgg tgaatttgtt 900
gctatgaaca gagataatga agatgataga gaaagatggc aagaatacta cattaaaaag 960
gctactgctt tgggtattcc atgtgttatt tgggataatg gttattttga aggtgaaggt 1020
gaaagatttg gtattattga tagaaagtct ttgaacgtta ttttcccaaa gttgattaat 1080
ggtttgatga aaggtttggg tgatgaaaaa ccaaaaacta ctattagaag aactactact 1140
actacagttc aagttcaacc aactattaac aacgaatgtt tctctactag attgggttat 1200
tcttgttgta atggtttcga tgttttgtac actgataatg atggtcaatg gggtgttgaa 1260
aatggtaatt ggtgtggtat taaatcttct tgtggtaaca atcaaagaca atgttggtct 1320
gaaagattag gttatccatg ttgtcaatac actactaatg ctgaatatac agacaacgac 1380
ggtagatggg gtgtagaaaa cggtaactgg tgcggaatat acttgtaagg cgcgcc 1436

<210> SEQ ID NO 51
<211> LENGTH: 1220
<212> TYPE: DNA
<213> ORGANISM: Irpex lacteus

<400> SEQUENCE: 51

```
ttaattaaaa tgaagtcttt gttgttgtct gctgctgcta ctttggcttt atctactcca     60

gctttttctg tttctgtttg gggtcaatgt ggtggtattg gttttactgg ttctactact    120

tgtgatgctg gtacttcttg tgttcatttg aacgattact actttcaatg tcaaccaggt    180

gctgctactt ctactgttca accaactact actgcttctt ctacttcttc tgctgcagct    240

ccatcttctt caggtaatgc tgtttgttct ggtactagaa acaagtttaa gttcttcggt    300

gttaatgaat ctggtgctga atttggtaac aatgttattc caggtacttt gggtactgat    360

tatacttggc catctccatc ttctattgat tttttcgttg gtaagggttt taatactttc    420

agagttccat tttgatgga aagattgtct ccacctgcta ctggtttgac tggtccattt    480

gattctactt atttgcaagg tttgaaaact attgtttctt acattactgg taaaggtggt    540

tatgctttgg ttgatccaca taactttatg atttacaacg gtgctactat ttctgatact    600

aatgcttttc aaacttggtg gcaaaatttg gctgctcaat ttaagactga ttctcatgtt    660

gttttcgatg ttatgaatga accacatgat attccagctc aaactgtttt taacttgaac    720

caagctgcta ttaatagaat tagagcttct ggtgctactt ctcaatctat tttggttgaa    780

ggtacttctt atactggtgc ttggacttgg actactactt ctggtaattc tcaagttttt    840

ggtgctattc atgatccaaa caacaatgtt gctattgaaa tgcatcaata cttggattct    900

gatggttctg gtacttctcc aacttgtgtt tctccaacta ttggtgctga aagattgcaa    960

gctgctactc aatggttgca acaaaacaat ttgaaaggtt tcttgggtga aattggtgct   1020

ggttctaatg ctgattgtat ttctgctgtt caaggtgctt tgtgtgaaat gcaacaatct   1080

gatgtttggt tgggtgcttt gtggtgggct gctggtccat ggtggggtga ttattttcaa   1140

tctattgaac caccatctgg tgttgctgtt tcttctattt tgccacaagc tttggaacca   1200

tttttgttat aaggcgcgcc                                                 1220


<210> SEQ ID NO 52
<211> LENGTH: 521
<212> TYPE: PRT
<213> ORGANISM: Aspergillus kawachii

<400> SEQUENCE: 52

Met Arg Ile Ser Asn Leu Ile Val Ala Ala Ser Ala Ala Thr Met Val
1               5                   10                  15

Ser Ala Leu Pro Ser Arg Gln Met Lys Lys Arg Asp Ser Gly Phe Lys
            20                  25                  30

Trp Val Gly Thr Ser Glu Ser Gly Ala Glu Phe Gly Ser Ala Leu Pro
        35                  40                  45

Gly Thr Leu Gly Thr Asp Tyr Thr Trp Pro Glu Thr Ser Lys Ile Gln
    50                  55                  60

Val Leu Arg Asn Lys Gly Met Asn Ile Phe Arg Ile Pro Phe Leu Met
65                  70                  75                  80

Glu Arg Leu Thr Pro Asp Gly Leu Thr Gly Ser Phe Ala Ser Thr Tyr
                85                  90                  95

Leu Ser Asp Leu Lys Ser Thr Val Glu Phe Val Thr Asn Ser Gly Ala
            100                 105                 110

Tyr Ala Val Leu Asp Pro His Asn Tyr Gly Arg Phe Asp Gly Ser Ile
        115                 120                 125

Ile Glu Ser Thr Ser Asp Phe Lys Thr Trp Trp Lys Asn Val Ala Thr
    130                 135                 140

Glu Phe Ala Asp Asn Asp Lys Val Ile Phe Asp Thr Asn Asn Glu Tyr
```

```
145                 150                 155                 160

His Asp Met Glu Gln Ser Leu Val Leu Asn Leu Asn Gln Ala Ala Ile
                165                 170                 175

Asn Gly Ile Arg Ala Ala Gly Ala Thr Thr Gln Tyr Ile Phe Val Glu
            180                 185                 190

Gly Asn Ala Tyr Thr Gly Ala Trp Asp Trp Thr Thr Tyr Asn Asp Asp
        195                 200                 205

Leu Ser Gly Leu Thr Asp Ser Glu Asp Lys Ile Ile Tyr Glu Met His
    210                 215                 220

Gln Tyr Leu Asp Ser Asp Ser Ser Gly Thr Ser Glu Thr Cys Val Ser
225                 230                 235                 240

Ser Thr Ile Gly Lys Glu Arg Ile Glu Lys Ala Thr Glu Trp Leu Lys
                245                 250                 255

Thr Asn Asn Lys Gln Gly Ile Ile Gly Glu Phe Ala Gly Gly Val Asn
            260                 265                 270

Ser Val Cys Glu Glu Ala Val Glu Gly Met Leu Ala Tyr Met Ser Glu
        275                 280                 285

Asn Ser Asp Val Trp Val Gly Ala Ser Trp Trp Ser Ala Gly Pro Trp
    290                 295                 300

Trp Gly Thr Tyr Met Tyr Ser Leu Glu Pro Thr Asp Gly Thr Ala Tyr
305                 310                 315                 320

Ser Thr Tyr Leu Pro Ile Leu Glu Lys Tyr Phe Pro Ser Gly Asp Ala
                325                 330                 335

Ser Ser Ser Ser Ser Ala Ser Ala Ser Val Ala Ala Ala Thr Ser Ala
            340                 345                 350

Val Ser Thr Thr Thr Thr Ala Ala Phe Glu Gln Thr Thr Thr Pro Ala
        355                 360                 365

Thr Gln Val Glu Ile Ala Ser Ser Ser Ser Ser Ser Ser Ala Val Ala
    370                 375                 380

Ala Ser Gln Thr Thr Leu Ser Lys Val Lys Ser Lys Ser Lys Ser Pro
385                 390                 395                 400

Cys Lys Leu Ser Ser Ala Thr Ser Ser Ala Val Ser Ser Ala Ala Ala
                405                 410                 415

Val Thr Thr Pro Ala Val Ala Ala Thr Thr Pro Ala Ala Ala Pro Thr
            420                 425                 430

Ser Ser Ser Val Ala Phe Ala Thr Thr Ser Val Tyr Val Pro Thr Thr
        435                 440                 445

Thr Ala Ala Ala Pro Ser Gln Val Ser Ser Ser Ala Ala Ala Ser Ser
    450                 455                 460

Ser Gly Val Val Gly Val Ser Asp Pro Gln Gly Pro Ser Ala Thr Asn
465                 470                 475                 480

Ser Ala Gly Glu Val Asn Gln Tyr Tyr Gln Cys Gly Gly Ile Asn Trp
                485                 490                 495

Thr Gly Pro Thr Val Cys Ala Ser Pro Tyr Thr Cys Lys Val Gln Asn
            500                 505                 510

Asp Tyr Tyr Tyr Gln Cys Val Ala Glu
        515                 520
```

<210> SEQ ID NO 53
<211> LENGTH: 419
<212> TYPE: PRT
<213> ORGANISM: Heterodera schachtii

<400> SEQUENCE: 53

-continued

```
Met His Trp Ala Asp Val Ala Cys Ser Arg Pro Pro Trp Pro Arg Asp
1               5                   10                  15

Ser Val Lys Ala Leu Lys Cys Asn Trp Asn Ala Asn Val Ile Arg Gly
            20                  25                  30

Ala Met Gly Val Asp Glu Gly Gly Tyr Leu Ser Asp Ala Asn Thr Ala
        35                  40                  45

Tyr Asn Leu Met Val Ala Val Ile Glu Ala Ala Ile Ser Asn Gly Ile
    50                  55                  60

Tyr Val Ile Val Asp Trp His Ala His Asn Ala His Pro Asp Glu Ala
65                  70                  75                  80

Val Lys Phe Phe Thr Arg Ile Ala Gln Ala Tyr Gly Ser Tyr Leu His
                85                  90                  95

Ile Leu Tyr Glu Asp Phe Asn Glu Pro Leu Asp Val Ser Trp Thr Asp
            100                 105                 110

Val Leu Val Pro Tyr His Lys Lys Val Ile Ala Ala Ile Arg Ala Ile
        115                 120                 125

Asp Lys Lys Asn Val Ile Ile Leu Gly Thr Pro Lys Trp Ser Gln Asp
    130                 135                 140

Val Asp Val Ala Ser Gln Asn Pro Ile Lys Asp Tyr Gln Asn Leu Met
145                 150                 155                 160

Tyr Thr Leu His Phe Tyr Ala Ser Ser His Phe Thr Ser Asp Leu Gly
                165                 170                 175

Ala Lys Leu Lys Thr Ala Val Asn Asn Gly Leu Pro Val Phe Val Thr
            180                 185                 190

Glu Tyr Gly Thr Cys Glu Ala Ser Gly Asn Gly Asn Leu Asn Thr Asp
        195                 200                 205

Ser Met Ser Ser Trp Trp Thr Leu Leu Asp Ser Leu Lys Ile Ser Tyr
    210                 215                 220

Ala Asn Trp Ala Ile Ser Asp Lys Ser Glu Ala Cys Ser Ala Leu Ser
225                 230                 235                 240

Pro Gly Thr Thr Ala Val Asn Val Gly Val Ser Ser Arg Trp Thr Ser
                245                 250                 255

Ser Gly Asn Met Val Ala Ser Tyr Tyr Lys Lys Lys Ser Thr Gly Ile
            260                 265                 270

Ser Cys Ser Gly Ser Ser Ser Gly Ser Ser Ser Gly Ser Ser Ser Gly
        275                 280                 285

Ser Ser Gly Thr Ser Ser Gly Ser Ser Gly Ser Ser Ser Gly Ser Ser
    290                 295                 300

Ser Gly Ser Ser Ser Gly Ser Ser Gly Ser Ser Ser Gly Ser Ser Ser
305                 310                 315                 320

Gly Ser Gly Ser Ala Ser Ile Ser Val Val Pro Ser Asn Thr Trp Asn
                325                 330                 335

Gly Gly Gly Arg Val Asn Phe Glu Ile Lys Asn Thr Gly Ser Val Pro
            340                 345                 350

Leu Cys Gly Val Val Phe Ser Val Ser Leu Pro Ser Gly Thr Thr Leu
        355                 360                 365

Gly Gly Ser Trp Asn Met Glu Ser Ala Gly Ser Gly Gln Tyr Ser Leu
    370                 375                 380

Pro Ser Trp Val Arg Ile Glu Ala Gly Lys Ser Ser Lys Asp Ala Gly
385                 390                 395                 400

Leu Thr Phe Asn Gly Lys Asp Lys Pro Thr Ala Lys Ile Val Thr Thr
                405                 410                 415

Lys Lys Cys
```

```
<210> SEQ ID NO 54
<211> LENGTH: 418
<212> TYPE: PRT
<213> ORGANISM: Hypocrea jecorina

<400> SEQUENCE: 54

Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
```

```
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys


<210> SEQ ID NO 55
<211> LENGTH: 471
<212> TYPE: PRT
<213> ORGANISM: Orpinomyces sp.

<400> SEQUENCE: 55

Met Lys Phe Leu Asn Ser Leu Ser Leu Leu Gly Leu Val Ile Ala Gly
1               5                   10                  15

Cys Glu Ala Met Arg Asn Ile Ser Ser Lys Glu Leu Val Lys Glu Leu
            20                  25                  30

Thr Ile Gly Trp Ser Leu Gly Asn Thr Leu Asp Ala Ser Cys Val Glu
        35                  40                  45

Thr Leu Asn Tyr Ser Lys Asp Gln Thr Ala Ser Glu Thr Cys Trp Gly
    50                  55                  60

Asn Val Lys Thr Thr Gln Glu Leu Tyr Tyr Lys Leu Ser Asp Leu Gly
65                  70                  75                  80

Phe Asn Thr Phe Arg Ile Pro Thr Thr Trp Ser Gly His Phe Gly Asp
                85                  90                  95

Ala Pro Asp Tyr Lys Ile Ser Asp Val Trp Met Lys Arg Val His Glu
            100                 105                 110

Val Val Asp Tyr Ala Leu Asn Thr Gly Gly Tyr Ala Ile Leu Asn Ile
        115                 120                 125

His His Glu Thr Trp Asn Tyr Ala Phe Gln Lys Asn Leu Glu Ser Ala
    130                 135                 140

Lys Lys Ile Leu Val Ala Ile Trp Lys Gln Ile Ala Ala Glu Phe Gly
145                 150                 155                 160

Asp Tyr Asp Glu His Leu Ile Phe Glu Gly Met Asn Glu Pro Arg Lys
                165                 170                 175

Val Gly Asp Pro Ala Glu Trp Thr Gly Gly Asp Gln Glu Gly Trp Asn
            180                 185                 190

Phe Val Asn Glu Met Asn Ala Leu Phe Val Lys Thr Ile Arg Ala Thr
        195                 200                 205

Gly Gly Asn Asn Ala Asn Arg His Leu Met Ile Pro Thr Tyr Ala Ala
    210                 215                 220

Ser Val Asn Asp Gly Ser Ile Asn Asn Phe Lys Tyr Pro Asn Gly Asp
225                 230                 235                 240

Asp Lys Val Ile Val Ser Leu His Ser Tyr Ser Pro Tyr Asn Phe Ala
                245                 250                 255

Leu Asn Asn Gly Pro Gly Ala Ile Ser Asn Phe Tyr Asp Gly Asn Glu
            260                 265                 270

Ile Asp Trp Val Met Asn Thr Ile Asn Ser Ser Phe Ile Ser Lys Gly
        275                 280                 285

Ile Pro Val Ile Ile Gly Glu Phe Val Ala Met Asn Arg Asp Asn Glu
    290                 295                 300

Asp Asp Arg Glu Arg Trp Gln Glu Tyr Tyr Ile Lys Lys Ala Thr Ala
305                 310                 315                 320

Leu Gly Ile Pro Cys Val Ile Trp Asp Asn Gly Tyr Phe Glu Gly Glu
```

```
                325                 330                 335

Gly Glu Arg Phe Gly Ile Ile Asp Arg Lys Ser Leu Asn Val Ile Phe
            340                 345                 350

Pro Lys Leu Ile Asn Gly Leu Met Lys Gly Leu Gly Asp Glu Lys Pro
        355                 360                 365

Lys Thr Thr Ile Arg Arg Thr Thr Thr Thr Thr Val Gln Val Gln Pro
    370                 375                 380

Thr Ile Asn Asn Glu Cys Phe Ser Thr Arg Leu Gly Tyr Ser Cys Cys
385                 390                 395                 400

Asn Gly Phe Asp Val Leu Tyr Thr Asp Asn Asp Gly Gln Trp Gly Val
                405                 410                 415

Glu Asn Gly Asn Trp Cys Gly Ile Lys Ser Ser Cys Gly Asn Asn Gln
            420                 425                 430

Arg Gln Cys Trp Ser Glu Arg Leu Gly Tyr Pro Cys Cys Gln Tyr Thr
        435                 440                 445

Thr Asn Ala Glu Tyr Thr Asp Asn Asp Gly Arg Trp Gly Val Glu Asn
    450                 455                 460

Gly Asn Trp Cys Gly Ile Tyr
465                 470


<210> SEQ ID NO 56
<211> LENGTH: 399
<212> TYPE: PRT
<213> ORGANISM: Irpex lacteus

<400> SEQUENCE: 56

Met Lys Ser Leu Leu Leu Ser Ala Ala Ala Thr Leu Ala Leu Ser Thr
1               5                   10                  15

Pro Ala Phe Ser Val Ser Val Trp Gly Gln Cys Gly Gly Ile Gly Phe
            20                  25                  30

Thr Gly Ser Thr Thr Cys Asp Ala Gly Thr Ser Cys Val His Leu Asn
        35                  40                  45

Asp Tyr Tyr Phe Gln Cys Gln Pro Gly Ala Ala Thr Ser Thr Val Gln
    50                  55                  60

Pro Thr Thr Thr Ala Ser Ser Thr Ser Ser Ala Ala Ala Pro Ser Ser
65                  70                  75                  80

Ser Gly Asn Ala Val Cys Ser Gly Thr Arg Asn Lys Phe Lys Phe Phe
                85                  90                  95

Gly Val Asn Glu Ser Gly Ala Glu Phe Gly Asn Asn Val Ile Pro Gly
            100                 105                 110

Thr Leu Gly Thr Asp Tyr Thr Trp Pro Ser Pro Ser Ser Ile Asp Phe
        115                 120                 125

Phe Val Gly Lys Gly Phe Asn Thr Phe Arg Val Pro Phe Leu Met Glu
    130                 135                 140

Arg Leu Ser Pro Pro Ala Thr Gly Leu Thr Gly Pro Phe Asp Ser Thr
145                 150                 155                 160

Tyr Leu Gln Gly Leu Lys Thr Ile Val Ser Tyr Ile Thr Gly Lys Gly
                165                 170                 175

Gly Tyr Ala Leu Val Asp Pro His Asn Phe Met Ile Tyr Asn Gly Ala
            180                 185                 190

Thr Ile Ser Asp Thr Asn Ala Phe Gln Thr Trp Trp Gln Asn Leu Ala
        195                 200                 205

Ala Gln Phe Lys Thr Asp Ser His Val Val Phe Asp Val Met Asn Glu
    210                 215                 220
```

```
Pro His Asp Ile Pro Ala Gln Thr Val Phe Asn Leu Asn Gln Ala Ala
225                 230                 235                 240

Ile Asn Arg Ile Arg Ala Ser Gly Ala Thr Ser Gln Ser Ile Leu Val
                245                 250                 255

Glu Gly Thr Ser Tyr Thr Gly Ala Trp Thr Trp Thr Thr Thr Ser Gly
            260                 265                 270

Asn Ser Gln Val Phe Gly Ala Ile His Asp Pro Asn Asn Asn Val Ala
        275                 280                 285

Ile Glu Met His Gln Tyr Leu Asp Ser Asp Gly Ser Gly Thr Ser Pro
    290                 295                 300

Thr Cys Val Ser Pro Thr Ile Gly Ala Glu Arg Leu Gln Ala Ala Thr
305                 310                 315                 320

Gln Trp Leu Gln Gln Asn Asn Leu Lys Gly Phe Leu Gly Glu Ile Gly
                325                 330                 335

Ala Gly Ser Asn Ala Asp Cys Ile Ser Ala Val Gln Gly Ala Leu Cys
            340                 345                 350

Glu Met Gln Gln Ser Asp Val Trp Leu Gly Ala Leu Trp Trp Ala Ala
        355                 360                 365

Gly Pro Trp Trp Gly Asp Tyr Phe Gln Ser Ile Glu Pro Pro Ser Gly
    370                 375                 380

Val Ala Val Ser Ser Ile Leu Pro Gln Ala Leu Glu Pro Phe Leu
385                 390                 395


<210> SEQ ID NO 57
<211> LENGTH: 42
<212> TYPE: PRT
<213> ORGANISM: Artificial Sequence
<220> FEATURE:
<223> OTHER INFORMATION: flexible linker sequence

<400> SEQUENCE: 57

Gly Gly Gly Gly Ser Gly Gly Gly Gly Ser Ala Trp His Pro Gln Phe
1               5                   10                  15

Gly Gly Glu Asn Leu Tyr Phe Gln Gly Asp Tyr Lys Asp Asp Asp Lys
            20                  25                  30

Gly Gly Gly Gly Ser Gly Gly Gly Gly Ser
        35                  40


<210> SEQ ID NO 58
<211> LENGTH: 37
<212> TYPE: PRT
<213> ORGANISM: Artificial Sequence
<220> FEATURE:
<223> OTHER INFORMATION: flexible linker sequence

<400> SEQUENCE: 58

Gly Gly Gly Gly Ser Gly Gly Gly Gly Ser Trp Ser His Pro Gln Phe
1               5                   10                  15

Glu Lys Gly Gly Glu Asn Leu Tyr Phe Gln Gly Gly Gly Gly Gly Ser
            20                  25                  30

Gly Gly Gly Gly Ser
        35


<210> SEQ ID NO 59
<211> LENGTH: 31
<212> TYPE: DNA
<213> ORGANISM: Artificial Sequence
<220> FEATURE:
<223> OTHER INFORMATION: sCBH1/2-L
```

<400> SEQUENCE: 59
gactgaattc ataatggtct ccttcacctc c 31

<210> SEQ ID NO 60
<211> LENGTH: 34
<212> TYPE: DNA
<213> ORGANISM: Artificial Sequence
<220> FEATURE:
<223> OTHER INFORMATION: sCBH1-R

<400> SEQUENCE: 60
gactctcgag ttacaaacat tgagagtagt atgg 34

<210> SEQ ID NO 61
<211> LENGTH: 31
<212> TYPE: DNA
<213> ORGANISM: Artificial Sequence
<220> FEATURE:
<223> OTHER INFORMATION: sCBH2 R

<400> SEQUENCE: 61
cagtctcgag ttacaagaaa gatgggttag c 31

<210> SEQ ID NO 62
<211> LENGTH: 63
<212> TYPE: DNA
<213> ORGANISM: Artificial Sequence
<220> FEATURE:
<223> OTHER INFORMATION: 395 Te cbh1 Synt1 PacI-ATG

<400> SEQUENCE: 62
gcgttggtac cgtttaaacg gggcccttaa ttaaacaatg ctaagaagag ctttactatt 60
gag 63

<210> SEQ ID NO 63
<211> LENGTH: 40
<212> TYPE: DNA
<213> ORGANISM: Artificial Sequence
<220> FEATURE:
<223> OTHER INFORMATION: 398 Te cbh1 synt core SmaI

<400> SEQUENCE: 63
cctcccccgg gttagaagca gtgaaagtgg agttgattgg 40

<210> SEQ ID NO 64
<211> LENGTH: 42
<212> TYPE: DNA
<213> ORGANISM: Artificial Sequence
<220> FEATURE:
<223> OTHER INFORMATION: 399Trcbh1 synt CBM5 MlyIHincII

<400> SEQUENCE: 64
gcgacgagtc aaccctccag gtggtaacag aggtactacc ac 42

<210> SEQ ID NO 65
<211> LENGTH: 46
<212> TYPE: DNA
<213> ORGANISM: Artificial Sequence
<220> FEATURE:
<223> OTHER INFORMATION: 400 Trcbh1 synt CBM AscIXhoI

<400> SEQUENCE: 65
gcgactcgag ggcgcgccta caaacattga gagtagtatg ggttta 46

<210> SEQ ID NO 66
<211> LENGTH: 47
<212> TYPE: DNA
<213> ORGANISM: Artificial Sequence
<220> FEATURE:
<223> OTHER INFORMATION: 379 ScPGK1prom -786 SacI ApaI

<400> SEQUENCE: 66
gcgttgagct cgggccctaa tttttatttt agattcctga cttcaac 47

<210> SEQ ID NO 67
<211> LENGTH: 45
<212> TYPE: DNA
<213> ORGANISM: Artificial Sequence
<220> FEATURE:
<223> OTHER INFORMATION: 380 ScPGK1prom EcoRI-PacI

<400> SEQUENCE: 67
gcgttgaatt cttaattaag taaaaagtag ataattactt ccttg 45

<210> SEQ ID NO 68
<211> LENGTH: 47
<212> TYPE: DNA
<213> ORGANISM: Artificial Sequence
<220> FEATURE:
<223> OTHER INFORMATION: 381 CBH2 WT EcoRI-PacI-ATG

<400> SEQUENCE: 68
gcgttgaatt cttaattaaa caatgattgt cggcattctc accacgc 47

<210> SEQ ID NO 69
<211> LENGTH: 45
<212> TYPE: DNA
<213> ORGANISM: Artificial Sequence
<220> FEATURE:
<223> OTHER INFORMATION: 386 CBH2 WT TAA-AscI-EcoRI

<400> SEQUENCE: 69
gcgatgaatt cggcgcgcct tacaggaacg atgggtttgc gtttg 45

<210> SEQ ID NO 70
<211> LENGTH: 31
<212> TYPE: DNA
<213> ORGANISM: Artificial Sequence
<220> FEATURE:
<223> OTHER INFORMATION: ENOBB-left

<400> SEQUENCE: 70
gatcggatcc caattaatgt gagttacctc a 31

<210> SEQ ID NO 71
<211> LENGTH: 34
<212> TYPE: DNA
<213> ORGANISM: Artificial Sequence
<220> FEATURE:
<223> OTHER INFORMATION: ENOBB-right

<400> SEQUENCE: 71
gtacaagctt agatctccta tgcggtgtga aata 34

<210> SEQ ID NO 72
<211> LENGTH: 31
<212> TYPE: DNA
<213> ORGANISM: Artificial Sequence
<220> FEATURE:
<223> OTHER INFORMATION: sCBH2 R -continued

```
<400> SEQUENCE: 72

cagtctcgag ttacaagaaa gatgggttag c                                    31


<210> SEQ ID NO 73
<211> LENGTH: 21
<212> TYPE: DNA
<213> ORGANISM: Artificial sequence
<220> FEATURE:
<223> OTHER INFORMATION: Primer FUR1-left

<400> SEQUENCE: 73

atttcttctt gaaccatgaa c                                               21


<210> SEQ ID NO 74
<211> LENGTH: 22
<212> TYPE: DNA
<213> ORGANISM: Artificial sequence
<220> FEATURE:
<223> OTHER INFORMATION: Primer FUR1-right

<400> SEQUENCE: 74

cttaatcaag acttctgtag cc                                              22
```

YEAST EXPRESSING CELLULASES FOR SIMULTANEOUS SACCHARIFICATION AND FERMENTATION USING CELLULOSE

This is a U.S. National Phase of International Appl. No. PCT/US2009/065571, filed Nov. 23, 2009, which claims the benefit of U.S. Provisional Appl. No. 61/116,981, filed Nov. 21, 2008, each of which is hereby incorporated by reference in its entirety.

REFERENCE TO A SEQUENCE LISTING SUBMITTED ELECTRONICALLY VIA EFS-WEB

The content of the electronically submitted substitute sequence listing (Name: 2608.0250001 sequencelisting.ascii.txt, Size: 169,791 bytes; and Date of Creation: Aug. 7, 2013) is herein incorporated by reference in its entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer, and engineering non-cellulolytic organisms that exhibit high product yields and titers to express a heterologous cellulase and hemicellulase system enabling cellulose and hemicellulose utilization.

Three major types of enzymatic activities are required for native cellulose degradation: The first type are endoglucanases (1,4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

Bakers' yeast (*Saccharomyces cerevisiae*) remains the preferred micro-organism for the production of ethanol (Hahn-Hägerdal, B., et al., *Adv. Biochem. Eng. Biotechnol.* 73, 53-84 (2001)). Favorable attributes of this microbe include (i) high productivity at close to theoretical yields (0.51 g ethanol produced/g glucose used), (ii) high osmo- and ethanol tolerance, (iii) natural robustness in industrial processes, and (iv) being generally regarded as safe (GRAS) due to its long association with wine and bread making, and beer brewing. Furthermore, *S. cerevisiae* exhibits tolerance to inhibitors commonly found in hydrolyzates resulting from biomass pretreatment.

One major shortcoming of *S. cerevisiae* is its inability to utilize complex polysaccharides such as cellulose, or its break-down products, such as cellobiose and cellodextrins. In attempt to address this problem, several heterologous cellulases from bacterial and fungal sources have been transferred to *S. cerevisiae*, enabling the degradation of cellulosic derivatives (Van Rensburg, P., et al., *Yeast* 14, 67-76 (1998)), or growth on cellobiose (Van Rooyen, R., et al., *J. Biotech.* 120, 284-295 (2005)); McBride, J. E., et al., *Enzyme Microb. Techol.* 37, 93-101 (2005)). However. current levels of expression and specific activity of cellulases heterologously expressed in yeast are still not sufficient to enable efficient growth and ethanol production by yeast on cellulosic substrates without externally added enzymes. There remains a significant need for improvement in the amount of cellulase activity in order to attain the goal of achieving a consolidated bioprocessing (CBP) system capable of efficiently and cost-effectively converting cellulosic substrates to ethanol.

Another major shortcoming of the use of *S. cerevisiae* is that externally produced cellulases function optimally at a higher temperature than the temperature at which *S. cerevisiae* function optimally. Thus, either the processing must be carried out in a two step process at two different temperatures or one temperature can be selected where both processes function to some extent, but at least one of the processes does not occur at optimal efficiency.

In order to address these limitations, the present invention provides for heterologous expression of wild-type and codon-optimized combinations of heterologous cellulases in yeast that allows efficient production of ethanol from cellulose sources. The invention also provides for expression of such heterologous cellulases in theromtolerant yeast and methods of using such transformed yeast for ethanol production.

BRIEF DESCRIPTION OF THE INVENTION

The present invention is directed to cellulytic host cells. The host cells of the invention expressing heterologous cellulases and are able to produce ethanol from cellulose.

In particular, in some embodiments, the invention provides a transformed thermotolerant yeast host cell comprising at least one heterologous polynucleotide comprising a nucleic acid encoding a cellulase, wherein the yeast host cell is capable of producing ethanol when grown using cellulose as a carbon source.

In another embodiment, the invention provides a transformed thermotolerant yeast host cell comprising: (a) at least one heterologous polynucleotide comprising a nucleic acid which encodes an endoglucanase; (b) at least one heterologous polynucleotide comprising a nucleic acid which encodes a β-glucosidase; (c) at least one heterologous polynucleotide comprising a nucleic acid which encodes a first cellobiohydrolase; and (d) at least one heterologous polynucleotide comprising a nucleic acid which encodes a second cellobiohydrolase.

In another embodiment, the invention provides a transformed yeast host cell comprising: (a) at least one heterologous polynucleotide comprising a nucleic acid which encodes a cellulase which is an endoglucanase; (b) at least one heterologous polynucleotide comprising a nucleic acid which encodes a cellulase which is a β-glucosidase; (c) at least one heterologous polynucleotide comprising a nucleic acid which encodes a cellulase which is a first cellobiohydrolase; and (d) at least one heterologous polynucleotide comprising a nucleic acid which encodes a cellulase which is a second cellobiohydrolase, wherein at least two of the cellulases are secreted by the cell.

In yet another embodiment, the invention provides a transformed yeast host cell comprising at least six heterologous polynucleotides, wherein each heterologous polynucleotide comprises a nucleic acid which encodes a cellulase.

In yet another embodiment, the invention provides a transformed yeast host cell comprising at least four heterologous polynucloeotides, wherein each heterologous polynucleotide comprises a nucleic acid which encodes an endogluconase.

In still another embodiment, the invention provides a co-culture comprising at least two yeast host cells wherein (a) at least one of the host cells comprises a first heterologous polynucleotide comprising a nucleic acid which encodes a cellulase which is an endoglucanase; (b) at least one of the host cells comprises a second heterologous polynucleotide comprising a nucleic acid which encodes a cellulase which is a β-glucosidase; (c) at least one of the host cells comprises a third heterologous polynucleotide comprising a nucleic acid which encodes a cellulase which is a first cellobiohydrolase; (d) at least one of the host cells comprises a fourth heterologous polynucleotide comprising a nucleic acid which encodes a cellulase which is a second cellobiohydrolase; wherein the first polynucleotide, the second polynucleotide, the third polynucleotide and the fourth polynucleotide are not in the same host cell; and wherein the co-culture is capable of producing ethanol from cellulose.

In some particular embodiments of the invention, the cellulose carbon source is insoluble cellulose, crystalline cellulose, cellulose derived from lignocellulose, hardwood, phosphoric acid swollen cellulose or microcrystalline cellulose.

In some embodiments, the host cells of the invention comprise a heterologous polynucleotide comprising a nucleic acid encoding a first cellobiohydrolase, a polynucleotide comprising a nucleic acid encoding an endoglucanase, a polynucleotide comprising a nucleic acid encoding a β-glucosidase and/or a polynucleotide comprising a nucleic acid encoding a second cellobiohydrolase.

In some embodiments, the cellulase, endoglucanase, β-glucosidase or cellobiohydrolase is a *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa*, or *Arabidopsis thaliana* cellulase, endoglucanase, β-glucosidase or cellobiohydrolase.

In some particular embodiments, the cellobiohydrolase is an *H. grisea* CBH1, a *T. aurantiacus* CBH1, a *T. emersonii* CBH1, a *T. reesei* CBH1, a *T. emersonii* CBH2, a *C. lucknowense* CBH2 or a *T. reesei* CBH2. In some embodiments, the heterologous polynucleotide comprising a nucleic acid which encodes a cellobiohydrolase, encodes a fusion protein comprising a cellobiohydrolase and a cellulose binding module (CBM). In some particular embodiments, the CBM is the CBM of *T. reesei* CBH2, the CBM of *T. reesei* CBH1 or the CBM of *C. lucknowense* CBH2b. In some particular embodiments, the CBM is fused to the cellobiohydrolase via a linker sequence. In some particular embodiments, the host cell expresses a first and a second cellobiohydrolase, wherein the first cellobiohydrolase is a *T. emersonii* CBH1 and CBD fusion, and the second cellobiohydrolase is a *C. lucknowense* CBH2b.

In other particular embodiments, the β-glucosidase is a *S. fibuligera* β-glucosidase. In another particular embodiment, the endoglucanase is a *C. formosanus* endoglucanase. In another particular embodiment, the endoglucanse is a *T. reesei* endoglucanase, e.g. *T. reesei* EG2.

In some embodiments of the invention, at least one or at least two of the cellulases is tethered. In other embodiments of the invention, at least one of the cellulases is secreted. In another embodiment, at least one of the cellulases is tethered and at least one of the cellulases is secreted. In another embodiment, all of the cellulases are secreted.

In some embodiments of the invention, the nucleic acid encoding a cellulase is codon optimized.

In some embodiments, the host cell can be a thermotolerant host cell. In some embodiments, the host cell is a *Issatchenkia orientalis, Pichia mississippiensis, Pichia mexicana, Pichia farinosa, Clavispora opuntiae, Clavispora lusitaniae, Candida mexicana, Hansenula polymorpha* or *Kluveryomyces* host cell. For example, in some embodiments, the host cell is a *K. lactis* or *K. marxianus* host cell. In some embodiments, the thermotolerant host cell is an *S. cerevisiae* host cell, wherein the *S. cerevisiae* is selected to be thermotolerant.

In some embodiments, the host cell can be an oleaginous yeast cell. In some particular embodiments, the oleaginous yeast cell is a *Blakeslea, Candida, Cryptococcus, Cunninghamella, Lipomyces, Mortierella, Mucor, Phycomces, Pythium, Rhodosporidium, Rhodotorula, Trichosporon* or *Yarrowia* cell.

In some embodiments, the host cell is a *Saccharomyces cerevisiae* cell.

In some particular embodiments, the host cell can produce ethanol from cellulose at temperatures above about 30° C., 35° C., 37° C., 42° C., 45° C. or 50° C.

In another particular embodiment, the host cell can produce ethanol at a rate of at least about 10 mg per hour per liter, at least about 30 mg per hour per liter, at least about 40 mg per hour per liter, at least about 50 mg per hour per liter, at least about 60 mg per hour per liter, at least about 70 mg per hour per liter, at least about 80 mg per hour per liter, at least about 90 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, or at least about 1 g per hour per liter.

The present invention also provides methods of using the host cells and co-cultures of the invention. For example, the present invention is also directed to a method for hydrolyzing a cellulosic substrate, comprising contacting said cellulosic substrate with a host cell or co-culture of the invention. The invention is also directed to a method of fermenting cellulose comprising culturing a host cell or co-culture of the invention in medium that contains insoluble cellulose under suitable conditions for a period sufficient to allow saccharification and fermentation of the cellulose. In some particular embodiments, the methods further comprise contacting the cellulosic substrate with externally produced cellulase enzymes.

In some particular methods of the invention, the cellulosic substrate is a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, Agave, and combinations thereof.

In some particular methods of the invention, the host cell or co-culture produces ethanol. The ethanol can be produced at a rate of at least about 10 mg per hour per liter, at least about 30 mg per hour per liter, at least about 40 mg per hour per liter, at least about 50 mg per hour per liter, at least about 60 mg per hour per liter, at least about 70 mg per hour per liter, at least about 80 mg per hour per liter, at least about 90 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, or at least about 1 g per hour per liter.

In other particular methods of the invention, the host cell or co-cultures contact a cellulosic substance at a temperature of at least about 37° C., least about 42° C., from about 42° C. to about 45° C., or from about 42° C. to about 50° C.

BRIEF DESCRIPTION OF THE DRAWINGS

FIG. 39 shows the genes modified in yeast strain M0509.

FIG. 40 shows the yeast strains used to contract M0509 and the relevant genetic modifications.

FIG. 41 shows the genealogy of yeast strain M1105.

FIG. 42 shows the genealogy of yeast strain M1254.

DETAILED DESCRIPTION OF THE INVENTION

Figure 1:
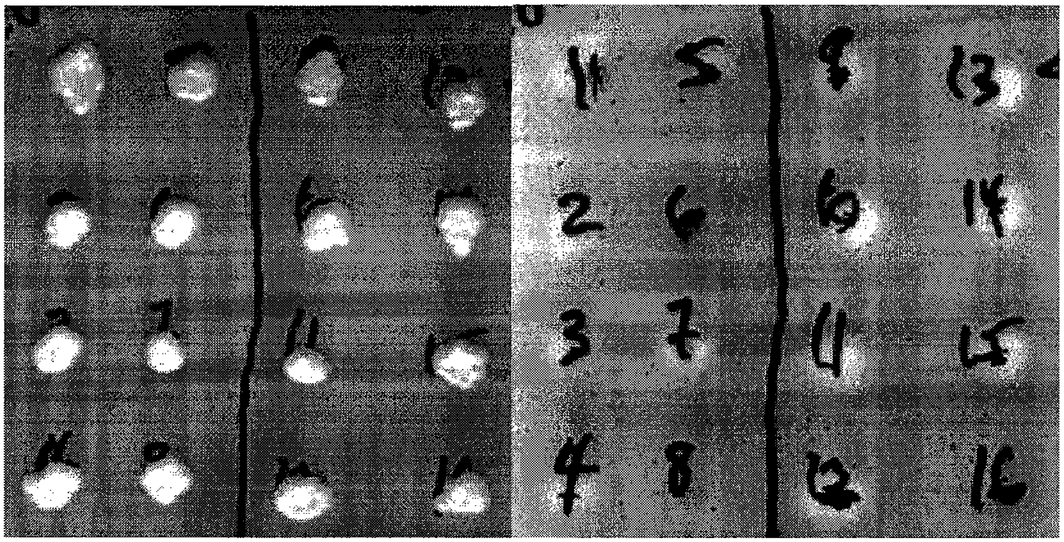
FIG. 1 shows an image of a CMC plate assay to detect endoglucanase I activity in *K. lactis* (colonies numbered 1-8) and *K. marxianus* strains (colonies numbered 9-16) transformed with heterologous cellulases. Strains 8 and 16 are untransformed negative controls. The plate on the left shows colony growth, and the plate on the right shows CMCase activity, indicated by the presence of a clearance zone. Clearance zones appear as white spots in the image.

The disclosed methods and materials are useful generally in the field of engineered yeast.

DEFINITIONS

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY-10). Default parameters for pairwise alignments using the Clustal method were KTUPLE 1, GAP PENALTY=3, WINDOW=5 and DIAGONALS SAVED-5.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and may have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease Si), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

Host Cells Expressing Heterologous Cellulases

In order to address the limitations of the previous systems, the present invention provides host cells expressing heterologous cellulases that can be effectively and efficiently utilized to produce ethanol from cellulose. In some embodiments, the host cells can be a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments of the present invention, the host cell is an oleaginous cell. According to the present invention, the oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantegeous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments of the present invention, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells of the invention can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments of the present invention, the host cell is a *Kluyveromyces* host cell. For example, the *Kluyveromyces* host cell can be a *K. lactis, K. marxianus, K. blattae, K. phaffii, K. yarrowii, K. aestuarii, K. dobzhanskii, K. wickerhamii K. thermotolerans*, or *K. waltii* host cell. In one embodiment, the host cell is a *K. lactis*, or *K. marxianus* host cell. In another embodiment, the host cell is a *K. marxianus* host cell.

In some embodiments of the present invention the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some methods described herein, the host cell has the ability to metabolize xylose. Detailed information regarding the development of the xylose-utilizing technology can be found in the following publications: Kuyper M et al. *FEMS Yeast Res.* 4: 655-64 (2004), Kuyper M et al. *FEMS Yeast Res.* 5:399-409 (2005), and Kuyper M et al. *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g. from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimise xylitol production.

According to the methods described herein, the host cells can contain antibiotic markers or can contain no antibiotic markers.

Host cells are genetically engineered (transduced or transformed or transfected) with the polynucleotides encoding cellulases of this invention which are described in more detail below. The polynucleotides encoding cellulases can be introduced to the host cell on a vector of the invention, which may be, for example, a cloning vector or an expression vector comprising a sequence encoding a heterologous cellulase. The host cells can comprise polynucleotides of the invention as integrated copies or plasmid copies.

In certain aspects, the present invention relates to host cells containing the polynucleotide constructs described below. The host cells of the present invention can express one or more heterologous cellulase polypeptides. In some embodiments, the host cell comprises a combination of polynucleotides that encode heterologous cellulases or fragments, variants or derivatives thereof. The host cell can, for example, comprise multiple copies of the same nucleic acid sequence, for example, to increase expression levels, or the host cell can comprise a combination of unique polynucleotides. In other embodiments, the host cell comprises a single polynucleotide that encodes a heterologous cellulase or a fragment, variant or derivative thereof. In particular, such host cells expressing a single heterologous cellulase can be used in co-culture with other host cells of the invention comprising a polynucleotide that encodes at least one other heterologous cellulase or fragment, variant or derivative thereof.

Introduction of a polynucleotide encoding a heterologous cellulase into a host cell can be done by methods known in the art. Introduction of polynucleotides encoding heterologous cellulases into, for example yeast host cells, can be effected by lithium acetate transformation, spheroplast transformation, or transformation by electroporation, as described in Current Protocols in Molecular Biology, 13.7.1-13.7.10.

Introduction of the construct in other host cells can be effected by calcium phosphate transfection, DEAE-Dextran mediated transfection, or electroporation. (Davis, L., et al., Basic Methods in Molecular Biology, (1986)).

The transformed host cells or cell cultures, as described above, can be examined for endoglucanase, cellobiohydrolase and/or βglucosidase protein content. For the use of secreted heterologous cellulases, protein content can be determined by analyzing the host (e.g., yeast) cell supernatants. In certain embodiments, high molecular weight material can be recovered from the yeast cell supernatant either by acetone precipitation or by buffering the samples with disposable de-salting cartridges. Proteins, including tethered heterologous cellulases, can also be recovered and purified from recombinant yeast cell cultures by methods including spheroplast preparation and lysis, cell disruption using glass beads, and cell disruption using liquid nitrogen for example. Additional protein purification methods include ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method or the protein assay method according to BioRad's manufacturer's protocol. Using such methods, the protein content of saccharolytic enzymes can be estimated. Additionally, to accurately measure protein concentration a heterologous cellulase can be expressed with a tag, for example a His-tag or HA-tag and purified by standard methods using, for example, antibodies against the tag, a standard nickel resin purification technique or similar approach.

The transformed host cells or cell cultures, as described above, can be further analyzed for hydrolysis of cellulose (e.g., by a sugar detection assay), for a particular type of cellulase activity (e.g., by measuring the individual endoglucanase, cellobiohydrolase or βglucosidase activity) or for total cellulase activity. Endoglucanase activity can be determined, for example, by measuring an increase of reducing ends in an endoglucanase specific CMC substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase and β-glucosidase, can hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose. Specific activity of cellulases can also be detected by methods known to one of ordinary skill in the art, such as by the Avicel assay (described supra) that would be normalized by protein (cellulase) concentration measured for the sample.

One aspect of the invention is thus related to the efficient production of cellulases to aid in the digestion of cellulose and generation of ethanol. A cellulase can be any enzyme involved in cellulase digestion, metabolism and/or hydrolysis, including an endoglucanase, exogluconase, or β-glucosidase.

In additional embodiments, the transformed host cells or cell cultures are assayed for ethanol production. Ethanol production can be measured by techniques known to one or ordinary skill in the art e.g. by a standard HPLC refractive index method.

Heterologous Cellulases

According to the present invention the expression of heterologous cellulases in a host cell can be used advantageously to produce ethanol from cellulosic sources. Cellulases from a variety of sources can be heterologously expressed to successfully increase efficiency of ethanol production. For example, the cellulases can be from fungi, bacteria, plant, protozoan or termite sources. In some embodiments, the cellulase is a *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa*, or *Arabidopsis thaliana* cellulase.

In some embodiments of the invention, multiple cellulases from a single organism are co-expressed in the same host cell. In some embodiments of the invention, multiple cellulases from different organisms are co-expressed in the same host cell. In particular, cellulases from two, three, four, five, six, seven, eight, nine or more organisms can be co-expressed in the same host cell. Similarly, the invention can encompass co-cultures of yeast strains, wherein the yeast strains express different cellulases. Co-cultures can include yeast strains expressing heterologous cellulases from the same organisms or from different organisms. Co-cultures can include yeast strains expressing cellulases from two, three, four, five, six, seven, eight, nine or more organisms.

Cellulases of the present invention include both endoglucanases or exoglucanases. The cellulases can be, for example, endoglucanases, β-glucosidases or cellobiohydrolases.

In certain embodiments of the invention, the endoglucanase(s) can be an endoglucanase I or an endoglucanase II isoform, paralogue or orthologue. In some embodiments, the endoglucanase expressed by the host cells of the present invention can be recombinant endo-1,4-β-glucanase. In particular embodiments, the endoglucanase is a *T. reesei, C. lacteus, C. formosanus, N. takasagoensis, C. acinaciformis, M. darwinensis, N. walkeri, R. speratus Aspergillus kawachii, Heterodera schachtii, H. jecorina, Orpinomycess, Irpex lacteus, C. lucknowense, C. globosum, Aspergillus terreus, Aspergillus fumigatus, Neurospora crassa* or *Acremonium thermophilum* endoglucanase. In one particular embodiment, the endoglucanase comprises an amino acid sequence selected from SEQ ID NOs: 30-39 or 52-56, as shown in Table 1 below. In certain other embodiments, the endoglucanase comprises an amino acid sequence that is at least about 70, about 80, about 90, about 95, about 96, about 97, about 98, about 99, or 100% identical to an amino acid sequence selected from SEQ ID NOs: 30-39 or 52-56.

As a practical matter, whether any polypeptide is at least 70%, 80%, 85%, 90%, 95%, 96%, 97%, 98%, 99% or 100% identical to a polypeptide of the present invention can be determined conventionally using known computer programs.

Methods for determining percent identity, as discussed in more detail below in relation to polynucleotide identity, are also relevant for evaluating polypeptide sequence identity.

In one particular embodiment, the endoglucanase is an endoglucanase I ("eg1") from *Trichoderma reesei*. In certain embodiments, the endoglucanase comprises an amino acid sequence at least about 70, about 80, about 90, about 95, about 96, about 97, about 98, about 99, or 100% identical to SEQ ID NO:39.

In another particular embodiment, the endoglucanase is an endoglucanase from *C. formosanus*. In certain embodiments, the endoglucanase comprises an amino acid sequence at least about 70, about 80, about 90, about 95, about 96, about 97, about 98, about 99, or 100% identical to SEQ ID NO:31.

In another particular embodiment, the endoglucanase is an endoglucanase from *H. jecorina*. In certain embodiments, the endoglucanase comprises an amino acid sequence at least about 70, about 80, about 90, about 95, about 96, about 97, about 98, about 99, or 100% identical to SEQ ID NO:54.

In certain embodiments, the β-glucosidase is a β-glucosidase I or a β-glucosidase II isoform, paralogue or orthologue. In certain embodiments of the present invention the β-glucosidase is derived from *Saccharomycopsis fibuligera*. In particular embodiments, the β-glucosidase comprises an amino acid sequence at least about 70, about 80, about 90, about 95, about 96, about 97, about 98, about 99, or 100% identical to SEQ ID NO:40.

In certain embodiments of the invention, the cellobiohydrolase(s) can be a cellobiohydrolase I and/or a cellobiohydrolase II isoform, paralogue or orthologue. In one particular embodiment, the cellobiohydrolase comprises an amino acid sequence selected from SEQ ID NOs: 21-29 or 46, as shown in Table 1 below. In particular embodiments of the present invention the cellobiohydrolase is a cellobiohydrolase I or II from *Trichoderma reesei*. In another embodiment, the cellobiohydrolase comprises a sequence at least about 70, about 80, about 90, about 95, about 96, about 97, about 98, about 99, or 100% identical to SEQ ID NO:27 or SEQ ID NO:28.

In other particular embodiments of the present invention the cellobiohydrolase is a cellobiohydrolase I or II from *T. emersonii*. In another embodiment, the cellobiohydrolase comprises a sequence at least about 70, about 80, about 90, about 95, about 96, about 97, about 98, about 99, or 100% identical to SEQ ID NO:23 or SEQ ID NO:24.

In another embodiment, the cellobiohydrolase of the invention is a *C. lucknowense* cellobiohydrolase. In a particular embodiment, the cellobiohydrolase is *C. lucknowense* cellobiohydrolase Cbh2b. In one embodiment, the cellobiohydrolase comprises a sequence at least about 70, about 80, about 90, about 95, about 96, about 97, about 98, about 99, or 100% identical to SEQ ID NO:25.

In some particular embodiments of the invention, the cellulase comprises a sequence selected from the sequences in Table 1 below. The cellulases of the invention also include cellulases that comprise a sequence at least about 70, about 80, about 90, about 95, about 96, about 97, about 98, about 99 or 100% identical to the sequences of Table 1.

Some embodiments of the invention encompass a polypeptide comprising at least 10, 20, 30, 40, 50, 60, 70, 80, 90, 100, 200, 300, 400, or 500 or more consecutive amino acids of any of SEQ ID NOs:21-40, 46 or 52-56, or domains, fragments, variants, or derivatives thereof.

TABLE 1

Cellulases used in Examples 1-11 as described below.

| Donor organism/ Gene | Codon-Optimized DNA sequence used | Accession number and amino acid sequence |
|---|---|---|
| | Cellobiohydrolases | |
| *Humicola grisea* cbh1 | GAATTCATGAGAACCGCTAAGTTCGCTACCTTGGCTGCCTTGGTTGCCTCT GCTGCTGCTCAACAAGCCTGTTCCTTGACTACTGAACGTCACCCATCTTTG TCTTGGAACAAGTGTACTGCTGGTGGTCAATGTCAAACTGTCCAAGCCTCC ATCACTTTGGACTCTAATTGGAGATGGACCCACCAAGTCTCTGGTAGTACT AACTGTTACACCGGTAATAAGTGGGACACTTCTATTTGTACTGACGCTAA GTCTTGTGCTCAAAATTGTTGTGTTGATGGTGCTGATTACACCTCCACTTA TGGTATTACCACCAACGGTGACTCTTTGTCCTTGAAGTTCGTTACTAAAGG TCAACATTCCACCAACGTCGGTTCTAGAACCTACTTAATGGACGGTGAAG ACAAGTACCAAACCTTCGAATTGTTGGGTAATGAATTTACCTTCGATGTCG ATGTGTCTAACATCGGTTGTGGTTTGAACGGTGCTTTATACTTCGTTTCTAT GGACGCCGACGGTGGTTTGTCTCGTTACCCAGGTAATAAGGCTGGTGCCA AGTATGGTACCGGTTACTGTGATGCTCAATGCCCAAGAGACATTAAGTTC ATCAACGGTGAAGCTAACATTGAAGGTTGGACTGGTTCTACCAACGACCC AAACGCTGGCGCCGGTAGATACGGTACCTGTTGTTCCGAAATGGACATTT GGGAAGCCAACAACATGGCTACTGCTTTTACTCCACACCCATGTACCATC ATTGGTCAATCCAGATGTGAAGGTGACTCCTGTGGCGGTACCTACTCCAA CGAAAGATACGCTGGTGTTTGTGATCCAGACGGTTGTGACTTCAACTCCTA CAGACAAGGTAACAAGACTTTCTATGGTAAGGGTATGACTGTCGATACCA CCAAGAAGATCACCGTCGTCACCCAATTCTTGAAGGACGCTAACGGTGAT TTAGGTGAAATTAAAAGATTCTACGTCCAAGATGGTAAGATCATCCCAAA CTCTGAATCTACCATTCCAGGTGTTGAAGGTAATTCCATCACTCAAGACTG GTGTGACAGACAAAAGGTTGCCTTCGGTGATATTGACGACTTCAACAGAA AGGGTGGTATGAAGCAAATGGGTAAGGCTTTGGCCGGTCCAATGGTCTTG GTTATGTCTATTTGGGACGATCACGCTTCCAACATGTTGTGGTTGGACTCC ACCTTCCCAGTTGATGCTGCTGGTAAGCCAGGTGCCGAAAGAGGTGCTTG TCCAACTACTTCCGGTGTCCCAGCTGAAGTTGAAGCCGAAGCTCCAAATT CTAACGTTGTCTTCTCTAACATCAGATTCGGTCCAATCGGTTCCACAGTCG CTGGTTTGCCAGGTGCTGGTAATGGTGGTAATAACGGTGGTAACCCACCA CCACCAACCACTACCACTTCTTCTGCCCCAGCTACTACCACCACCGCTTCT GCTGGTCCAAAGGCTGGTAGATGGCAACAATGTGGTGGTATTGGTTTCAC CGGTCCAACCCAATGTGAAGAACCATACATCTGTACCAAGTTGAACGACT GGTACTCTCAATGTTTATAACTCGAG (SEQ ID NO: 1) | CAA35159 MRTAKFATLAALVASAAAQQA CSLTTERHPSLSWNKCTAGGQC QTVQASITLDSNWRWTHQVSGS TNCYTGNKWDTSICTDAKSCAQ NCCVDGADYTSTYGITTNGDSLS LKFVTKGQHSTNVGSRTYLMDG EDKYQTFELLGNEFTFDVDVSNI GCGLNGALYFVSMDADGGLSR YPGNKAGAKYGTGYCDAQCPR DIKFINGEANIEGWTGSTNDPNA GAGRYGTCCSEMDIWEANNMA TAFTPHPCTIIGQSRCEGDSCGGT YSNERYAGVCDPDGCDFNSYRQ GNKTFYGKGMTVDTTKKITVVT QFLKDANGDLGEIKRFYVQDGK IIPNSESTIPGVEGNSITQDWCDR QKVAFGDIDDFNRKGGMKQMG KALAGPMVLVMSIWDDHASNM LWLDSTFPVDAAGKPGAERGAC PTTSGVPAEVEAEAPNSNVVFSN IRFGPIGSTVAGLPGAGNGGNNG GNPPPPTTTTSSAPATTTTASAGP KAGRWQQCGGIGFTGPTQCEEP YICTKLNDWYSQCL (SEQ ID NO: 21) |

TABLE 1-continued

Cellulases used in Examples 1-11 as described below.

| Donor organism/ Gene | Codon-Optimized DNA sequence used | Accession number and amino acid sequence |
|---|---|---|
| *Thermoascus aurantiacus* cbh1 | GAATTCATGTACCAAAGAGCTCTATTGTTCTCCTTCTTCTTGGCCGCCGCT<br>AGAGCTCATGAAGCCGGTACTGTCACCGCCGAAAACCACCCATCCTTGAC<br>TTGGCAACAATGTTCCTCTGGTGGTTCTTGTACTACTCAAAACGGGAAGGT<br>TGTTATTGACGCTAACTGGAGATGGGTTCACACTACCTCCGGTTACACCAA<br>CTGTTACACTGGTAACACTTGGGATACTTCCATCTGTCCAGACGACGTTAC<br>CTGTGCTCAAAACTGTGCTTTGGACGGTGCTGACTACTCCGGTACTTACGG<br>TGTCACTACCTCTGGCAACGCGTTGAGATTGAACTTCGTCACCCAATCTTC<br>TGGTAAGAACATCGGTTCTAGATTGTACTTGTTGCAAGACGATACTACTTA<br>CCAAATCTTCAAGTTGTTGGGTCAAGAGTTCACTTTCGACGTTGATGTTTC<br>CAACTTGCCTTGTGGTTTGAACGGTGCTTTGTACTTCGTTGCTATGGACGC<br>CGACGGTAACTTATCCAAGTACCCAGGTAACAAGGCCGGTGCCAAGTACG<br>GTACCGGTTACTGTGATTCTCAATGTCCAAGAGACCTAAAATTCATTAACG<br>GTCAAGCTAACGTCGAAGGTTGGCAACCATCTGCTAACGATCCAAACGCC<br>GGTGTCGGTAATCACGGTTCCTCCTGTGCTGAAATGGACGTTTGGGAAGC<br>TAACTCTATCTCCACCGCCGTCACTCCACATCCATGTGATACCCCAGGTCA<br>AACCATGTGTCAAGGTGATGATTGTGGTGGTACCTACTCTTCCACTAGATA<br>CGCTGGTACCTGTGACACCGACGGTTGTGATTTCAACCCATACCAACCAG<br>GTAACCACTCTTTCTACGGTCCAGGTAAGATTGTCGATACTTCTTCTAAGT<br>TCACTGTTGTCACTCAATTCATTACCGACGATGGTACCCCATCTGGTACCC<br>TAACTGAAATTAAGAGATTCTACGTCCAAAACGGTAAAGTCATTCCACAA<br>TCCGAAAGCACCATTTCCGGTGTTACCGGTAACTCCATCACCACTGAATAC<br>TGTACCGCTCAAAAGGCCGCCTTTGACAACACCGGTTTCTTCACCCATGGT<br>GGTTTGCAAAAGATTTCTCAAGCCTTGGCTCAAGGTATGGTTTTGGTCATG<br>TCCTTGTGGGATGACCACGCTGCTAACATGTTGTGGTTGGATTCTACTTAC<br>CCAACTGACGCTGATCCAGACACCCCAGGTGTTGCTAGAGGTACTTGTCC<br>AACCACTTCTGGTGTTCCAGCTGACGTCGAATCTCAAAACCCTAACTCTTA<br>CGTTATCTACTCTAACATCAAGGTGGGTCCAATTAACTCCACCTTCACTGC<br>TAACTAACTCGAG (SEQ ID NO: 2) | AAL83303<br>MYQRALLFSFFLAAARAHEAGT<br>VTAENHPSLTWQQCSSGGSCTT<br>QNGKVVIDANWRWVHTTSGYT<br>NCYTGNTWDTSICPDDVTCAQN<br>CALDGADYSGTYGVTTSGNALR<br>LNFVTQSSGKNIGSRLYLLQDDT<br>TYQIFKLLGQEFTFDVDVSNLPC<br>GLNGALYFVAMDADGNLSKYP<br>GNKAGAKYGTGYCDSQCPRDL<br>KFINGQANVEGWQPSANDPNAG<br>VGNHGSSCAEMDVWEANSISTA<br>VTPHPCDTPGQTMCQGDDCGGT<br>YSSTRYAGTCDTDGCDFNPYQP<br>GNHSFYGPGKIVDTSSKFTVVTQ<br>FITDDGTPSGTLTEIKRFYVQNG<br>KVIPQSESTISGVTGNSITTEYCT<br>AQKAAFDNTGFFTHGGLQKISQ<br>ALAQGMVLVMSLWDDHAANM<br>LWLDSTYPTDADPDTPGVARGT<br>CPTTSGVPADVESQNPNSYVIYS<br>NIKVGPINSTFTAN (SEQ ID<br>NO: 22) |
| *Talaromyces emersonii* cbh1 | GAATTCATGCTAAGAAGAGCTTTACTATTGAGCTCTTCTGCTATCTTGGCC<br>GTTAAGGCTCAACAAGCCGGTACCGCTACTGCTGAAAACCACCCTCCATT<br>GACCTGGCAAGAATGTACCGCTCCAGGTTCTTGTACCACCCAAAACGGTG<br>CTGTCGTCTTGGACGCTAACTGGAGATGGGTCCACGACGTCAACGGTTAC<br>ACTAACTGTTACACCGGTAACACCTGGGACCCAACTTACTGTCCAGACGA<br>CGAAACTTGCGCTCAAAACTGTGCCTTGGACGGTGCTGACTACGAAGGTA<br>CTTACGGTGTTACCTCCTCTGGTTCTTCCTTGAAGTTGAACTTCGTCACTGG<br>TTCTAACGTCGGTTCCAGATTGTATTTGTTGCAAGATGACTCCACTTACCA<br>AATCTTCAAGTTGTTGAACAGAGAATTTTCTTTCGACGTCGATGTGTCCAA<br>CTTGCCTTGTGGTTTGAACGGTGCTCTATACTTCGTTGCTATGGACGCTGA<br>TGGTGGTGTTTCCAAGTACCCAAACAACAAGGCTGGTGCCAAATACGGTA<br>CTGGTTACTGTGACTCTCAATGTCCACGTGACTTGAAGTTTATTGATGGTG<br>AAGCTAATGTCGAAGGTTGGCAACCATCTTCTAACAACGCTAACACTGGC<br>ATCGGTGACCACGGTTCTTGCTGTGCCGAAATGGACGTTTGGGAAGCCAA<br>CTCCATTTCCAACGCCGTCACTCCACACCCATGTGACACTCCAGGTCAAAC<br>TATGTGTTCCGGCGATGACTGTGGTGGTACTTACTCTAACGATAGATACGC<br>TGGTACCTGTGATCCAGACGGTTGCGACTTCAATCCATACAGAATGGGTA<br>ACACTTCCTTTTACGGTCCAGGCAAGATCATCGACACTACTAAGCCATTCA<br>CTGTTGTCACCCAATTCTTGACCGACGATGGTACTGATACCGGTACTTTGT<br>CCGAAATCAAGAGATTCTACATCCAAAACTCTAACGTCATCCCACAACCA<br>AATTCCGACATCTCTGGTGTCACTGGTAACTCCATTACCACCGAATTTTGT<br>ACCGCCCAAAAGCAAGCTTTCGGTGACACCGACGACTTCTCTCAACACGG<br>TGGTTTGGCTAAGATGGGTGCTGCTATGCAACAAGGTATGGTTTTGGTCAT<br>GTCTTTGTGGGACGACTACGCTGCTCAAATGTTGTGGTTGGACTCCGATTA<br>CCCAACCGATGCCGACCCAACCACCCCTGGTATCGCTAGAGGTACCTGTC<br>CAACTGACTCTGGTGTTCCATCTGACGTCGAATCCCAATCTCCAAACTCCT<br>ACGTCACTTACTCCAACATTAAATTCGGTCCAATCAACTCCACTTTCACTG<br>CTTCTTAACTCGAG (SEQ ID NO: 3) | AAL89553<br>MLRRALLLSSSAILAVKAQQAG<br>TATAENHPPLTWQECTAPGSCTT<br>QNGAVVLDANWRWVHDVNGY<br>TNCYTGNTWDPTYCPDDETCAQ<br>NCALDGADYEGTYGVTSSGSSL<br>KLNFVTGSNVGSRLYLLQDDST<br>YQIFKLLNREFSFDVDVSNLPCG<br>LNGALYFVAMDADGGVSKYPN<br>NKAGAKYGTGYCDSQCPRDLKF<br>IDGEANVEGWQPSSNNANTGIG<br>DHGSCCAEMDVWEANSISNAVT<br>PHPCDTPGQTMCSGDDCGGTYS<br>NDRYAGTCDPDGCDFNPYRMG<br>NTSFYGPGKIIDTTKP<br>FTVVTQFLTDDGTDTGTLSEIKR<br>FYIQNSNVIPQPNSDISGVTGNSI<br>TTEFCTAQKQAFGDTDDFSQHG<br>GLAKMGAAMQQGMVLVMSLW<br>DDYAAQMLWLDSDYPTDADPT<br>TPGIARGTCPTDSGVPSDVESQSP<br>NSYVTYSNIKFGPINSTFTAS<br>(SEQ ID NO: 23) |
| *Talaromyces emersonii* cbh2 | GAATTCATGCGTAACTTGTTGGCCTTGGCTCCAGCCGCTTTGTTGGTTGGT<br>GCTGCCGAAGCTCAACAATCCTTGTGGGGTCAATGCGGTGGTTCCTCCTG<br>GACTGGTGCAACTTCCTGTGCCGCTGGTGCCACCTGTTCCACCATTAACCC<br>ATACTACGCTCAATGTGTTCCAGCCACTGCCACTCCAACTACCTTGACTAC<br>CACCACTAAGCCAACCTCCACCGGTGGTGCTGCTCCAACCACTCCACCAC<br>CAACTACTACCGGTACTACCACCTCTCCAGTCGTCACCAGACCTGCCTCCG<br>CCTCCGGTAATCCATTCGAAGGTTATCAATTGTACGCTAACCCTTACTACG<br>CTTCTGAAGTCATTTCCTTGGCTATCCCATCTTTGAGCTCCGAGTTGGTCCC<br>AAAGGCCTCCGAAGTTGCTAAGGTCCCTTCATTTGTCTGGTTAGATCAAGC<br>TGCCAAGGTTCCATCTATGGGTGATTACTTGAAGGATATTCAATCTCAAAA<br>CGCTGCTGGTGCTGATCCACCAATCGCCGGTATTTTCGTTGTTTACGATTT<br>GCCAGATAGAGACTGTGCCGCCGCTGCTTCTAACGGTGAATTTTCTATCGC<br>CAACAACGGTGTCGCTTTATACAAACAATATATCGATTCCATTAGAGAAC<br>AATTAACCACTTACTCCGACGTCCATACCATCTTGGTTATCGAACCAGACT<br>CTTTGGCTAACGTTGTCACTAACTTGAACGTTCCAAAATGTGCTAACGCTC<br>AAGATGCTTACTTGGAATGTATCAACTACGCTATTACCCAATTGGACTTGC | AAL78165<br>MRNLLALAPAALLVGAAEAQQS<br>LWGQCGGSSWTGATSCAAGAT<br>CSTINPYYAQCVPATATPTTLTT<br>TTKPTSTGGAAPTTPPPTTTGTTT<br>SPVVTRPASASGNPFEGYQLYAN<br>PYYASEVISLAIPSLSSELVPKAS<br>EVAKVPSFVWLDQAAKVPSMG<br>DYLKDIQSQNAAGADPPIAGIFV<br>VYDLPDRDCAAAASNGEFSIAN<br>NGVALYKQYIDSIREQLTTYSDV<br>HTILVIEPDSLANVVTNLNVPKC<br>ANAQDAYLECINYAITQLDLPNV<br>AMYLDAGHAGWLGWQANLAP<br>AAQLFASVYKNASSPASVRGLA<br>TNVANYNAWSISRCPSYTQGDA |

TABLE 1-continued

| Cellulases used in Examples 1-11 as described below. | | |
|---|---|---|
| Donor organism/ Gene | Codon-Optimized DNA sequence used | Accession number and amino acid sequence |
| | CAAACGTTGCTATGTACTTGGACGCTGGTCACGCCGGTTGGTTGGGTTGGC<br>AAGCCAACTTGGCCCCAGCTGCTCAATTATTCGCTTCTGTTTACAAGAACG<br>CCTCTTCCCCAGCCTCTGTTAGAGGTTTGGCTACCAACGTGGCTAACTACA<br>ACGCCTGGTCCATTTCTAGATGTCCATCCTACACTCAAGGTGACGCTAACT<br>GTGATGAAGAAGATTACGTTAACGCTTTGGGTCCATTGTTCCAAGAACAA<br>GGTTTCCCAGCTTACTTCATCATCGACACTTCCCGTAACGGTGTCAGACCA<br>ACTAAGCAATCTCAATGGGGTGACTGGTGTAACGTTATTGGTACCGGTTTC<br>GGTGTTAGACCAACCACCGACACTGGTAACCCATTGGAAGACGCTTTCGT<br>TTGGGTCAAGCCAGGTGGTGAATCCGACGGTACCTCCAACACTACTAGCC<br>CACGTTACGATTACCACTGTGGTTTGTCTGACGCTTTGCAACCAGCTCCAG<br>AAGCTGGTACCTGGTTCCAAGCCTACTTCGAACAATTGTTGACTAACGCC<br>AACCCATTGTTCTAACTCGAG (SEQ ID NO: 4) | NCDEEDYVNALGPLFQEQGFPA<br>YFIIDTSRNGVRPTKQSQWGDW<br>CNVIGTGFGVRPTTDTGNPLEDA<br>FVWVKPGGESDGTSNTTSPRYD<br>YHCGLSDALQPAPEAGTWFQAY<br>FEQLLTNANPLF (SEQ ID NO: 24) |
| *Chrysosporium lucknowense* CBH2b | ATGGCCAAGAAGTTGTTCATTACCGCTGCCTTAGCTGCCGCAGTGCTTGCT<br>GCACCAGTGATCGAAGAGAGACAAAATTGCGGAGCCGTCTGGACACAGT<br>GCGGAGGCAACGGCTGGCAAGGCCCAACATGTTGTGCTTCTGGCTCAACG<br>TGCGTGGCACAGAACGAGTGGTATTCCCAGTGCCTTCCAAACTCCCAGGT<br>GACTTCTTCAACAACCCCCAGCTCAACGTCTACTTCACAGAGATCCACAA<br>GTACCTCTTCTAGCACAACCAGAAGTGGCTCATCCTCATCTAGCAGTACG<br>ACCCCTCCACCCGTATCAAGTCCTGTCACGAGTATCCCTGGCGGAGCAAC<br>CTCAACAGCCAGTTATTCCGGCAATCCTTTCTCTGGAGTGAGATTATTTGC<br>AAACGACTATTATAGATCAGAGGTTCACAACCTTGCAATTCCTTCTATGAC<br>GGGAACCCTAGCCGCAAAGGCTTCCGCCGTAGCAGAAGTCCCTAGTTTCC<br>AATGGCTTGACAGAAACGTTACAATAGATACACTTATGGTACAGACTTTA<br>TCTCAGGTTAGAGCTTTGAATAAGGCCGGTGCCAACCCACCTTATGCTGCC<br>CAATTAGTAGTCTATGACTTGCCAGATAGAGACTGTGCTGCCGCAGCTTCT<br>AATGGTGAATTTTCCATCGCAAATGGCGGAGCTGCAAACTATAGATCATA<br>CATTGATGCAATAAGAAAACACATCATTGAGTATTCTGATATTAGAATAA<br>TCCTTGTGATTGAACCAGACTCCATGGCTAATATGGTTACCAACATGAATG<br>TAGCCAAGTGTTCTAACGCAGCTTCCACATACCATGAGCTAACCGTATAT<br>GCATTAAAACAACTGAATCTACCTAACGTTGCTATGTACTTAGATGCCGGT<br>CATGCCGGATGGTTGGGCTGGCCTGCAAATATCCAACCCGCAGCTGAATT<br>GTTCGCTGGAATCTACAACGACGCCGGAAAGCCCGCTGCCGTTAGAGGCT<br>TAGCCACAAATGTTGCAAATTACAACGCTTGGTCAATTGCTAGTGCCCCTT<br>CTTATACCTCACCAAATCCTAACTACGATGAGAAACATTACATAGAAGCA<br>TTTTCCCCATTGTTAAACTCCGCTGGATTCCCTGCCAGATTCATCGTGGAT<br>ACCGGTAGAAACGGCAAACAACCAACTGGACAACAACAATGGGGAGATT<br>GGTGTAACGTCAAGGGAACCGGCTTCGGCGTCAGGCCTACGGCAAACACC<br>GGACACGAGCTAGTCGACGCTTTTGTATGGGTTAAGCCAGGTGGCGAAAG<br>TGACGGAACAAGTGACACGAGTGCTGCAAGATACGATTACCACTGTGGTC<br>TGTCCGACGCTTTACAGCCCGCCCCCGAGGCTGGACAATGGTTCCAGGCT<br>TATTTTGAACAATTGTTAACGAACGCAAATCCACCATTCTAA (SEQ ID<br>NO: 5) | MAKKLFITAALAAAVLAAPVIEE<br>RQNCGAVWTQCGGNGWQGPTC<br>CASGSTCVAQNEWYSQCLPNSQ<br>VTSSTTPSSTSTSQRSTSTSSSTTR<br>SGSSSSSSTTPPPVSSPVTSIPGGA<br>TSTASYSGNPFSGVRLFANDYYR<br>SEVHNLAIPSMTGTLAAKASAV<br>AEVPSFQWLDRNVTIDTLMVQT<br>LSQVRALNKAGANPPYAAQLVV<br>YDLPDRDCAAAASNGEFSIANG<br>GAANYRSYIDAIRKHIIEYSDIRII<br>LVIEPDSMANMVTNMNVAKCS<br>NAASTYHELTVYALKQLNLPNV<br>AMYLDAGHAGWLGWPANIQPA<br>AELFAGIYNDAGKPAAVRGLAT<br>NVANYNAWSIASAPSYTSPNPN<br>YDEKHYIEAFSPLLNSAGFPARFI<br>VDTGRNGKQPTGQQQWGDWC<br>NVKGTGFGVRPTANTGHELVDA<br>FVWVKPGGESDGTSDTSAARYD<br>YHCGLSDALQPAPEAGQWFQAY<br>FEQLLTNANPPF (SEQ ID NO: 25) |
| *Talaromyces emersonii* cbh1 with CBD | ATGCTAAGAAGAGCTTTACTATTGAGCTCTTCTGCTATCTTGGCCGTTAAG<br>GCTCAACAAGCCGGTACCGCTACTGCTGAAAACCACCCTCCATTGACCTG<br>GCAAGAATGTACCGCTCCAGGTTCTTGTACCACCCAAAACGGTGCTGTCG<br>TCTTGGACGCTAACTGGAGATGGGTCCACGACGTCAACGGTTACACTAAC<br>TGTTACACCGGTAACACCTGGGACCCAACTTACTGTCCAGACGACGAAAC<br>TTGCGCTCAAAACTGTGCCTTGGACGGTGCTGACTACGAAGGTACTTACG<br>GTGTTACCTCCTCTGGTTCTTCCTTGAAGTTGAACTTCGTCACTGGTTCTAA<br>CGTCGGTTCCAGATTGTATTTGTTGCAAGATGACTCCACTTACCAAATCTT<br>CAAGTTGTTGAACAGAGAATTTTCTTTCGACGTCGATGTGTCCAACTTGCC<br>TTGTGGTTTGAACGGTGCTCTATACTTCGTTGCTATGGACGCTGATGGTGG<br>TGTTTCCAAGTACCCAAACAACAAGGCTGGTGCCAAATACGGTACTGGTT<br>ACTGTGACTCTCAATGTCCACGTGACTTGAAGTTTATTGATGGTGAAGCTA<br>ATGTCGAAGGTTGGCAACCATCTTCTAACAACGCTAACACTGGCATCGGT<br>GACCACGGTTCTTGCTGTGCCGAAATGGACGTTTGGGAAGCCAACTCCAT<br>TTCCAACGCCGTCACTCCACACCCATGTGACACTCCAGGTCAAACTATGTG<br>TTCCGGCGATGACTGTGGTGGTACTTACTCTAACGATAGATACGCTGGTAC<br>CTGTGATCCAGACGGTTGCGACTTCAATCCATACAGAATGGGTAACACTT<br>CCTTTTACGGTCCAGGCAAGATCATCGACACTACTAAGCCATTCACTGTTG<br>TCACCCAATTCTTGACCGACGATGGTACTGATACCGGTACTTTGTCCGAAA<br>TCAAGAGATTCTACATCCAAAACTCTAACGTCATCCCACAACCAAATTCC<br>GACATCTCTGGTGTCACTGGTAACTCCATTACCACCGAATTTTGTACCGCC<br>CAAAAGCAAGCTTTCGGTGACACCGACGACTTCTCTCAACACGGTGGTTT<br>GGCTAAGATGGGTGCTGCTATGCAACAAGGTATGGTTTTGGTCATGTCTTT<br>GTGGGACGACTACGCTGCTCAAATGTTGTGGTTGGACTCCGATTACCCAA<br>CCGATGCCGACCCAACCACCCCTGGTATCGCTAGAGGTACCTGTCCAACT<br>GACTCTGGTGTTCCATCTGACGTCGAATCCCAATCTCCAAACTCCTACGTC<br>ACTTACTCCAACATTAAATTCGGTCCAATCAACTCCACTTTCACTGCTTCT<br>AACCCTCCAGGTGGTAACAGAGGTACTACCACTACTCGTAGGCCAGCTAC<br>TACAACTGGTTCTTCCCCAGGCCCAACCCAATCCCACTACGGTCAATGTGG<br>TGGTATCGGTTACTCTGGTCCAACCGTCTGTGCTTCTGGTACTACCTGTCA<br>AGTTTTAAACCCATACTACTCTCAATGTTTGTAG (SEQ ID NO: 6) | MLRRALLLSSSAILAVKAQQAG<br>TATAENHPPLTWQECTAPGSCTT<br>QNGAVVLDANWRWVHDVNGY<br>TNCYTGNTWDPTYCPDDETCAQ<br>NCALDGADYEGTYGVTSSGSSL<br>KLNFVTGSNVGSRLYLLQDDST<br>YQIFKLLNREFSFDVDVSNLPCG<br>LNGALYFVAMDADGGVSKYPN<br>NKAGAKYGTGYCDSQCPRDLKF<br>IDGEANVEGWQPSSNNANTGIG<br>DHGSCCAEMDVWEANSISNAVT<br>PHPCDTPGQTMCSGDDCGGTYS<br>NDRYAGTCDPDGCDFNPYRMG<br>NTSFYGPGKIIDTTKPFTVVTQFL<br>TDDGTDTGTLSEIKRFYIQNSNVI<br>PQPNSDISGVTGNSITTEFCTAQK<br>QAFGDTDDFSQHGGLAKMGAA<br>MQQGMVLVMSLWDDYAAQML<br>WLDSDYPTDADPTTPGIARGTCP<br>TDSGVPSDVESQSPNSYVTYSNI<br>KFGPINSTFTASNPPGGNRGTTTT<br>RRPATTTGSSPGPTQSHYGQCGG<br>IGYSGPTVCASGTTCQVLNPYYS<br>QCL (SEQ ID NO: 26) |

TABLE 1-continued

| Cellulases used in Examples 1-11 as described below. | | |
|---|---|---|
| Donor organism/ Gene | Codon-Optimized DNA sequence used | Accession number and amino acid sequence |
| *Trichoderma reesei* CBH1 | ATGGTCTCCTTCACCTCCCTGCTGGCCGGCGTTGCCGCTATCTCTGGTGTC<br>CTAGCAGCCCCTGCCGCAGAAGTTGAACCTGTCGCAGTTGAGAAACGTGA<br>GGCCGAAGCAGAAGCTCAATCCGCTTGTACCCTACAATCCGAAACTCACC<br>CACCATTGACCTGGCAAAAGTGTTCTAGCGGTGGAACTTGTACTCAACAA<br>ACTGGTTCTGTTGTTATCGACGCTAACTGGAGATGGACACACGCCACTAA<br>CTCTTCTACCAACTGTTACGACGGTAACACTTGGTCTTCCACTTTATGTCC<br>AGATAACGAAACTTGTGCTAAGAATTGCTGTTTGGACGGTGCCGCCTACG<br>CTTCTACCTACGGTGTTACCACCTCCGGTAACTCCTTGTCTATTGGTTTCGT<br>CACTCAATCCGCTCAAAAGAACGTTGGTGCTAGATTGTACTTGATGGCTTC<br>TGACACTACTTATCAAGAATTTACTTTGTTGGGTAACGAATTTTCTTTCGA<br>TGTTGACGTTTCCCAATTGCCATGTGGCTTGAACGGTGCTTTGTACTTTGT<br>CTCTATGGATGCTGACGGTGGTGTTTCTAAGTACCCAACTAACACTGCCGG<br>TGCTAAGTACGGTACTGGTTACTGTGATTCTCAATGTCCACGTGACTTGAA<br>GTTCATTAACGGTCAAGCCAACGTCGAAGGTTGGGAACCATCCTCCAACA<br>ACGCTAACACCGGTATCGGTGGTCACGGTTCCTGTTGTTCCGAAATGGAC<br>ATCTGGGAAGCTAACAGTATTTCTGAAGCTTTGACACCACACCCATGCAC<br>CACTGTCGGTCAAGAAATTTGTGAAGGTGATGGATGTGGTGGAACCTACT<br>CTGATAACAGATACGGTGGTACTTGTGACCCAGACGGTTGTGACTGGAAC<br>CCATACAGATTGGGTAACACTTCTTTCTATGGTCCAGGTTCTTCTTTCACCT<br>TGGATACCACCAAGAAGTTGACTGTTGTTACCCAATTCGAAACTTCTGGTG<br>CTATCAACAGATACTACGTTCAAAACGGTGTCACCTTCCAACAACCAAAC<br>GCTGAATTGGGTTCTTACTCTGGTAATGAATTGAACGACGACTACTGTACC<br>GCTGAAGAAGCTGAATTTGGTGGTTCCTCTTTCTCCGACAAGGGTGGTTTG<br>ACCCAATTCAAGAAGGCTACCTCCGGTGGTATGGTTTTGGTTATGTCCTTG<br>TGGGATGATTACTACGCAAACATGTTATGGTTAGACAGTACTTACCCAAC<br>TAACGAAACCTCCTCTACTCCAGGTGCTGTCAGAGGTTCCTGTTCTACCTC<br>TTCTGGTGTTCCAGCTCAAGTTGAATCTCAATCTCCAAACGCTAAGGTCAC<br>TTTCTCCAACATCAAGTTCGGTCCAATCGGTTCCACTGGTAATCCATCTGG<br>TGGAAACCCTCCAGGTGGTAACAGAGGTACTACCACTACTCGTAGGCCAG<br>CTACTACAACTGGTTCTTCCCCAGGCCCAACCCAATCCCACTACGGTCAAT<br>GTGGTGGTATCGGTTACTCTGGTCCAACCGTCTGTGCTTCTGGTACTACCT<br>GTCAAGTTTTAAACCCATACTACTCTCAATGTTTGTAA (SEQ ID NO: 7) | ACCESSION NO.: CAA49596<br>MVSFTSLLAGVAAISGVLAAPA<br>AEVEPVAVEKREAEAEAQSACT<br>LQSETHPPLTWQKCSSGGTCTQ<br>QTGSVVIDANWRWTHATNSSTN<br>CYDGNTWSSTLCPDNETCAKNC<br>CLDGAAYASTYGVTTSGNSLSIG<br>FVTQSAQKNVGARLYLMASDTT<br>YQEFTLLGNEFSFDVDVSQLPCG<br>LNGALYFVSMDADGGVSKYPTN<br>TAGAKYGTGYCDSQCPRDLKFI<br>NGQANVEGWEPSSNNANTGIGG<br>HGSCCSEMDIWEANSISEALTPH<br>PCTTVGQEICEGDGCGGTYSDN<br>RYGGTCDPDGCDWNPYRLGNTS<br>FYGPGSSFTLDTTKKLTVVTQFE<br>TSGAINRYYVQNGVTFQQPNAE<br>LGSYSGNELNDDYCTAEEAEFG<br>GSSFSDKGGLTQFKKATSGGMV<br>LVMSLWDDYYANMLWLDSTYP<br>TNETSSTPGAVRGSCSTSSGVPA<br>QVESQSPNAKVTFSNIKFGPIGST<br>GNPSGGNPPGGNRGTTTTRRPAT<br>TTGSSPGPTQSHYGQCGGIGYSG<br>PTVCASGTTCQVLNPYYSQCL<br>(SEQ ID NO: 27)<br>[SECRETION SIGNAL: 1-33<br>CATALYTIC DOMAIN: 41-465<br>CELLULOSE-BINDING DOMAIN:<br>503-535] |
| *Trichoderma reesei* CBH2 | ATGGTCTCCTTCACCTCCCTGCTGGCCGGCGTTGCCGCTATCTCTGGTGTC<br>CTAGCAGCCCCTGCCGCAGAAGTTGAACCTGTCGCAGTTGAGAAACGTGA<br>GGCCGAAGCAGAAGCTGTCCCATTAGAAGAAAGACAAGCCTGCTCCTCTG<br>TTTGGGGTCAATGTGGTGGTCAAAACTGGTCTGGTCCAACTTGTTGTGCTT<br>CCGGTTCTACCTGTGTTTACTCCAACGACTACTATTCCCAATGTTTGCCAG<br>GTGCTGCTTCCTCTTCCTCTTCAACTAGAGCTGCTTCTACAACTTCTAGGGT<br>CTCCCCAACCACTTCCAGATCCTCTTCTGCTACTCCACCACCAGGTTCTAC<br>TACCACTAGAGTTCCACCAGTCGGTTCCGGTACTGCTACTTACTCTGGTAA<br>CCCTTTCGTCGGTGTTACTCCATGGGCTAACGCTTACTACGCTTCTGAAGT<br>TTCTTCTTTGGCTATCCCATCTTTGACTGGTGCTATGGCTACCGCTGCTGCT<br>GCTGTCGCCAAAGTTCCATCCTTCATGTGGTTGGACACCTTGGACAAAACT<br>CCATTAATGGAACAAACCTTGGCAGACATAAGGACTGCTAACAAGAACG<br>GCGGTAACTACGCTGGTCAATTTGTTGTGTACGACTTGCCAGACAGAGAC<br>TGTGCTGCTTTGGCTTCCAACGGTGAATACTCCATCGCTGACGGTGGTGTC<br>GCCAAGTACAAGAACTACATTGATACCATTAGACAAATCGTTGTCGAATA<br>CTCTGACATCAGAACCTTGTTAGTCATCGAACCAGATTCTTTAGCCAATTT<br>AGTCACCAACTTGGGTACTCCAAAGTGTGCTAACGCTCAATCTGCCTACTT<br>AGAATGTATCAATTATGCAGTTACCCAATTGAACTTGCCAAACGTTGCTAT<br>GTACTTGGACGCTGGTCACGCCGGTTGGTTGGGTTGGCCAGCTAACCAAG<br>ACCCAGCCGCTCAATTATTCGCCAACGTTTACAAGAATGCCTCTTCTCCTA<br>GAGCCTTGCGTGGTTTGGCTACTAACGTCGCTAACTACAACGGTTGGAAC<br>ATCACTTCTCCACCATCTTACACCCAAGGTAACGCTGTTTACAACGAAAA<br>GTTGTACATTCACGCTATCGGTCCATTATTGGCTAACCATGGTTGGTCTAA<br>CGCCTTCTTCATCACCGACCAAGGTAGATCCGGTAAACAACCAACTGGTC<br>AACAACAATGGGGTGATTGGTGTAACGTCATCGGTACTGGTTTCGGTATC<br>AGACCATCCGCTAACACTGGTGATTCCTTGTTGGATTCCTTCGTCTGGGTT<br>AAGCCAGGTGGTGAATGTGATGGCACCTCTGATTCCTCTGCTCCAAGATTC<br>GATTCCCACTGCGCCTTGCCAGACGCTTTGCAACCAGCCCCACAAGCTGG<br>TGCATGGTTCCAAGCTTACTTTGTCCAATTGTTGACCAACGCTAACCCATC<br>TTTCTTGTAA (SEQ ID NO: 8) | ACCESSION NO.:<br>AAA72922AAA34210<br>MIVGILTTLATLATLAASVPLEE<br>RQACSSVWGQCGGQNWSGPTC<br>CASGSTCVYSNDYYSQCLPGAA<br>SSSSSTRAASTTSRVSPTTSRSSS<br>ATPPPGSTTTRVPPVGSGTATYS<br>GNPFVGVTPWANAYYASEVSSL<br>AIPSLTGAMATAAAAVAKVPSF<br>MWLDTLDKTPLMEQTLADIRTA<br>NKNGGNYAGQFVVYDLPDRDC<br>AALASNGEYSIADGGVAKYKNY<br>IDTIRQIVVEYSDIRTLLVIEPDSL<br>ANLVTNLGTPKCANAQSAYLEC<br>INYAVTQLNLPNVAMYLDAGHA<br>GWLGWPANQDPAAQLFANVYK<br>NASSPRALRGLATNVANYNGW<br>NITSPPSYTQGNAVYNEKLYIHAI<br>GRLLANHGWSNAFFITDQGRSG<br>KQPTGQQQWGDWCNVIGTGFGI<br>RPSANTGDSLLDSFVWVKPGGE<br>CDGTSDSSAPRFDSHCALPDALQ<br>PAAQAGAWFQAYFVQLLTNAN<br>PSFL (SEQ ID NO: 28) |
| *Chaetomium thermophilum* CBH1 | TTAATTAAACAATGATGTACAAGAAATTTGCAGCCCTAGCTGCTTTAGTTG<br>CAGGAGCTTCCGCTCAACAGGCATGTTCATTGACTGCCGAAAATCATCCA<br>TCCTTAACGTGGAAGAGATGCACGTCAGGAGGTTCATGCTCCACTGTAAA<br>CGGAGCTGTCACAATAGATGCAAATTGGAGATGGACCCACACTGTGTCCG<br>GTAGTACAAACTGCTACACCGGTAATCAATGGGATACGTCTTTGTGTACA<br>GATGGAAAGTCATGCGCTCAGACCTGTTGCGTGGATGGAGCAGACTACTC<br>TTCTACTTACGGAATCACGACATCAGGTGACAGTCTTAATTTGAAATTCGT<br>AACCAAGCACCAGTACGGAACAAATGTAGGCTCCAGAGTGTACTTAATGG<br>AGAACGATACCAAATATCAAATGTTCGAGTTATTAGGCAATGAGTTTACC<br>TTTGACGTAGACGTTAGCAATTTGGGTTGCGGATTAAACGGCGCCCTTTAC | AM711862<br>MMYKKFAALAALVAGASAQQA<br>CSLTAENHPSLTWKRCTSGGSCS<br>TVNGAVTIDANWRWTH<br>TVSGSTNCYTGNQWDTSLCTDG<br>KSCAQTCCVDGADYSSTYGITTS<br>GDSLNLKFVTKHQYG<br>TNVGSRVYLMENDTKYQMFELL<br>GNEFTFDVDVSNLGCGLNGALY<br>FVSMDADGGMSKYSGN |

TABLE 1-continued

| Donor organism/ Gene | Codon-Optimized DNA sequence used | Accession number and amino acid sequence |
|---|---|---|
| Cellulases used in Examples 1-11 as described below. | | |
| | TTCGTGTCTATGGATGCTGACGGAGGTATGTCAAAGTATTCTGGTAACAA<br>AGCCGGAGCAAAGTACGGTACAGGTTATTGTGACGCTCAGTGCCCTAGAG<br>ATTTGAAGTTTATCAACGGAGAAGCCAACGTTGGTAACTGGACGCCAAGT<br>ACTAACGACGCAAACGCTGGATTCGGCAGATACGGTAGTTGTTGCTCAGA<br>AATGGACGTGTGGGAGGCCAATAACATGGCAACCGCTTTTACTCCTCACC<br>CATGTACAACTGTTGGACAATCTAGATGTGAAGCCGACACGTGCGGTGGC<br>ACCTACAGTAGCGATAGGTATGCAGGAGTATGTGATCCTGACGGTTGCGA<br>TTTCAATGCTTATAGACAAGGAGACAAAACGTTTTATGGTAAAGGTATGA<br>CCGTCGATACTAACAAGAAGATGACTGTGGTTACCCAGTTCCACAAGAAC<br>TCAGCTGGAGTATTGTCTGAAATTAAAAGATTCTACGTCCAGGATGGAAA<br>GATTATTGCTAATGCCGAGAGTAAGATACCAGGTAACCCTGGAAATAGTA<br>TCACACAGGAATACTGTGACGCTCAGAAGGTAGCTTTTAGCAACACCGAT<br>GACTTCAATAGAAAGGGTGGAATGGCTCAAATGAGTAAGGCTTTAGCCGG<br>TCCAATGGTGTTGGTGATGTCTGTTTGGGATGATCACTATGCAAACATGCT<br>TTGGCTTGACAGCACCTATCCTATCGACCAAGCCGGAGCCCCAGGTGCTG<br>AAAGGGGTGCATGTCCAACCACGAGTGGTGTGCCCGCCGAGATTGAAGCT<br>CAAGTGCCTAATAGTAACGTTATCTTTTCCAATATAAGATTCGGACCAATC<br>GGATCCACTGTTCCAGGTTTGGATGGATCTAATCCTGGCAACCCAACAAC<br>CACGGTAGTCCCTCCAGCTTCAACTTCCACAAGTAGACCAACAAGTTCAA<br>CGTCCAGTCCAGTGTCTACTCCTACCGGACAACCAGGAGGCTGTACCACT<br>CAGAAATGGGGTCAATGCGGTGGAATTGGCTATACAGGTTGTACGAATTG<br>CGTTGCAGGAACCACTTGTACACAGTTAAACCCTTGGTACTCACAATGCCT<br>ATAAGGCGCGCC (SEQ ID NO: 9) | KAGAKYGTGYCDAQCPRDLKFI<br>NGEANVGNWTPSTNDANAGFG<br>RYGSCCSEMDVWEANNM<br>ATAFTPHPCTTVGQSRCEADTCG<br>GTYSSDRYAGVCDPDGCDFNAY<br>RQGDKTFYGKGMTVD<br>TNKKMTVVTQFHKNSAGVLSEI<br>KRFYVQDGKIIANAESKIPGNPG<br>NSITQEYCDAQKVAF<br>SNTDDFNRKGGMAQMSKALAG<br>PMVLVMSVWDDHYANMLWLD<br>STYPIDQAGAPGAERGACP<br>TTSGVPAEIEAQVPNSNVIFSNIR<br>FGPIGSTVPGLDGSNPGNPTTTV<br>VPPASTSTSRPTS<br>STSSPVSTPTGQPGGCTTQKWGQ<br>CGGIGYTGCTNCVAGTTCTQLN<br>PWYSQCL (SEQ ID NO: 29) |
| *Acremonium thermophilum* CBH1 | ATGTATACCAAATTTGCTGCATTGGCCGCTTTAGTTGCAACAGTAAGAGGT<br>CAAGCCGCTTGTTCTCTAACCGCAGAAACTCACCCATCTCTACAATGGCA<br>GAAATGCACAGCCCCTGGATCTTGTACAACTGTCTCCGGCCAAGTCACCA<br>TTGACGCTAATTGGAGATGGCTTCACCAAACTAACTCTTCAACGAATTGTT<br>ATACCGGTAACGAATGGGATACTTCCATATGTTCATCCGATACAGACTGC<br>GCAACGAAATGTTGTTTAGATGGAGCAGACTATACGGGAACTTATGGTGT<br>TACAGCCTCAGGTAATTCCCTAAACCTTAAGTTCGTAACTCAAGGACCAT<br>ATAGTAAGAATATCGGCTCTAGAATGTACTTGATGGAAAGTGAGAGCAAA<br>TATCAGGGTTTTACGTTATTGGGACAAGAGTTTACATTTGATGTTGATGTG<br>AGTAACTTAGGTTGCGGCCTAAACGGCGCCTTGTACTTCGTTTCTATGGAT<br>CTTGATGGAGGTGTATCAAAATACACGACCAACAAGGCTGGAGCCAAATA<br>TGGTACGGGATATTGTGACAGCCAATGCCCTAGAGACTTAAAGTTCATTA<br>ACGGTCAGGCAAATATTGACGGCTGGCAACCAAGCAGTAACGACGCTAAT<br>GCCGGACTAGGTAACCATGGCTCATGTTGTTCCGAAATGGATATCTGGGA<br>AGCCAATAAGGTGTCCGCTGCCTACACCCCCCATCCATGCACGACAATCG<br>GTCAGACAATGTGTACCGGTGATGACTGTGGAGGCACATACTCAAGTGAT<br>AGGTACGCCGGTATATGTGATCCTGACGGTTGCGATTTCAACTCTTATAGA<br>ATGGGAGATACATCCTTTTACGGCCCCGGTAAAACAGTTGATACGGGTAG<br>TAAGTTCACTGTTGTTACTCAGTTCTTAACAGGTTCAGACGGCAATCTTAG<br>TGAAATCAAAAGATTCTACGTTCAGAATGGAAAAGTCATTCCTAATTCCG<br>AGAGTAAGATTGCTGGTGTGTCTGGTAACAGTATCACGACCGACTTCTGT<br>ACCGCCCAAAAGACTGCCTTTGGAGATACGAATGTTTTCGAGGAAAGGGG<br>CGGTCTTGCTCAAATGGGCAAGGCTTTGGCCGAACCAATGGTATTAGTCC<br>TATCCGTTTGGGATGATCATGCAGTGAATATGCTTTGGCTTGATAGCACCT<br>ACCCTACTGACAGCACCAAGCCAGGAGCTGCCAGAGGTGACTGTCCTATC<br>ACAAGTGGCGTTCCAGCAGATGTAGAGAGCCAAGCTCCAAACTCCAATGT<br>GATCTATTCTAACATCAGATTTGGCCCCATTAATAGTACCTATACAGGAAC<br>GCCCTCTGGTGGTAACCCTCCAGGCGGAGGCACCACAACTACCACGACCA<br>CAACGACTTCAAAGCCTTCTGGCCCTACGACAACTACCAATCCTTCCGGA<br>CCACAGCAAACTCACTGGGGTCAGTGTGGAGGCCAAGGATGGACGGGTC<br>CTACCGTGTGTCAATCACCTTACACATGCAAATACAGTAATGACTGGTACT<br>CTCAGTGTTTATAA (SEQ ID NO: 45) | MYTKFAALAALVATVRGQAAC<br>SLTAETHPSLQWQKCTAPGSCTT<br>VSGQVTIDANWRWLHQTNSSTN<br>CYTGNEWDTSICSSDTDCATKC<br>CLDGADYTGTYGVTASGNSLNL<br>KFVTQGPYSKNIGSRMYLMESES<br>KYQGFTLLGQEFTFDVDVSNLG<br>CGLNGALYFVSMDLDGGVSKYT<br>TNKAGAKYGTGYCDSQCPRDLK<br>FINGQANIDGWQPSSNDANAGL<br>GNHGSCCSEMDIWEANKVSAAY<br>TPHPCTTIGQTMCTGDDCGGTYS<br>SDRYAGICDPDGCDFNSYRMGD<br>TSFYGPGKTVDTGSKFTVVTQFL<br>TGSDGNLSEIKRFYVQNGKVIPN<br>SESKIAGVSGNSITTDFCTAQKT<br>AFGDTNVFEERGGLAQMGKAL<br>AEPMVLVLSVWDDHAVNMLWL<br>DSTYPTDSTKPGAARGDCPITSG<br>VPADVESQAPNSNVIYSNIRFGPI<br>NSTYTGTPSGGNPPGGGTTTTTT<br>TTTSKPSGPTTTTNPSGPQQTHW<br>GQCGGQGWTGPTVCQSPYTCK<br>YSNDWYSQCL (SEQ ID NO: 46) |
| Endoglucanases | | |
| *Coptotermes lacteus* EG | ATGAGATTTCCTTCCATATTCACCGCTGTTTTGTTCGCAGCCTCAAGTGCTT<br>TAGCAGAATGTACTAAGGGTGGATGTACTAACAAGAATGGATACATAGTT<br>CATGATAAGCACGTCGGTGACATCCAGAATAGAGACACTTTGGACCCTCC<br>AGACTTAGATTATGAAAAGGACGTGGGAGTAACCGTGTCCGGTGGAACCC<br>TTAGTCAAAGATTAGTCTCAACTTGGAACGGTAAGAAAGTCGTGGGAAGT<br>AGATTGTATATTGTGGACGAAGCCGACGAGAAATATCAATTATTCACATTT<br>GTCGGTAAGGAGTTCACCTATACCGTTGATATGTCCCAGATCCAATGTGGA<br>ATCAATGCCGCATTATACACAGTGGAAATGCCTGCCGCTGGAAAGACCCC<br>TGGAGGTGTTAAGTATGGATATGGATATTGTGATGCCAACTGCGTGGATG<br>GAGATTGTTGTATGGAGTTCGATATCCAAGAAGCTTCTAACAAGGCAATC<br>GTTTACACCACCCATTCCTGTCAAAGTCAAACTTCAGGTTGCGATACCTCA<br>GGATGCGGTTACAACCCTTACAGAGACAGTGGTGACAAGGCATTCTGGGG<br>AACAACTATAAACGTAAACCAGCCTGTGACAATTGTAACACAGTTTATCG<br>GTTCTGGTAGTTCCTTAACTGAAGTCAAAAGATTGTGCGTGCAAGGTGGA<br>AAGACCTTCCCTCCAGCCAAATCATTAACCGACAGTTATTGTAATGCCAAC | MRFPSIFTAVLFAASSALAECTK<br>GGCTNKNGYIVHDKHVGDIQNR<br>DTLDPPDLDYEKDVGVTVSGGT<br>LSQRLVSTWNGKKVVGSRLYIV<br>DEADEKYQLFTFVGKEFTYTVD<br>MSQIQCGINAALYTVEMPAAGK<br>TPGGVKYGYGYCDANCVDGDC<br>CMEFDIQEASNKAIVYTTHSCQS<br>QTSGCDTSGCGYNPYRDSGDKA<br>FWGTTINVNQPVTIVTQFIGSGSS<br>LTEVKRLCVQGGKTFPPAKSLT<br>DSYCNANDYRSLRTMGASMAR<br>GHVVVFSLWDSNGMSWMDGG<br>NAGPCTSYNIESLESSQPNLKVT<br>WSNVKYGEIDSPY (SEQ ID |

TABLE 1-continued

Cellulases used in Examples 1-11 as described below.

| Donor organism/ Gene | Codon-Optimized DNA sequence used | Accession number and amino acid sequence |
|---|---|---|
| | GACTATAGAAGTTTGAGAACTATGGGTGCATCCATGGCTAGAGGACACGT<br>TGTTGTGTTTTCTTTGTGGGATTCTAATGGTATGAGTTGGATGGATGGAGG<br>TAACGCCGGTCCTTGTACCTCATATAATATTGAATCTTTGGAATCCAGTCA<br>GCCAAACTTAAAGGTCACATGGTCAAACGTGAAATACGGAGAGATCGATT<br>CTCCTTATTAA (SEQ ID NO: 10) | NO: 30) |
| *Coptotermes formosanus* EG | ATGAGATTCCCTTCCATTTTCACTGCTGTTTTGTTCGCAGCCTCAAGTGCTT<br>TAGCAGCCTATGACTACAAGACAGTATTGAAGAACTCCTTGTTGTTCTACG<br>AAGCTCAAAGAAGTGGAAAATTGCCTGCAGACCAGAAGGTGACCTGGAG<br>AAAAGATTCCGCATTAAACGACAAGGGACAGAAGGGAGAGGACTTAACT<br>GGAGGTTATTACGACGCCGGAGACTTTGTGAAGTTCGGTTTTCCAATGGCA<br>TACACAGTTACCGTGTTGGCCTGGGGTTTAGTCGATTATGAATCTGCTTAC<br>AGTACTGCGGGTGCCTTGGATGATGGTAGAAAGGCCTTGAAATGGGGTAC<br>AGATTATTTCTTGAAAGCACATACCGCTGCCAATGAGTTTTACGGACAGGT<br>GGGTCAGGGAGATGTGGATCATGCTTACTGGGGACGTCCTGAGGACATGA<br>CTATGTCTAGACCAGCTTACAAGATCGATACATCAAAACCTGGTAGTGACT<br>TAGCTGCAGAAACAGCAGCCGCTTTAGCAGCAACCGCAATAGCTTACAAG<br>TCAGCCGATTCTACCTACAGTAACAACTTAATTACTCATGCAAAGCAGTTG<br>TTCGATTTTGCAAACAATTATAGAGGAAAGTACTCTGATAGTATTACCGAT<br>GCCAAGAATTTCTATGCATCCGGTGATTATAAGGACGAATTAGTATGGGCT<br>GCAGCCTGGTTGTATAGAGCTACAAATGATAACACTTACTTAACCAAAGC<br>CGAATCATTGTATAATGAATTTGGTTTAGGATCTTGGAACGGTGCATTCAA<br>TTGGGATAACAAGATATCCGGAGTTCAGGTCTTATTAGCCAAATTGACATC<br>CAAACAAGCATACAAAGATAAAGTTCAGGGTTATGTTGATTACTTAGTCTC<br>CTCTCAAAAGAAAACTCCAAAGGGATTGGTCTATATTGACCAATGGGGAA<br>CCTTAAGACACGCAGCTAATAGTGCCTTGATCGCTTTACAGGCCGCTGATT<br>TGGGTATAAACGCTGCTAGTTATAGACAATACGCAAAGAAGCAAATTGAT<br>TATGCCTTAGGTGACGGAGGTCGTTCTTACGTGGTCGGATTCGGAACTAAC<br>CCTCCAGTAAGACCTCATCATAGATCCAGTTCCTGTCCTGACGCACCAGCC<br>GCTTGCGACTGGAATACTTACAACTCTGCCGGACCAAATGCCCACGTCTTG<br>ACCGGAGCCTTAGTAGGTGGACCAGATTCCAACGATAGTTACACAGATTC<br>ACGTTCTGATTATATCAGTAACGAAGTCGCTACTGATTACAATGCCGGTTT<br>CCAATCTGCAGTTGCTGGTTTGTTGAAAGCCGGAGTATAA (SEQ ID NO: 11) | BAB40697<br>MRFPSIFTAVLFAASSALAAYDY<br>KTVLKNSLLFYEAQRSGKLPAD<br>QKVTWRKDSALNDKGQKGEDL<br>TGGYYDAGDFVKFGFPMAYTV<br>TVLAWGLVDYESAYSTAGALD<br>DGRKALKWGTDYFLKAHTAAN<br>EFYGQVGQGDVDHAYWGRPED<br>MTMSRPAYKIDTSKPGSDLAAE<br>TAAALAATAIAYKSADSTYSNN<br>LITHAKQLFDFANNYRGKYSDSI<br>TDAKNFYASGDYKDELVWAAA<br>WLYRATNDNTYLTKAESLYNEF<br>GLGSWNGAFNWDNKISGVQVL<br>LAKLTSKQAYKDKVQGYVDYL<br>VSSQKKTPKGLVYIDQWGTLRH<br>AANSALIALQAADLGINAASYR<br>QYAKKQIDYALGDGGRSYVVG<br>FGTNPPVRPHHRSSSCPDAPAAC<br>DWNTYNSAGPNAHVLTGALVG<br>GPDSNDSYTDSRSDYISNEVATD<br>YNAGFQSAVAGLLKAGV (SEQ<br>ID NO: 31) |
| *Nasutitermes takasagoensis* EG | ATGAGATTTCCATCTATTTTCACTGCCGTCTTATTTGCAGCCTCCAGTGCAT<br>TAGCAGCCTATGATTATAAACAAGTTTTGAGAGATTCCTTATTGTTCTACG<br>AAGCTCAGAGAAGCGGTAGATTACCAGCAGACCAGAAGGTCACTTGGAG<br>AAAAGATTCAGCCTTGAATGATCAGGGAGATCAAGGTCAAGACTTAACCG<br>GAGGTTATTTTGACGCCGGTGATTTTGTGAAATTTGGTTTCCCAATGGCAT<br>ATACTGCTACCGTCTTGGCCTGGGGTTTAATCGATTTTGAGGCAGGATACA<br>GTTCCGCTGGTGCCTTGGATGACGGTAGAAAAGCAGTAAAGTGGGCAACT<br>GATTACTTTATAAAGGCCCACACTTCACAGAATGAGTTTTACGGACAAGTC<br>GGTCAGGGTGACGCTGATCACGCTTTCTGGGGACGTCCTGAAGATATGAC<br>CATGGCTAGACCAGCCTACAAGATTGACACCAGCAGACCAGGTAGTGACT<br>TAGCGGGTGAAACCGCAGCGGCATTGGCAGCTGCCAGTATCGTGTTTAGA<br>AATGTTGATGGTACATACTCTAACAACTTACTTACTCATGCCAGACAATTA<br>TTTGACTTTGCAAATAACTACAGAGGAAAATACTCAGATTCCATAACCGA<br>CGCTAGAAACTTTTACGCCAGTGCAGATTACCGTGACGAATTGGTTTGGGC<br>TGCCGCATGGTTGTACAGAGCTACAAATGACAACACTTACTTGAATACCG<br>CAGAATCCTTGTATGATGAATTTGGATTGCAGAACTGGGGTGGAGGGTTA<br>AACTGGGATTCAAAGGTGTCTGGTGTCCAGGTCTTGTTAGCAAAATTGACC<br>AACAAACAGGCTTACAAAGATACTGTGCAGTCTTACGTGAATTACCTGATT<br>AATAACCAGCAAAAGACCCCAAAAGGATTGTTATACATTGATATGTGGGG<br>TACATTGAGACACGCCGCAAATGCTGCATTCATCATGTTGGAAGCTGCCG<br>AGTTGGGTTTATCCGCATCATCTTACAGACAGTTTGCTCAAACTCAGATCG<br>ACTACGCTTTGGGTGACGGTGGAAGTTTCGTCTGTGGTTTTGGTTCAA<br>ACCCTCCTACAAGACCACATCATCGTTCTTCCAGTTGCCCGCCTGCCCCAG<br>CAACTTGTGACTGGAATACATTCAACTCACCTGACCCAAATTACCACGTGT<br>TATCTGGAGCTTTGGTAGGAGGACCAGATCAAAACGATAATTATGTGGAT<br>GATAGATCCGACTACGTCCATAACGAAGTGGCAACCGACTACAACGCCGG<br>ATTTCAGAGTGCTTTGGCAGCCTTAGTTGCTTTGGGTTATTAA (SEQ ID<br>NO: 12) | MRFPSIFTAVLFAASSALAAYDY<br>KQVLRDSLLFYEAQRSGRLPAD<br>QKVTWRKDSALNDQGDQGQDL<br>TGGYFDAGDFVKFGFPMAYTAT<br>VLAWGLIDFEAGYSSAGALDDG<br>RKAVKWATDYFIKAHTSQNEFY<br>GQVGQGDADHAFWGRPEDMT<br>MARPAYKIDTSRPGSDLAGETA<br>AALAAASIVFRNVDGTYSNNLL<br>THARQLFDFANNYRGKYSDSIT<br>DARNFYASADYRDELVWAAAW<br>LYRATNDNTYLNTAESLYDEFG<br>LQNWGGGLNWDSKVSGVQVLL<br>AKLTNKQAYKDTVQSYVNYLIN<br>NQQKTPKGLLYIDMWGTLRHA<br>ANAAFIMLEAAELGLSASSYRQF<br>AQTQIDYALGDGGRSFVCGFGS<br>NPPTRPHHRSSSCPPAPATCDWN<br>TFNSPDPNYHVLSGALVGGPDQ<br>NDNYVDDRSDYVHNEVATDYN<br>AGFQSALAALVALGY (SEQ ID<br>NO: 32) |
| *Coptotermes acinaciformis* EG | ATGAGATTCCCTAGTATTTTCACTGCCGTCTTATTTGCAGCCAGTTCTGCTT<br>TAGCCGCATATGATTATACCACAGTTTTGAAAAGTTCCTTATTGTTCTACG<br>AAGCTCAAAGATCCGGTAAGTTGCCAGCCGACCAGAAGGTCACTTGGAGA<br>AAAGATTCAGCATTAGACGATAAAGGAAATAATGGAGAGGACTTAACAG<br>GAGGTTATTATGACGCTGGTGATTTTGTGAAGTTTGGTTTTCCTTTAGCATA<br>CACCGCTACTGTTTTAGCCTGGGGTTTGGTGGACTATGAAGCGGGTTACTC<br>ATCCGCTGGAGCCACAGATGACGGTAGAAAGGCAGTGAAATGGGCAACC<br>GACTATTTGTTGAAGGCACATACTGCCGCTACCGAGTTATACGGACAGGTC<br>GGGGACGGTGACGCCGATCACGCATATTGGGGACGTCCTGAAGATATGAC<br>TATGGCTAGACCAGCATACAAGATCGACGCTAGCAGACCAGGATCTGACT<br>TAGCGGGTGAAACCGCTGCCGCTTTAGCCGCTGCATCCATAGTTTTCAAAG | MRFPSIFTAVLFAASSALAAYDY<br>TTVLKSSLLFYEAQRSGKLPADQ<br>KVTWRKDSALDDKGNNGEDLT<br>GGYYDAGDFVKFGFPLAYTATV<br>LAWGLVDYEAGYSSAGATDDG<br>RKAVKWATDYLLKAHTAATEL<br>YGQVGDGDADHAYWGRPEDM<br>TMARPAYKIDASRPGSDLAGET<br>AAALAAASIVFKGVDSSYSDNL<br>LAHAKQLFDFADNYRGKYSDSI<br>TQASNFYASGDYKDELVWAAT |

TABLE 1-continued

| Cellulases used in Examples 1-11 as described below. | | |
|---|---|---|
| Donor organism/ Gene | Codon-Optimized DNA sequence used | Accession number and amino acid sequence |
| | GTGTAGATTCTTCATATTCTGACAACTTGTTAGCTCACGCTAAACAGTTAT<br>TTGATTTCGCTGACAATTATAGAGGAAAATACAGTGATTCCATAACACAA<br>GCTTCAAACTTTTACGCCTCCGGAGATTACAAAGACGAGTTAGTCTGGGCT<br>GCCACTTGGTTGTACAGAGCAACCAACGATAATACATATTTGACCAAAGC<br>AGAATCCTTGTACAACGAGTTCGGATTAGGAAACTGGAACGGAGCCTTTA<br>ATTGGGACAACAAGGTGTCCGGTGTTCAGGTGTTGTTAGCCAAATTGACCT<br>CCAAGCAGGCTTATAAAGACACCGTTCAAGGATACGTCGATTATTTGATTA<br>ACAATCAGCAAAAGACCCCAAAGGGTTTGTTATACATAGACCAATGGGGG<br>ACCTTGAGACACGCAGCTAATGCTGCCTTAATAATCTTACAGGCTGCTGAT<br>TTGGGTATTTCTGCCGACAGTTATAGACAATTCGCAAAGAAGCAAATAGA<br>TTACGCTTTAGGTGACGGAGGTAGATCATATGTAGTTGGTTTTGGAGACAA<br>TCCTCCAACACATCCTCATCACCGTTCTTCCTCATGCCCTGACGCCCCAGC<br>AGTATGCGATTGGAATACTTTCAATTCACCTGATCCAAACTTTCATGTCTT<br>AACCGGAGCTTTAGTGGGAGGTCCTGATCAGAACGATAACTACGTTGATG<br>ATCGTTCTGACTACGTGTCCAACGAGGTTGCAACCGACTATAATGCAGGAT<br>TCCAAAGTGCTGTGGCCGCTTTAGTTACTTTAGGAGTTTAA (SEQ ID NO: 13) | WLYRATNDNTYLTKAESLYNEF<br>GLGNWNGAFNWDNKVSGVQV<br>LLAKLTSKQAYKDTVQGYVDY<br>LINNQQKTPKGLLYIDQWGTLR<br>HAANAALIILQAADLGISADSYR<br>QFAKKQIDYALGDGGRSYVVGF<br>GDNPPTHPHHRSSSCPDAPAVC<br>DWNTFNSPDPNFHVLTGALVGG<br>PDQNDNYVDDRSDYVSNEVAT<br>DYNAGFQSAVAALVTLGV (SEQ ID NO: 33) |
| *Mastotermes darwinensis* EG | ATGAGATTCCCAAGTATATTTACTGCTGTTTTGTTCGCAGCCAGTTCTGCTT<br>TAGCAGCCTATGATTACAATGACGTATTAACCAAAAGTTTGTTGTTCTACG<br>AAGCTCAAAGATCCGGTAAGTTACCTTCTGATCAGAAAGTCACCTGGAGA<br>AAAGATTCAGCATTAAACGATAAGGGACAAAATGGTGAGGACTTAACTGG<br>TGGATATTATGACGCCGGTGATTACGTGAAGTTTGGTTTTCCAATGGCATA<br>TACTGCTACCGTTTTGGCTTGGGGTTTAGTGGACCATCCTGCCGGATACAG<br>TTCTGCGGGTGTCTTGGATGATGGTAGAAAAGCTGTGAAGTGGGTTACCG<br>ATTACTTAATCAAAGCCCACGTATCAAAGAACGAATTATACGGACAGGTC<br>GGTGACGGTGACGCAGATCACGCTTATTGGGGACGTCCAGAGGATATGAC<br>AATGGCAAGACCAGCATACAAAATAGACACTTCAAGACCAGGTTCCGACT<br>TAGCGGGTGAAACCGCAGCGGCATTGGCTGCTGCATCTATTGTGTTTAAGT<br>CAACAGATTCTAATTACGCCAACACCTTATTGACCCACGCAAAACAATTAT<br>TCGACTTTGCCAATAACTATAGAGGTAAGTATAGTGATTCCATAACACAG<br>GCATCTAATTTCTACAGTAGTTCCGACTATAAAGATGAATTGGTTTGGGCA<br>GCTGTATGGTTGTACAGAGCCACTAACGATCAGACCTATTTGACAACTGCA<br>GAGAAGTTATACTCAGACTTGGGATTACAGTCCTGGAACGGAGGTTTCAC<br>ATGGGACACCAAAATTAGTGGAGTAGAAGTGTTATTGGCTAAGATTACTG<br>GTAAACAGGCATATAAGGACAAAGTAAAGGGATATTGTGATTATATCTCA<br>GGATCTCAGCAGAAAACACCTAAAGGATTAGTTTACATAGATAAGTGGGG<br>TTCCTTAAGAATGGCCGCAAACGCCGCATATATTTGCGCTGTAGCCGCAGA<br>CGTCGGAATCAGTTCAACAGCTTACAGACAGTTCGCCAAAACACAGATTA<br>ATTACATATTGGGTGATGCCGGACGTTCTTTTGTGGTTGGTTACGGAAACA<br>ACCCACCTACACACCCACATCACAGATCCAGTTCATGTCCTGACGCCCCAG<br>CAACATGCGATTGGAATAACTACAACAGTGCTAACCCTAATCCACATGTTT<br>TATACGGTGCATTAGTTGGTGGACCAGATTCCAACGATAATTATCAAGACT<br>TAAGATCAGATTATGTCGCCAACGAAGTGGCAACAGACTACAATGCAGCC<br>TTCCAGTCATTGTTAGCATTAATCGTGGACTTAGGTTTGTAA (SEQ ID NO: 14) | MRFPSIFTAVLFAASSALAAYDY<br>NDVLTKSLLFYEAQRSGKLPSD<br>QKVTWRKDSALNDKGQNGEDL<br>TGGYYDAGDYVKFGFPMAYTA<br>TVLAWGLVDHPAGYSSAGVLD<br>DGRKAVKWVTDYLIKAHVSKN<br>ELYGQVGDGDADHAYWGRPED<br>MTMARPAYKIDTSRPGSDLAGE<br>TAAALAAASIVFKSTDSNYANT<br>LLTHAKQLFDFANNYRGKYSDS<br>ITQASNFYSSSDYKDELVWAAV<br>WLYRATNDQTYLTTAEKLYSDL<br>GLQSWNGGFTWDTKISGVEVLL<br>AKITGKQAYKDKVKGYCDYISG<br>SQQKTPKGLVYIDKWGSLRMA<br>ANAAYICAVAADVGISSTAYRQ<br>FAKTQINYILGDAGRSFVVGYG<br>NNPPTHPHHRSSSCPDAPATCD<br>WNNYNSANPNPHVLYGALVGG<br>PDSNDNYQDLRSDYVANEVAT<br>DYNAAFQSLLALIVDLGL (SEQ ID NO: 34) |
| *Nasutitermes walkeri* EG | ATGAGATTTCCATCTATTTTCACTGCCGTCTTATTTGCAGCCTCAAGTGCTT<br>TAGCAGCCTATGATTACAAACAAGTATTGAGAGATTCCTTATTGTTCTACG<br>AAGCTCAGAGAAGCGGTAGATTACCAGCAGACCAGAAGGTCACCTGGAG<br>AAAAGATTCCGCCTTGAATGATCAGGGAGAGCAAGGTCAAGACTTAACCG<br>GAGGTTATTTTGACGCCGGTGATTTTGTGAAGTTTGGATTCCCAATGGCTT<br>ATACAGCAACCGTTTTGGCCTGGGGTTTAATCGACTTTGAAGCCGGTTACT<br>CTTCTGCTGGTGCCTTGGACGATGGTAGAAAAGCAGTAAAGTGGGCTACT<br>GATTACTTTATAAAAGCCCATACTTCTCAAAACGAGTTTTACGGACAAGTC<br>GGTCAGGGTGACGTAGATCACGCATATTGGGGACGTCCTGAAGATATGAC<br>AATGGCTAGACCAGCCTACAAGATTGATACCAGCAGACCAGGTAGTGACT<br>TAGCAGGAGAAACTGCTGCAGCTTTGGCTGCCGCATCCATCGTTTTCAAGA<br>ATGTAGATGGTACATATTCCAACAACTTACTTACTCATGCTAGACAGTTGT<br>TTGATTTCGCCAACAATTACAGAGGAAAATACTCTGATAGTATTACCGATG<br>CAAGAAACTTTTACGCTAGTGCCGACTATAGAGATGAGTTAGTCTGGGCA<br>GCTGCCTGGTTGTACAGAGCAACCAACGACAATTCTTACTTGAACACTGCT<br>GAATCATTATACAACGAGTTTGGATTGCAAAATTGGGGTGGAGGGTTAAA<br>CTGGGATTCTAAAGTGAGTGGTGTTCAAGTTTTGTTAGCCAAGTTGACCAA<br>CAAACAAGAGTATAAGGACACTATTCAATCATACGTGAATTACTTAATCA<br>ATAACCAACAGAAAACTCCAAAGGGATTGTTATACATTGACATGTGGGGG<br>ACCTTGAGACACGCAGCTAACGCAGCCTTTATAATGTTAGAAGCTGCCGA<br>CTTAGGTTTATCCGCTTCATCTTATAGACAGTTCGCCCAAACACAAATAGA<br>CTACGCATTGGGGGACGGTGGACGTTCTTTTGTCTGTGGTTTCGGTTCTAA<br>TCCTCCAACTAGACCTCATCATAGATCCAGTTCATGCCCGCCTGCTCCAGC<br>TACCTGTGATTGGAATACATTCAATTCTCCTGACCCAAACTACAATGTTTT<br>ATCCGGTGCCTTGGTTGGTGGTCCTGACCAGAATGATAACTACGTGGACG<br>ATAGAAGTGATTATGTCCATAATGAGGTAGCAACTGACTACAATGCCGGT<br>TTCCAATCAGCCTTAGCCGCTTTAGTCGCCTTAGGTTACTAA (SEQ ID NO: 15) | MRFPSIFTAVLFAASSALAAYDY<br>KQVLRDSLLFYEAQRSGRLPAD<br>QKVTWRKDSALNDQGEQGQDL<br>TGGYFDAGDFVKFGFPMAYTAT<br>VLAWGLIDFEAGYSSAGALDDG<br>RKAVKWATDYFIKAHTSQNEFY<br>GQVGQGDVDHAYWGRPEDMT<br>MARPAYKIDTSRPGSDLAGETA<br>AALAAASIVFKNVDGTYSNNLL<br>THARQLFDFANNYRGKYSDSIT<br>DARNFYASADYRDELVWAAAW<br>LYRATNDNSYLNTAESLYNEFG<br>LQNWGGGLNWDSKVSGVQVLL<br>AKLTNKQEYKDTIQSYVNYLIN<br>NQQKTPKGLLYIDMWGTLRHA<br>ANAAFIMLEAADLGLSASSYRQ<br>FAQTQIDYALGDGGRSFVCGFG<br>SNPPTRPHHRSSSCPPAPATCDW<br>NTFNSPDPNYNVLSGALVGGPD<br>QNDNYVDDRSDYVHNEVATDY<br>NAGFQSALAALVALGY (SEQ ID NO: 35) |

TABLE 1-continued

Cellulases used in Examples 1-11 as described below.

| Donor organism/ Gene | Codon-Optimized DNA sequence used | Accession number and amino acid sequence |
|---|---|---|
| *Reticulitermes speratus EG* | ATGAGATTCCCAAGTATATTTACTGCCGTCTTATTTGCAGCCTCCAGTGCA<br>TTAGCCGCTTATGACTACAAAACAGTATTGTCCAATTCCTTGTTGTTCTAC<br>GAAGCTCAAAGATCCGGTAAGTTACCTTCTGACCAGAAAGTGACCTGGAG<br>AAAGGATTCAGCATTAAACGACAAAGGACAAAAGGGTGAGGACTTAACC<br>GGTGGATATTACGACGCCGGAGACTTTGTGAAATTTGGTTTTCCAATGGCT<br>TACACAGTTACCGTATTGGCATGGGGTGTTATTGATTACGAATCCGCCTAC<br>TCTGCCGCAGGAGCTTTAGATTCAGGTAGAAAGGCCTTGAAATATGGGAC<br>CGACTATTTCTTAAAGGCACATACAGCAGCTAACGAGTTTTACGGACAGG<br>TGGGTCAAGGTGACGTTGACCACGCATACTGGGGACGTCCTGAAGATATG<br>ACCATGAGCAGACCAGCATACAAAATAGACACTTCTAAGCCTGGTTCCGA<br>CTTAGCTGCAGAGACTGCAGCTGCATTAGCAGCCACAGCTATTGCATACA<br>AATCTGCCGATGCAACATATTCCAACAATTTGATAACACATGCAAAACAA<br>TTATTCGACTTTGCCAACAATTACAGAGGAAAATATTCCGATAGTATTACC<br>GATGCCAAGAACTTTTATGCTTCTGGTGATTACAAAGACGAATTGGTATGG<br>GCCGCTGCATGGTTGTACAGAGCAACCAATGACAACACATATTTGACTAA<br>GGCAGAATCCTTATACAATGAATTTGGTTTGGGAAACTTCAATGGTGCCTT<br>CAATTGGGATAACAAAGTCTCCGGAGTCCAGGTGTTATTGGCCAAGTTAA<br>CCTCAAAACAAGTGTATAAGGATAAGGTACAGTCTTACGTGGACTATTTG<br>ATCTCCTCACAAAAAAAGACACCAAAAGGTTTAGTGTACATCGATCAATG<br>GGGTACTTTAAGACACGCAGCTAATTCTGCTTTGATCGCTTTGCAGGCAGC<br>TGACTTAGGAATTAACGCTGCTACTTACAGAGCCTACGCAAAGAAGCAAA<br>TCGACTATGCTTTGGGTGATGGTGGAAGATCCTATGTTATTGGATTTGGGA<br>CCAACCCTCCAGTAAGACCACATCACAGAAGTTCATCTTGCCCAGATGCA<br>CCAGCTGTCTGCGATTGGAACACCTATAACTCCGCTGGTCCAAACGCCCAC<br>GTGTTAACCGGTGCATTGGTTGGAGGACCTGATAGTAATGATAGTTATACC<br>GATGCTCGTTCTGACTACATATCCAACGAAGTGGCAACTGATTACAATGCG<br>GGTTTCCAATCCGCTGTCGCTGGATTATTGAAGGCGGGTGTCTAA<br>(SEQ ID NO: 16) | AB019095<br>MRFPSIFTAVLFAASSALAAYDY<br>KTVLSNSLLFYEAQRSGKLPSDQ<br>KVTWRKDSALNDKGQKGEDLT<br>GGYYDAGDFVKFGFPMAYTVT<br>VLAWGVIDYESAYSAAGALDSG<br>RKALKYGTDYFLKAHTAANEFY<br>GQVGQGDVDHAYWGRPEDMT<br>MSRPAYKIDTSKPGSDLAAETA<br>AALAATAIAYKSADATYSNNLIT<br>HAKQLFDFANNYRGKYSDSITD<br>AKNFYASGDYKDELVWAAAWL<br>YRATNDNTYLTKAESLYNEFGL<br>GNFNGAFNWDNKVSGVQVLLA<br>KLTSKQVYKDKVQSYVDYLISS<br>QKKTPKGLVYIDQWGTLRHAA<br>NSALIALQAADLGINAATYRAY<br>AKKQIDYALGDGGRSYVIGFGT<br>NPPVRPHHRSSSCPDAPAVCDW<br>NTYNSAGPNAHVLTGALVGGPD<br>SNDSYTDARSDYISNEVATDYN<br>AGFQSAVAGLLKAGV (SEQ ID<br>NO: 36) |
| *Neosartorya fischeri* EG | ATGAGATTTCCATCTATTTTCACTGCAGTTTTGTTCGCAGCCAGTTCCGCTT<br>TGGCCCAACAGATCGGGTCCATCGCCGAAAATCATCCTGAGTTGACAACC<br>TATAGATGCTCCTCTCAAGCTGGATGCGTAGCACAGAGTACTTCCGTCGTG<br>TTAGATATTAACGCTCATTGGATTCATCAAAACGGTGCCCAAACAAGTTGC<br>ACTACCTCAAGTGGATTGGACCCTTCATTGTGCCCTGATAAAGTCACCTGT<br>TCTCAGAACTGCGTAGTCGAAGGAATAACCGACTACTCATCTTTTGGTGTG<br>CAAAACTCCGGAGATGCAATGACATTAAGACAGTATCAAGTTCAAAATGG<br>ACAGATCAAAACATTGCGTCCTAGAGTGTACTTGTTAGCTGAGGATGGAA<br>TCAATTACTCCAAATTGCAGTTGTTGAACCAAGAGTTTACTTTCGATGTGG<br>ACGCTTCCAAATTGCCTTGTGGTATGAATGGAGCTTTATATTTGTCAGAAA<br>TGGATGCTTCTGGTGGACGTTCTGCCTTGAACCCAGCGGGTGCCACATATG<br>GAACAGGTTACTGTGATGCCCAGTGCTTCAACCCAGGTCCATGGATAAAT<br>GGAGAAGCAAATACTGCTGGAGCCGGTGCATGTTGCCAAGAGATGGACTT<br>ATGGGAAGCCAACTCCCGTTCTACCATTTTCAGTCCTCACCCATGTACAAC<br>TGCGGGTTTGTATGCCTGTACTGGAGCTGAGTGCTACTCAATCTGTGACGG<br>TTATGGTTGCACTTACAACCCTTATGAATTAGGAGCCAAAGATTACTATGG<br>TTACGGTTTGACTATTGACACCGCAAAGCCAATAACAGTGGTTACTCAGTT<br>TATGACCGCTGATAATACAGCAACCGGTACATTAGCAGAGATCAGAAGAT<br>TATATGTTCAAGATGGTAAAGTAATCGGAAATACAGCCGTGGCCATGACC<br>GAGGCATTTTGTAGTTCTAGTAGAACATTTGAAGAGTTAGGTGGTTTGCAA<br>AGAATGGGAGAAGCTTTAGGTAGAGGAATGGTGCCAGTTTTCTCAATATG<br>GGACGATCCTGGTTTGTGGATGCATTGGTTAGATTCTGACGGTGCAGGACC<br>TTGTGGTAATACTGAAGGTGATCCTGCCTTCATTCAGGCTAACTACCCAAA<br>TACCGCCGTAACATTCTCCAAGGTGAGATGGGGAGATATCGGTTCTACCTA<br>TAGTTCTTAA (SEQ ID NO: 17) | XM_001258277<br>MRFPSIFTAVLFAASSALAQQIG<br>SIAENHPELTTYRCSSQAGCVAQ<br>STSVVLDINAHWIHQNGAQTSC<br>TTSSGLDPSLCPDKVTCSQNCVV<br>EGITDYSSFGVQNSGDAMTLRQ<br>YQVQNGQIKTLRPRVYLLAEDG<br>INYSKLQLLNQEFTFDVDASKLP<br>CGMNGALYLSEMDASGGRSAL<br>NPAGATYGTGYCDAQCFNPGP<br>WINGEANTAGAGACCQEMDLW<br>EANSRSTIFSPHPCTTAGLYACT<br>GAECYSICDGYGCTYNPYELGA<br>KDYYGYGLTIDTAKPITVVTQF<br>MTADNTATGTLAEIRRLYVQDG<br>KVIGNTAVAMTEAFCSSSRTFEE<br>LGGLQRMGEALGRGMVPVFSI<br>WDDPGLWMHWLDSDGAGPCG<br>NTEGDPAFIQANYPNTAVTFSKV<br>RWGDIGSTYSS (SEQ ID NO: 37) |
| *Reticulitermes flavipes* EG | ATGAGATTTCCATCTATTTTCACTGCTGTTTTGTTCGCAGCCTCAAGTGCTT<br>TAGCACAATGGATGCAGATCGGTGGTAAGCAGAAATATCCTGCCTTTAAG<br>CCAGGTGCTAAGTACGGAAGAGGTTATTGTGACGGACAGTGCCCTCACGA<br>CATGAAGGTGTCTAGTGGAAGAGCAAACGTTGACGGATGGAAGCCACAA<br>GACAACGACGAAAATAGTGGAAATGGAAAATTGGGTACATGTTGCTGGGA<br>GATGGATATATGGGAAGGAAACTTAGTGTCCCAAGCCTACACCGTTCACG<br>CTGGTTCCAAGTCCGGACAATATGAGTGTACTGGAACACAATGCGGTGAC<br>ACCGACAGTGGTGAAAGATTCAAGGGAACATGCGATAAAGATGGTTGTGA<br>TTTCGCAAGTTACAGATGGGGAGCTACAGACTATTACGGTCCTGGAAAGA<br>CCGTGGACACCAAACAGCCAATGACAGTCGTGACCCAGTTCATTGGTGAC<br>CCTTTGACTGAGATAAAGAGAGTTTATGTACAAGGAGGAAAAGTCATAAA<br>CAATTCCAAAACATCTAACTTAGGTTCAGTGTACGATTCTTTGACTGAGGC<br>CTTCTGCGATGACACCAAACAGGTTACAGGTGATACAAATGACTTTAAGG<br>CTAAAGGAGGTATGTCTGGATTCTCCAAGAACTTAGACACCCCACAAGTTT<br>TGGTGATGTCTTTATGGGATGACCATACAGCTAATATGTTATGGTTAGATT<br>CTACTTATCCTACCGATAGTACAAAGCCAGGTGCCGCAAGAGGTACTTGT<br>GCCGTCACCTCCGGGGACCCTAAAGATGTGGAATCCAAGCAAGCCAACTC<br>TCAGGTAGTTTACAGTGACATTAAGTTTGGTCCTATTAATTCAACATACAA<br>AGCAAATTAA (SEQ ID NO: 18) | DQ014512<br>MRFPSIFTAVLFAASSALAQWM<br>QIGGKQKYPAFKPGAKYGRGYC<br>DGQCPHDMKVSSGRANVDGWK<br>PQDNDENSGNGKLGTCCWEMD<br>IWEGNLVSQAYTVHAGSKSGQY<br>ECTGTQCGDTDSGERFKGTCDK<br>DGCDFASYRWGATDYYGPGKT<br>VDTKQPMTVVTQFIGDPLTEIKR<br>VYVQGGKVINNSKTSNLGSVYD<br>SLTEAFCDDTKQVTGDTNDFKA<br>KGGMSGFSKNLDTPQVLVMSL<br>WDDHTANMLWLDSTYPTDSTK<br>PGAARGTCAVTSGDPKDVESKQ<br>ANSQVVYSDIKFGPINSTYKAN<br>(SEQ ID NO: 38) |

TABLE 1-continued

Cellulases used in Examples 1-11 as described below.

| Donor organism/ Gene | Codon-Optimized DNA sequence used | Accession number and amino acid sequence |
|---|---|---|
| *Trichoderma reesei* EGI | ATGGTCTCCTTCACCTCCCTGCTGGCCGGCGTTGCCGCTATCTCTGGTGTCC<br>TAGCAGCCCCTGCCGCAGAAGTTGAACCTGTCGCAGTTGAGAAACGTGAG<br>GCCGAAGCAGAAGCTCAACAACCAGGAACATCAACACCAGAAGTCCATC<br>CAAAGTTAACAACCTATAAATGTACTAAGAGTGGAGGGTGTGTAGCGCAG<br>GACACAAGTGTGGTCTTAGACTGGAATTATCGTTGGATGCATGATGCCAAT<br>TATAATTCCTGTACTGTTAACGGCGGTGTTAACACTACGTTATGCCCCGAT<br>GAAGCGACTTGTGGTAAGAATTGTTTTATTGAAGGGGTTGACTACGCCGCT<br>AGTGGTGTTACGACGAGTGGGTCATCCTTGACGATGAATCAATACATGCCT<br>TCTTCTAGTGGTGGGTATTCCTCTGTGTCTCCAAGGCTGTATTTATTGGATT<br>CCGATGGGGAATATGTTATGTTAAAATTAAATGGGCAAGAACTGAGTTTT<br>GATGTGGATCTATCTGCATTACCTTGTGGAGAAAATGGTAGTCTTTATTTA<br>TCACAAATGGACGAAAACGGCGGAGCCAATCAGTACAATACAGCTGGTGC<br>TAATTATGGTTCAGGCTATTGTGATGCTCAATGTCCAGTGCAGACTTGGAG<br>GAATGGCACCTTAAACACATCACATCAAGGATTTTGCTGTAACGAAATGG<br>ACATATTAGAAGGTAATTCAAGAGCTAATGCACTAACTCCGCACTCTTGTA<br>CTGCGACCGCATGTGATTCTGCCGGTTGTGGTTTCAACCCTTATGGTTCTG<br>GTTATAAGAGTTACTACGGTCCGGGAGACACCGTGGATACGTCAAAGACC<br>TTCACTATAATCACTCAGTTTAACACAGATAACGGATCTCCGAGTGGTAAT<br>TTGGTGAGTATTACTAGGAAATATCAGCAGAACGGTGTTGATATTCCGTCC<br>GCGCAGCCAGGCGGTGACACTATATCTAGCTGTCCTTCCGCCAGTGCCTAT<br>GGCGGACTTGCTACAATGGGTAAGGCATTGTCCTCAGGTATGGTCCTAGTA<br>TTTTCTATTTGGAATGATAATTCACAATACATGAATTGGCTGGATTCTGGT<br>AATGCAGGCCCTTGCTCCTCTACAGAAGGTAACCCAAGCAATATACTAGC<br>TAATAACCCAAATACTCATGTTGTCTTTAGTAATATTAGATGGGGCGATAT<br>AGGTAGCACTACGAACAGTACCGCACCTCCTCCTCCACCTGCTAGCTCCAC<br>GACATTTTCCACTACTAGAAGGTCCAGCACTACCAGCTCATCACCATCTTG<br>TACTCAAACCCATTGGGGACAGTGTGGTGGTATAGGTTACAGCGGTTGCA<br>AAACTTGCACATCTGGTACTACATGCCAATACAGTAATGACTATTACTCAC<br>AATGTTAA (SEQ ID NO: 19) | AB003694<br>MVSFTSLLAGVAAISGVLAAPA<br>AEVEPVAVEKREAEAEAQQPGT<br>STPEVHPKLTTYKCTKSGGCVA<br>QDTSVVLDWNYRWMHDANYN<br>SCTVNGGVNTTLCPDEATCGKN<br>CFIEGVDYAASGVTTSGSSLTMN<br>QYMPSSSGGYSSVSPRLYLLDSD<br>GEYVMLKLNGQELSFDVDLSAL<br>PCGENGSLYLSQMDENGGANQ<br>YNTAGANYGSGYCDAQCPVQT<br>WRNGTLNTSHQGFCCNEMDILE<br>GNSRANALTPHSCTATACDSAG<br>CGFNPYGSGYKSYYGPGDTVDT<br>SKTFTIITQFNTDNGSPSGNLVSI<br>TRKYQQNGVDIPSAQPGGDTISS<br>CPSASAYGGLATMGKALSSGM<br>VLVFSIWNDNSQYMNWLDSGN<br>AGPCSSTEGNPSNILANNPNTHV<br>VFSNIRWGDIGSTTNSTAPPPPPA<br>SSTTFSTTRRSSTTSSSPSCTQTH<br>WGQCGGIGYSGCKTCTSGTTCQ<br>YSNDYYSQC (SEQ ID NO: 39) |
| *Aspergillus kawachii* EgA | TTAATTAAAATGAGAATTTCTAACTTGATTGTTGCTGCTTCTGCTGCTACTA<br>TGGTTTCTGCTTTGCCATCTAGACAAATGAAAAAGAGGGATTCTGGTTTTA<br>AATGGGTTGGTACTTCTGAATCTGGTGCTGAATTTGGTTCTGCTTTACCAG<br>GTACTTTGGGTACTGATTATACTTGGCCAGAAACTTCTAAAATTCAAGTTT<br>TGAGAAACAAGGGTATGAACATTTTTAGAATACCATTCTTGATGGAAAGA<br>TTAACTCCAGATGGTTTGACTGGTTCTTTTGCTTCTACTTACTTGTCTGATT<br>TGAAGTCAACTGTTGAATTTGTTACTAATTCTGGTGCTTATGCTGTTTTAGA<br>TCCACATAATTACGGTAGATTCGATGGTTCTATTATTGAATCTACTTCTGAT<br>TTTAAGACTTGGTGGAAAAATGTTGCTACTGAATTTGCTGATAACGATAAG<br>GTTATTTTCGATACAAACAACGAATATCATGATATGGAACAATCTTTGGTT<br>TTGAATTTGAACCAAGCTGCTATTAATGGTATTAGAGCTGCTGGTGCTACT<br>ACTCAATACATTTTCGTTGAAGGTAATGCTTATACTGGTGCTTGGGATTGG<br>ACTACTTACAATGATGATTTGTCTGGTTTAACTGATTCTGAAGATAAGATA<br>ATATACGAAATGCATCAATACTTGGATTCTGATTCTTCTGGTACATCTGAA<br>ACTTGTGTTTCTTCTACTATTGGTAAAGAAAGAATTGAAAAGGCTACTGAA<br>TGGTTGAAAACTAACAACAAGCAAGGTATTATTGGTGAATTTGCAGGTGG<br>TGTTAATTCTGTTTGTGAAGAGGCTGTTGAAGGAATGTTGGCTTATATGTC<br>TGAAAATTCTGATGTTTGGGTTGGTGCTTCTTGGTGGTCTGCTGGTCCATG<br>GTGGGGTACTTACATGTATTCTTTGGAACCAACTGATGGTACTGCTTATTC<br>TACTTATTTGCCAATTTTGGAAAAATACTTCCCATCTGGTGATGCTTCATCA<br>TCTTCATCTGCTTCAGCTTCAGTTGCAGCCGCTACTTCTGCTGTTTCTACTA<br>CTACTACAGCTGCATTTGAACAAACTACTACTCCAGCTACTCAAGTTGAAA<br>TTGCTTCTTCTTCATCTTCATCATCAGCTGTTGCTGCTTCACAAACTACTTT<br>GTCTAAGGTTAAGTCTAAATCTAAATCTCCATGTAAATTGTCATCTGCTAC<br>TTCATCTGCTGTTTCATCAGCTGCTGCAGTTACTACACCTGCAGTTGCAGCT<br>ACAACTCCAGCTGCTGCTCCAACTTCTTCTTCTGTTGCTTTTGCTACTACTT<br>CTGTTTACGTTCCAACTACTACTGCTGCTGCACCATCTCAAGTTTCATCTTC<br>AGCTGCAGCTTCATCTTCAGGTGTTGTTGGTGTTTCTGATCCACAAGGTCC<br>ATCTGCTACTAATTCTGCTGGTGAAGTTAATCAATATTACCAATGTGGTGG<br>TATTAATTGGACTGGTCCAACTGTTTGTGCTTCTCCATATACTTGTAAGGTT<br>CAAAACGATTACTACTATCAATGTGTTGCTGAATTATAAGGCGCGCC (SEQ<br>ID NO: 47) | MRISNLIVAASAATMVSALPSRQ<br>MKKRDSGFKWVGTSESGAEFGS<br>ALPGTLGTDYTWPETSKIQVLR<br>NKGMNIFRIPFLMERLTPDGLTG<br>SFASTYLSDLKSTVEFVTNSGAY<br>AVLDPHNYGRFDGSIIESTSDFK<br>TWWKNVATEFADNDKVIFDTN<br>NEYHDMEQSLVLNLNQAAINGI<br>RAAGATTQYIFVEGNAYTGAW<br>DWTTYNDDLSGLTDSEDKIIYE<br>MHQYLDSDSSGTSETCVSSTIGK<br>ERIEKATEWLKTNNKQGIIGEFA<br>GGVNSVCEEAVEGMLAYMSEN<br>SDVWVGASWWSAGPWWGTYM<br>YSLEPTDGTAYSTYLPILEKYFPS<br>GDASSSSSASASVAAATSAVSTT<br>TTAAFEQTTTPATQVEIASSSSSS<br>SAVAASQTTLSKVKSKSKSPCKL<br>SSATSSAVSSAAAVTTPAVAATT<br>PAAAPTSSSVAFATTSVYVPTTT<br>AAAPSQVSSSAAASSSGVVGVS<br>DPQGPSATNSAGEVNQYYQCGG<br>INWTGPTVCASPYTCKVQNDYY<br>YQCVAE (SEQ ID NO: 52) |
| *Heterodera schachtii* Eng1 | TTAATTAAAATGCATTGGGCTGATGTTGCTTGTTCTAGACCACCATGGCCA<br>AGAGATTCTGTTAAAGCTTTGAAGTGTAATTGGAACGCTAATGTTATTAGA<br>GGTGCTATGGGTGTTGATGAAGGTGGTTATTTGTCTGATGCTAATACTGCT<br>TACAATTTGATGGTTGCTGTTATTGAAGCTGCTATTTCTAATGGTATCTACG<br>TTATTGTTGATTGGCATGCTCATAATGCTCATCCAGATGAAGCTGTTAAAT<br>TCTTTACTAGAATTGCTCAAGCTTATGGTTCTTACTTGCATATTTTGTACGA<br>AGATTTCAATGAACCATTGGATGTTTCTTGGACTGATGTTTTGGTTCCATA<br>CCATAAAAAAGTTATTGCTGCCATTAGAGCTATTGATAAGAAGAACGTTA<br>TTATCTTGGGTACTCCAAAATGGTCACAAGATGTTGATGTTGCTTCTCAAA<br>ATCCAATTAAGGATTACCAAAACTTGATGTACACTTTGCATTTTTACGCTT<br>CATCTCATTTTACATCTGATTTGGGTGCTAAATTGAAAACTGCTGTTAACA | MHWADVACSRPPWPRDSVKAL<br>KCNWNANVIRGAMGVDEGGYL<br>SDANTAYNLMVAVIEAAISNGIY<br>VIVDWHAHNAHPDEAVKFFTRI<br>AQAYGSYLHILYEDFNEPLDVS<br>WTDVLVPYHKKVIAAIRAIDKK<br>NVIILGTPKWSQDVDVASQNPIK<br>DYQNLMYTLHFYASSHFTSDLG<br>AKLKTAVNNGLPVFVTEYGTCE<br>ASGNGNLNTDSMSSWWTLLDS<br>LKISYANWAISDKSEACSALSPG |

TABLE 1-continued

Cellulases used in Examples 1-11 as described below.

| Donor organism/ Gene | Codon-Optimized DNA sequence used | Accession number and amino acid sequence |
|---|---|---|
| | ATGGTTTGCCAGTTTTTGTTACTGAATATGGTACTTGTGAAGCTTCTGGTAATGGTAATTTGAATACTGATTCTATGTCATCTTGGTGGACTTTGTTGGATTCTTTGAAAATTTCTTACGCTAATTGGGCTATTTCTGATAAATCTGAAGCTTGTTCTGCTTTGTCTCCAGGTACTACTGCTGTTAATGTTGGTGTTTCTTCTAGATGGACTTCTTCTGGTAATATGGTTGCTTCTTACTACAAAAAAAAGTCCACTGGTATTTCTTGTTCTGGTAGTTCTTCAGGTTCTTCAAGTGGTTCATCTAGTGGTTCTTCCGGTACATCTTCTGGTTCTAGTGGTTCATCTAGTGGTAGTTCTTCCGGTAGTTCTAGTGGTAGTTCTGGTTCAAGTTCTGGTTCCTCCTCTGGTTCTGGTTCTGCATCTATTTCTGTTGTTCCATCTAATACTTGGAATGGTGGTGGTAGAGTTAATTTTGAAATTAAGAACACTGGTTCTGTTCCATTGTGTGGTGTTGTTTTTTCTGTTTCTTTGCCATCTGGTACTACTTTGGGTGGTTCTTGGAATATGGAATCTGCTGGTTCTGGTCAATATTCTTTACCATCTTGGGTTAGAATTGAAGCTGGTAAATCTTCTAAAGATGCTGGTTTGACTTTTAATGGTAAAGATAAGCCAACTGCTAAAATTGTTACCACCAAGAAGTGCTTATAAGGCGCGCC (SEQ ID NO: 48) | TTAVNVGVSSRWTSSGNMVASYYKKKSTGISCSGSSSGSSSGSSSGSSGTSSGSSGSSSGSSSGSSSGSSGSSSGSSSGSGSASISVVPSNTWNGGGRVNFEIKNTGSVPLCGVVFSVSLPSGTTLGGSWNMESAGSGQYSLPSWVRIEAGKSSKDAGLTFNGKDKPTAKIVTTKKC (SEQ ID NO: 53) |
| *Hypocrea jecorina* (anamorph: *Trichoderma reesei*) Eg2 | TTAATTAAAATGAACAAGTCTGTTGCTCCATTGTTGTTGGCTGCTTCTATTTTGTATGGTGGTGCTGTTGCTCAACAAACTGTTTGGGGTCAATGTGGTGGTATTGGTTGGTCTGGTCCAACTAATTGTGCTCCAGGTTCTGCTTGTTCTACTTTGAATCCATATTATGCTCAATGTATTCCAGGTGCTACTACTATTACTACTTCTACTAGACCACCATCTGGTCCAACAACTACTACTAGAGCTACTTCTACATCTTCTTCTACTCCACCAACTTCATCTGGTGTTAGATTTGCTGGTGTTAACATTGCTGGTTTTGATTTTGGTTGTACTACTGATGGTACTTGTGTTACTTCTAAAGTTTACCCACCATTGAAAAATTTCACTGGTTCTAACAATTATCCAGATGGTATTGGTCAAATGCAACATTTTGTTAACGAAGATGGTATGACTATTTTTAGATTGCCAGTTGGTTGGCAATATTTGGTTAACAACAATTTGGGTGGTAATTTGGATTCTACTTCTATTTCTAAGTACGATCAATTGGTTCAAGGTTGTTTGTCTTTGGGTGCTTACTGTATTGTTGATATTCATAATTATGCTAGATGGAATGGTGGTATTATTGGTCAAGGTGGTCCAACAAATGCTCAATTTACTTCTTTGTGGTCACAATTGGCTTCAAAATATGCTTCTCAATCTAGAGTTTGGTTTGGTATTATGAATGAACCACATGATGTTAACATTAATACTTGGGCTGCTACTGTTCAAGAAGTTGTTACTGCTATTAGAAATGCTGGTGCTACTTCTCAATTCATTTCTTTGCCAGGTAATGATTGGCAATCTGCTGGTGCTTTTATTTCTGATGGTTCTGCTGCTGCTTTGTCTCAAGTTACTAATCCAGATGGTTCTACTACTAATTTGATCTTCGATGTTCATAAGTACTTGGATTCTGATAATTCTGGTACTCATGCTGAATGTACTACAAACAATATTGATGGTGCTTTTTCTCCATTGGCTACTTGGTTGAGACAAAACAATAGACAAGCTATTTTGACTGAAACTGGTGGTGGTAATGTTCAATCTTGTATCCAAGATATGTGCCAACAAATTCAATACTTGAACCAAAATTCTGATGTTTATTTGGGTTACGTTGGTTGGGGTGCTGGTTCTTTTGATTCTACTTACGTTTTAACTGAAACTCCAACTTCTTCTGGTAATTCTTGGACTGATACTTCTTTGGTTTCTTCATGTTTGGCTAGAAAGTTATAAGGCGCGCC (SEQ ID NO: 49) | MNKSVAPLLLAASILYGGAVAQQTVWGQCGGIGWSGPTNCAPGSACSTLNPYYAQCIPGATTITTSTRPPSGPTTTTRATSTSSSTPPTSSGVRFAGVNIAGFDFGCTTDGTCVTSKVYPPLKNFTGSNNYPDGIGQMQHFVNEDGMTIFRLPVGWQYLVNNNLGGNLDSTSISKYDQLVQGCLSLGAYCIVDIHNYARWNGGIIGQGGPTNAQFTSLWSQLASKYASQSRVWFGIMNEPHDVNINTWAATVQEVVTAIRNAGATSQFISLPGNDWQSAGAFISDGSAAALSQVTNPDGSTTNLIFDVHKYLDSDNSGTHAECTTNNIDGAFSPLATWLRQNNRQAILTETGGGNVQSCIQDMCQQIQYLNQNSDVYLGYVGWGAGSFDSTYVLTETPTSSGNSWTDTSLVSSCLARK (SEQ ID NO: 54) |
| *Orpinomyces* sp.PC-2 CelB | TTAATTAAAATGAAGTTCTTGAACTCTTTGTCTTTGTTGGGTTTGGTTATTGCTGGTTGTGAAGCTATGAGAAACATTTCTTCTAAAGAATTGGTTAAAGAATTGACTATTGGTTGGTCTTTGGGTAATACTTTGGATGCTTCTTGTGTTGAAACTTTGAACTACTCTAAAGATCAAACTGCTTCTGAAACTTGTTGGGGTAATGTTAAAACTACTCAAGAATTGTACTACAAATTGTCTGATTTGGGTTTCAATACTTTCAGAATACCAACTACTTGGTCTGGTCATTTTGGTGATGCTCCAGATTACAAAATTTCTGATGTTTGGATGAAAAGAGTTCACGAAGTTGTTGATTATGCTTTGAATACTGGTGGTTACGCTATTTTGAACATTCATCATGAAACTTGGAATTACGCTTTTCAAAAGAATTTGGAATCTGCTAAAAAGATTTTGGTTGCTATTTGGAAACAAATTGCTGCTGAATTTGGTGATTACGATGAACATTTGATTTTTGAAGGTATGAATGAACCAAGAAAAGTTGGTGATCCAGCTGAATGGACTGGTGGTGATCAAGAAGGTTGGAATTTTGTTAATGAAATGAACGCTTTGTTCGTTAAAACTATTAGAGCTACTGGTGGTAACAATGCTAATAGACATTTGATGATTCCAACTTATGCTGCTTCTGTTAATGATGGTTCTATTAACAATTTTAAGTACCCAAATGGTGATGATAAAGTTATTGTTTCTTTGCATTCTTACTCTCCATACAATTTTGCTTTGAACAATGGTCCAGGTGCTATTTCTAATTTCTACGATGGTAACGAAATTGATTGGGTTATGAACACTATTAACTCTTCATTCATTTCTAAGGGTATTCCAGTTATTATTGGTGAATTTGTTGCTATGAACAGAGATAATGAAGATGATAGAGAAAGATGGCAAGAATACTACATTAAAAAGGCTACTGCTTTGGGTATTCCATGTGTTATTTGGGATAATGGTTATTTTGAAGGTGAAGGTGAAAGATTTGGTATTATTGATAGAAAGTCTTTGAACGTTATTTTCCCAAAGTTGATTAATGGTTTGATGAAAGGTTTGGGTGATGAAAAACCAAAAACTACTATTAGAAGAACTACTACTACTACAGTTCAAGTTCAACCAACTATTAACAACGAATGTTTCTCTACTAGATTGGGTTATTCTTGTTGTAATGGTTTCGATGTTTTGTACACTGATAATGATGGTCAATGGGGTGTTGAAAATGGTAATTGGTGTGGTATTAAATCTTCTTGTGGTAACAATCAAAGACAATGTTGGTCTGAAAGATTAGGTTATCCATGTTGTCAATACACTACTAATGCTGAATATACAGACAACGACGGTAGATGGGGTGTAGAAAACGGTAACTGGTGCGGAATATACTTGTAAGGCGCGCC (SEQ ID NO: 50) | MKFLNSLSLLGLVIAGCEAMRNISSKELVKELTIGWSLGNTLDASCVETLNYSKDQTASETCWGNVKTTQELYYKLSDLGFNTFRIPTTWSGHFGDAPDYKISDVWMKRVHEVVDYALNTGGYAILNIHHETWNYAFQKNLESAKKILVAIWKQIAAEFGDYDEHLIFEGMNEPRKVGDPAEWTGGDQEGWNFVNEMNALFVKTIRATGGNNANRHLMIPTYAASVNDGSINNFKYPNGDDKVIVSLHSYSPYNFALNNGPGAISNFYDGNEIDWVMNTINSSFISKGIPVIIGEFVAMNRDNEDDRERWQEYYIKKATALGIPCVIWDNGYFEGEGERFGIIDRKSLNVIFPKLINGLMKGLGDEKPKTTIRRTTTTTVQVQPTINNECFSTRLGYSCCNGFDVLYTDNDGQWGVENGNWCGIKSSCGNNQRQCWSERLGYPCCQYTTNAEYTDNDGRWGVENGNWCGIY (SEQ ID NO: 55) |

TABLE 1-continued

Cellulases used in Examples 1-11 as described below.

| Donor organism/ Gene | Codon-Optimized DNA sequence used | Accession number and amino acid sequence |
|---|---|---|
| *Irpex lacteus* En1 | TTAATTAAAATGAAGTCTTTGTTGTTGTCTGCTGCTGCTACTTTGGCTTTAT<br>CTACTCCAGCTTTTTCTGTTTCTGTTTGGGGTCAATGTGGTGGTATTGGTTT<br>TACTGGTTCTACTACTTGTGATGCTGGTACTTCTTGTGTTCATTTGAACGAT<br>TACTACTTTCAATGTCAACCAGGTGCTGCTACTTCTACTGTTCAACCAACT<br>ACTACTGCTTCTTCTACTTCTTCTGCTGCAGCTCCATCTTCTTCAGGTAATG<br>CTGTTTGTTCTGGTACTAGAAACAAGTTTAAGTTCTTCGGTGTTAATGAAT<br>CTGGTGCTGAATTTGGTAACAATGTTATTCCAGGTACTTTGGGTACTGATT<br>ATACTTGGCCATCTCCATCTTCTATTGATTTTTTCGTTGGTAAGGGTTTTAA<br>TACTTTCAGAGTTCCATTTTTGATGGAAAGATTGTCTCCACCTGCTACTGGT<br>TTGACTGGTCCATTTGATTCTACTTATTTGCAAGGTTTGAAAACTATTGTTT<br>CTTACATTACTGGTAAAGGTGGTTATGCTTTGGTTGATCCACATAACTTTA<br>TGATTTACAACGGTGCTACTATTTCTGATACTAATGCTTTTCAAACTTGGTG<br>GCAAAATTTGGCTGCTCAATTTAAGACTGATTCTCATGTTGTTTTCGATGTT<br>ATGAATGAACCACATGATATTCCAGCTCAAACTGTTTTTAACTTGAACCAA<br>GCTGCTATTAATAGAATTAGAGCTTCTGGTGCTACTTCTCAATCTATTTTGG<br>TTGAAGGTACTTCTTATACTGGTGCTTGGACTTGGACTACTACTTCTGGTA<br>ATTCTCAAGTTTTTGGTGCTATTCATGATCCAAACAACAATGTTGCTATTG<br>AAATGCATCAATACTTGGATTCTGATGGTTCTGGTACTTCTCCAACTTGTG<br>TTTCTCCAACTATTGGTGCTGAAAGATTGCAAGCTGCTACTCAATGGTTGC<br>AACAAAACAATTTGAAAGGTTTCTTGGGTGAAATTGGTGCTGGTTCTAATG<br>CTGATTGTATTTCTGCTGTTCAAGGTGCTTTGTGTGAAATGCAACAATCTG<br>ATGTTTGGTTGGGTGCTTTGTGGTGGGCTGCTGGTCCATGGTGGGGTGATT<br>ATTTTCAATCTATTGAACCACCATCTGGTGTTGCTGTTTCTTCTATTTTGCC<br>ACAAGCTTTGGAACCATTTTTGTTATAAGGCGCGCC (SEQ ID NO: 51) | MKSLLLSAAATLALSTPAFSVSV<br>WGQCGGIGFTGSTTCDAGTSCV<br>HLNDYYFQCQPGAATSTVQPTT<br>TASSTSSAAAPSSSGNAVCSGTR<br>NKFKFFGVNESGAEFGNNVIPGT<br>LGTDYTWPSPSSIDFFVGKGFNT<br>FRVPFLMERLSPPATGLTGPFDS<br>TYLQGLKTIVSYITGKGGYALV<br>DPHNFMIYNGATISDTNAFQTW<br>WQNLAAQFKTDSHVVFDVMNE<br>PHDIPAQTVFNLNQAAINRIRAS<br>GATSQSILVEGTSYTGAWTWTT<br>TSGNSQVFGAIHDPNNNVAIEM<br>HQYLDSDGSGTSPTCVSPTIGAE<br>RLQAATQWLQQNNLKGFLGEIG<br>AGSNADCISAVQGALCEMQQSD<br>VWLGALWWAAGPWWGDYFQS<br>IEPPSGVAVSSILPQALEPFL (SEQ<br>ID NO: 56) |
| | β-Glucosidases | |
| S.f.BGLI | ATGGTCTCCTTCACCTCCCTCCTCGCCGGCGTCGCCGCCATCTCGGGCGTC<br>TTGGCCGCTCCCGCCGCCGAGGTCGAATCCGTGGCTGTGGAGAAGCGCTC<br>GGACTCGCGAGTCCCAATTCAAAACTATACCCAGTCTCCATCCCAGAGAG<br>ATGAGAGCTCCCAATGGGTGAGCCCGCATTATTATCCAACTCCACAAGGT<br>GGTAGGCTCCAAGACGTCTGGCAAGAAGCATATGCTAGAGCAAAAGCCAT<br>CGTTGGCCAGATGACTATTGTTGAAAAGGTCAATTTGACCACTGGTACCGG<br>TTGGCAATTAGATCCATGTGTTGGTAATACCGGTTCTGTTCCAAGATTCGG<br>CATCCCAAACCTTTGCCTACAAGATGGGCCATTGGGTGTTCGATTCGCTGA<br>CTTTGTTACTGGCTATCCATCCGGTCTTGCTACTGGTGCAACGTTCAATAA<br>GGATTTGTTTCTTCAAAGAGGTCAAGCTCTCGGTCATGAGTTCAACAGCAA<br>AGGTGTACATATTGCGTTGGGCCCTGCTGTTGGCCCACTTGGTGTCAAAGC<br>CAGAGGTGGCAGAAATTTCGAAGCCTTTGGTTCCGACCCATATCTCCAAG<br>GTACTGCTGCTGCTGCAACCATCAAAGGTCTCCAAGAGAATAATGTTATG<br>GCTTGTGTCAAGCACTTTATTGGTAACGAACAAGAAAAGTACAGACAGCC<br>AGATGACATAAACCCTGCCACCAACCAAACTACTAAAGAAGCTATTAGTG<br>CCAACATTCCAGACAGAGCCATGCATGAGTTGTACTTGTGGCCATTTGCCG<br>ATTCGGTTCGAGCAGGTGTTGGTTCTGTTATGTGCTCTTATAACAGAGTCA<br>ACAACACTTACGCTTGCGAAAACTCTTACATGATGAACCACTTGCTTAAAG<br>AAGAGTTGGGTTTTCAAGGCTTTGTTGTTTCGGACTGGGGTGCACAATTAA<br>GTGGGGTTTATAGCGCTATCTCGGGCTTAGATATGTCTATGCCTGGTGAAG<br>TGTATGGGGGATGGAACACCGGCACGTCTTTCTGGGGTCAAAACTTGACG<br>AAAGCTATTTACAATGAGACTGTTCCGATTGAAAGATTAGATGATATGGC<br>AACCAGGATCTTGGCTGCTTTGTATGCTACCAATAGTTTCCCAACAGAAGA<br>TCACCTTCCAAATTTTTCTTCATGGACAACGAAAGAATATGGCAATAAATA<br>TTATGCTGACAACACTACCGAGATTGTCAAAGTCAACTACCATGTGGACCC<br>ATCAAATGACTTTACGGAGGACACAGCTTTGAAGGTTGCTGAGGAATCTA<br>TTGTGCTTTTAAAAAATGAAAACAACACTTTGCCAATTTCTCCCGAAAAGG<br>CTAAAAGATTACTATTGTCGGGTATTGCTGCAGGCCCTGATCCGATAGGTT<br>ATCAGTGTGAAGATCAATCTTGCACAAATGGCGCTTTGTTTCAAGGTTGGG<br>GTTCTGGCAGTGTTGGTTCTCCAAAATATCAAGTCACTCCATTTGAGGAAA<br>TTTCTTATCTTGCAAGAAAAAACAAGATGCAATTTGATTATATTCGGGAGT<br>CTTACGACTTAGCTCAAGTTACTAAAGTAGCTTCCGATGCTCATTTGTCTA<br>TAGTTGTTGTCTCTGCTGCAAGCGGTGAGGGTTATATAACCGTTGACGGTA<br>ACCAAGGTGACAGAAGAAATCTCACTTTGTGGAACAACGGTGATAAATTG<br>ATTGAAACAGTTGCTGAAAACTGTGCCAATACTGTTGTTGTTGTTACTTCT<br>ACTGGTCAAATTAATTTTGAAGGCTTTGCTGATCACCCAAATGTTACCGCA<br>ATTGTCTGGGCCGGCCCATTAGGTGACAGATCCGGGACTGCTATCGCCAAT<br>ATTCTTTTTGGTAAAGCGAACCCATCAGGTCATCTTCCATTCACTATTGCTA<br>AGACTGACGATGATTACATTCCAATTGAAACCTACAGTCCATCGAGTGGT<br>GAACCTGAAGACAACCACTTGGTTGAAAATGACTTGCTTGTTGACTATAG<br>ATATTTTGAAGAGAAGAATATTGAGCCAAGATACGCATTTGGTTATGGCTT<br>GTCTTACAATGAGTATGAAGTTAGCAATGCAAAGGTCTCGGCAGCCAAAA<br>AAGTTGATGAGGAGTTGCCTGAACCAGCTACCTACTTATCGGAGTTTAGCT<br>ATCAAAATGCAAAAGACAGCAAAAATCCAAGTGATGCTTTTGCTCCAACA<br>GATTTAAACAGAGTTAATGAGTACCTTTATCCATATTTAGATAGCAATGTT<br>ACCTTAAAAGACGGAAACTATGAGTATCCCGATGGCTACAGCACTGAGCA<br>AAGAACAACACCTATCCAACCTGGGGGCGGCTTGGGAGGCAACGATGCTT | FJ028723<br>MVSFTSLLAGVAAISGVLAAPA<br>AEVESVAVEKRSDSRVPIQNYT<br>QSPSQRDESSQWVSPHYYPTPQ<br>GGRLQDVWQEAYARAKAIVGQ<br>MTIVEKVNLTTGTGWQLDPCVG<br>NTGSVPRFGIPNLCLQDGPLGVR<br>FADFVTGYPSGLATGATFNKDL<br>FLQRGQALGHEFNSKGVHIALG<br>PAVGPLGVKARGGRNFEAFGSD<br>PYLQGTAAAATIKGLQENNVMA<br>CVKHFIGNEQEKYRQPDDINPAT<br>NQTTKEAISANIPDRAMHELYL<br>WPFADSVRAGVGSVMCSYNRV<br>NNTYACENSYMMNHLLKEELG<br>FQGFVVSDWGAQLSGVYSAISG<br>LDMSMPGEVYGGWNTGTSFWG<br>QNLTKAIYNETVPIERLDDMATR<br>ILAALYATNSFPTEDHLPNFSSW<br>TTKEYGNKYYADNTTEIVKVNY<br>HVDPSNDFTEDTALKVAEESIVL<br>LKNENNTLPISPEKAKRLLLSGIA<br>AGPDPIGYQCEDQSCTNGALFQ<br>GWGSGSVGSPKYQVTPFEEISYL<br>ARKNKMQFDYIRESYDLAQVTK<br>VASDAHLSIVVVSAASGEGYITV<br>DGNQGDRRNLTLWNNGDKLIET<br>VAENCANTVVVVTSTGQINFEG<br>FADHPNVTAIVWAGPLGDRSGT<br>AIANILFGKANPSGHLPFTIAKTD<br>DDYIPIETYSPSSGEPEDNHLVEN<br>DLLVDYRYFEEKNIEPRYAFGY<br>GLSYNEYEVSNAKVSAAKKVDE<br>ELPEPATYLSEFSYQNAKDSKNP<br>SDAFAPTDLNRVNEYLYPYLDS<br>NVTLKDGNYEYPDGYSTEQRTT<br>PIQPGGGLGGNDALWEVAYKVE<br>VDVQNLGNSTDKFVPQLYLKHP<br>EDGKFETPIQLRGFEKVELSPGE<br>KKTVEFELLRRDLSVWDTTRQS<br>WIVESGTYEALIGVAVNDIKTSV<br>LFTI (SEQ ID NO: 40) |

TABLE 1-continued

Cellulases used in Examples 1-11 as described below.

| Donor organism/ Gene | Codon-Optimized DNA sequence used | Accession number and amino acid sequence |
|---|---|---|
| | TGTGGGAGGTCGCTTATAAAGTTGAAGTGGACGTTCAAAACTTGGGTAAC TCCACTGATAAGTTTGTTCCACAGTTGTATTTGAAACACCCTGAGGATGGC AAGTTTGAAACCCCTATTCAATTGAGAGGGTTTGAAAAGGTTGAGTTGTCC CCGGGTGAGAAGAAGACAGTTGAGTTTGAGCTTTTGAGAAGAGATCTTAG TGTGTGGGATACCACCAGACAGTCTTGGATCGTTGAATCTGGTACTTATGA GGCCTTAATTGGTGTTGCTGTTAATGATATCAAGACATCTGTCCTGTTTACT ATT (SEQ ID NO: 20) | |

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 80%, 85%, 90%, 95%, 96%, 97%, 98%, 99% similar to the polypeptide of any of SEQ ID NOs: 21-40, 46, or 52-56 and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide of any of SEQ ID NOs: 21-40, 46, or 52-56.

Fragments or portions of the polypeptides of the present invention may be employed for producing the corresponding full-length polypeptide by peptide synthesis. Therefore, the fragments may be employed as intermediates for producing the full-length polypeptides.

Fragments of cellobiohydrolase, endoglucanase or beta-glucosidase polypeptides encompass domains, proteolytic fragments, deletion fragments and in particular, fragments of *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase polypeptides which retain any specific biological activity of the cellobiohydrolase, endoglucanase or beta-glucosidase proteins. Polypeptide fragments further include any portion of the polypeptide which retains a catalytic activity of cellobiohydrolase, endoglucanase or beta-glucosidase proteins.

The variant, derivative or analog of the polypeptide of any of SEQ ID NOs: 21-40, 46, or 52-56, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase protein.

The allelic variants, the conservative substitution variants, and members of the endoglucanase, cellobiohydrolase or β-glucosidase protein families, can have an amino acid sequence having at least 75%, at least 80%, at least 90%, at least 95% amino acid sequence identity with a *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Aspergil-*

*lus kawachii, Heterodera schachtii, H. jecorina, Orpinomyces* sp., *Irpex lacteus, Acremonium thermophilum, R. flavipes*, or *Neosartorya fischeri* cellobiohydrolase, endoglucanase or beta-glucosidase amino acid sequence set forth in any one of SEQ ID NOs: 21-40, 46, or 52-56. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the proteins and peptides of the present invention include molecules comprising the amino acid sequence of SEQ ID NOs: 21-40, 46 and 52-56 or fragments thereof having a consecutive sequence of at least about 3, 4, 5, 6, 10, 15, 20, 25, 30, 35 or more amino acid residues of the *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Aspergillus kawachii, Heterodera schachtii, H. jecorina, Orpinomyces* sp., *Irpex lacteus, Acremonium thermophilum, R. flavipes*, or *Neosartorya fischeri* cellobiohydrolase, endoglucanase or beta-glucosidase polypeptide sequences; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to bacterial, fungal, insect, rabbit, rat, porcine, bovine, ovine, equine and non-human primate species, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the cellulase polypeptides. For instance, one or more amino acids can be deleted from the N-terminus or C-terminus of the secreted protein without substantial loss of biological function.

Thus, the invention further includes *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes* or *Arabidopsis thaliana* cellobiohydrolase, endoglucanase or beta-glucosidase polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase polypeptide, but retaining essential properties thereof. Generally, derivatives and analogs are overall closely similar, and, in many regions, identical to the *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum,*

*Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase polypeptides. The terms "derivative" and "analog" when referring to *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes* or *Arabidopsis thaliana* cellobiohydrolase, endoglucanase or beta-glucosidase polypeptides include any polypeptides which retain at least some of the activity of the corresponding native polypeptide, e.g., the exoglucanase activity, or the activity of the catalytic domain.

Derivatives of *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase polypeptides, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *H. grisea, T. aurantiacus, T. emersonii, T. reesei, C. lacteus, C. formosanus, N. takasagoensis, C. acinaciformis, M. darwinensis, N. walkeri, S. fibuligera, C. lucknowense, R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellobiohydrolase, endoglucanase or beta-glucosidase polypeptide of the present invention. An "analog" also retains substantially the same biological function or activity as the polypeptide of interest, e.g., functions as a cellobiohydrolase. An analog includes a proprotein which can be activated by cleavage of the proprotein portion to produce an active mature polypeptide.

The polypeptide of the present invention may be a recombinant polypeptide, a natural polypeptide or a synthetic polypeptide. In some particular embodiments, the polypeptide is a recombinant polypeptide.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-40, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

Consensus Sequence Cellulases

In some embodiments of the present invention, the host cells express at least one heterologous cellulase that is not derived from any one particular organism, but instead has an artificial amino acid sequence that is a consensus cellulase sequence. The consensus cellulase sequence can be an endoglucanase consensus sequence, a β-glucosidase consensus sequence, or a cellobiohydrolase consensus sequence.

In one particular embodiment, the heterologous cellulase is a CBH1 consensus sequence. Therefore, in one embodiment, the invention is directed to a polypeptide sequence which comprises a sequence that is at least 80%, 85%, 90%, 95%, 98% or 99% identical to the consensus CBH1 sequence of SEQ ID NO: 43. In some embodiments, the invention is directed to a polypeptide which comprises the sequence of SEQ ID NO: 43.

The invention is also directed to host cells that comprise a polypeptide sequence which comprises a sequence that is at least 80%, 85%, 90%, 95%, 98% 99% or 100% identical to the consensus CBH1 sequence of SEQ ID NO: 43. The invention further directed to host cells that comprise a polynucleotide that encodes a polypeptide sequence which comprises a sequence that is at least 80%, 85%, 90%, 95%, 98% 99% or 100% identical to the consensus CBH1 sequence of SEQ ID NO: 43. In some embodiments the host cell comprises at least one polynucleotide that encodes a polypeptide sequence which comprises a sequence that is at least 80%, 85%, 90%, 95%, 98%, 99% or 100% identical to the consensus CBH1 sequence of SEQ ID NO: 43 and at least a second polynucleotide that encodes a heterologous cellulase. The second polynucleotide can encode a endoglucanase, a β-glucosidase, a cellobiohydrolase, an endoglucanase consensus sequence, a β-glucosidase consensus sequence, or a cellobiohydrolase consensus sequence. In some embodiments the host cell comprising the polynucleotide that encodes a polypeptide sequence which comprises a sequence that is at least 80%, 85%, 90%, 95%, 98%, 99%, or 100% identical to the consensus CBH1 sequence of SEQ ID NO: 43 is capable of producing ethanol when grown using cellulose as a carbon source.

Combinations of Cellulases

In some embodiments of the present invention the host cells express a combination of heterologous cellulases. For example, the host cell can contain at least two heterologous cellulases, at least three heterologous cellulases, at least four heterologous cellulases, at least five heterologous cellulases, at least six heterologous cellulases, at least seven heterologous cellulases, at least eight heterologous cellulases, at least nine heterologous cellulases, at least ten heterologous cellulases, at least eleven heterologous cellulases, at least twelve heterologous cellulases, at least thirteen heterologous cellulases, at least fourteen heterologous cellulases or at least fifteen heterologous cellulases. The heterologous cellulases in the host cell can be from the same or from different species.

In some embodiments of the present invention, the host cells express a combination of heterologous cellulases which includes at least one endoglucanase, at least one β-glucosidase and at least one cellobiohydrolase. In another embodiment of the invention, the host cells express a combination of heterologous cellulases which includes at least one endoglucanase, at least one β-glucosidase and at least two cellobiohydrolases. The at least two cellobiohydrolases can be both be cellobiohydrolase I, can both be cellobiohydrolase II, or can be one cellobiohydrolase I and one cellobiohydrolase II.

In one particular embodiment of the invention, the host cells express a combination of cellulases that includes a *C. formosanus* endoglucanase I and an *S. fibuligera* β-glucosidase I. In another embodiment of the invention, the host cells express a combination of cellulases that includes a *T. emersonii* cellobiohydrolase I, and a *T. reesei* cellobiohydrolase II.

In yet another embodiment the host cells express a combination of cellulases that includes a *C. formosanus* endoglucanase I, an *S. fibuligera* β-glucosidase I, a *T. emersonii* cellobiohydrolase I, and a *C. lucknowense* cellobiohydrolase IIb. In still another embodiment, the host cells express a combination of cellulases that includes a *C. formosanus* endoglucanase I, an *S. fibuligera* β-glucosidase I, a *T. emersonii* cellobiohydrolase I, and a *T. reesei* cellobiohydrolase II. In still another embodiment, the host cells express a combination of cellulases that includes an *H. jecorina* endogluconase 2, an *S. fibuligera* β-glucosidase I, a *T. emersonii* cellobiohydrolase I, and a *T. reesei* cellobiohydrolase II. In still another embodiment, the host cells express a combination of cellulases that includes an *H. jecorina* endogluconase 2, an *S. fibuligera* β-glucosidase I, a *T. emersonii* cellobiohydrolase I, and a *C. lucknowense* cellobiohydrolase II.

Tethered and Secreted Cellulases

According to the present invention, the cellulases may be either tethered or secreted. As used herein, a protein is "tethered" to an organism's cell surface if at least one terminus of the protein is bound, covalently and/or electrostatically for example, to the cell membrane or cell wall. It will be appreciated that a tethered protein may include one or more enzymatic regions that may be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering may, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein maybe tethered at its amino terminal end or optionally at its carboxy terminal end.

As used herein, "secreted" means released into the extracellular milieu, for example into the media. Although tethered proteins may have secretion signals as part of their immature amino acid sequence, they are maintained as attached to the cell surface, and do not fall within the scope of secreted proteins as used herein.

As used herein, "flexible linker sequence" refers to an amino acid sequence which links two amino acid sequences, for example, a cell wall anchoring amino acid sequence with an amino acid sequence that contains the desired enzymatic activity. The flexible linker sequence allows for necessary freedom for the amino acid sequence that contains the desired enzymatic activity to have reduced steric hindrance with respect to proximity to the cell and may also facilitate proper folding of the amino acid sequence that contains the desired enzymatic activity.

In some embodiments of the present invention, the tethered cellulase enzymes are tethered by a flexible linker sequence linked to an anchoring domain. In some embodiments, the anchoring domain is of CWP2 (for carboxy terminal anchoring) or FLO1 (for amino terminal anchoring) from *S. cerevisiae.*

In some embodiments, heterologous secretion signals may be added to the expression vectors of the present invention to facilitate the extra-cellular expression of cellulase proteins. In some embodiments, the heterologous secretion signal is the secretion signal from *T. reesei* Xyn2.

Fusion Proteins Comprising Cellulases

The present invention also encompasses fusion proteins. For example, the fusion proteins can be a fusion of a heterologous cellulase and a second peptide. The heterologous cellulase and the second peptide can be fused directly or indirectly, for example, through a linker sequence. The fusion protein can comprise for example, a second peptide that is N-terminal to the heterologous cellulase and/or a second peptide that is C-terminal to the heterologous cellulase. Thus, in certain embodiments, the polypeptide of the present invention comprises a first polypeptide and a second polypeptide, wherein the first polypeptide comprises a heterologous cellulase.

According to the present invention, the fusion protein can comprise a first and second polypeptide wherein the first polypeptide comprises a heterologous cellulase and the second polypeptide comprises a signal sequence. According to another embodiment, the fusion protein can comprise a first and second polypeptide, wherein the first polypeptide comprises a heterologous cellulase and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, a MYC-tag, or a fluorescent protein.

According to yet another embodiment, the fusion protein can comprise a first and second polypeptide, wherein the first polypeptide comprises a heterologous cellulase and the second polypeptide comprises an anchoring peptide. In some embodiments, the anchoring domain is of CWP2 (for carboxy terminal anchoring) or FLO1 (for amino terminal anchoring) from *S. cerevisiae.*

According to yet another embodiment, the fusion protein can comprise a first and second polypeptide, wherein the first polypeptide comprises a heterologous cellulase and the second polypeptide comprises a cellulose binding module (CBM). In some embodiments, the CBM is from, for example, *T. reesei* Cbh1 or Cbh2, from *H. grisea* Cbh1, or from *C. lucknowense* Cbh2b. In some particular embodiments, the CBM is fused to a cellobiohydrolase. In one particular embodiment, the fusion protein comprises a first and second polypeptide, wherein the first polypeptide comprises a heterologous cellobiohydrolase and the second polypeptide comprises a CBM. In yet another particular embodiment, the cellobiohydrolase is *T. emersonii* cellobiohydrolase I and the CBM is a *T. reesei* cellobiohydrolase CBM. In yet another particular embodiment, the cellobiohydrolase is *T. emersonii* cellobiohydrolase I and the CBM is a *H. grisea* cellobiohydrolase CBM. In some embodiments, the CBM of *H. grisea* comprises amino acids 492-525 of SEQ ID NO: 21.

In certain embodiments, the polypeptide of the present invention encompasses a fusion protein comprising a first polypeptide and a second polypeptide, wherein the first polypeptide is a cellobiohydrolase, and the second polypeptide is a domain or fragment of a cellobiohydrolase. In certain embodiments, the polypeptide of the present invention encompasses a fusion protein comprising a first polypeptide, where the first polypeptide is a *T. emersonii* Cbh1, *H. grisea* Cbh1, *T. aurantiacusi* Cbh1, *T. emersonii* Cbh2, *T. reesei* Cbh1 *T. reesei* Cbh2, *C. lucknowense* Cbh2b, or domain, fragment, variant, or derivative thereof, and a second polypeptide, where the second polypeptide is a *T. emersonii* Cbh1, *H. grisea* Cbh1, or *T. aurantiacusi* Cbh1, *T. emersonii* Cbh2, *T. reesei* Cbh1 or *T. reesei* Cbh2, *C. lucknowense* Cbh2b, or domain, fragment, variant, or derivative thereof. In particular embodiments the first polypeptide is *T. emersonii* Cbh1 and the second polynucleotide is a CBM from *T. reesei* Cbh1 or Cbh2 or from *C. lucknowense* Cbh2b. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae* or *Kluveromyces*. In particular embodiments, the first polynucleotide is a codon-optimized *T. emersonii* cbh1 and the second polynucleotide encodes for a codon-optimized CBM from *T. reesei* Cbh1 or Cbh2. In another particular embodiments, the first polynucleotide is a codon-optimized *T. emersonii* cbh1 and the second polynucleotide encodes for a codon-optimized CBM from *C. lucknowense* or Cbh2b.

In certain other embodiments, the first polypeptide and the second polypeptide are fused via a linker sequence. The linker sequence can, in some embodiments, be encoded by a codon-optimized polynucleotide. (Codon-optimized polynucleotides are described in more detail below.) An amino acid sequence corresponding to a codon-optimized linker 1 according to the invention is a flexible linker-strep tag-TEV site-FLAG-flexible linker fusion and corresponds to GGGGSGGGGS AWHPQFGG ENLYFQG DYKDDDK GGGGSGGGGS (SEQ ID NO:57)

The DNA sequence is as follows:

```
                                        (SEQ ID NO: 41)
GGAGGAGGTGGTTCAGGAGGTGGTGGGTCTGCTTGGCAT

CCACAATTTGGAGGAGGCGGTGGTGAAAATCTGTATTTC

CAGGGAGGCGGAGGTGATTACAAGGATGACGACAAAGG

AGGTGGTGGATCAGGAGGTGGTGGCTCC
```

An amino acid sequence corresponding to optimized linker 2 is a flexible linker-strep tag-linker-TEV site-flexible linker and corresponds to GGGGSGGGGS WSHPQFEK GG ENLYFQG GGGGSGGGGS (SEQ ID NO:58). The DNA sequence is as follows:

```
                                        (SEQ ID NO: 42)
ggtggcggtggatctggaggaggcggttcttggtctcacccacaatttga

aaagggtggagaaaacttgtactttcaaggcggtggtggaggttctggcg

gaggtggctccggctca
```

Co-Cultures

The present invention is also directed to co-cultures comprising at least two yeast host cells wherein the at least two yeast host cells each comprise an isolated polynucleotide encoding a heterologous cellulase. As used herein, "co-culture" refers to growing two different strains or species of host cells together in the same vessel. In some embodiments of the invention, at least one host cell of the co-culture comprises a heterologous polynucleotide comprising a nucleic acid which encodes an endoglucanase, at least one host cell of the co-culture comprises a heterologous polynucleotide comprising a nucleic acid which encodes a β-glucosidase and at least one host cell comprises a heterologous polynucleotide comprising a nucleic acid which encodes a cellobiohydrolase. In a further embodiment, the co-culture further comprises a host cell comprising a heterologous polynucleotide comprising a nucleic acid which encodes a second cellobiohydrolase.

The co-culture can comprise two or more strains of yeast host cells and the heterologous cellulases can be expressed in any combination in the two or more strains of host cells. For example, according to the present invention, the co-culture can comprise two strains: one strain of host cells that expresses an endoglucanase and a second strain of host cells that expresses a β-glucosidase, a cellobiohydrolase and a second cellobiohydrolase. According to the present invention, the co-culture can also comprise four strains: one strain of host cells which expresses an endoglucanase, one strain of host cells that expresses a β-glucosidase, one strain of host cells which expresses a first cellobiohydrolase, and one strain of host cells which expressess a second cellobiohydrolase. Similarly, the co-culture can comprise one strain of host cells that expresses two cellulases, for example an endoglucanase and a beta-glucosidase and a second strain of host cells that expresses one or more cellulases, for example one or more cellobiohydrolases. The co-culture can, in addition to the at least two host cells comprising heterologous cellulases, also include other host cells which do not comprise heterologous cellulases.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells may be present in equal or unequal numbers.

The co-cultures of the present invention can include tethered cellulases, secreted cellulases or both tethered and secreted cellulases. For example, in some embodiments of the invention, the co-culture comprises at least one yeast host cell comprising a polynucleotide encoding a secreted heterologous cellulase. In another embodiment, the co-culture comprises at least one yeast host cell comprising a polynucleotide encoding a tethered heterologous cellulase. In one embodiment, all of the heterologous cellulases in the co-culture are secreted, and in another embodiment, all of the heterologous cellulases in the co-culture are tethered. In addition, other cellulases, such as externally added cellulases may be present in the co-culture.

Polynucleotides Encoding Heterologous Cellulases

The present invention also includes isolated polynucleotides encoding cellulases of the present invention. Thus, the polynucleotides of the invention can encode endoglucanases or exoglucanases. The polynucleotides can encode endoglucanases, β-glucosidases or cellobiohydrolases.

In some particular embodiments of the invention, the polynucleotide encodes an endoglucanase which is an endo-1,4-β-glucanase. In particular embodiments, the polynucleotide encodes an endoglucanase I from *Trichoderma reesei*. In certain other embodiments, the endoglucanase is encoded by a polynucleotide comprising a sequence at least about 70, about 80, about 90, about 95, about 96, about 97, about 98, about 99, or 100% identical to SEQ ID NO:19. In particular embodiments, the polynucleotide encodes an endoglucanase I from *C. formosanus*. In certain other embodiments, the endoglucanase is encoded by a polynucleotide comprising a sequence at least about 70, about 80, about 90, about 95, about 96, about 97, about 98, about 99, or 100% identical to SEQ ID NO:11. In particular embodiments, the polynucleotide encodes an endoglucanase I from *Trichoderma reesei*. In certain other embodiments, the endoglucanase is encoded by a polynucleotide comprising a sequence at least about 70, about 80, about 90, about 95, about 96, about 97, about 98, about 99, or 100% identical to SEQ ID NO:19. In particular embodiments, the polynucleotide encodes an endoglucanase 2 from *H. jecorina*. In certain other embodiments, the endoglucanase is encoded by a polynucleotide comprising a sequence at least about 70, about 80, about 90, about 95, about 96, about 97, about 98, about 99, or 100% identical to SEQ ID NO:54.

In certain embodiments, the polynucleotide encodes a β-glucosidase I or a β-glucosidase II isoform, paralogue or orthologue. In certain embodiments of the present invention the polynucleotide encodes a β-glucosidase derived from *Saccharomycopsis fibuligera*. In particular embodiments, the β-glucosidase is encoded by a polynucleotide comprising a sequence at least about 70, about 80, about 90, about 95, about 96, about 97, about 98, about 99, or 100% identical to SEQ ID NO:20.

In certain embodiments of the invention, the polynucleotide encodes a cellobiohydrolase I and/or an cellobiohydrolase II isoform, paralogue or orthologue. In particular embodiments of the present invention, the polynucleotide encodes the cellobiohydrolase I or II from *Trichoderma reesei*. In particular embodiments of the present invention, the polynucleotide encodes the cellobiohydrolase I or II from *Trichoderma emersonii*. In another embodiment, the cellobiohydrolase is encoded by a polynucleotide comprising a sequence at least about 70, about 80, about 90, about 95, about 96, about 97, about 98, about 99, or 100% identical to SEQ ID NO:7 or SEQ ID NO:8. In particular embodiments of the present invention, the polynucleotide encodes a cellobiohydrolase from *C. lucknowense*. In another embodiment, the cellobiohydrolase is encoded by a polynucleotide comprising a sequence at least about 70, about 80, about 90, about 95, about 96, about 97, about 98, about 99, or 100% identical to SEQ ID NO:5.

In further embodiments the polynucleotide is a polypeptide comprising a sequence at least about 70, about 80, about 90, about 95, about 96, about 97, about 98, about 99, or 100% identical to a nucleotide sequence listed in Table 1. In certain aspects the polynucleotide can encode an endoglucanase, cellobiohydrolase or β-glucosidase derived from, for example, a fungal, bacterial, protozoan or termite source.

In certain aspects, the present invention relates to a polynucleotide comprising a nucleic acid encoding a functional or structural domain of *T. emersonii, H. grisea, T. aurantiacus, C. lucknowense* or *T. reesei* Cbh1 or Cbh2. For example, the domains of *T. reesei* Cbh1 include, without limitation: (1) a signal sequence, from amino acid 1 to 33 of SEQ ID NO: 27; (2) a catalytic domain (CD) from about amino acid 41 to about amino acid 465 of SEQ ID NO: 27; and (3) a cellulose binding module (CBM) from about amino acid 503 to about amino acid 535 of SEQ ID NO: 27. The domains of *T. reesei* Cbh 2 include, without limitation: (1) a signal sequence, from amino acid 1 to 33 of SEQ ID NO: 27; (2) a catalytic domain (CD) from about amino acid 145 to about amino acid 458 of SEQ ID NO: 27; and (3) a cellulose binding module (CBM) from about amino acid 52 to about amino acid 83 of SEQ ID NO: 27.

The present invention also encompasses an isolated polynucleotide comprising a nucleic acid that is at least about 70%, 75%, or 80% identical, at least about 90% to about 95% identical, or at least about 96%, 97%, 98%, 99% or 100% identical to a nucleic acid encoding a *T. emersonii, H. grisea, T. aurantiacus, C. lucknowense* or *T. reesei* Cbh1 or Cbh2 domain, as described above.

The present invention also encompasses variants of the cellulase genes, as described above. Variants may contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, and *Arabidopsis thaliana* cellulase polynucleotide variants can be produced for a variety of reasons, e.g., to optimize codon expression for a particular host. Codon-optimized polynucleotides of the present invention are discussed further below.

The present invention also encompasses an isolated polynucleotide encoding a fusion protein. In certain embodiments, the nucleic acid encoding a fusion protein comprises a first polynucleotide encoding for a *T. emersonii* cbh1, *H. grisea* cbh1, *T. aurantiacusi* cbh1 or *T. emersonii* cbh1 and a second polynucleotide encoding for the CBM domain of *T. reesei* cbh1 or *T. reesei* cbh2 or *C. lucknowense* cbh2b. In particular embodiments of the nucleic acid encoding a fusion protein, the first polynucleotide encodes *T. emersonii* cbh1 and the second polynucleotide encodes for a CBM from *T. reesei* Cbh1 or Cbh2.

In further embodiments, the first and second polynucleotides are in the same orientation, or the second polynucleotide is in the reverse orientation of the first polynucleotide. In additional embodiments, the first polynucleotide encodes a polypeptide that is either N-terminal or C-terminal to the polypeptide encoded by the second polynucleotide. In certain other embodiments, the first polynucleotide and/or the second polynucleotide are encoded by codon-optimized polynucleotides, for example, polynucleotides codon-optimized for *S. cerevisiae, Kluyveromyces* or for both *S. cerevisiae* and *Kluyveromyces*. In particular embodiments of the nucleic acid encoding a fusion protein, the first polynucleotide is a codon-optimized *T. emersonii* cbh1 and the second polynucleotide encodes for a codon-optimized CBM from *T. reesei* Cbh1 or Cbh2.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-20, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of any of SEQ ID NOs:1-20, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs:1-20, or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded can be the coding strand or non-coding (anti-sense) strand. The coding sequence which encodes the mature polypeptide can be identical to the coding sequence encoding SEQ ID NO:21-40, 46, or 52-56, or may be a different coding sequence which coding sequence, as a result of the redundancy or degeneracy of the genetic code, encodes the same mature polypeptide as the DNA of any one of SEQ ID NOs:21-40, 46, or 52-56.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NOs: 21-40, 46, or 52-56.

The polynucleotide encoding for the mature polypeptide of SEQ ID NOs: 21-40, 46, or 52-56 or may include: only the coding sequence for the mature polypeptide; the coding sequence of any domain of the mature polypeptide; and the coding sequence for the mature polypeptide (or domain-encoding sequence) together with non coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences.

In further aspects of the invention, nucleic acid molecules having sequences at least about 90%, 95%, 96%, 97%, 98% or 99% identical to the nucleic acid sequences disclosed herein, encode a polypeptide having cellobiohydrolase ("Cbh"), endoglucanase ("Eg") or beta-gluconase ("Bgl") functional activity. By "a polypeptide having Cbh, Eg or Bgl functional activity" is intended polypeptides exhibiting activity similar, but not necessarily identical, to a functional activity of the Cbh, Eg or Bgl polypeptides of the present invention, as measured, for example, in a particular biological assay. For example, a Cbh, Eg or Bgl functional activity can routinely be measured by determining the ability of a Cbh, Eg or Bgl polypeptide to hydrolyze cellulose, or by measuring the level of Cbh, Eg or Bgl activity.

Of course, due to the degeneracy of the genetic code, one of ordinary skill in the art will immediately recognize that a large portion of the nucleic acid molecules having a sequence at least 90%, 95%, 96%, 97%, 98%, or 99% identical to the nucleic acid sequence of any of SEQ ID NOs: 1-20, or fragments thereof, will encode polypeptides having Cbh, Eg or Bgl functional activity. In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Cbh, Eg or Bgl functional activity.

The polynucleotides of the present invention also comprise nucleic acids encoding a *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes* or *Arabidopsis thaliana* cellulase, or domain, fragment, variant, or derivative thereof, fused to a polynucleotide encoding a marker sequence which allows for detection of the polynucleotide of the present invention. In one embodiment of the invention, expression of the marker is independent from expression of the cellulase. The marker sequence may be a yeast selectable marker selected from the group consisting of URA3, HIS3, LEU2, TRP1, LYS2 or ADE2. Casey, G. P. et al., "A convenient dominant selection marker for gene transfer in industrial strains of *Saccharomyces* yeast: SMR1 encoded resistance to the herbicide sulfometuron methyl," *J. Inst. Brew.* 94:93-97 (1988).

Codon Optimized Polynucleotides

According to one embodiment of the invention, the polynucleotides encoding heterologous cellulases can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 4, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, Bg1II, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 2

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA **Ter** | TGA **Ter** |
| | TTG Leu (L) | TCG Ser (S) | TAG **Ter** | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | **ATG** Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, and these tables can be adapted in a number of ways. See Nakamura, Y., et al. "Codon usage tabulated from the international DNA sequence databases: status for the year 2000" *Nucl. Acids Res.* 28:292 (2000). Codon usage tables for yeast, calculated from GenBank Release 128.0 [15 Feb. 2002], are reproduced below as Table 3. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 3

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Total | | | |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Total | | | |
| Ile | AUU | 196893 | 30.1 |
| Ile | AUC | 112176 | 17.2 |
| Ile | AUA | 116254 | 17.8 |
| Total | | | |
| Met | AUG | 136805 | 20.9 |
| Total | | | |
| Val | GUU | 144243 | 22.1 |
| Val | GUC | 76947 | 11.8 |
| Val | GUA | 76927 | 11.8 |
| Val | GUG | 70337 | 10.8 |
| Total | | | |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Total | | | |
| Pro | CCU | 88263 | 13.5 |
| Pro | CCC | 44309 | 6.8 |
| Pro | CCA | 119641 | 18.3 |
| Pro | CCG | 34597 | 5.3 |
| Total | | | |
| Thr | ACU | 132522 | 20.3 |
| Thr | ACC | 83207 | 12.7 |
| Thr | ACA | 116084 | 17.8 |
| Thr | ACG | 52045 | 8.0 |
| Total | | | |
| Ala | GCU | 138358 | 21.2 |
| Ala | GCC | 82357 | 12.6 |
| Ala | GCA | 105910 | 16.2 |
| Ala | GCG | 40358 | 6.2 |
| Total | | | |
| Tyr | UAU | 122728 | 18.8 |
| Tyr | UAC | 96596 | 14.8 |
| Total | | | |
| His | CAU | 89007 | 13.6 |
| His | CAC | 50785 | 7.8 |
| Total | | | |
| Gln | CAA | 178251 | 27.3 |
| Gln | CAG | 79121 | 12.1 |
| Total | | | |
| Asn | AAU | 233124 | 35.7 |
| Asn | AAC | 162199 | 24.8 |
| Total | | | |
| Lys | AAA | 273618 | 41.9 |
| Lys | AAG | 201361 | 30.8 |
| Total | | | |
| Asp | GAU | 245641 | 37.6 |
| Asp | GAC | 132048 | 20.2 |
| Total | | | |
| Glu | GAA | 297944 | 45.6 |
| Glu | GAG | 125717 | 19.2 |
| Total | | | |
| Cys | UGU | 52903 | 8.1 |
| Cys | UGC | 31095 | 4.8 |
| Total | | | |
| Trp | UGG | 67789 | 10.4 |
| Total | | | |
| Arg | CGU | 41791 | 6.4 |

TABLE 3-continued

Codon Usage Table for *Saccharomyces cerevisiae* Genes

| Amino Acid | Codon | Number | Frequency per hundred |
|---|---|---|---|
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Total | | | |
| Gly | GGU | 156109 | 23.9 |
| Gly | GGC | 63903 | 9.8 |
| Gly | GGA | 71216 | 10.9 |
| Gly | GGG | 39359 | 6.0 |
| Total | | | |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 3 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 3 for frequency of usage in the *S. cerevisiae*, about 5, or 5% of the leucine codons would be CUC, about 11, or 11% of the leucine codons would be CUG, about 12, or 12% of the leucine codons would be CUU, about β, or β% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences. Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae* or *Kluveromyces*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be, for example, versions encoding a cellobiohydrolase, endoglucanase or beta-glucosidase from *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana*, or domains, fragments, variants, or derivatives thereof.

Codon optimization is carried out for a particular species by methods described herein, for example, in certain embodiments codon-optimized coding regions encoding polypeptides of *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H. jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellulases, or domains, fragments, variants, or derivatives thereof are optimized according to yeast codon usage, e.g., *Saccharomyces cerevisiae, Kluyveromyces lactis* and/or *Kluyveromyces marxianus*. Also provided are polynucleotides, vectors, and other expression constructs comprising codon-optimized coding regions encoding polypeptides of *H. grisea, T. aurantiacus, T. emersonii, T. reesei, C. lacteus, C. formosanus, N. takasagoensis, C. acinaciformis, M. darwinensis, N. walkeri, S. fibuligera, C. luckowense R. speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Aspergillus kawachii, Heterodera schachtii, H.*

*jecorina, Orpinomyces* sp., *Irpex lacteus, Acremonium thermophilum, Neosartorya fischeri, Chaetomium globosum, Chaetomium thermophilum, Aspergillus fumigatus, Aspergillus terreus, Neurospora Crassa, R. flavipes*, or *Arabidopsis thaliana* cellulases or domains, fragments, variants, or derivatives thereof, and various methods of using such polynucleotides, vectors and other expression constructs.

In certain embodiments described herein, a codon-optimized coding region encoding any of SEQ ID NOs:21-40, 46, or 52-56 or domain, fragment, variant, or derivative thereof, is optimized according to codon usage in yeast (*Saccharomyces cerevisiae, Kluyveromyces lactis* or *Kluyveromyces marxianus*). In some embodiments, the sequences are codon-optimized specifically for expression in *Saccharomyces cerevisiae*. In some embodiments, the sequences are codon-optimized for expression in *Kluyveromyces*. In some embodiments, a sequence is simultaneously codon-optimized for optimal expression in both *Saccharomyces cerevisiae* and in *Kluyveromyces*. Alternatively, a codon-optimized coding region encoding any of SEQ ID NOs: 21-40, 46, or 52-56 may be optimized according to codon usage in any plant, animal, or microbial species.

Vectors and Methods of Using Vectors in Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

| Gene | Organism | Systematic name | Reason for use/benefits |
|---|---|---|---|
| PGK1 | *S. cerevisiae* | YCR012W | Strong constitutive promoter |
| ENO1 | *S. cerevisiae* | YGR254W | Strong constitutive promoter |
| TDH3 | *S. cerevisiae* | YGR192C | Strong constitutive promoter |
| TDH2 | *S. cerevisiae* | YJR009C | Strong constitutive promoter |
| TDH1 | *S. cerevisiae* | YJL052W | Strong constitutive promoter |
| ENO2 | *S. cerevisiae* | YHR174W | Strong constitutive promoter |
| GPM1 | *S. cerevisiae* | YKL152C | Strong constitutive promoter |
| TPI1 | *S. cerevisiae* | YDR050C | Strong constitutive promoter |

Additionally, promoter sequences from stress and starvation response genes are useful in the present invention. In some embodiments, promoter regions from the *S. cerevisiae* genes GAC1, GET3, GLC7, GSH1, GSH2, HSF1, HSP12, LCB5, LRE1, LSP1, NBP2, PIL1, PIM1, SGT2, SLG1, WHI2, WSC2, WSC3, WSC4, YAP1, YDC1, HSP104, HSP26, ENA1, MSN2, MSN4, SIP2, SIP4, SIP5, DPL1, IRS4, KOG1, PEP4, HAP4, PRB1, TAX4, ZPR1, ATG1, ATG2, ATG10. ATG11, ATG12, ATG13, ATG14, ATG15, ATG16, ATG17, ATG18, and ATG19 may be used. Any suitable promoter to drive gene expression in the host cells of the invention may be used. Additionally the *E. coli*, lac or trp, and other promoters known to control expression of genes in prokaryotic or lower eukaryotic cells can be used.

In addition, the expression vectors may contain one or more selectable marker genes to provide a phenotypic trait for selection of transformed host cells such as URA3, HIS3, LEU2, TRP1, LYS2 or ADE2, dihydrofolate reductase, neomycin (G418) resistance or zeocin resistance for eukaryotic cell culture, or tetracycline or ampicillin resistance in *E. coli*.

The expression vector may also contain a ribosome binding site for translation initiation and/or a transcription terminator. The vector may also include appropriate sequences for amplifying expression, or may include additional regulatory regions.

The vector containing the appropriate DNA sequence as herein, as well as an appropriate promoter or control sequence, may be employed to transform an appropriate host to permit the host to express the protein.

Thus, in certain aspects, the present invention relates to host cells containing the above-described constructs. The host cell can be a host cell as described elsewhere in the application. The host cell can be, for example, a lower eukaryotic cell, such as a yeast cell, e.g., *Saccharomyces cerevisiae* or *Kluyveromyces*, or the host cell can be a prokaryotic cell, such as a bacterial cell.

As representative examples of appropriate hosts, there may be mentioned: bacterial cells, such as *E. coli, Streptomyces, Salmonella typhimurium*; thermophilic or mesophlic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is selected from the group consisting of *Saccharomyces cerevisiae, Kluyveromyces lactis, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schwanniomyces occidentalis, Issatchenkia orientalis, Kluyveromyces marxianus, Blakeslea, Candida, Cryptococcus, Cunninghamella, Lipomyces, Mortierella, Mucor, Phycomces, Pythium, Rhodosporidium, Rhodotorula, Trichosporon* and *Yarrowia*.

Methods of Using Host Cells to Produce Ethanol

The present invention is also directed to use of host cells and co-cultures to produce ethanol from cellulosic substrates.

Such methods can be accomplished, for example, by contacting a cellulosic substrate with a host cell or a co-culture of the present invention.

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a host cell of the invention. In some embodiments, the invention is directed to a method for hydrolyzing a cellulosic substrate, for example a cellulosic substrate as described above, by contacting the cellulosic substrate with a co-culture comprising yeast cells expressing heterologous cellulases.

In some embodiments, the invention is directed to a method for fermenting cellulose. Such methods can be accomplished, for example, by culturing a host cell or co-culture in a medium that contains insoluble cellulose to allow saccharification and fermentation of the cellulose.

The production of ethanol can, according to the present invention, be performed at temperatures of at least about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a cellulosic substrate with a host cell or co-culture of the invention and additionally contacting the cellulosic substrate with externally produced cellulase enzymes. Exemplary externally produced cellulase enzymes are commercially available and are known to those of skill in the art.

Therefore, the invention is also directed to methods of reducing the amount of externally produced cellulase enzymes required to produce a given amount of ethanol from cellulose comprising contacting the cellulose with externally produced cellulases and with a host cell or co-culture of the invention. In some embodiments, the same amount of ethanol production can be achieved using at least about 5%, 10%, 15%, 20%, 25%, 30%, or 50% less externally produced cellulases. In some embodiments, no external cellulase is added, or less than about 5% of the cellulase is externally added cellulase, or less than about 10% of the cellulase is externally added cellulase, or less than about 15% of the cellulase is externally added cellulase.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter more than a control strain (lacking heterologous cellulases) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

The following embodiments of the invention will now be described in more detail by way of these non-limiting examples.

EXAMPLES

The present invention presents a number of important steps forward for creating a yeast capable of consolidated bioprocessing. It describes improved cellulolytic yeast created by expressing combinations of heterologous cellulases. The present invention demonstrates for the first time, the ability of transformed *Kluyveromyces* to produce ethanol from cellulose, the ability of yeast strains expressing only secreted heterologous cellulases to produce ethanol from cellulose, and the ability of co-cultures of multiple yeast strains expressing different cellulases to produce ethanol from cellulose. In addition such yeast strains and co-cultures of yeast strains can increase the efficiency of simultaneous saccharification and fermentation (SSF) processes.

General Protocols

General Strain Cultivation and Media

*Escherichia coli* strain DH5α (Invitrogen), or NEB 5 alpha (New England Biolabs) was used for plasmid transformation and propagation. Cells were grown in LB medium (5 g/L yeast extract, 5 g/L NaCl, 10 g/L tryptone) supplemented with ampicillin (100 mg/L), kanamycin (50 mg/L), or zeocin (20 mg/L). When zeocin selection was desired LB was adjusted to pH 7.0. Also, 15 g/L agar was added when solid media was desired.

Yeast strains were routinely grown in YPD (10 g/L yeast extract, 20 g/L peptone, 20 g/L glucose), YPC (10 g/L yeast extract, 20 g/L peptone, 20 g/L cellobiose), or YNB+glucose (6.7 g/L Yeast Nitrogen Base without amino acids, and supplemented with appropriate amino acids for strain, 20 g/L glucose) media with either G418 (250 mg/L unless specified) or zeocin (20 mg/L unless specified) for selection. 15 g/L agar was added for solid media.

Molecular Methods

Standard protocols were followed for DNA manipulations (Sambrook et al. 1989).

PCR was performed using Phusion polymerase (New England Biolabs) for cloning, and Taq polymerase (New England Biolabs) for screening transformants, and in some cases Advantage Polymerase (Clontech) for PCR of genes for correcting auxotrophies. Manufacturers guidelines were followed as supplied. Restriction enzymes were purchased from New England Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA. Sequencing was performed by the Molecular Biology Core Facility at Dartmouth College. Yeast mediated ligation (YML) was used to create some constructs (Ma et al. *Gene* 58:201-216 (1987)). This was done by creating DNA fragments to be cloned with 20-40 bp of homology with the other pieces to be combined and/or the backbone vector. A backbone vector (pRS426), able to replicate in yeast, and with the Ura3 gene for selection, was then transformed into yeast by standard methods with the target sequences for cloning. Transformed yeast recombine these fragments to form a whole construct and the resulting plasmid allows selection on media without uracil.

Vectors

Plasmid constructs vectors in the experiments detailed below are summarized in Table 4, and the primers used in vector construction are shown in Table 5.

TABLE 4

Plasmids used.

| Plasmid | Genotype |
|---|---|
| pBKD1-BGLI | bla KanMX PGK1$_P$-S.f. bgl1-PGK1$_T$ |
| pBKD2-sEGI | bla KanMX ENO1$_P$-sT.r. egl-ENO1$_T$ |
| pBKD1-BGLI-sEGI | bla KanMX ENO1$_P$-sT.r. egl-ENO1$_T$ & PGK1$_P$-S.f. bgl1-PGK1$_T$ |
| YEpENO-BBH | bla URA3 ENO1$_{PT}$ |
| pJC1 La grange et al. (1996) | bla URA3 PGK$_{PT}$ |

TABLE 4-continued

Plasmids used.

| Plasmid | Genotype |
|---|---|
| pRDH101 | bla URA3 ENO1$_P$-sT.r.cbh1-ENO1$_T$ |
| pRDH103 | bla URA3 ENO1$_P$-sH.g.cbh1-ENO1$_T$ |
| pRDH104 | bla URA3 ENO1$_P$-sT.a.cbh1-ENO1$_T$ |
| pRDH105 | bla URA3 ENO1$_P$-sT.e.cbh1-ENO1$_T$ |
| pRDH106 | bla URA3 ENO1$_P$-sT.e.cbh2-ENO1$_T$ |
| pRDH107 | bla URA3 PGK1$_P$-sT.r.cbh2-PGK1$_T$ |
| pRDH108 | bla URA3 PGK1$_P$-sT.r.cbh2-PGK1$_T$ & ENO1$_P$-sT.e.cbh1-ENO1$_T$ |
| pRDH118 | bla URA3 PGK1$_P$-sT.r.cbh2-PGK1$_T$ & ENO1$_P$-sH.g.cbh1-ENO1$_T$ |
| pRDH120 | bla URA3 PGK1$_P$-sT.r.cbh2-PGK1$_T$ & ENO1$_P$-sT.a.cbh1-ENO1$_T$ |
| pDF1 La Grange et al. (1996) | bla fur1::LEU2 |
| pCEL5 Den Haan et al. 2007 | 2 micron vector for expression of SfBGLI and TrEGI (native sequence) |
| pMU185 | pUG66 (loxp-zeo-loxp) |
| pKLAC1 New England Biolabs | *K. lactis* expression vector for integration at the lac4 locus, acetamide selection |
| pRS426 | 2 micron vector for yeast mediated ligation (YML) |
| pMU289 | pRS426 with portion of pKLAC1 for insertion of TrEG1 (from pBKD_11621, as detailed in example 1) into lac4 locus created by YML |
| pMU291 | pRS426 with portion of pKLAC1 for insertion of TrCBH2 (from pBZD_20641, as detailed in example 1) into lac4 locus created by YML |
| pMU398 | ENO1$_P$-sT.e.cbh1-ENO1$_T$ from pRDH105 into pMU289 (cloning by YML) |
| pMU451 | pRDH105 with PacI/AscI linker (formed using primers) inserted into EcoRI/XhoI |
| pMU458 | synthetic construct for N.f. EG inserted into pMU451 (PacI/AscI digest of both pieces) |
| pMU463 | TrEG1 from pBKD1-BGLI-sEGI into pMU451 (PacI/AscI digest of both pieces) |
| pMU465 | synthetic construct for C.l.(a) EG inserted into pMU451 (PacI/AscI digest of both pieces) |
| pMU469 | synthetic construct for R.f.EG inserted into pMU451 (PacI/AscI digest of both pieces) |
| pMU471 | synthetic construct for C.f.EG inserted into pMU451 (PacI/AscI digest of both pieces) |
| pMU472 | synthetic construct for N.t.EG inserted into pMU451 (PacI/AscI digest of both pieces) |
| pMU473 | synthetic construct for C.a.EG inserted into pMU451 (PacI/AscI digest of both pieces) |
| pMU475 | synthetic construct for T.r. CBH2 derived from pBKD_20641 with tether removed (from example 1) inserted into pMU451 (PacI/AscI digest of both pieces) |
| pMU499 | synthetic construct for M.d. EG inserted into pMU451 (PacI/AscI digest of both pieces) |
| pMU500 | synthetic construct for R.s. EG inserted into pMU451 (PacI/AscI digest of both pieces) |
| pMU503 | synthetic construct for N.w. EG inserted into pMU451 (PacI/AscI digest of both pieces) |
| pMU624/pMI529 | 2 micron vector for expression of T.e. CBH1 w/CBD (PCR fragments for chimeric enzyme with PmlI-XhoI digested pRDH105) |
| pMU326 | synthetic construct for R.s. EG from Codon Devices |
| pMU784/pMI574 | 2 micron vector for expression of C.l.(b) CBH2 (synthetic construct for C.l.(b) CBH2 inserted into PacI/AscI digested pMU624) |
| pMU562 | pBKD_2 with loxp-zeo-loxp inserted (NotI digest of both pieces) |
| pMU576 | ENO1p-T.r.cbh1-ENO1$_T$ (from pMU291) in pMU562 (PacI/AscI digest of both pieces) |
| pMU577 | ENO1p-T.e.cbh1-ENO1$_T$ in (from pMU398) pMU562 (PacI/AscI digest of both pieces) |
| pMU661 | ENO1p-T.r. EG1-ENO1$_T$ (from pMU463) in pMU562 (PacI/AscI digest of both pieces) |
| pMU662 | ENO1p-C.l.(a) EG1-ENO1$_T$ (from pMU465) in pMU562 (PacI/AscI digest of both pieces) |

TABLE 4-continued

Plasmids used.

| Plasmid | Genotype |
|---|---|
| pMU663 | ENO1p-C.f. EG1-ENO1$_T$ (from pMU471) in pMU562 (PacI/AscI digest of both pieces) |
| pMU664 | ENO1p-N.t. EG1-ENO1$_T$ (from pMU472) in pMU562 (PacI/AscI digest of both pieces) |
| pMU665 | ENO1p-C.a. EG1-ENO1$_T$ (from pMU473) in pMU562 (PacI/AscI digest of both pieces) |
| pMU666 | ENO1p-T.r.CBH2-ENO1$_T$ (from pMU475) in pMU562 (PacI/AscI digest of both pieces) |
| pMU667 | ENO1p-M.d.-EG1-ENO1$_T$ (from pMU499) in pMU562 (PacI/AscI digest of both pieces) |
| pMU668 | ENO1p-N.w.-EG1-ENO1$_T$ (from pMU503) in pMU562 (PacI/AscI digest of both pieces) |
| pMU755 | ENO1p-T.e.CBH1 w/CBD-ENO1$_T$ (from pMU624) in pMU562 (PacI/AscI digest of both pieces) |
| pMU750 | ENO1p-R.s.-EG2-ENO1$_T$ (from pMU326) in pMU562 (PacI/AscI digest of both pieces) |
| pMU809 | ENO1p-C.l.(b) CBH2b-ENO1$_T$ (from pMU784) in pMU562 (PacI/AscI digest of both pieces) |
| pMU721 | pMU562 with hph gene (hygromycin resistance marker) replacing zeocin marker (NotI digest for both fragments) |
| pMU760 | ENO1p-T.e.CBH1 w/CBD-ENO1$_T$ from pMU624 in pMU721 (MheI/AscI digest for both fragments) |
| pMU761 | ENO1p-T.r.CBH2-ENO1$_T$ from pMU291in pMU721 (PacI/AscI digest for both fragments) |
| pMI553 | 2 micron vector for expression of T.r. CBH2 and T.e. CBH1 + CBM |
| pMI568 | 2 micron vector for expression of T.r. EG1, please see text for description of how this construct was built. |
| pMI574 | 2 micron vector for expression of C.l.(b) CBH2 |
| pMI577 | 2 micron vector for expression of T.r. CBH2 and H.g. CBH1 |
| pMI578 | 2 micron vector for expression of T.r. CBH2 and T.e. CBH1 |
| pMI579 | 2 micron vector for expression of T.r. CBH2 and C.l.(b) CBH1 |
| pMI580 | 2 micron vector for expression of C.l.(b) CBH2 and T.e. CBH1 + CBM |
| pMI581 | 2 micron vector for expression of C.l.(b) CBH2 and T.e. CBH1 |
| pMI582 | 2 micron vector for expression of C.l.(b) CBH2 and H.g. CBH1 |
| pMI583 | 2 micron vector for expression of C.l.(b) CBH2 and C.t. CBH1 |

Abbreviations:
ENO1$_{P/T}$ = Enolase 1 gene promoter/terminator;
PGK1$_{P/T}$ = phosphoglycerate kinase 1 gene promoter & terminator;
T.r. = *Trichoderma reesei*;
H.g. = *Humicola grisea*;
T.a. = *Thermoascus aurantiacus*;
T.e. = *Talaromyces emersonii*,
S.f. = *Saccharomycopsis fibuligera*;
C.l. (a) = *Coptotermes lacteus*;
C.f. = *Coptotermes formosanus*;
N.t. = *Nasutitermes takasagoensis*;
C.a. = *Coptotermes acinaciformis*;
M.d. = *Mastotermes darwinensis*;
N.w. = *Nasutitermes walkeri*;
R.s. = *Reticulitermes speratus*;
C.l. (b) = *Chrysosporium lucknowense*;
N.f. = *Neosartorya fischeri*;
R.f. = *Reticulitermes flavipes*;
C.t. = *Chaetomium thermophilum*

TABLE 5

Primers Used

| | |
|---|---|
| sCBH1/2-L | GACTGAATTCATAATGGTCTCCTTCACCTCC (SEQ ID NO: 59) |
| sCBH1-R | GACTCTCGAGTTACAAACATTGAGAGTAGTATGG (SEQ ID NO: 60) |
| sCBH2-R | CAGTCTCGAGTTACAAGAAAGATGGGTTAGC (SEQ ID NO: 61) |
| 395 Te cbh1 Synt1 PacI-ATG | GCGTTGGTACCGTTTAAACGGGGCCCTTAATTAAACAATGCTAAGAAGAGCTTTACTATTGAG (SEQ ID NO: 62) |
| 398 Te cbh1 synt core SmaI | CCTCCCCCGGGTTAGAAGCAGTGAAAGTGGAGTTGATTGG (SEQ ID NO: 63) |
| 399 Trcbh1 synt CBM5 MlyIHincII | GCGACGAGTCAACCCTCCAGGTGGTAACAGAGGTACTACCAC (SEQ ID NO: 64) |
| 400 Trcbh1 synt CBM AscIXhoI | GCGACTCGAGGGCGCGCCTACAAACATTGAGAGTAGTATGGGTTTA (SEQ ID NO: 65) |
| 379 ScPGK1prom -786 SacI + ApaI | GCGTTGAGCTCGGGCCCTAATTTTTATTTTAGATTCCTGACTTCAAC (SEQ ID NO: 66) |
| 380 ScPGK1prom EcoRI-PacI | GCGTTGAATTCTTAATTAAGTAAAAAGTAGATAATTACTTCCTTG (SEQ ID NO: 67) |
| 381 CBH2 WT EcoRI-PacI-ATG | GCGTTGAATTCTTAATTAAACAATGATTGTCGGCATTCTCACCACGC (SEQ ID NO: 68) |
| 386 CBH2 WT TAA-AscI-EcoRI | gcgatgaattcggcgcgccTTACAGGAACGATGGGTTTGCGTTTG (SEQ ID NO: 69) |

The yeast expression vector YEpENO-BBH was created to facilitate heterologous expression under control of the *S. cerevisiae enolase* 1 (ENO1) gene promoter and terminator. The vector was also useful because the expression__ cassette from this vector could be simply excised using a BamHI, BglII digest. YEpENO1 (Den Haan et al., *Metabolic Engineering.* 9: 87-942007) contains the YEp352 backbone with the ENO1 gene promoter and terminator sequences cloned into the BamHI and HindIII sites. This plasmid was digested with BamHI and the overhang filled in with Klenow polymerase and dNTPs to remove the BamHI site. The plasmid was re-ligated to generate YEpENO-B. Using the same method, the BglII and then the HindIII sites were subsequently destroyed to create YEpENO-BBHtemplate. YEpENO-BBHtemplate was used as template for a PCR reaction with primers ENOBB-left (5'-GATCGGATCCCAATTAATGT-GAGTTACCTCA-3'; SEQ ID NO:70) and ENOBB-right (5'-GTACAAGCTTAGATCTCCTATGCGGTGTGAAATA-3': SEQ ID NO:71) in which the ENO1 cassette was amplified together with a 150 by flanking region upstream and 220 bp downstream. This product was digested with BamHI and HindIII and the over hangs filled in by treatment with Klenow polymerase and dNTPs and cloned between the two PvuII sites on yENO1 effectively replacing the original ENO1 cassette and generating YEpENO-BBH.

The yeast expression vector YEpENO-BBH was created to facilitate heterologous expression under control of the *S. cerevisiae* enolase 1 (ENO1) gene promoter and terminator. The vector was also useful because the expression cassette from this vector could be simply excised using a BamHI, BglII digest. YEpENO1 (Den Haan et al., *Metabolic Engineering.* 9: 87-942007) contains the YEp352 backbone with the ENO1 gene promoter and terminator sequences cloned into the BamHI and HindIII sites. This plasmid was digested with BamHI and the overhang filled in with Klenow polymerase and dNTPs to remove the BamHI site. The plasmid was re-ligated to generate YEpENO-B. Using the same method, the BglII and then the HindIII sites were subsequently destroyed to create YEpENO-BBHtemplate. YEpENO-BBHtemplate was used as template for a PCR reaction with primers ENOBB-left (5'-GATCGGATCCCAATTAATGT-GAGTTACCTCA-3'; SEQ ID NO:70) and ENOBB-right (5'-GTACAAGCTTAGATCTCCTATGCGGTGTGAAATA-3': SEQ ID NO:71) in which the ENO1 cassette was amplified together with a 150 bp flanking region upstream and 220 bp downstream. This product was digested with BamHI and HindIII and the over hangs filled in by treatment with Klenow polymerase and dNTPs and cloned between the two PvuII sites on yENO1 effectively replacing the original ENO1 cassette and generating YEpENO-BBH.

Codon optimized versions of *Humicola grisea* cbh1 (Hgcbh1), *Thermoascus aurantiacus* cbh1 (Tacbh1) and *Talaromyces emersonii* cbh1 and cbh2 (Tecbh1 and Tecbh2) were designed and synthetic genes were ordered from GenScript Corporation (Piscataway, N.J., USA). These four synthetic cbh encoding genes received from GenScript Corporation were cloned onto the plasmid pUC57. The resulting vectors were digested with EcoRI and XhoI to excise the cbh genes which were subsequently cloned into an EcoRI and XhoI digested YEpENO-BBH. This created the plasmids pRDH103 (with Hgcbh1), pRDH104 (with Tacbh1), pRDH105 (with Tecbh1) and pRDH106 (with Tecbh2) with the cbh encoding genes under transcriptional control of the ENO1 promoter and terminator. Additionally, pRDH101 was created to express the *T. reesei* CBH1 from pBZD__10631__20641. Takara ExTaq enzyme was used as directed and to amplify the sTrcbh1 from pBZD__10631__20641 using primers sCBH1/2 L and sCBH1R. The fragment was then isolated and digested with EcoRI and XhoI. YEpENO-BBH was also digested with EcoRI and XhoI and the relevant bands were isolated and ligated. A 1494 bp fragment encoding the *T. reesei* cbh2 gene was amplified from the plasmid pBZD__10631__20641, with primers sCBH1/2-L and sCBH2 R (5'-CAGTCTCGAGTTACAAGAAAGATGGGTTAGC-3': SEQ ID NO:72), digested with EcoRI and XhoI and cloned into the EcoRI and XhoI sites of pJC1 (Crouse et al., *Curr. Gen.* 28: 467-473 (1995)) placing it under transcriptional control of *S. cerevisiae* phosphoglycerate kinase 1 (PGK1) gene promoter and terminator. This plasmid was designated pRDH107. Subsequently the expression cassettes from pRDH103, pRDH104 and pRDH105 were excised with BamHI and BglII digestion and cloned into the BamHI site of pRDH107 to yield pRDH118, pRDH120, pRDH108 and pRDH109, respectively. pRDH109 contains the same expression cassettes as pRDH108 but in pRDH108 the gene expression cassettes are in the reverse orientation relative to each other. These plasmids and their basic genotypes are summarized in Table 4.

Two additional 2-micron vectors for expression of *Chrysosporium lucknowense* CBH2b and the *T. emersonii* CBH1 with a c-terminal fusion of the CBM of *T. reesei* CBH1 were also created. The fusion between *T. emersonii* cbh1 and the CBM of *T. reesei* cbh1 was generated by ligation of three fragments. Table 5 lists the oligonucleotides used for these constructs. A PCR product was amplified with the oligonucleotides 395 Te cbh1 Synt1 PacI-ATG and 398 Te cbh1 synt core SmaI using pRDH105 as the template, digested with Pm1I and SmaI and the 800 bp fragment was isolated. A second PCR product was amplified with oligonucleotides 399 Trcbh1 synt CBM5 MlyIHincII and 400 Trcbh1 synt CBM AscIXhoI with pRDH101 as the template, digested with MlyI and XhoI and the 180 bp fragment was isolated. The two PCR fragments were ligated with the 6.9 kb Pm1I-XhoI fragment of pRDH105 resulting in pMU624.

The genomic 3900 bp DNA sequence of *Chrysosporium lucknowense* cbh2b gene (described in Published United States Patent Application No: 2007/0238155) was analyzed for putative introns using the NetAspGene 1.0 Server. Removal of the predicted introns from the genomic sequence resulted in an open reading frame of 482 amino acids which was synthesized at Codon Devices and codon optimized for expression in *S. cerevisiae* and cloned into pUC57 vector. Plasmid pAJ401 (Saloheimo et al. *Mol. Microbiol.* 13:219-228, 1994), which contains the PGK1 promoter and terminator, was modified for expression of *T. reesei* cbh2 between PacI and AscI restrictions sites. The PGK1 promoter was amplified with primers 379 ScPGK1prom −786 SacI+ApaI and 380 ScPGK1prom EcoRI-PacI and pAJ410 as the template and digested with PacI and EcoRI. The *T. reesei* cbh2 ORF was amplified from pTTc01 (Teeri et al., *Gene* 51:43-52, 1987) with oligonucleotides 381 CBH2 WT EcoRI-PacI-ATG and 386 CBH2 WT TAA-AscI-EcoRI, digested with PacI and EcoRI, and ligated with the SacI-EcoRI digested pAJ401 resulting in pMI508. The PacI-AscI fragment in pMI508 was replaced by a synthetic 1.4 kb *T. reesei* egl1 gene resulting in pMI522. The 1.9 kb fragment of pMI522 was digested with PmlI and XhoI and ligated to the 6.4 kb PmlI-XhoI fragment of pRDH107 resulting in pMI568. pMI568 was digested with PacI and AscI and the 7 kb fragment was ligated to the 1.5 kb fragment of pMI558 producing pMU784 for the expression of *C. lucknowense* cbh2b.

A set of 2-micron vectors was also constructed for the expression of endoglucanases in *S. cerevisiae*, as well as related plasmids to act as controls. pMU451 was created as a control vector and for cloning the cellulases under control of the ENO1 promoter and terminator. This was done by adding a PacI/AscI linker into the EcoRI/XhoI site of pMU451. Synthetic genes ordered from Codon Devices and received in pUC57 were cloned into this vector as PacI/AscI fragments. Vectors created this way and listed in Table 4 are: pMU458, pMU463, pMU465, pMU469, pMU471, pMU472, pMU473, pMU475, pMU499, pMU500, and pMU503.

Vectors for integrating secreted versions of cellulases at the delta integration sites in *S. cerevisiae*, or for integration into the genome of *K. marxianus* were created from the pBKD_1 and pBKD_2 constructs. The *S. fibuligera* BGL1 (SfBGLI) was cloned by PCR from ySFI (van Rooyen et al., *J. Biotechnol.* 120: 284-95 (2005)). The endoglucanase (TrEGI) used was the sequence give in Table 1. The cellulase encoding genes were cloned via PCR (using PacI and AscI sites) into pBKD_1 and pBKD_2- to create pBKD1-BGL1 and pBKD2-sEG1. The ENO1P-sEG1-ENO1T cassette from pBKD2-sEG1 was subsequently sub cloned as a SpeI, NotI fragment to pBKD1-BGL1 to create pBKD1-BGL1-sEG1.

pMU562, used for integrating cellulases into *K. marxianus*, was generated by cutting with pMU185 (pUG66) with Not1 and isolating a 1190 bp lox P ZeoR containing insert. This insert was ligated into a Not1 digested 4.5 Kb delta-integration vector to produce pMU562. pMU576 was generated by cutting *T. reesei* CBH2 containing plasmid pMU291 with Asc1/Pac1, isolating a 1491 bp CBH2 gene and ligating it into delta-integration vector pMU562 cut with Asc1/Pac1. pMU577 was generated by cutting *T. emersonii* CBH1 from pMU398 with Asc1/Pac1, isolating a 1380 bp CBH1 gene and ligating into delta-integration vector pMU562 cut with Asc1/Pac1. Similarly, a set of recombinant cellulase constructs (pMU661 to pMU668 and pMU750, pMU755, pMU809—see Table 4), including a variety of endoglucanases and cellobiohydrolases, was incorporated into pMU562 for co-transformation. Synthetic seqeuences for these cellulase genes were originally obtained from Codon Devices and subsequently cloned into 2μ expression vectors for use in *S. cerevisiae*. They were then transferred from these vectors to the integrating vectors as detailed (including digests used) in Table X. Together these constructs formed a library that could be transformed separately or together and then screened by activity assay. Constructs were digested with enzymes that cut inside of, or very closely outside of, the delta sequences for integration. Similar constructs for integrating cellulases using the hygromycin marker (pMU721, pMU760, and pMU761) were also built.

Yeast Transformation

For routine transformation of whole plasimds in *S. cerevisiae*, standard chemical transformation was used (Sambrook et al. *Molecular cloning: A laboratory manual*. New York: Cold Spring Harbor Laboratory Press (1989)). For some transformations, a modified protocol described by Hill et al. (*Nucleic Acids Res.* 19: 5791 (1991)) was used.

A protocol for electrotransformation of yeast was developed based on Cho et al. (1999) and on Ausubel et al. (1994). Linear fragments of DNA were created by digesting pBD1-BGL1-sEG1 with AccI. AccI has a unique site in the ϵ sequence. The fragments were purified by precipitation with 3M NaAc and ice cold ethanol, subsequent washing with 70% ethanol, and resuspension in USB dH2O (DNAse and RNAse free, sterile water) after drying in a 70° C. vacuum oven.

*S. cerevisiae* cells for transformation were prepared by growing to saturation in 5 mL YPD cultures. 4 mL of the culture was sampled, washed 2× with cold distilled water, and resuspended in 640 μL cold distilled water. 80 μL of 100 mM Tris-HCl, 10 mM EDTA, pH 7.5 (10× TE buffer—filter sterilized) and 80 μL of 1 M lithium acetate, pH 7.5 (10× LiAc—filter sterilized) were added, and the cell suspension was incubated at 30° C. for 45 min. with gentle shaking. 20 μL of 1M DTT was added and incubation continued for 15 min. The cells were then centrifuged, washed once with cold distilled water, and once with electroporation buffer (1M sorbitol, 20 mM HEPES), and finally resuspended in 267 μL electroporation buffer. The same protocol was used for transforming *K. lactis* and *K. marxianus* strains, except that 50 mLs of YPD was inoculated with 0.5 mL from an overnight culture, grown for 4 hours at 37° C., and then centrifuged and prepared as above. Additionally, incubations and recovery steps were carried out at 37° C.

For electroporation, 10 μg of linearized DNA (measured by estimation on a gel) was combined with 50 μL of the cell suspension in a sterile 1.5 mL microcentrifuge tube. The mixture was then transferred to a 0.2 cm electroporation cuvette, and a pulse of 1.4 kV (200μ, 25 μF) was applied to the sample using the Biorad Gene Pulser device. 1 mL of YPD with 1M sorbitol adjusted to pH 7.0 (YPDS) was placed in the cuvette and the cells were allowed to recover for ~3 hrs. 100-200 μL cell suspension were spread out on YPDS agar plates with appropriate antibiotic, which were incubated at 30° C. for 3-4 days until colonies appeared.

Yeast Strains

The yeast strains listed in Table 6 were created using the vectors and transformation protocols as described.

TABLE 6

Yeast Strains.

| Name | Background strain | Genes expressed and/or knocked out | Constructs |
|---|---|---|---|
| M0013 | *Saccharomyces cerevisiae* Y294 (ATCC 201160) | Genotype: α, leu2-3, 112 ura3-52 his3 trp1-289 | None |
| M0243 | M0013 | SfBGLI, TrEGI | pBKD1-BGLI-sEGI |
| M0244 | M0013 | SfBGLI, TrEGI (native sequence) | pCEL5 |
| M0247 | M0013 | TeCBH1; delta FUR1 | pRDH105 |
| M0248 | M0013 | TrCBH2, TeCBH1; delta FUR1 | pRDH108; pDF1 |
| M0249 | M0013 | None (control); delta FUR1 | pJC1; pDF1 |
| M0265 | M0013 | HgCBHI; delta FUR1 | pRDH103; pDF1 |
| M0266 | M0013 | TaCBHI; delta FUR1 | pRDH104; pDF1 |
| M0282 | M0248 | SfBGLI, TrEGI, TrCBH2, TeCBH1; delta FUR1 | pBKD1-BGLI-sEGI; pRDH108; pDF1 |
| M0284 | M0243 | SfBGLI, TrEGI, TrCBH2, HgCBH1; delta FUR1 | pBKD1-BGLI-sEGI; pRDH118; pDF1 |

TABLE 6-continued

| Name | Background strain | Genes expressed and/or knocked out | Constructs |
|---|---|---|---|
| Yeast Strains. | | | |
| M0286 | M0243 | SfBGLI, TrEGI, TrCBH2, TaCBH1; delta FUR1 | pBKD1-BGLI-sEGI; pRDH120; pDF1 |
| M0288 | M0243 | SfBGLI, TrEGI, TrCBH2, TeCBH1; delta FUR1 | pBKD1-BGLI-sEGI; pRDH108; pDF1 |
| M0289 | M0013 | TrCBH2, HgCBH1; delta FUR1 | pRDH118; pDF1 |
| M0291 | M0013 | TrCBH2, TaCBH1; delta FUR1 | pRDH120; pDF1 |
| M0358 | M0282 | SfBGLI, TrEGI, TrCBH2, TeCBH1; delta FUR1; Trp1; His3 | pBKD1-BGLI-sEGI; pRDH108; pDF1 |
| M0359 | M0288 | SfBGLI, TrEGI, TrCBH2, TeCBH1; delta FUR1; Trp1; His3 | pBKD1-BGLI-sEGI; pRDH108; pDF1 |
| M0361 | M0249 | None (control); delta FUR1; Trp1; His3 | pJC1; pDF1 |
| M0157 | *Kluyveromyces marxianus* (ATCC #10606) | None | None |
| M0158 | *Kluyveromyces lactis* (ATCC #34440) | None | None |
| M0411 | M0158 (colony #1) | SfBGLI, TrEGI | pBKD1-BGLI-sEGI; |
| M0412 | M0158 (colony #2) | SfBGLI, TrEGI | pBKD1-BGLI-sEGI; |
| M0413 | M0157 (Colony #1) | SfBGLI, TrEGI | pBKD1-BGLI-sEGI; |
| M0414 | M0157 (Colony #2) | SfBGLI, TrEGI | pBKD1-BGLI-sEGI; |
| M0491 | M0414 | SfBGLI, TrEGI, TeCBH1, TrCBH2 | pBKD1-BGLI-sEGI; pMU576 and pMU577 |
| M0599 | M0414 | SfBGLI, TrEGI, TeCBH1, TrCBH2 | pBKD1-BGLI-sEGI; pMU760 and pMU761 |
| M0600 | M0414 | SfBGLI, TrEGI, TeCBH1, TrCBH2 | pBKD1-BGLI-sEGI; pMU760 and pMU761 |
| M0601 to M0604; M0611 to M0617 | M0414 (11 colonies displaying highest avicelase activity) | SfBGLI, TrEGI, Cl(a)EG, CfEG, NtEG, CaEG, MdEG, NwEG, RsEG, TeCBH1, TeCBH1 + CBD, TrCBH2, Cl(b)CBH2 | pBKD1-BGLI-sEGI; pMU663, pMU755, pMU809, pMU576, pMU661, pMU662, pMU664, pMU665, pMU667, pMU668, pMU750, pMU577 |
| M0618 to M0625 | M0157 (8 colonies displaying highest avicelase activity) | Cl(a)EG, CfEG, NtEG, CaEG, MdEG, NwEG, RsEG, TeCBH1, TeCBH1 + CBD, TrCBH2, Cl(b)CBH2 | pMU663, pMU755, pMU809, pMU576, pMU661, pMU662, pMU664, pMU665, pMU667, pMU668, pMU750, pMU577 |
| yENO1 | M0013 | ENO1 P/T | YEpENO-BBH; pDF1 |
| M0419 | M0013 | ENO1 P/T | pMU451 |
| M0420 | M0013 | TeCBH1 | pMU272 |
| M0423 | M0013 | TrEG1 | pMU463 |
| M0424 | M0013 | SfBGL1 | pMU464 |
| M0426 | M0013 | RfEG | pMU469 |
| M0446 | M0013 | Cl(a)EG | pMU465 |
| M0449 | M0013 | CfEG | pMU471 |
| M0450 | M0013 | NtEG | pMU472 |
| M0460 | M0013 | MdEG | pMU499 |
| M0461 | M0013 | RsEG | pMU500 |
| M0464 | M0013 | NwEG | pMU503 |
| M0476 | M0013 | NfEG | pMU458 |
| Y294/pMI529 fur1Δ | M0013 | TeCBH1 + CBM | pMU624 |
| Y294/pMI553 fur1Δ | M0013 | TrCBH2, TeCBH1 + CBM | pMI553 |
| Y294/pMI574 fur1Δ | M0013 | Cl(b)CBH2 | pMI574 |
| Y294/pMI577 fur1Δ | M0013 | TrCBH2, HgCBH1 | pMI577 |
| Y294/pMI578 fur1Δ | M0013 | TrCBH2, TeCBH1 | pMI578 |
| Y294/pMI579 fur1Δ | M0013 | TrCBH2, Cl(b)CBH1 | pMI579 |
| Y294/pMI580 fur1Δ | M0013 | Cl(b)CBH2, TeCBH1 + CBM | pMI580 |
| Y294/pMI581 fur1Δ | M0013 | Cl(b)CBH2, TeCBH1 | pMI581 |

TABLE 6-continued

| Yeast Strains. | | | |
|---|---|---|---|
| Name | Background strain | Genes expressed and/or knocked out | Constructs |
| Y294/pMI582 fur1Δ | M0013 | Cl(b)CBH2, HgCBH1 | pMI582 |
| Y294/pMI583 fur1Δ | M0013 | Cl(b)CBH2, Cl(b)CBH1 | pMI583 |

The plasmid pBKD1-BGL1-sEG1 (pMU276) was digested with AccI and transformed to *S. cerevisiae* Y294 by electrotransformation to create a strain with delta integrated copies of the SfBGLI and TrEGI, designated M0243. Episomal plasmids were then transformed to *S. cerevisiae* Y294 and/or M0243.

To create autoselective *S. cerevisiae* strains, i.e. strains that can be grown in medium without requiring selective pressure to maintain the episomal plasmid, strains were transformed with NsiI & NcoI digested pDFI and selected on SC-ura-leu plates. This lead to the disruption of the FUR1 gene of *S. cerevisiae*. PCR was used to confirm FUR1 disruption with primers FUR1-left (5'-ATTTCTTCTTGAACCATGAAC-3' SEQ ID NO:73) and FUR1-right (5'-CTTAATCAAGACT-TCTGTAGCC-3'; SEQ ID NO:74), where a 2568 bp indicated a disruption.

M0282 was created by transforming M0248 with AccI digested pBKD1-BGLI-sEGI, as described above, except that the transformation mixture was spread on plated containing 10 g/L BMCC with 10 g/L yeast extract and 20 g/L peptone.

The presence of integrated genes was verified by colony PCR for *Kluyveromyces* strains. Selected yeast strains were made prototrophic by transforming with PCR products for genes to complement their auxotrophies.

Cellulosic Substrates for Enzyme Assays

Bacterial microcrystalline cellulose (BMCC) was a gift from CP Kelco company. BMCC as received was stirred O/N at 4 C in water. After the substrate was rehydrated, it was washed 6 times with water and resuspended in water. The dry weight of the substrate was measured by drying samples at 105 C until constant weight was obtained.

Avicel PH105 (FMC Biopolymers) was used as provided by the manufacturer.

Pretreated mixed hardwoods were generated by autohydrolysis of the substrate at 160 PSI for 10 minutes. Pretreated material was washed 5 times to remove inhibitors and soluble sugars and resuspended in distilled water. Samples were dried overnight at 105 C to determine the dry weight. Analysis of sugar content by quantitative saccharification showed a 50% glucan content.

Phosphoric acid swollen cellulose (PASC) was prepared as in Zhang and Lynd (2006), with only slight modifications. Avicel PH105 (10 g) was wetted with 100 mL of distilled water in a 4 L flask. 800 mL of 86.2% phosphoric acid was added slowly to the flask with a first addition of 300 mL followed by mixing and subsequent additions of 50 mL aliquots. The transparent solution was kept at 4° C. for 1 hour to allow complete solubilization of the cellulose, until no lumps remained in the reaction mixture. Next, 2 L of ice-cooled distilled water was added in 500 mL aliquots with mixing between additions. 300 mL aliquots of the mixture were centrifuged at 5,000 rpm for 20 minutes at 2° C. and the supernatant removed. Addition of 300 mL cold distilled water and subsequent centrifugation was repeated 4×. 4.2 mL of 2M sodium carbonate and 300 mL of water were added to the cellulose, followed by 2 or 3 washes with distilled water, until the final pH was ~6. Samples were dried to constant weight in a 105° C. oven to measure the dry weight.

Enzyme Assays

β-glucosidase activity was measured in a manner similar to McBride, J. E., et al., (*Enzyme Microb. Techol.* 37: 93-101 (2005)), except that the volume of the assay was decreased and the reaction performed in a microtiter plate. Briefly, yeast strains were grown to saturation in YPD or YPC media with or without appropriate antibiotics, the optical density at 600 nm (OD(600)) was measured, and an 0.5 mL sample of the cultures was taken. This sample was centrifuged, the supernatant was separated and saved, and the cell pellet was washed 2× 50 mM citrate buffer, pH 5.0. Reactions for supernatants were made up of 50 μL sample, 50 μL citrate buffer, and 50 μL 20 mM p-nitrophenyl-β-D-glucopyranoside (PNPG) substrate. Reactions with washed cells consisted of 25 μL of cells, 75 μL citrate buffer, and 50 μL PNPG substrate. If the activity was too high for the range of the standard curve, a lower cell concentration was used and the assay was re-run. The standard curve consisted of a 2-fold dilution series of nitrophenol (PNP) standards, starting at 500 nM, and ending at 7.8 nM, and a buffer blank was included. After appropriate dilutions of supernatant or cells were prepared, the microtiter plate was incubated at 37° C. for 10 minutes along with the reaction substrate. The reaction was carried out by adding the substrate, incubating for 30 min., and stopping with 150 μL of 2M $Na_2CO_3$. The plate was then centrifuged at 2500 rpm for 5 minutes, and 150 μL of supernatant was transferred to another plate. The absorbance at 405 nm was read for each well.

Endoglucanase activity was qualitatively detected by observing clearing zones on synthetic complete media (as above, but including 20 g/L glucose) plates with 0.1% carboxymethyl cellulose (CMC) stained with congo red (Beguin, *Anal. Biochem.* 131: 333-6 (1983)). Cells were grown for 2-3 days on the plates and were washed off the plate with 1M Tris-HCL buffer pH 7.5. The plates were then stained for 10 minutes with a 0.1% Congo red solution, and extra dye was subsequently washed off with 1M NaCl.

CBH1 activity was detected using the substrate 4-Methylumbelliferyl-β-D-lactoside (MULac). Assays were carried out by mixing 50 μL of yeast supernatant with 50 μL of a 4 mM MUlac substrate solution made in 50 mM citrate buffer pH 5.5. The reaction was allowed to proceed for 30 minutes and then stopped with 1M $Na_2CO_3$. The fluorescence in each well was read in a microtiter plate reader (ex. 355 nm and em. 460 nm).

Quantification of Enzyme Activity

Enzyme activity on PASC and Avicel were measured using the protocol described in Den Haan et al., *Enzyme and Microbial Technology* 40: 1291-1299 (2007). Briefly, yeast supernatants were incubated with cellulose at 4° C. to bind the cellulase. The cellulose was then filtered from the yeast supernatant, resuspended in citrate buffer and sodium azide, and incubated at 37° C. Accumulation of sugar was measured in the reaction by sampling and performing a phenol-sulfuric acid assay. (See Example 10 and Table 9.)

Avicel activity levels were also generated using a 96-well plate method. (See Example 2.) Strains to be tested were grown in YPD in deep-well 96 well plates at 35° C. with shaking at 900 RPM. After growing, plates were centrifuged at 4000 rpm for 10 min. 300 μL substrate (2% avicel, 50 mM sodium acetate buffer, 0.02% sodium azide, β-glucosidase-1 μL per mL) was added to a new 96-well deep well plate, without allowing the avicel to settle. 300 μL of yeast supernatant was added to this substrate, and 100 μL was taken for an initial sample. The assay plate is incubated at 35° C., with shaking at 800 rpm, and samples were taken at 24 and 48 hours. Samples were placed in 96-well PCR plates, and spun at 2000 rpm for 2 minutes. 50 μL of supernatant was then added to 100 μL of DNS reagent previously placed in a separate 96 well PCR plate, mixed, and heated to 99° C. for 5 minutes in a PCR machine, followed by cooling to 4° C. 50 μL was transferred to a microtiter plate and the absorbance was measured at 565 nm. The conversion of avicel was calculated as follows:

$$Y = (OD(T = 24 \text{ or } 48) - OD(T = 0)) \times 100\% = \frac{\Delta OD \times 100}{S \times A} = \frac{\Delta OD \times 100}{0.1 \times 10}$$

Y—% of Avicel converted at 24 or 48 hrs

S—DNS/glucose calibration slope that is 0.1 for DNS at 565 nm

A—Avicel concentration at T=0 that is 10 g/L for 1% Avicel

Example 1

Production of *Kluyveromyces* Expressing Heterologous β-Glucosidase and Endoglucanase In order to test the ability of *Kluyveromyces* to express functional heterologous cellulases, two *Kluyveromyces strains, Kluyveromyces marxianus* (ATCC strain #10606; MO157) and *Kluyveromyces lactis* (ATCC strain #34440), were transformed with vectors encoding heterolgous cellulases.

Vectors containing yeast delta integration sequences, the KanMX marker and sequences encoding S.f. BGLI and T.r. EGI (pBKD-BFLI-sEG1) were transformed into *Kluyveromyces* according to the yeast transformation protocol as described above, and selected on G418. Transformants were verified by PCR and then tested by CMC assay. The results are shown in FIG. 1. The presence of the heterologous cellulase activity is indicated by a clearing zone on the CMC plate. As shown in FIG. 1, neither an untransformed *K. lactis* strain (colony 8) or an untransformed *K. marxianus* strain (colony 16) showed endoglucanase activity. However, 6 of 7 transformed *K. lactis* colonies showed CMCase activity, and all 7 transformed *K. marxianus* colonies showed CMCase activity. MO413 and MO414 were identified as two *K. marxianus* colonies showing CMCase activity.

Example 2

Production of *Kluyveromyces* Expressing CBH1 and CBH2

The ability of *Kluyveromyces* to express functional heterologous cellobiohydrolases was also examined. In these experiments, *K. marxianus* (MO157) was transformed with constructs containing *T. reesei* CBH2, *T. emersonii* CBH1 or both. Similarly, MO414 (*K. marxianus* transformed with Sf. BGLI and T.r. EGI) was transformed with constructs containing *T. reesei* CBH2, *T. emersonii CBH*1 or both.

Figure 2:
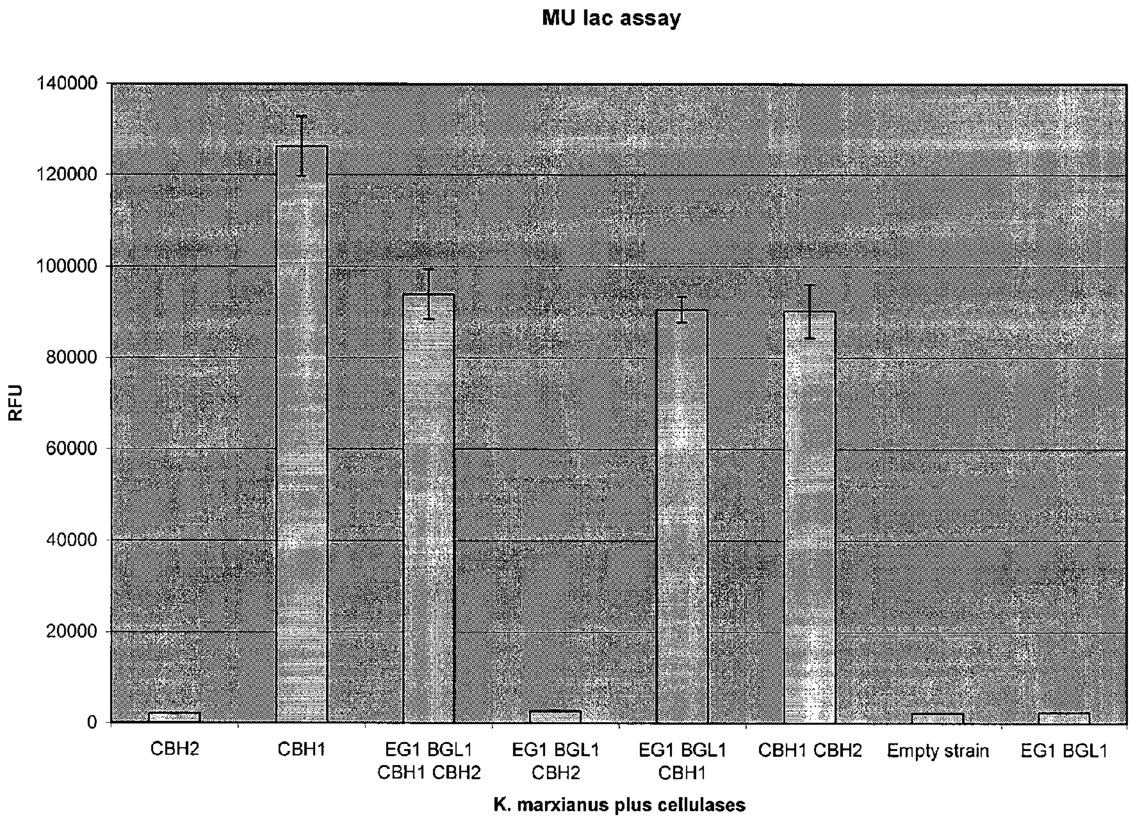
FIG. 2 depicts the results of an MU-lac assay to detect CBH1 activity in *K. marxianus* strains transformed with heterologous cellulases.

Transformations were performed as described in above. CBH1 activity was then detected using the substrate 4-Methylumbelliferyl-β-D-lactoside (MU-Lac) as described above. The assay was performed on eight colonies of each transformant and the three colonies showing the highest activity were averaged. The results are shown in FIG. 2 and demonstrate that strains transformed with *T. emersonii* CBH1 had high MU-lac activity.

Figure 3:
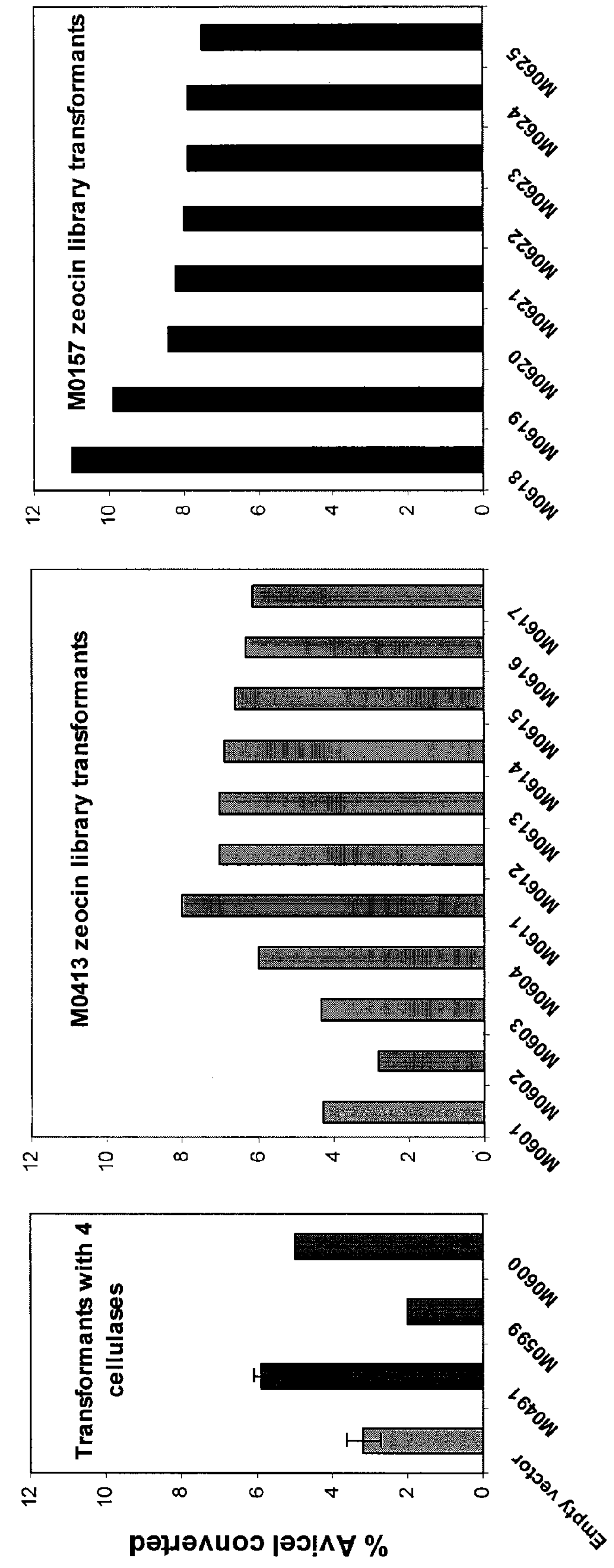
FIG. 3 depicts the percent of Avicel converted by several strains of *K. marxianus* expressing heterologous cellulases.

The activity of *Kluveromyces* strains expressing heterologous cellobiohydrolases on Avicel was also assessed. In one experiment, MO413 was transformed with vectors containing *T. reesei* CBH2 and *T. emersonii* CBH1 coding sequences along with a zeocin marker. Novel strain MO491 was created by this transformation and showed MU-lactoside activity. In a second experiment, MO413 was transformed with vectors containing *T. reesei* CBH2 and *T. emersonii* CBH1 coding sequences along with a hygromycin marker, and strains MO599 and MO600 were isolated from this transformation. Activity on Avicel was assessed at 48 hours as described above, and the results, shown in FIG. 3, demonstrate that *Kluveryomces* expressing heterologous cellulases have Avicelase activity at 35° C. Avicelase activity at 45° C. was also demonstrated (data not shown).

Example 3

Production of *Kluyveromyces* Expressing a Library of Cellulases

*Kluveromyces* strains were also created by transforming yeast with a library of cellulases (creation of library was described above). For example, MO413 was transformed with a library of cellulases containing a zeocin marker to produce novel strains MO601-MO604 and MO611-MO617. In addition, MO157 (*K. marxianus*) was transformed with the same library and novel strains MO618-MO625 were identified. Activity on Avicel was assessed at 48 hours as described above, and the results, shown in FIG. 3, demonstrate that *Kluveryomces* transformed with a library of heterologous cellulases also have Avicelase activity at 35° C. Tranformants of MO157 with the library showed the highest activity. Avicelase activity at 45° C. was also demonstrated (data not shown).

Example 4

Ethanol Production by Transformed *Kluyveromyces*

In order to determine if *Kluyveromyces* expressing heterologous cellulases could produce ethanol from Avicel, precultures were grown in for 24 hours in YPD (YPD as above, with 20 g/L glucose; 25 mL in a 250 mL shake flask) with shaking at 300 rpm at 35° C. After 24 and 48 hours, 40 g/L of additional glucose was added. At 72 hours, the pH of the cultures was adjusted to ~5.0 with citrate buffer (initial pH of buffer was 5.5, final concentration was 50 mM), and the culture was added to a sealed plastic shake flask containing 5.5 grams of Avicel (final concentration 10% (w/v). Avicel PH105 (FMC Biopolymers) was used as provided by the manufacturer. The culture was incubated at 35° C. with shaking at 150 rpm.

Quantification of ethanol in fermentation samples was carried out by HPLC analysis, and initial ethanol concentrations in bottles (from precultures) was subtracted from all subsequent data points (initial ethanol concentrations ranged between 0 and about 6 g/L). The initial glucose concentration for all strains except MO603 was 0.000 g/L. For this strain it was 0.069 g/L, which would result in a maximum in 0.035 g/L of ethanol from the initial sugar.

Figure 4:
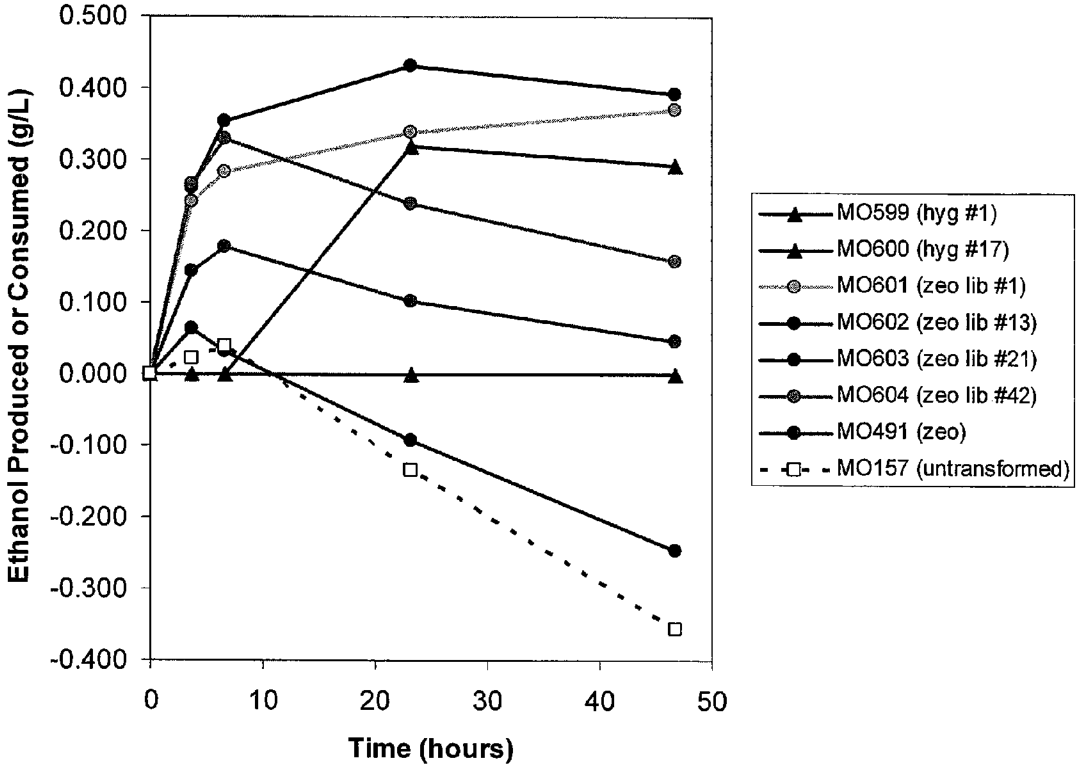
FIG. 4 depicts the ethanol production/consumption from Avicel by several strains of *K. marxianus* expressing heterologous cellulases.

The results, as shown in FIG. 4, demonstrate that Engineered *K. marxianus* strains were also able to produce ethanol directly from Avicel. Strain MO157, the untransformed control, showed a steady decrease in ethanol concentration over the course of the experiment. This is due to ethanol consumption by the strain because of the presence of a small amount of oxygen in the flasks.

Of the two strains transformed with *T. reesei* CBH2 and *T. emersonii* CBH1 with the hygromycin marker (MO599 and M600), one (MO599) showed ethanol production. In addition, of the five strains transformed with *T. reesei* CBH2 and *T. emersonii* CBH1 with the zeocin marker, four (MO601, MO602, MO604 and MO491) showed ethanol production. This demonstrates that engineered thermotolerant *K. marxianus* are capable of producing ethanol directly from the recalcitrant crystalline cellulose, Avicel.

Example 5

Production of *S. cerevisiae* Expressing Heterologous Cellulases

*S. cerevisiae* expressing heterologous cellulases were also produced and tested for their ability to grow on media containing bacterial microcrystalline cellulose (BMCC). In these experiments, microaerobic conditions were maintained by growing strains on BMCC in sealed hungate tubes with an air atomosphere.

Strains expressing *T. emersonii* CBH1 and *T. reesei* CBH2 (MO248) were transformed with a construct allowing *T. reesei* EGI and *S. fibuligera* BGLI expression (pKD-BGLI-sEGI). That transformation was plated on a BMCC solid agar plate and five colonies appeared on the plate after seven days (data not shown). Yeast from the largest of the five colonies was isolated as strain MO282. (MO282 is described in more detail above.) The three control strains were tested for growth on the same plates. One strain expressed with *T. emersonii* CBH1 and *T. reesei* CBH2, and two strains expressed *T. reesei* EGI and *S. fibuligera* BGLI. No colonies appeared on plates with control yeast strains (data not shown).

Figure 5:
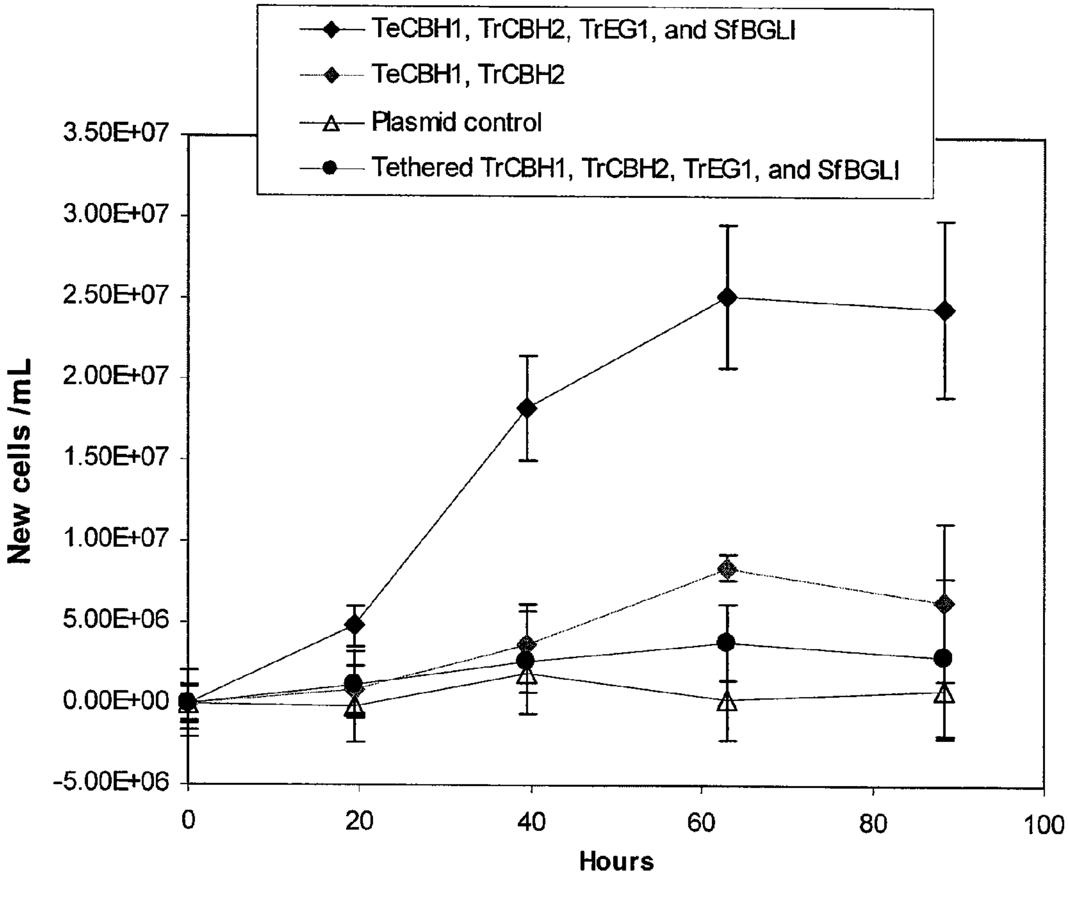
FIG. 5 depicts the growth of *S. cerevisiae* expressing heterologous cellulases on bacterial microcrystalline cellulose (BMCC).

The ability of MO282 to grow on BMCC was also tested using liquid media. FIG. 5 shows that MO282, which expresses all 4 secreted cellulases grew to a much greater extent on BMCC than a plasmid only control (MO249), a strain expressing only *T. emersonii* CBH1 and *T. reesei* CBH2 (MO249), and a strain expressing 4 tethered cellulases (M0144).

These results indicate that yeast expressing secreted *T. emersonii* CBH1, *T. reesei CBH2*, *T. reesei* EGI and *S. fibuligera* BGLI heterologously are able to grow on bacterial microcrystalline cellulose.

Example 6

*S. cerevisiae* Expressing Heterologous Cellulases can Produce Ethanol from Avicel and Pretreated Hardwood In order to determine if transformed *S. cerevisiae* can produce ethanol directly from cellulose without exogenously added cellulase enzymes, transformed strains were grown on Avicel as the sole carbon source. Avicel PH105 (FMC Biopolymers) was used as provided by the manufacturer.

Avicel media was made using the non-glucose components of synthetic complete medium for yeast including, yeast nitrogen base without amino acids-6.7 g/L, and supplemented with a complete amino acid mix (complete supplemental mixture). In some cases yeast extract (10 g/L) and peptone (20 g/L) (YP) were used as supplements in growth experiments. Cultivation conditions were anaerobic and were maintained by flushing sealed glass bottles with N2 after carbon source addition and before autoclaving. Non-carbon media components were added as 10× solutions by filter sterilizing after autoclaving. Inoculation into Avicel cultures was done at 20% by volume. Quantification of ethanol in fermentation samples was carried out by HPLC analysis, and initial ethanol concentrations in bottles (from precultures) was subtracted from all subsequent data points.

Figure 6:
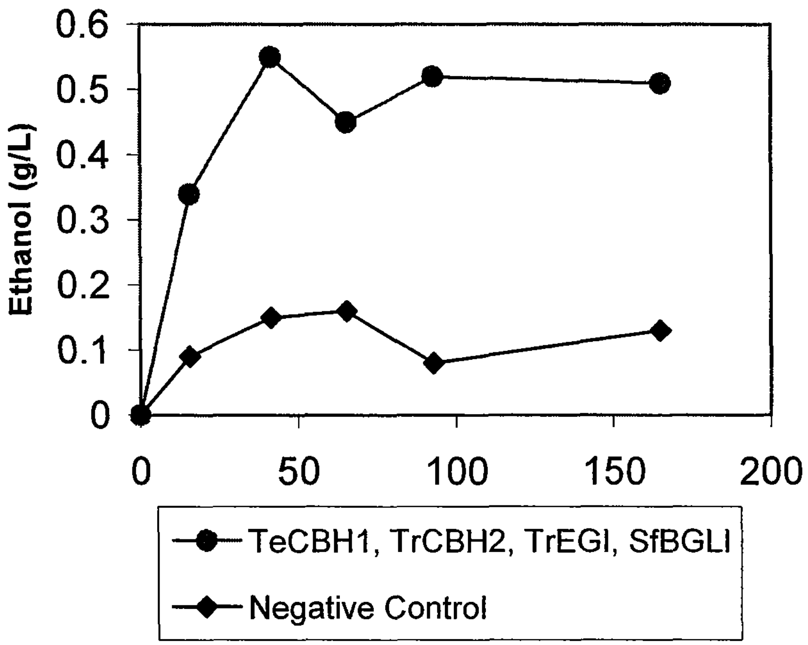
FIG. 6 depicts the ethanol production from Avicel by an *S. cerevisiae* strain expressing heterologous cellulases.

As shown in FIG. 6, Strain MO288 (expressing *S. fibuligera* BGLI, *T. reesei* EGI, *T. reesei* CBH2, and *T. emersonii* CBH1) was able to produce ethanol directly from avicel PH105 as compared to the control strain (MO249) when YNB media components were used.

The ability of MO288 to produce ethanol from cellulose was also demonstrated using pretreated hardwoods. Pretreated mixed hardwoods were generated by autohydrolysis of the substrate at 160 PSI for 10 minutes. Pretreated material was washed 5 times to remove inhibitors and soluble sugars and resuspended in distilled water. Samples were dried overnight at 105° C. to determine the dry weight. Analysis of sugar content by quantitative saccharification showed a 50% glucan content. Media and culture conditions were as described above for Avicel experiments except that cultures were inoculated at 10% by volume.

Figure 7:
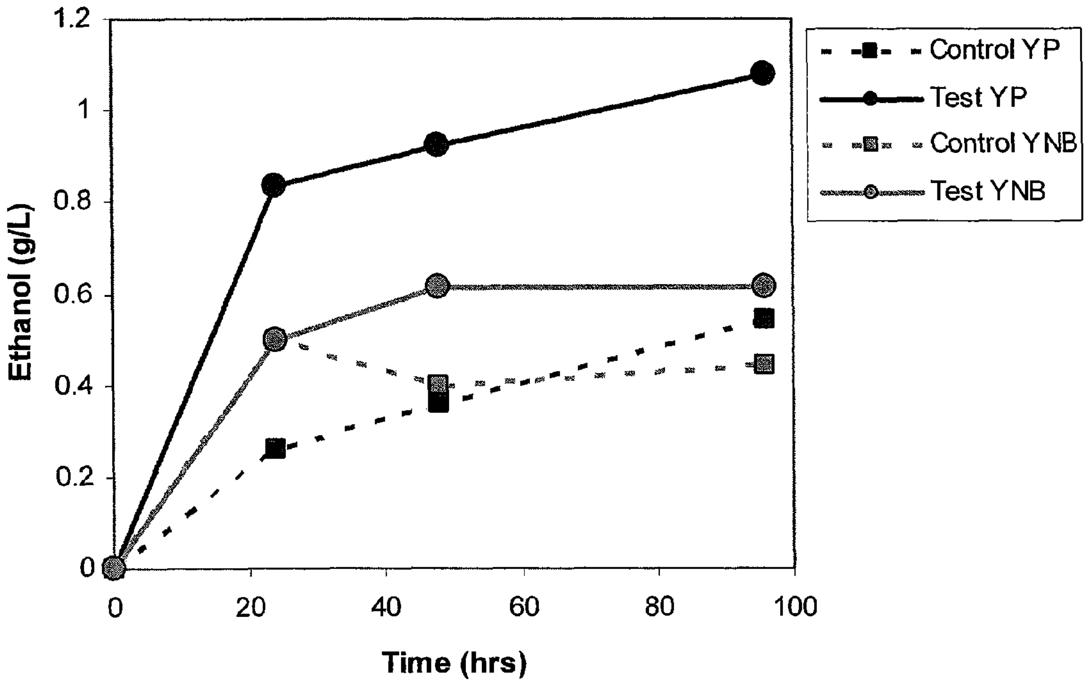
FIG. 7 depicts the ethanol production from pretreated hardwood (5% based on a dry weight percentage) by an *S. cerevisiae* strain expressing heterologous cellulases.

The data presented in FIG. 7 demonstrates that MO288 was also able to make ethanol from pretreated hardwoods without added enzyme. The strain made ~0.5 g/L more than the control when YP was used as media, and ~0.2 g/L when YNB was used.

These data demonstrate that yeast expressing secreted *T. emersonii* CBH1, *T. reesei* CBH2, *T. reesei* EGI and *S. fibuligera* BGLI heterologously are able to produce ethanol from cellulose without the addition of any exogenous cellulases.

Example 7

Transformed Yeast Strains and Externally Added Cellulases Act Synergistically to Produce Ethanol from Pretreated Mixed Hardwoods Production of ethanol from biomass is currently achieved using an SSF type of process where cellulase enzymes are added exogenously to a reaction containing pretreated cellulosic biomass, yeast growth media, and yeast. In order to determine if yeast expressing recombinant cellulases could improve this process, recombinant yeast expressing secreted cellulases were cultured in the presence of a range of exogenously added cellulase concentrations. Growth and media conditions were as described in previous examples.

Figure 8:
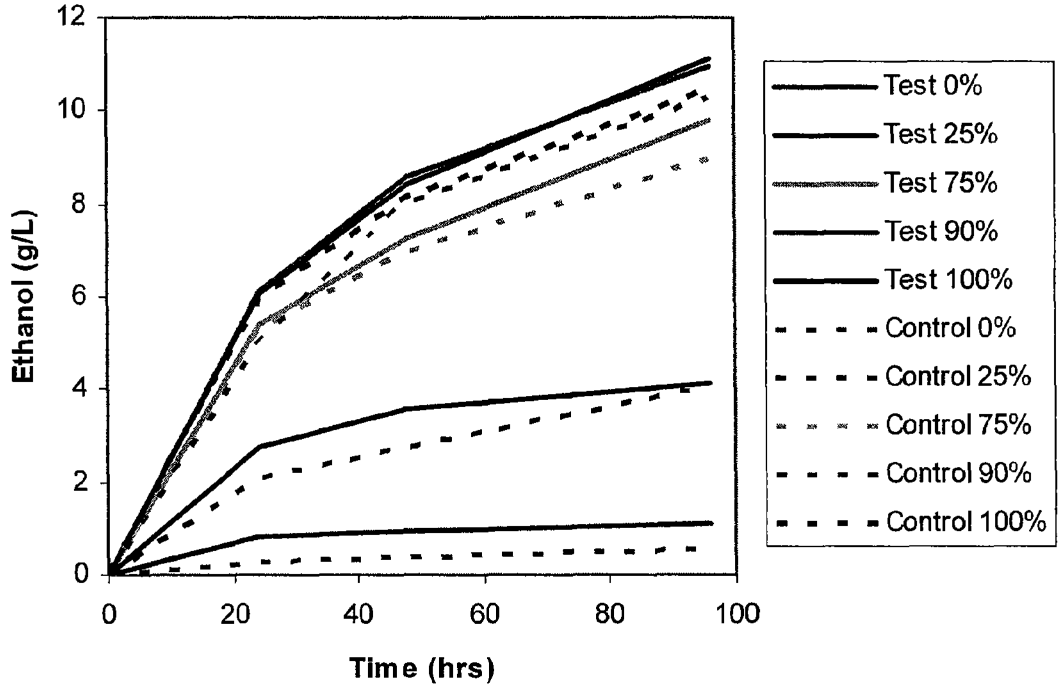
FIG. 8 depicts the ethanol production from pretreated hardwood (5% based on a dry weight percentage) by an *S. cerevisiae* expressing heterologous cellulases in the presence of various concentrations of exogenously added cellulases.

In these experiments, a recombinant yeast strain expressing four secreted cellulases (MO288) was compared directly to the control strain (MO249) under the same conditions. External cellulases were added at concentrations of 25 mg cellulase per gram cellulose (100%), 22.5 mg cellulase per gram cellulose (90%), 18.75 mg cellulase per gram cellulose (75%) or 6.25 mg cellulase per gram cellulose (25%). Experiments were also performed without adding any external cellulases (0%). Pretreated mixed hardwoods (prepared as described in examples above) at an initial solids concentration of 5% were used as a cellulose source. The data is presented in FIG. 8. From this data, it is clear that the strain producing cellulases makes additional ethanol relative to the control strain for each of the cellulase loading concentrations tested.

Figure 9:
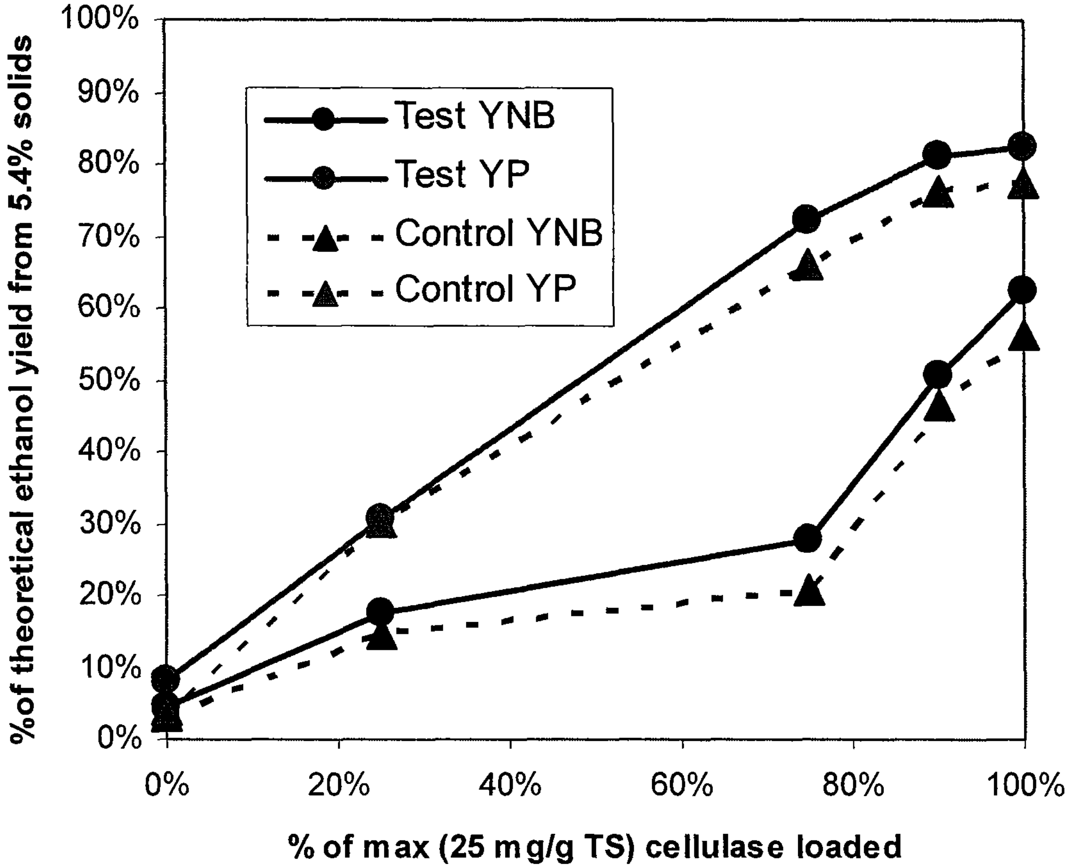
FIG. 9 depicts the ethanol production from Avicel by MO288 (circles) and a control strain (triangles) in both YP media and YNB media.

In order to examine this effect in more detail, ethanol production at different external cellulase concentrations was evaluated in two different types of media using pretreated mixed hardwood. The results are shown in FIG. 9. In YP media, MO288 makes 6-9% more ethanol at the higher cellulase loadings, only 1% more at a 25% loading, and 100% more when no cellulase is loaded. In YNB media MO288 makes 20-40% more ethanol at low cellulase loadings, and ~10% more ethanol at higher cellulase loadings. These results can be used to determine the amount of cellulase that can be removed from the process with the same overall ethanol yield being achieved. For YP media cellulase loading can be reduced ~15% compared to the control, and for YNB media, cellulase loading can be reduced ~5%. At non-zero cellulase loadings ethanol productivity was increased between 5 and 20% for strains expressing cellulases in YP media as compared to the control. It was increased between 10 and 20% for strains cultured in YNB media compared to the control.

These data demonstrate that previous SSF processes can be improved in terms of ethanol yield from biomass and ethanol productivity if strains expressing secreted cellulases are used in combination with exogenously added cellulases. Similarly, cellulase loadings required to achieve a particular percentage of theoretical ethanol yield can be reduced when strains expressing recombinant cellulases are added.

Example 8

Figure 10:
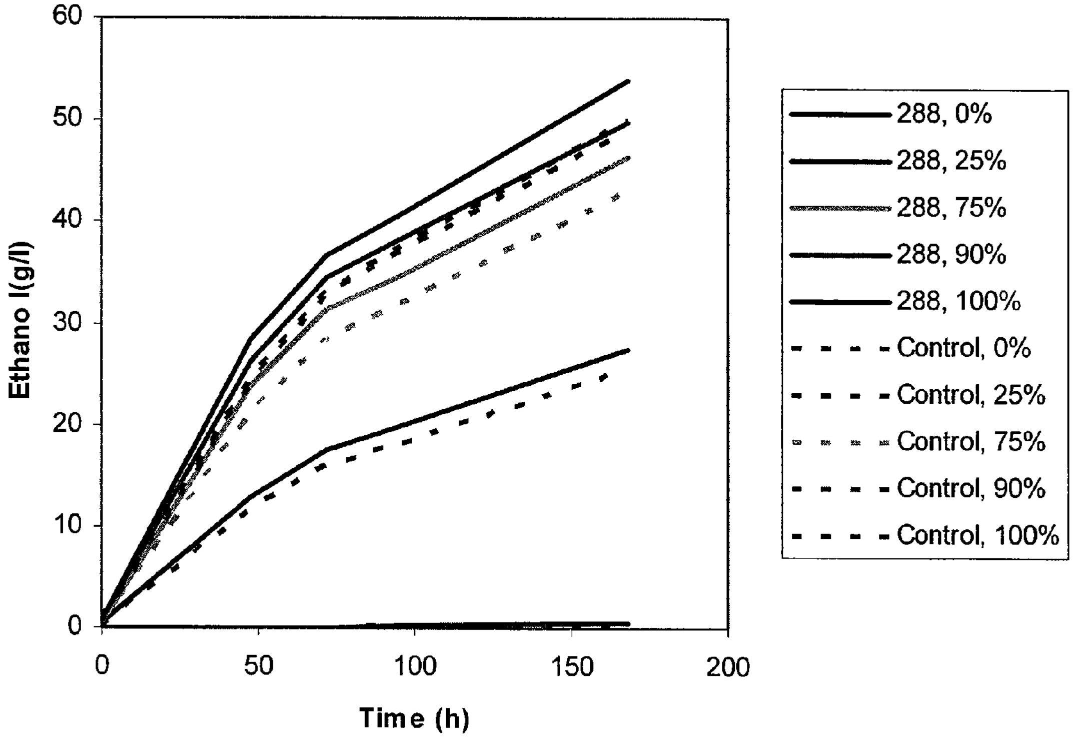
FIG. 10 depicts the ethanol yield from Avicel (15% based on a dry weight percentage) by a small scale simultaneous saccharification and fermentation (SSF) process using *S. cerevisiae* supplemented with external cellulases. The yield from a yeast strain expressing heterologous cellulases (MO288) is compared to the yield from a control strain (MO249) at a variety of external cellulase concentrations over 150 hours. (100% cellulase loading indicates 25 mg/g total solids; initial solids concentration was 15%.)
Figure 11:
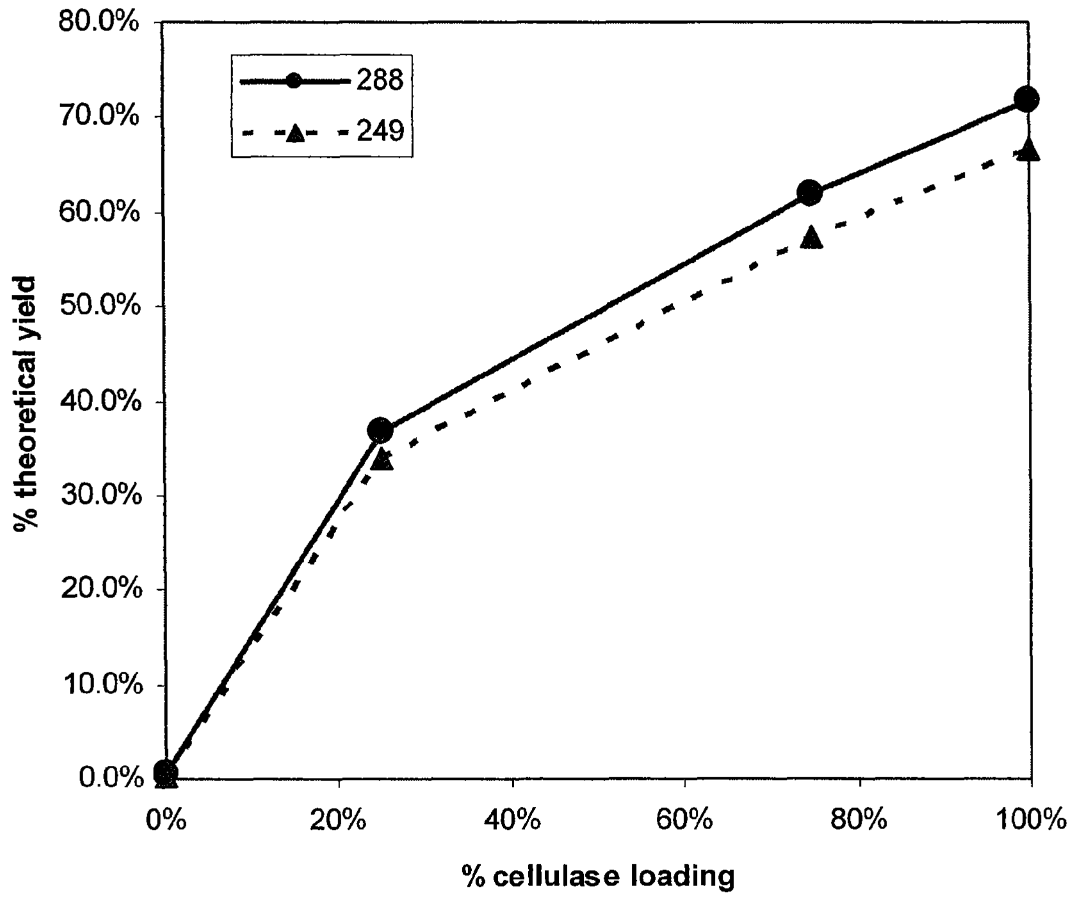
FIG. 11 depicts the theoretical ethanol yield from a simultaneous saccharification and fermentation (SSF) process using *S. cerevisiae* supplemented with external cellulases. The yield from a yeast strain expressing heterologous cellulases (MO288) is compared to the yield from a control strain (MO249).

Transformed Yeast Strains Also Increase Efficiency of Externally Added Cellulases in the Production of Ethanol from Avicel To test whether this same trend would hold at high substrate concentrations these experiments were repeated using 15% Avicel PH105 as substrate instead of 5% pretreated mixed hardwood. The results are shown in FIGS. 10 and 11. The strain making cellulases (MO288) routinely produced more ethanol from Avicel than the control yeast strain (MO249) under identical conditions, even at increased ethanol concentrations (FIG. 10). For example, when 25 mg cellulase per gram cellulose was loaded in the SSF reaction, the test strain (MO288) produced 54 g/L, while the control (MO249) produced 50 g/L.

Figure 12:
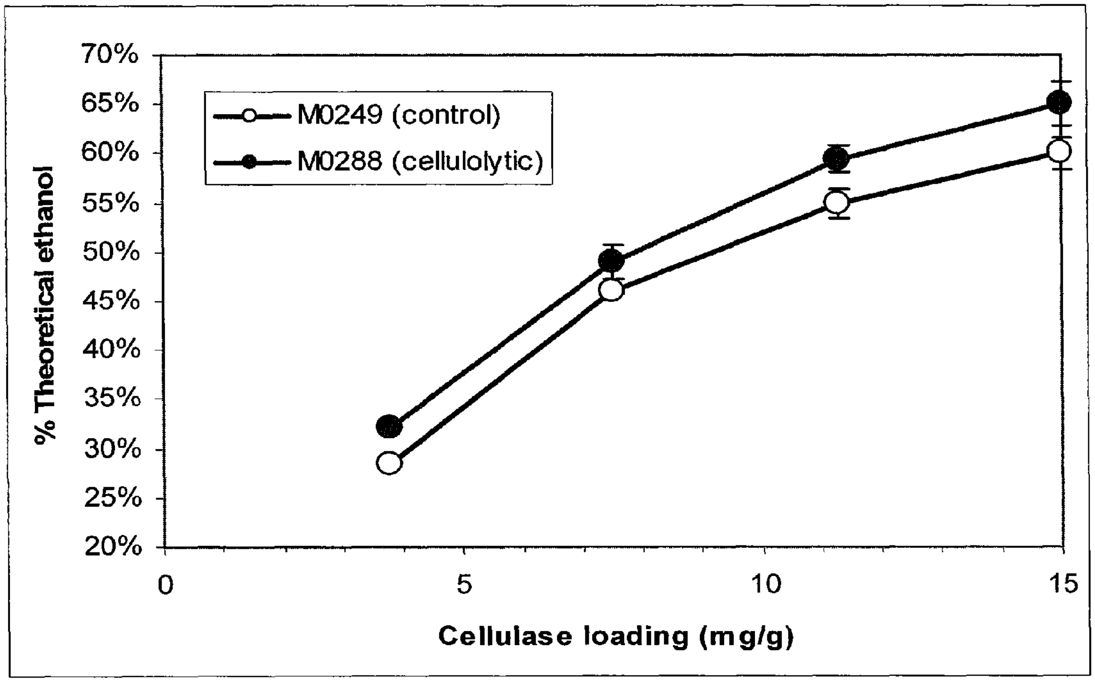
FIG. 12 illustrates the predicted cellulase enzyme savings based on ethanol yield at 168 hours of simultaneous saccharification and fermentation (SSF) process.
Figure 13:
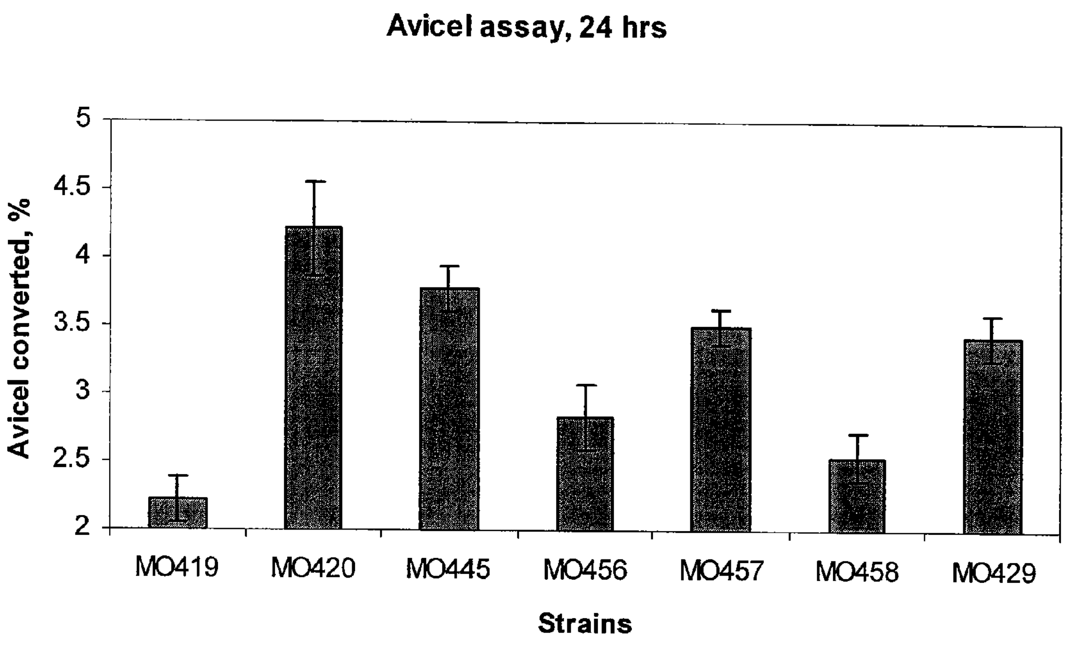
FIG. 13 shows the activity of an artificial cellulase in the Avicel conversion assay as described in Example 9. The MO429 strain was transformed the CBH1 consensus sequence "CBH1cons," and the MO419 strain was transformed with empty pMU451 vector as a negative control. Descriptions of other strains are found in Table 8 of Example 9.

To examine cellulase displacement the percentage of theoretical ethanol yield achieved at different cellulase loadings was determined. The results presented in FIG. 12 were repeated in triplicate for MO288 and MO249, allowing standard deviations for the increased ethanol yields to be calculated. The data that can be used for calculating cellulase displacement is presented in FIG. 12. FIG. 12 presents cellulase enzyme savings based on theoretical ethanol yield at 168 hours in an SSF experiment. SSF was performed in 30 ml of nitrogen purged YP+15% Avicel in pressure bottles. External cellulase mix at a ratio of 5 Spyzme:1 Novozyme-188 was used. The experiment was continued for 168 hours and sampling was done each day for ethanol estimation by HPLC. The arrows in the figure depict the necessary cellulase loading needed to achieve the same ethanol production from cellulose as the control. This loading is consistently lower than for the control (i.e. the ethanol yield is consistently higher). For data at 168 hours, the average cellulase displacement (amount less that needs to be loaded) is 13.3%±4.9%.

Example 9

Use of Artificial Cbh1 to Produce Ethanol

In order to design a CBH1 protein with efficient cellulase activity, 17 CBH1 protein sequences from NCBI database (Table 7) were aligned.

TABLE 7

Fungal CBH1 genes used for alignment.

| Organism | Genbank# |
|---|---|
| *Neosartorya fischeri* | XM_001258277 |
| *Gibberella zeae* | AY196784 |
| *Penicillium janthinellum* | X59054 |
| *Nectria haematococca* | AY502070 |
| *Fusarium poae* | AY706934 |
| *Chaetomium thermophilum* | AY861347 |
| *Aspergillus terreus* | XM_001214180 |
| *Penicillium chrysogenum* | AY790330 |
| *Neurospora crassa* | X77778 |
| *Trichoderma viride* | AY368686 |
| *Humicola grisea* | X17258 |
| *Thermoascus aurantiacus* | AF421954 |
| *Talaromyces emersonii* | AAL89553 |
| *Trichoderma reesei* | P62694 |
| *Phanerochaete chrysosporium* | Z29653 |
| *Aspergillus niger* | XM_001391971 |
| *Aspergillus niger* | XM_001389539 |

The artificial protein sequence was designed as a consensus (the most common) sequence for these proteins. The predicted signal sequence was exchanged by *S. cerevisiae* alpha mating factor pre signal sequence, and the sequence of the consensus CBH1 protein is shown below. Capital letters indicate the *S. cerevisiae* alpha mating factor pre signal sequence.

```
                                                  (SEQ ID NO: 43)
MRFPSIFTAVLFAASSALAqqagtltaethpsltwqkctsggscttvngs

vvidanwrwvhatsgstncytgntwdttlcpddvtcaqncaldgadysst

ygvttsgnslrlnfvtqgsqknvgsrlylmeddttyqmfkllgqeftfdv

dvsnlpcglngalyfvamdadggmskypgnkagakygtgycdsqcpr

dlkfingqanvegwepssndanagignhgsccaemdiweansistaf

tphpcdtigqtmcegdscggtyssdryggtcdpdgcdfnpyrmgnktf

ygpgktvdttkkvtvvtqfitgssgtlseikrfyvqngkvipnsestisg

vsgnsittdfctaqktafgdtddfakkgglegmgkalaqgmvlvmslwdd

haanmlwldstyptdatsstpgaargscdtssgvpadveanspnsyvtfs

nikfgpigstftg.
```

An *S. cerevisiae* and *K. lactis* codon optimized sequence for expressing the CBH1 consensus sequence (SEQ ID NO:44) was developed and is shown below.

```
                                                  (SEQ ID NO: 44)
atgagatttccttcaatcttcactgctgttttgttcgcagcctcaagtgc

tttagcacaacaggccggaacattgacagcagaaactcatccttccttaa
```

-continued

```
cctggcaaaagtgcacttctggaggttcatgcactacagtgaatggatct
gtcgtgatcgatgcaaactggagatgggttcacgcaacttcaggttctac
caactgttataccggaaacacttgggacaccacattgtgcccagatgacg
tcacgtgcgctcagaactgtgctttggatggagctgattacagttcaacc
tatggtgtaactacatccggaaactctttgagattaaacttcgttactca
aggaagtcaaaagaacgttggttctagattgtacttaatggaggacgata
caacctatcaaatgttcaaattgttaggtcaggagttcacctttgacgta
gatgtcagtaacttgccatgtgggttaaacggagctttatactttgtggc
```

-continued

```
aatggatgctgacggtggaatgtccaagtatccaggaaacaaagccggtg
caaagtacggtacaggatattgtgattcacagtgccctagagatttgaag
ttcattaacggtcaagcaaatgtggagggttgggaaccatctagtaacga
tgccaatgcgggtattggtaatcatgggtcctgttgcgctgagatggata
tctgggaggccaactcaatatctactgcctttacccctcacccatgcgat
acaattggtcaaactatgtgcgagggtgattcatgtggtggaacctactc
ctctgatagatacggaggtacatgcgatccagatggttgcgactttaatc
catacagaatgggaaacaaaaccttttacggtcctggaaagacagttgat
actaccaagaaagtaacagtcgtgacccagtttatcaccggtagttctgg
aaccttatccgaaatcaaaagattctacgttcagaacggtaaagtaattc
caaacagtgaatctacaatttcaggagtgagtggtaattctattactacc
gacttttgtacagctcagaaaacagcatttggtgacaccgatgactttgc
taagaagggtggattagaaggtatgggtaaagctttggcccagggaatgg
tgttagttatgtctttatgggatgatcacgccgcaaatatgttatggttg
gattcaacatatccaactgatgccacaagtagtacacctggagctgccag
aggttcttgtgatacatcttccggtgttccagccgatgtagaagcaaatt
ctcctaactcctatgttaccttctccaatataaagtttggtccaatcggt
tcaacattcactggttaa
```

The codon optimized sequence was inserted into the episomal yeast expression vector (pMU451) under control of ENO1 promoter and terminator into PacI/AscI sites. The resulting expression constructs (pMU505) was transformed into MO375 host strain that derived from Y294 (MO013) in which His3 and Trp1 auxotrophies were rescued by transformation with *S. cerevisiae* His3 and Trp1 PCR products. The resulting strain expressing the CBH1 consensus sequence was named MO429.

Figure 14:
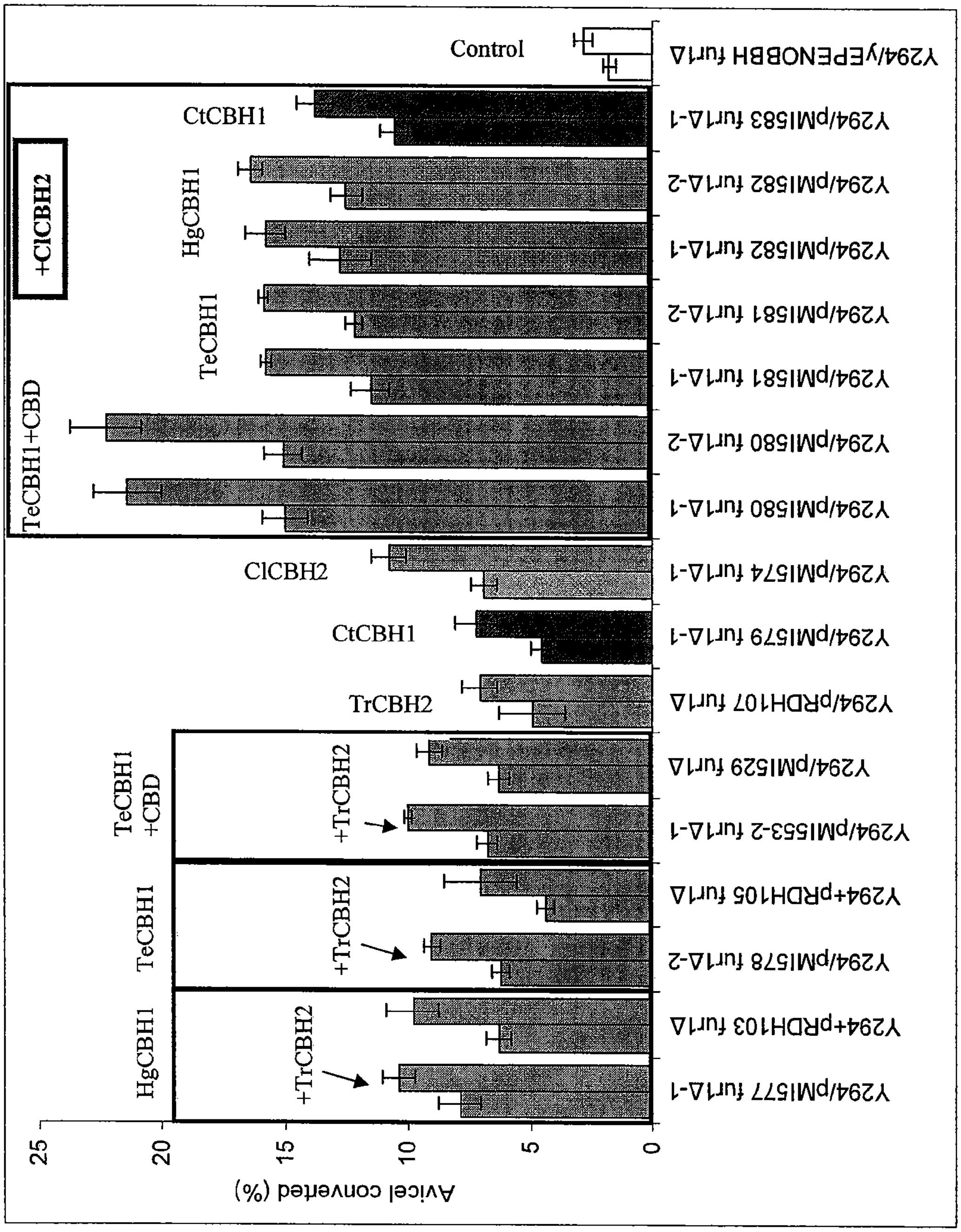
FIG. 14 demonstrates the activity of yeast expressing various combinations of CBH1 and CBH2 enzymes on Avicel as described in Example 10.

In order to determine if MO429 had cellulase activity, an Avicel conversion assay was performed as described above and measured at 24 hours. As shown in FIG. 14, *S. cerevisiae* expressing the consensus Cbh1 sequence (MO429) showed cellulase activity as compared to a negative control transformed with an empty vector (MO419). The cellulase activity of MO429 was also compared to that of yeast strains expressing other heterologous cellulases. The strains tested are summarized in Table 8 below.

TABLE 8

Cellulytic Strains Used in Avicel Conversion Assay

| Strain # | Description | Cellulase | Family | Organism | Activity | Signal |
|---|---|---|---|---|---|---|
| M0419 | MO375 + pMU451 | none | | | none | |
| M0420 | MO375 + pMU272 | CBH1 | Fungi | *Talaromyces emersonii* | exo | native |
| M0429 | MO375 + pMU505 | fungal CBH1 consensus | Fungi | N/A | exo | S.c.αMFpre |
| M0445 | MO375 + pMU459 | CBH1 | Fungi | *Neosartorya fischeri* | exo | S.c.αMFpre |
| M0456 | MO375 + pMU495 | CBH1 | Fungi | *Chaetomium thermophilum* | exo | S.c.αMFpre |
| M0457 | MO375 + pMU496 | CBH1 | Fungi | *Aspergillus terreus* | exo | S.c.αMFpre |
| M0458 | MO375 + pMU497 | CBH1 | Fungi | *Penicillium chrysogenum* | exo | S.c.αMFpre |

All of the strains in Table 8 were derived from the same parental MO375 strain and were transformed with an episomal yeast vector. MO420, MO429, MO445, MO456, MO457 and MO458 were created using episomal yeast vectors containing the heterologous cellulase genes as listed in the table which were codon optimized for expression in *S. cerevisiae* and *K. lactis*. The cellulases in MO429, MO445, MO456, MO457 and MO458 were expressed under control of *S. cerevisiae* ENO1 promoter and terminator. *T. emersonii* CBH1 was expressed with its own native signal sequence. As shown in FIG. 14, the secreted activity on Avicel of the consensus CBH1 was comparable with activity of other fungal CBH1s expressed in the same vector and in the same host strain.

Example 10

Comparison of Cellulase Activity in *S. cerevisiae*

*S. cerevisiae* were transformed with polynucleotides encoding a number of different heterologous cellobiohydrolases and their activity on PASC and Avicel was assessed as described above. The results are shown in the table below:

TABLE 9

Cellobiohydrolase activity in *S. cerevisiae*.

| Plasmid | Expression Cassette(s) | Act. (PASC) (mU/gDCW) | Act. (Avicel) (mU/gDCW) |
|---|---|---|---|
| yENO1 | ENO1p/t | 2.68 ± 1.1 | 2.99 ± 0.7 |
| M0265 | ENO1p/t-sH.g.cbh1 | 32.82 ± 6.5 | 34.85 ± 2.0 |
| M0266 | ENO1p/t-sT.a.cbh1 | 38.56 ± 5.9 | 38.15 ± 4.1 |
| M0247 | ENO1p/t-sT.e.cbh1 | 75.60 ± 13.1 | 21.42 ± 6.1 |
| M0248 | PGK1p/t-sT.r.cbh2 & ENO1p/t-sT.e.cbh1 | 174.35 ± 6.5 | 40.5 ± 4.9 |
| M0289 | PGK1p/t-sT.r.cbh2 & ENO1p/t-sH.g.cbh1 | Not measured | 106.2 ± 6.8 |
| M0291 | PGK1p/t-sT.r.cbh2 & ENO1p/t-sT.a.cbh1 | Not measured | 32.7 ± 5.7 |

In addition, activity on Avicel was assayed using a 96-plate assay, and the results are shown in FIG. 14. In the Figure, for each strain, the first bar indicates the sugar released at 24 hours, and the second bar indicates the sugar released by 48 hours. CBH1s expressed individually, or in combination with *T. reesei* CBH2 showed some avicel activity—reaching 10% conversion of avicel in 48 hours. Combinations of CBH1 with CBH2 from *C. lucknowense* reached much higher avicel conversions of about 22% conversion in 48 hours in combination with *T. emersonii* CBH1 with CBD attached.

Figure 15:
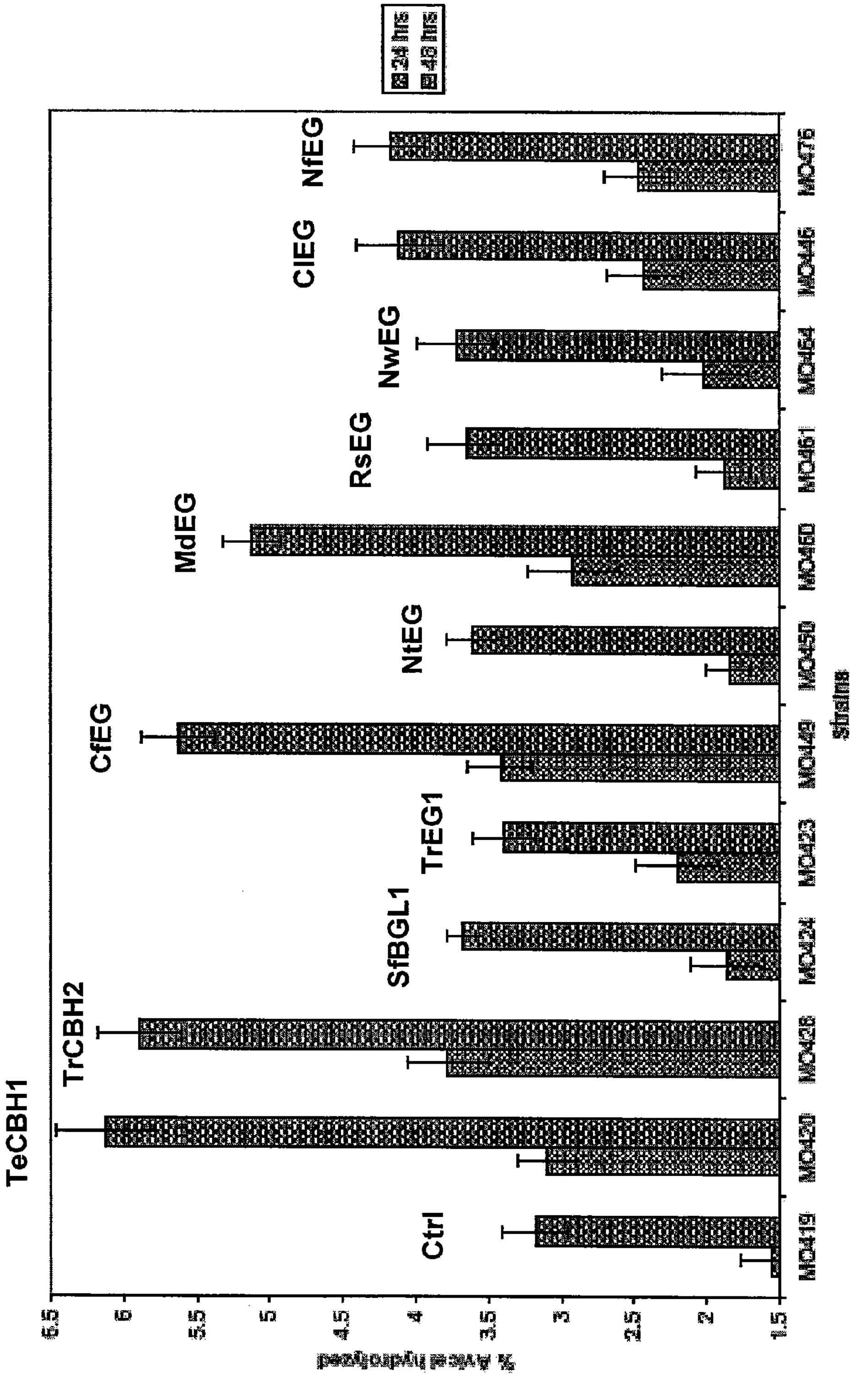
FIG. 15 demonstrates the activity of yeast expressing various cellulase enzymes on Avicel as described in Example 10.

The avicel activity data for endoglucanases tested in *S. cerevisiae* is shown in FIG. 15. The data demonstrate that among the EGs tested the *C. formosanus* EG demonstrated the highest avicel activity when expressed in *S. cerevisiae.*

Example 11

Figure 16:
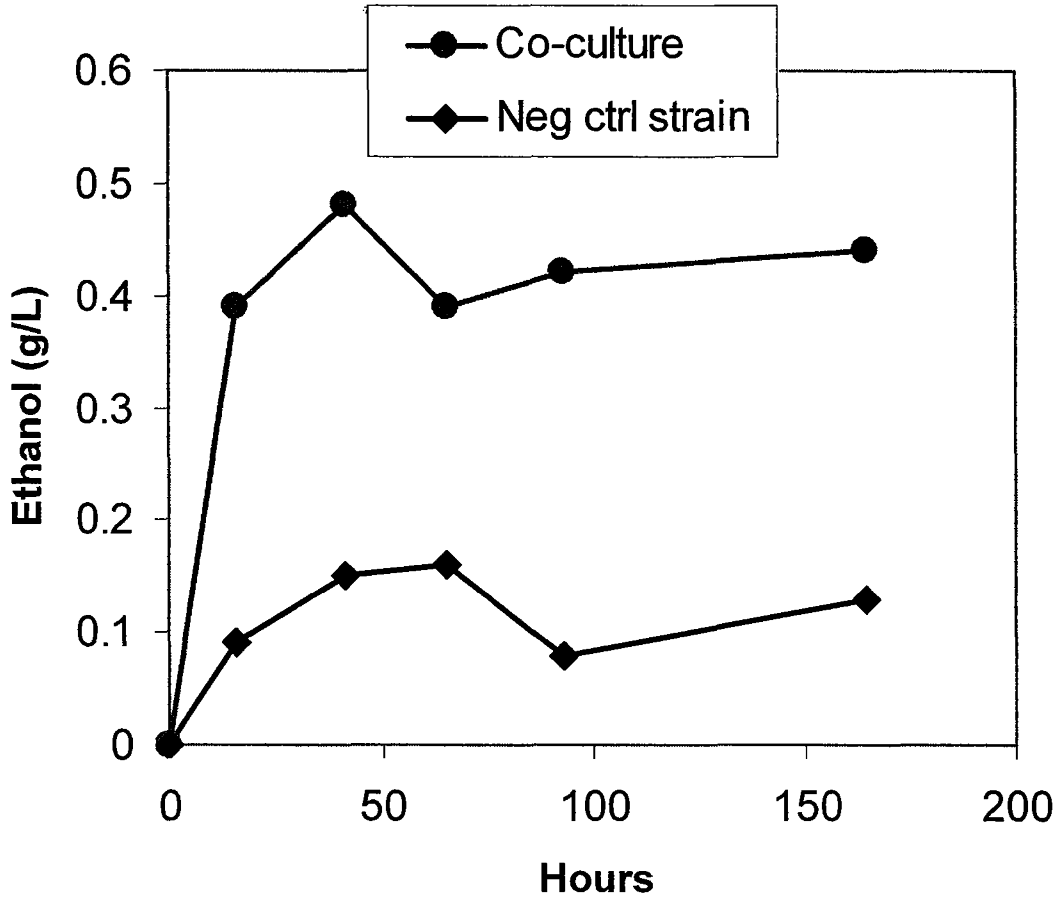
FIG. 16 depicts the ethanol production from Avicel by a co-culture of five *S. cerevisiae* strains expressing heterologous cellulases.

Co-Cultures of Yeast Strains Expressing Different Heterologous Cellulases Produce Ethanol from Avicel A co-culture of a number of cellulase producing yeast strains also showed the ability to make ethanol from Avicel PH105 in YNB media (FIG. 16). In this experiment 5 strains independently producing *T. emersonii* CBH1 (MO247), *T. aurantiacus* CBH1 (MO266), *H. grisea* CBH1 (MO265), a combination of *T. emersonii* CBH1 and *T. reesei* CBH2 (MO248), and a combination of *T. reesei* EGI and *S. fibuligera* BGLI (MO244) were mixed in equal proportion by volume and then inoculated at 20% by volume. Each of the heterologously expressed cellulases in each of these strains was secreted. Media and culture conditions were as described above for Avicel experiments. The data in FIG. 16 demonstrate that heterologous cellulases do not need to be expressed in an individual yeast strain in order to produce ethanol from cellulose. Instead, yeast strains expressing different secreted heterologous cellulases can be cultured together in order to produce ethanol from cellulose without the addition of any exogenous cellulases.

A co-culture using a different combination of cellulases was also evaluated. In this set of co-culture experiments, four yeast strains were cultured together: M0566 (M0424 with FUR deletion): Secreted SfBGLI; M0592 (M0449 with FUR deletion): Secreted CfEGI; M0563 (same as Y294/pMI574 furl Δ): Secreted Cl CBH2b; and M0567 (same as Y294/pMI529 furl Δ): Secreted TeCBH1+CBD. These strains were grown in liquid YPD for 3 days, until the culture was saturate for pre-culture. At this point they were used to inoculate experiments where avicel (10%) was used as the substrate, and the 4 strains were mixed at equal volume prior to inoculation.

Figure 17:
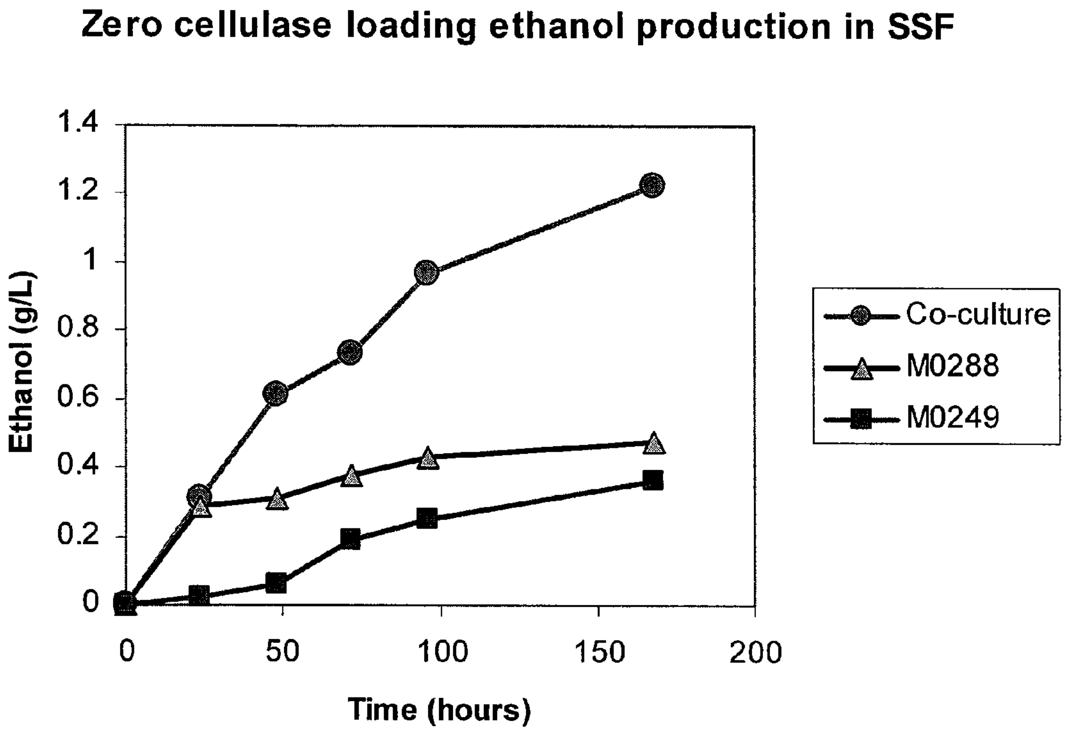
FIG. 17 depicts the ethanol production from Avicel by a co-culture of four *S. cerevisiae* strains expressing heterologous cellulases as well as the ethanol production from strain MO288, which is expressing four cellulases.

FIG. 17 demonstrates that the co-cultured strains are capable of producing ethanol directly from avicel in the absence of any added cellulase enzyme. The co-culture produces about 4-fold more ethanol after 168 hours as compared to the control strain, and about 3-fold more than MO288.

This co-culture was also used in SSF experiments where Zoomerase cellulase enzyme cocktail was used at 5 different loadings (10 mg protein/g avicel, 7.5 mg/g, 5 mg/g, and 2.5 mg/g, and 0 mg/g), and strains were inoculated at 10% by volume.

Figure 18:
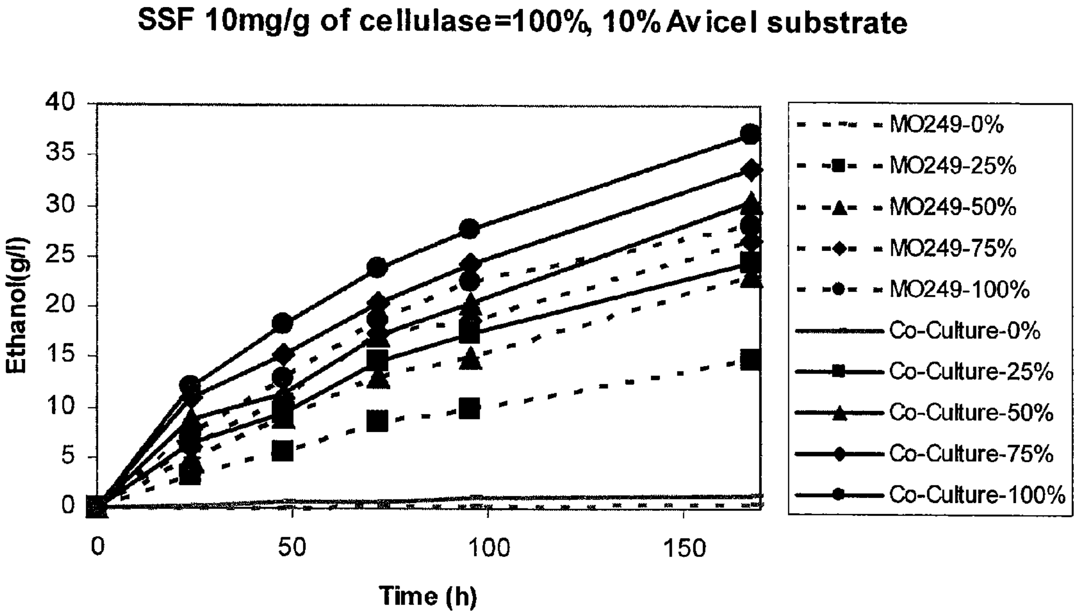
FIG. 18 depicts the ethanol production from Avicel by a co-culture of four *S. cerevisiae* strains expressing heterologous cellulases in combination with externally added cellulase.
Figure 18:
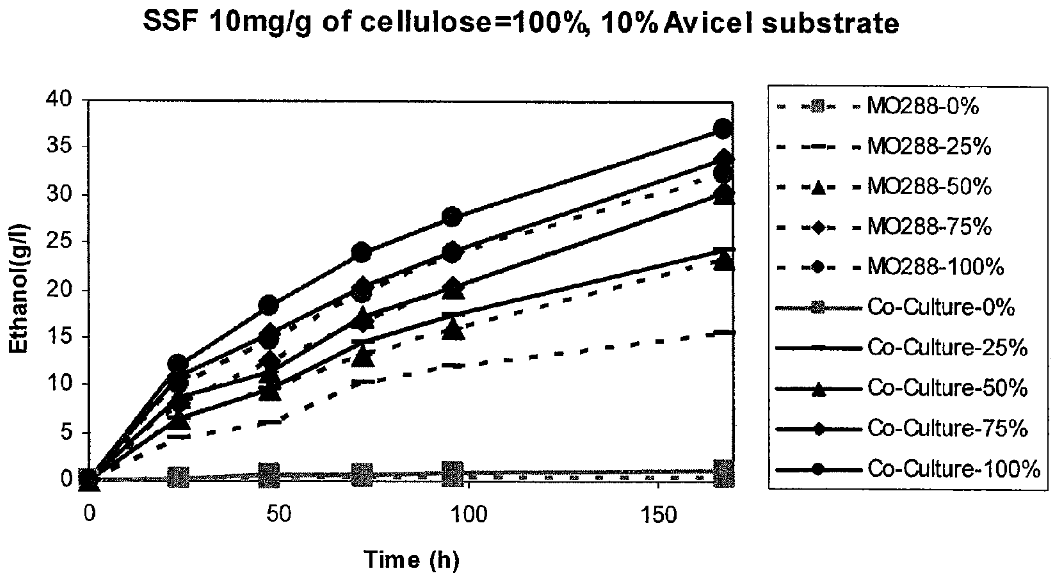
Figure 19:
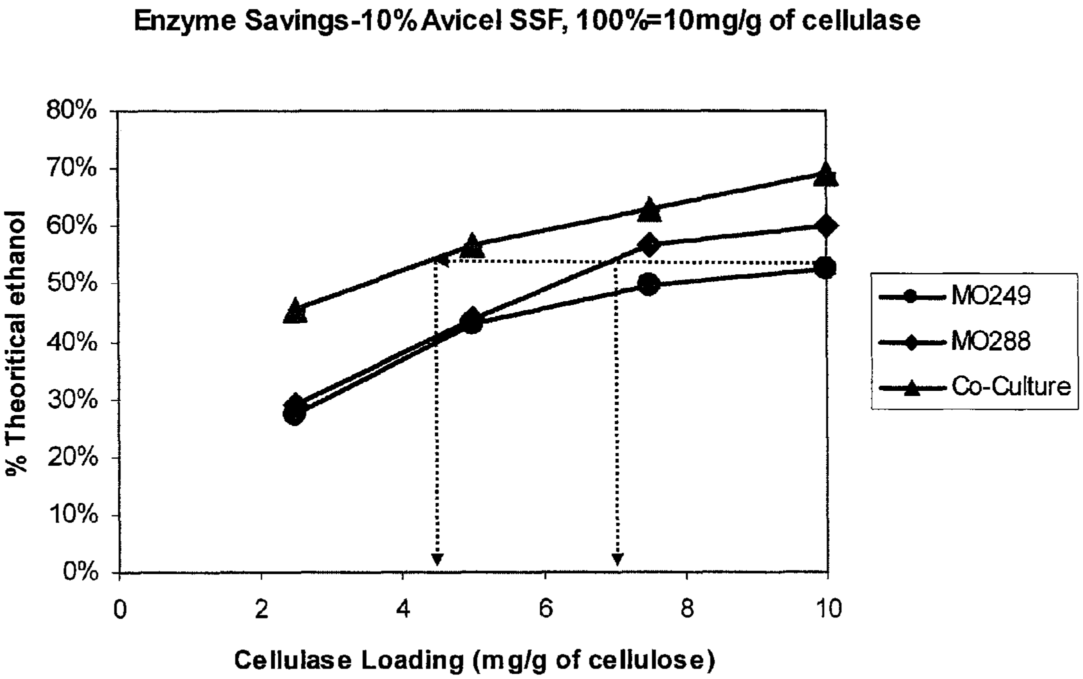
FIG. 19 depicts the calculated enzyme savings using a co-culture of four *S. cerevisiae* strains expressing heterologous cellulases or MO288 as compared to untransformed *S. cerevisiae.*

FIG. 18 presents the raw data for ethanol production at a variety of cellulase loadings by the co-culture, MO288, and MO249. FIG. 18A shows that at all cellulase loadings tested, the co-cultured strains produced significantly more ethanol than a control not producing cellulase. FIG. 18B shows that at all cellulase loadings tested, the co-culture produced more ethanol than the previously tested strain MO288. FIG. 19 shows the percentage of the theoretical yield of ethanol that could be achieved with each of these cultures after 168 hours of SSF using a variety of cellulase loadings. The data demonstrate that the co-cultured strains would achieve about a 2-fold reduction in cellulase relative to the control strain, and approximately a 35% reduction compared to MO288.

These data demonstrate that the combination of cellulases in this co-culture is highly efficient in the production of ethanol.

Example 12

Construction of a Robust Xylose-Utilizing Strain

M0509 (ATCC deposit designation PTA-10493, deposited on Nov. 23, 2009) is a strain of *Saccharomyces cerevisiae* that combines the ability to metabolize xylose with the robustness required to ferment sugars in the presence of pretreated hardwood inhibitors. M0509 was created in a three-step process. First, industrial strains of *S. cerevisiae* were benchmarked to identify strains possessing a level of robustness/hardiness sufficient for simultaneous saccharification and fermentation (SSF) of pretreated mixed hardwood substrates. Strain M0086, a diploid strain of strain of *S. cerevisiae*, satisfied this first requirement. Second, M0086 was genetically engineered with the ability to utilize xylose, resulting in strain M0407. Third, M0407 was adapted for several weeks in a chemostat containing xylose media with pretreatment inhibitors, generating strain M0509.

Strain M0407 was genetically engineered from M0086 to utilize xylose. This engineering required seven genetic modifications. The primary modification was the functional expression of the heterologous xylose isomerase gene, XylA, isolated from the anaerobic fungus *Piromyces* sp. E2. The *S. cerevisiae* structural genes coding for all five enzymes involved in the conversion of xylulose to glycolytic intermediates were also overexpressed: xylulokinase, ribulose 5-phosphate isomerase, ribulose 5-phosphate epimerase, transketolase and transaldolase. In addition, the GRE3 gene encoding aldose reductase was deleted to minimise xylitol production. The seven modified genes are listed in FIG. 39. The genetic modifications at the GRE3, RKI1, RPE1, TAL1, and TKL1 loci were designed to leave behind minimal vector DNA and no antibiotic markers. Each locus' DNA was sequenced to confirm the expected results. Each of the seven genetic modifications were sequentially introduced into strain M0086. FIG. 40 shows the progression of modifications from top to bottom together with the designations for the strain at each step in the process, starting with M0086 and finishing with M0407.

The deletion of GRE3 and the increased expression of RKI1, RPE1, TAL1, and TKL1 involve modifications of the endogenous *S. cerevisiae* loci. In the case of GRE3, both alleles were deleted. For the other four loci, only a single allele was modified. All of the modifications of endogenous loci required the use of selectable antibiotic markers including $kan^r$ from the *Escherichia coli* transposon Tn903 (confers resistance to G418), nat1 from *Streptomyces noursei* (confers resistance to clonNAT/nourseothricin), and dsdA from *Escherichia coli* (confers resistance to D-serine.) After selection for a desired genomic modification, the antibiotic marker was excised from the genome using the loxP/cre recombinase system. The cre recombinase was carried on plasmid pMU210 which contains a zeocin resistance marker. Loss of pMU210 as well as all antibiotic markers was tested on the appropriate selective media. Subsequent PCR genotyping and DNA sequencing confirmed removal of the antibiotic markers from the modified genomic loci.

The overexpression of RKI1, RPE1, TAL1, and TKL1 was achieved by placing the *S. cerevisiae* triose phosphate isomerase promoter, TPI, immediately 5' of each of the four ORFs. For TAL1 and RKI1, small portions of their endogenous promoters were deleted. To avoid disruption of adjacent ORFs and possible transcriptional regulatory elements, the introduction of the TPI promoter at the RPE1 and TKL1 loci was done such that the RPE1 and TKL1 loci were duplicated with the duplicate copies of both loci being regulated by the TPI promoter.

In order to boost M0407's xylose-utilization and increase its pretreatment inhibitor tolerance, the strain was maintained in a chemostat for four weeks under the following sequential conditions described in Table 10.

TABLE 10

Conditions to Improve M0407.

| Duration (days) | Residence Time (h) | Media |
|---|---|---|
| 5 | 24 | YPX, 20 g/L xylose |
| 5 | 18 | YPX, 20 g/L xylose |
| 7 | 24 | YPX + 25% of a 30% MS129 washate (21.5 g/L xylose) |
| 14 | 24 | YPX + 75% of a 30% MS129 washate (~22% solids equivalent) |

An aliquot of the adapted chemostat culture was plated on YPXi50% and nine M0407 "adapted" colonies were screened in YPDXi media (100 g/L glucose, 50 g/L xylose, 25% MS149 pressate). M0407 and M0228 (a xylose-utilizing strain created at Mascoma containing XlyA and XKS1 on plasmids) were included as controls. At 24 hours, the glucose had been entirely consumed by all strains. M0407 and M0228 had utilized 30 and 25 g/L of xylose respectively. All nine M0407 "adapted" colonies had utilized more than 44 g/L of xylose. The highest amount of xylose consumed was 48 g/L. This strain was designated M0509.

18S rDNA sequencing was used to confirm strain M0509 as *Saccharomyces cerevisiae* (Kurtzman C P and Robnett, C J; FEMS Yeast Research 3 (2003) 417-432). A 1774 bp fragment spanning the 18S rDNA was amplified from M0509 genomic DNA and sent for sequencing. The 1753 bp of M0509 18S rDNA sequence exhibited a 100% match to the NCBI sequence for *S. cerevisiae* 18S (nucleotide accession #Z75578).

Since strain M0509 was obtained by cultivating M0407 in a chemostat for four weeks, the length of cultivation separating the two strains provides a means to asses the stability of the engineered genetic modifications. Comparision of the DNA sequence of M0407 and M0509 at the GRE3, RKI1, RPE1, TAL1, and TKL1 loci showed no changes. This suggests that the genetic modifications at these loci are genetically stable, at least under the growth conditions used.

Real Time PCR analysis was used to estimate the copy number of integrations of the XylA/XKS1 vector. M0407 has approximately 10 copies of the vector, whereas M0509 has approximately 20 copies. This suggests that the copy number of the XylA/XKS1 vector can be increased by extended cultivation on xylose media.

To further asses the stability of the XylA/XKS1 integrations, M0509 was cultivated for ~50 generations in liquid media with either glucose or xylose as the sole carbon source. After 50 generations, an individual colony was isolated from each culture and the number of XylA/XKS1 integrations quantified and compared to the original M0509 freezer stock. The colony isolated from the xylose-culture had ~20 copies of XylA/XKS1, the same as the freezer stock. The glucose-cultured colony exhibited a slightly decreased copy number, ~16.

Figure 20:
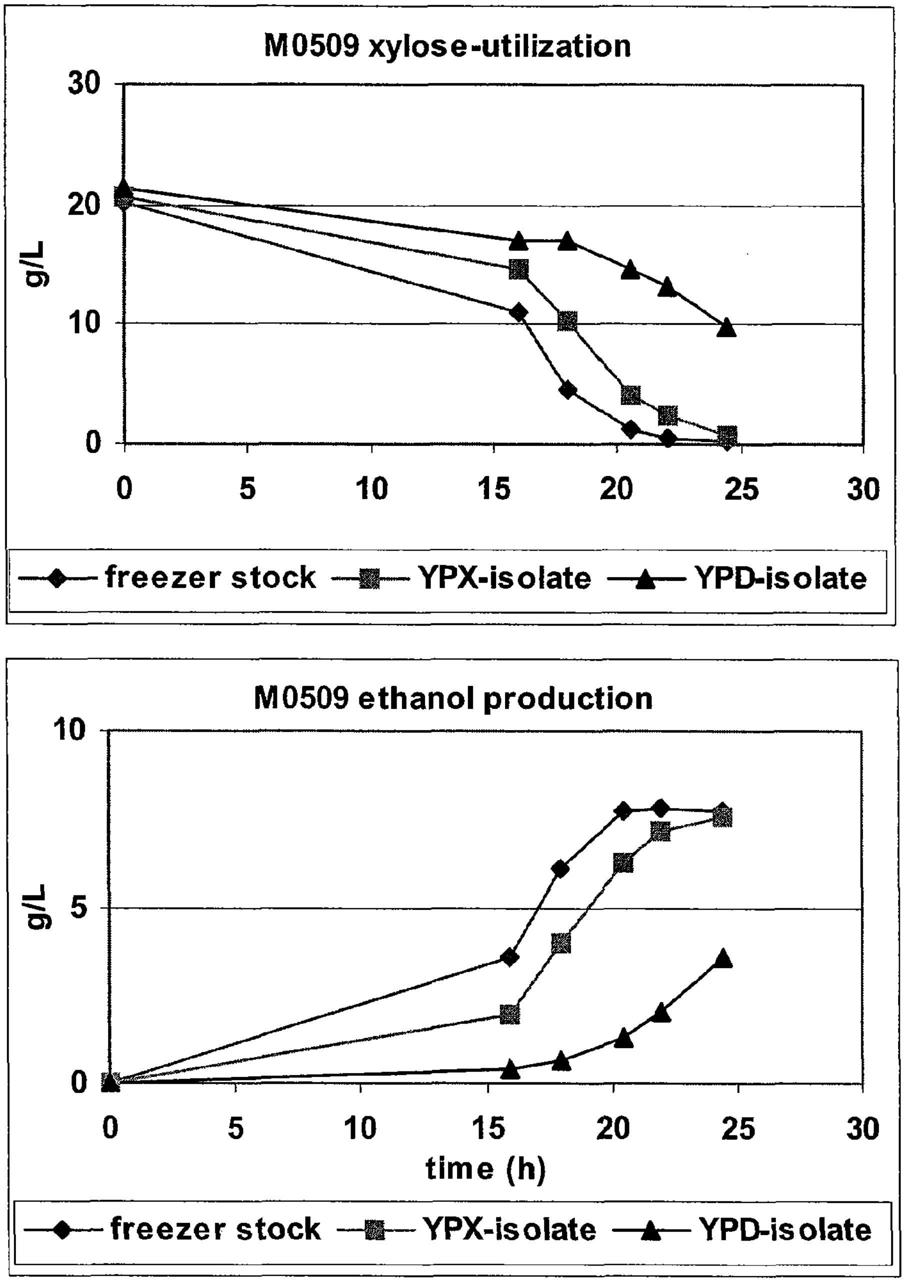
FIG. 20 depicts the xylose utilization and ethanol production of M0509 freezer stock, YPX-isolate and YPD-isolate.

The slight decrease in XylA/XKS1 copy number of the glucose-colony raises the question of the strain's performance. To partially address this question, xylose consumption was compared between the xylose-isolate, glucose-isolate, and freezer stock. The freezer and xylose-propagated isolates utilized all of the xylose in 24 hours and produced identical amounts of ethanol, but the glucose-propagated strain consumed only half as much xylose. FIG. 20.

Example 13

Selection of a Thermotolerant, Robust, Xylose-Utilizing Strain

M1105 is capable of fermentation at temperatures above 40° C. in the presence of 8 g/L acetate. M1105 was constructed in a M0509 background and is therefore an industrially robust strain capable of converting both glucose and xylose into ethanol.

M1105 was isolated following four rounds of selection/adaptation in a cytostat as outlined in FIG. 41 and described as follows. The temperature was increased from 38° C. to 41° C. during the course of the experiment. M1017 (ATCC deposit designation PTA-10492, deposited on Nov. 23, 2009) was isolated from this first cytostat run and was later confirmed by PCR of the GRE3 locus to be a descendant of M0509. M1017 was used to inoculate a second cytostat run using YMX media (yeast nitrogen base, 2 g/L xylose) at 41° C. M1046 was isolated from this second cytostat run. At 42° C. on YPX50, M1046 grew slowly yet with a doubling time 36% shorter than M1017. M1080 was isolated from a cytostat inoculated with M1046 and YMX media at 40° C. M1080 grew with a specific growth rate of $0.22\ h^{-1}$ on YMX at 40° C. M1105 was isolated from M1080 based on selection in the cytostat using YPD2X10+acetate media (2 g/L glucose, 10 g/L xylose, 8 g/L acetate, pH 5.4) at 39° C.

Figure 21:
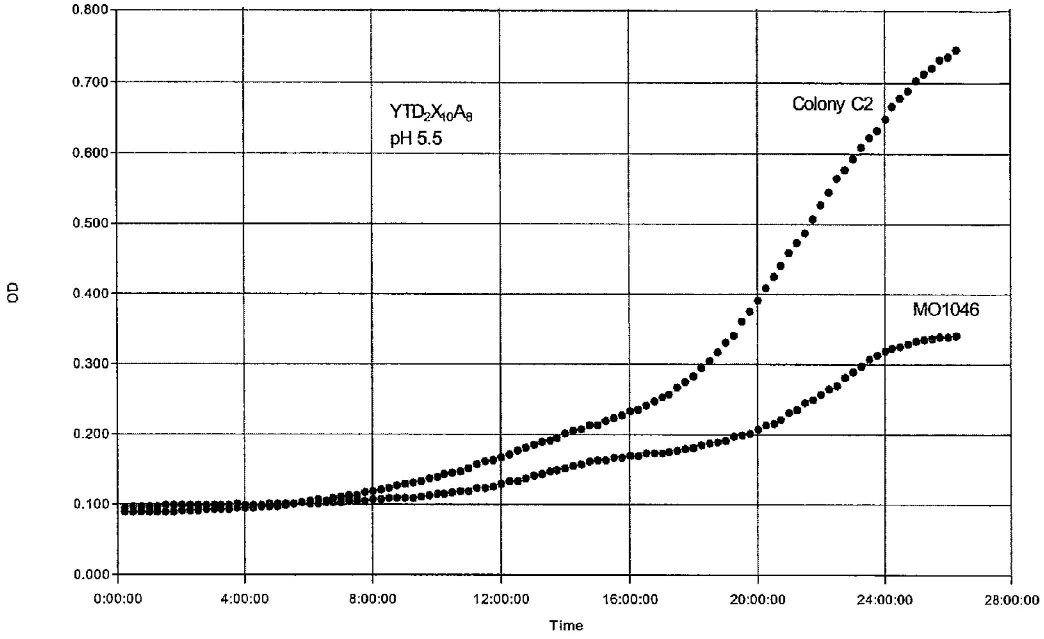
FIG. 21 depicts the growth of M1105 (labeled "colony C2") and MO1046 in the presence of the same medium and 8 g/L acetate at 40° C.

M1105 grows 10-20% faster than M0509 in rich media at 35° C. In addition, M1105 has increased acetate tolerance as the strain can grow more quickly than its ancestral strains in the presence of acetate. FIG. 21. While the parental strains required glucose for tolerance to acetate at high temperatures, M1105 does not require glucose or complex medium components to grow in the presence of 7 g/L acetate at pH 5.4.

Figure 22:
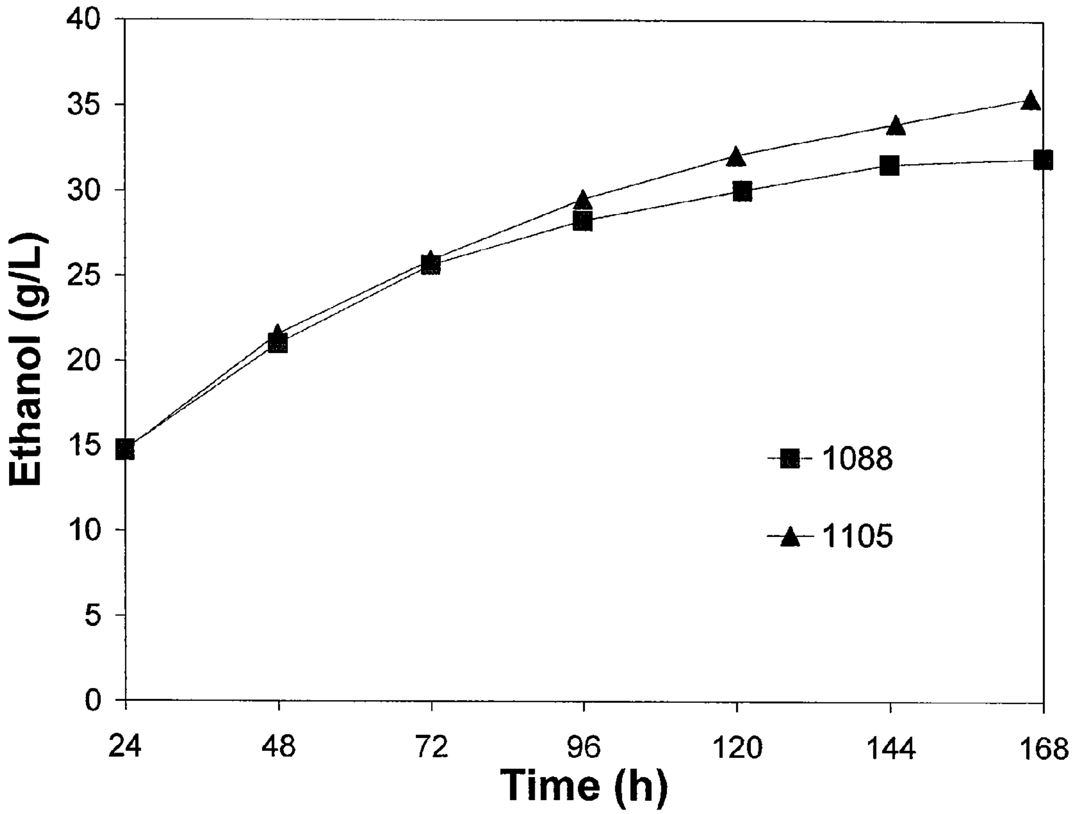
FIG. 22 depicts the ethanol production by M1105 (triangles) and M1088 (squares) on 18% TS MS419. The experiment with M1105 had 10% lower enzyme dose and half the inoculated cell density, but produced a higher ethanol titer. The experiment with MO1105 was performed at 40° C., and the experiment with M1088 was performed at 35° C.
Figure 23:
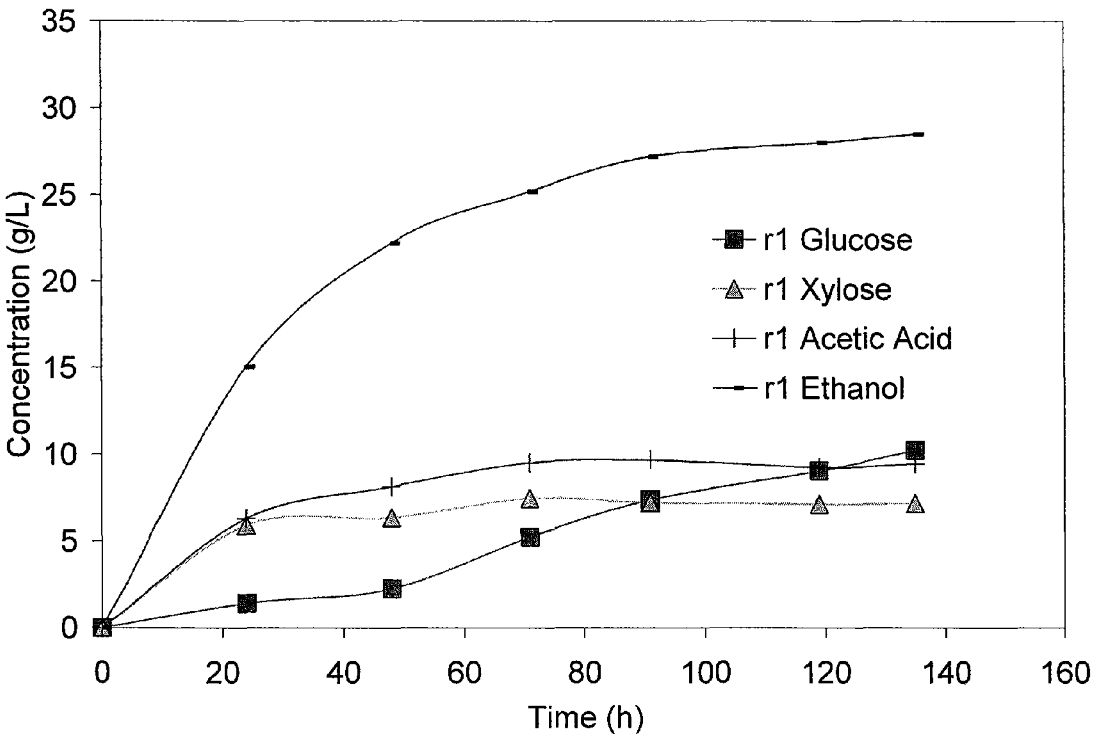
FIG. 23 depicts the ethanol production of M1105 where the fermentation was only inoculated with 0.15 g/L DCW and resulted in some sugar accumulation and 29 g/L ethanol.

To test fermentation performance, M1105 was inoculated at approximately 0.7 g/L DCW in 18% MS419 using 3.8 mg Zoomerase/g feedstock at 40° C. M1105 produced 3.55% (w/v) ethanol by 168 hours. The time course is presented in FIG. 22 along with a similar run performed with M1088 (described below) for comparison. A similar run using only 0.15 g/L DCW for inoculum resulted in 2.9% (w/v) ethanol and some sugar accumulation during the experiment. FIG. 23.

Example 14

Adaptation of a Thermotolerant, Robust, Xylose-Utilizing Strain

M1254 is capable of fermentation at temperatures above 40° C. in the presence of 12 g/L acetate, exhibiting an increased robustness relative to the thermotolerant strain M1105.

M1254 was isolated following three rounds of selection/adaptation in a cytostat as outlined in Table 11 and FIG. 42 and described as follows. The first cytostat run was inoculated with M1105. YMX media (yeast nitrogen base w/o amino acids, 20 g/L xylose) plus 8 g/L acetate was used at pH 5.5 and 40° C. M1155 was isolated from this first cytostat run and used to inoculate a second cytostat containing YPD media (yeast extract, peptone, 20 g/L glucose) plus 12 g/L acetate at pH 5.4 and 41° C. M1202 was isolated from this second cytostat run. M1254 was isolated from a third cytostat run inoculated with both M1155 and M1202 in yeast nitrogen base w/o amino acids+5% solids equivalent MS419 hydrolysate media at pH 4.8, 39° C.

TABLE 11

Evolutionary Conditions to Generate M1254 from M1105.

| Parental Strain(s) | Evolutionary Condition | New Strain |
|---|---|---|
| M1105 | Xylose minimal + 8 g/L acetate, pH 5.5, 40° C. | M1155 |
| M1155 | Complex glucose + 12 g/L acetate, pH 5.4, 41° C. | M1202 |
| M1155 + M1202 | 5% solids equivalent MS419 hydrolysate + yeast nitrogen base w/o amino acids, pH 4.8, 39° C. | M1254 |

Figure 24:
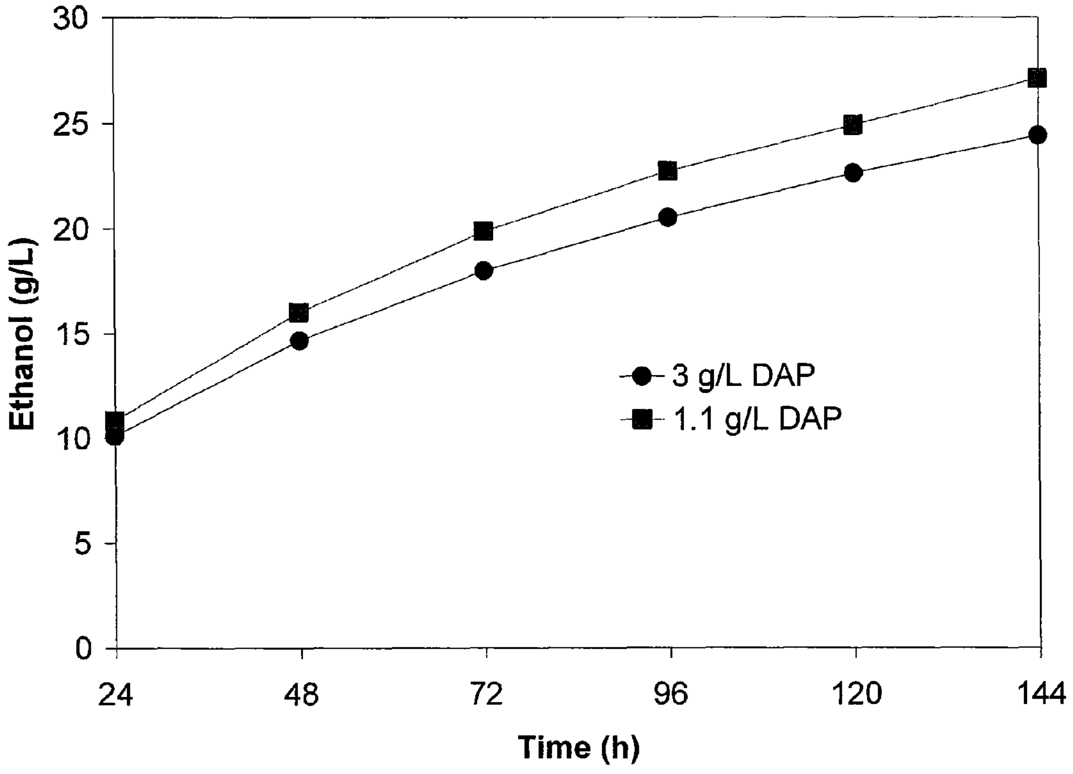
FIG. 24 depicts the ethanol production of M1254 is standard IFM (circles) and low ammonium IFM (squares) conditions.

M1254 grows 7.3±0.9% faster than M1202 and 17±2.0% faster than M1155 in 5% solids equivalent MS419 hydrolysate, which is the condition under which strain M1254 was selected. However, standard fermentation medium limits fermentation performance. Accordingly, use of this strain should be with lower ammonium concentrations, such as 1.1 g/L diammonium phosphate (DAP) or lower than 3 g/L DAP. FIG. 24 demonstrates the higher fermentation rate using the lower DAP concentration. The fermentations were performed using 18% MS149, 4 mg external cellulase/g TS, 40° C., 0.5 g/L inoculation DCW M1254 and pH 5.4. The pH was controlled using 5 M potassium hydroxide, and 1 g/L magnesium carbonate was fed with each solids feeding. All enzyme was front loaded, while the solids were fed at five time points (0, 3, 6, 24, and 48 hours) in equal size feedings of 3.6% TS.

MO1360 was created from M1254 using the evolutionary conditions described in Table 12 below.

TABLE 12

Conditions to Generate M1360 from M1254.

| Parental Strain(s) | Evolutionary Condition | New Strain |
|---|---|---|
| M1254 | Complex with low xylose + 8 g/L acetate, pH 5.4, 40° C. | M1339 |
| M1339 | Complex xylose + synthetic inhibitor mixture (including 8 g/L acetate), pH 5.4, 40° C. | M1360 |

Figure 25:
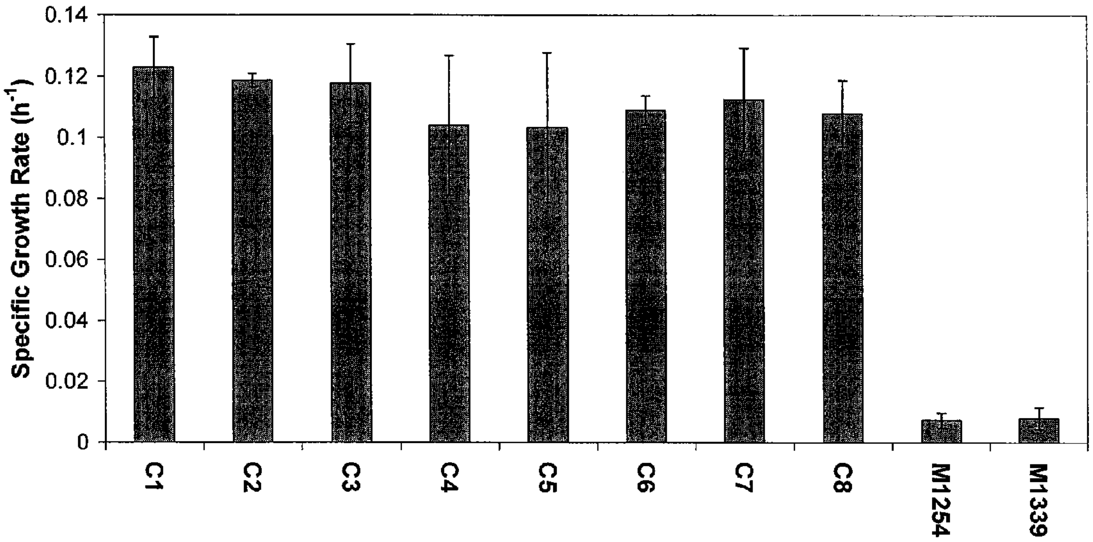
FIG. 25 depicts the specific growth rate of single colonies compared to M1254 and M1339 on complex xylose medium supplemented with a synthetic inhibitor mixture (which included 8 g/L acetate) at 40° C. The single colonies were screened at the same conditions as the evolution occurred. Colony C1 was renamed M1360.
Figure 26:
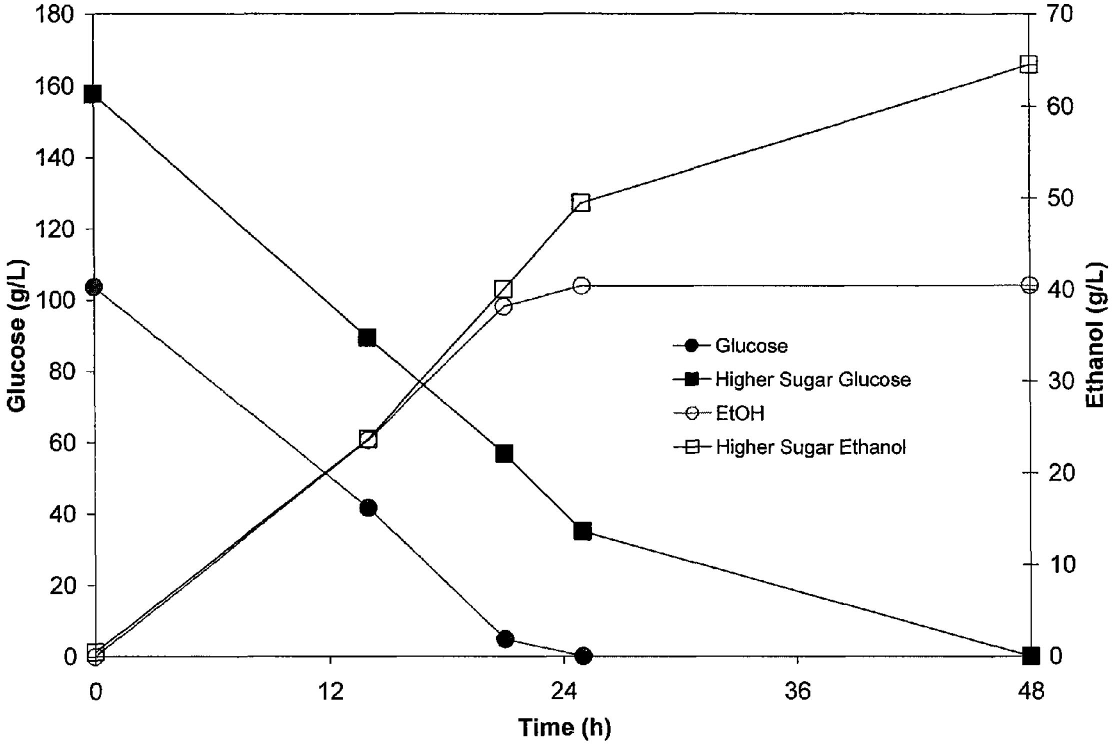
FIG. 26 depicts the fermentation performance of M1360 at 40° C. on industrially relevant fermentation medium supplemented with glucose. The fermentation was inoculated with 60 mg/L dry cell weight of M1360.

M1360, while still substantially inhibited by the synthetic inhibitor mixture, grows at 40° C. with a doubling time of approximately 5 hours. FIG. 25. In industrially relevant medium, M1360 is able to generate over 60 g/L ethanol from glucose along with g/L dry cell weight in 48 h at 40° C. beginning with only 60 mg/L dry cell weight. FIG. 26.

Figure 27:
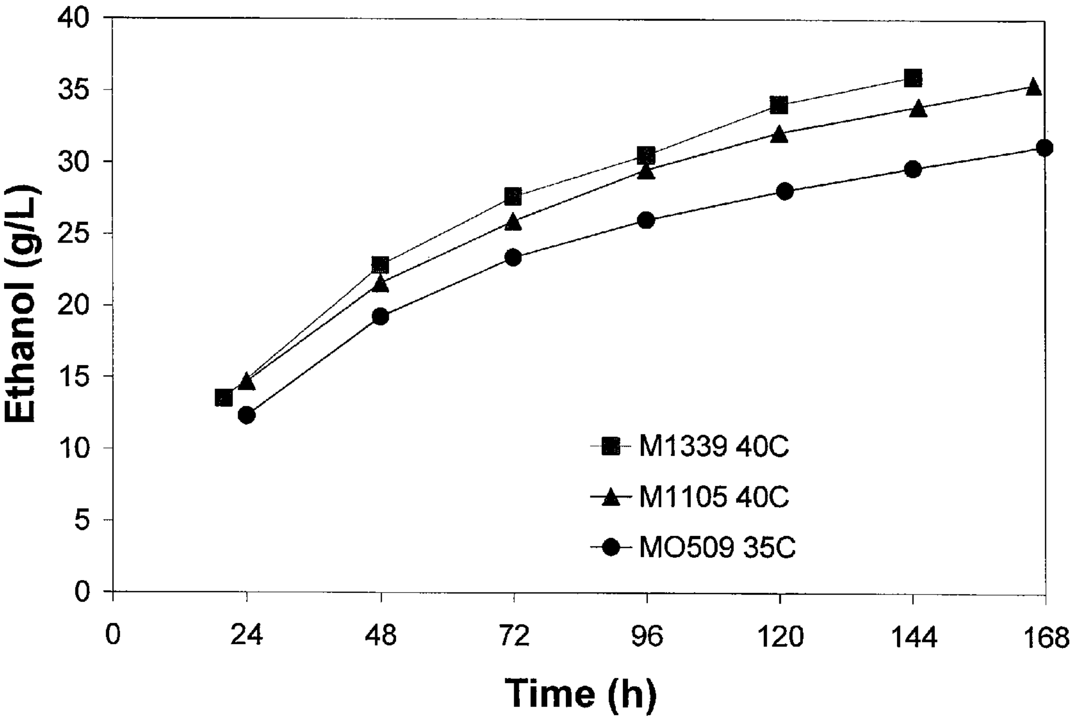
FIG. 27 depicts the ethanol production in SSF runs on PHW (18% solids, unwashed MS149) at 35° C. and 40° C. by several strains. All reactions were loaded with 4 mg/g "zoomerase" (Novozyme 22c).

Enzyme activity is known to increase as temperature increases, and thus it is desirable to have thermotolerant *S. cerevisiae* strains. FIG. 27 shows three equivalent SSFs with 18% PHW solids loaded. The reactions carried out at 40° C. show approximately 17% more ethanol produced than the control reaction carried out at 35° C., when both reactions were carried out at the same external enzyme loading (4 mg/g). This increased performance represents a substantial cost savings for the process.

Example 15

Expression of Cellulases in a Robust Xylose-Utilizing Strain

M1088 is capable of secreting three distinct cellulolytic enzymes: β-glucosidase from *S. fibuligera* (SfBGL), cellobiohydrolase 2b from *C. lucknowense* (C1CBH2b), and cellobiohydrolase I from *T. emersonii* fused to the *T. reesei* cellobiohydrolase I cellulose binding domain (TeCBH1+CBDTrCBH1). The M1088 genome also contains genes that encode for polypeptides capable of providing resistance to the following antibiotics: kanamycin, nourseothricin, and hygromycin B. Plasmid pMU624, which is also present in M1088, contains a gene encoding for a polypeptide capable of providing resistance to ampicillin. The steps used to generate M1088 and M0963 from M0509 are summarized in Table 13 below.

TABLE 13

Strains Used to Generate Strains M1088 and M0963

| Strain | Genotype | Parent | Description |
|---|---|---|---|
| M0509 | gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta | | |
| M0539 | URA-3/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta | M0509 | A single copy of the genomic URA-3 gene was deleted and replaced with a kanMX cassette. The KanMX gene cassette provides resistance to kanamycin (an aminoglycoside antibiotic). |
| M0544 | ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta | M0539 | The second copy of the genomic URA-3 gene was deleted and replaced with a kanMX cassette. |
| M0749 | ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta (pMU782)fur1::nat | M0544 | A single copy of the genomic FUR-1 gene was deleted and replaced with a *Streptomyces noursei* nat1 cassette. The nat1 gene cassette provides resistance to the antibiotic nourseothricin/clonNAT (an aminoglycoside antibiotic). |

TABLE 13-continued

Strains Used to Generate Strains M1088 and M0963

| Strain | Genotype | Parent | Description |
|---|---|---|---|
| M0867 | FUR-1/fur-1::nat ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta (pMU782)fur1::nat; [pMU624] | M0749 | The plasmid pMU624 was transformed into the strain. pMU624 can replicate in *S. cerevisiae* (2 micron ori and URA-3) and *E. coli* (pBMR ori and ampicillin resistance gene: beta-lactam antibiotic). pMU624 also carries the *T. emersonii* CBH1 + CBDTrCBH1 gene regulated by the ENO1 promoter and terminator. |
| M0759 | fur-1::hyg/fur-1::nat ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta (pMU782) fur1::nat; [pMU624]; (pMU1037) fur1::hyg | M0867 | The second copy of the genomic FUR-1 gene was deleted and replaced with a hygMX cassette. The hygMX gene cassette encodes for a hygromycin B phosphotransferase that confers resistance to hygromycin B (an aminoglycoside antibiotic). |
| M1088 | fur-1::hyg/fur-1::nat ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta [pMU624] (pMU1260) delta::PGKprom-SfBGL-PGKterm, ENO1prom-TeCBH + TrCBD-ENO1term (pMU1169) delta::PGKprom-SfBGL-PGKterm, ENO1prom-ClCBH2-ENO1term | M0759 | Two distinct integration cassettes were transformed into the strain and multiple copies were integrated into the genome at delta site. One cassette contained the cellulolytic genes *S. fibuligeria* BGL and C. lucknowense CBH2b. The other cassette contained the cellulolytic genes *S. fibuligeria* BGL and a *T. emersonii* chimeric CBH1. |
| M0963 | fur-1::hyg/fur-1::nat ura-3::kanMX/ura-3::kanMX gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PADH1-XKS::delta (pMU782) fur1::nat; [pMU624]; (pMU1037) fur1::hyg; (pMU755) delta::ZeoMX, ENO1prom-TeCBH1w/TrCBD-ENO1term; (pMU809) delta::ZeoMX, ENO1prom-ClCBH2b-ENO1term; (pMU663) delta::ZeoMX, ENO1prom-CfEG-ENO1term; (pMU864) delta::ZeoMX, ENO1prom-SfBGL-ENO1term | M0759 | Linear DNA from the 4 plasmids shown was transformed into M0759. 24 of the resulting colonies were then passaged for a week in YPD media containing zeocin at a low level (50 ug/mL), and assayed. The resulting strain M0963 was the best of those found in the avicel assay. |

Example 16

Selection of an Endogluconase for Expression in a Robust Xylose-Utilizing Strain Endoglucanases augment the activity of cellobiohydrolases, and therefore, the ability of family 5 endoglucanases to complement the previously identified CBH1 and CBH2 was invetigated. Five family 5 endoglucanses were selected and cloned under control of the ENO1 promoter/terminator using the pRDH122 expression plasmid as shown in Table 14.

TABLE 14

Family 5 endoglucanases expressed in *S. cerevisiae.*

| Organism & Gene: | CBM domain: | Expression plasmid: | Theoretical enzyme size Da* |
|---|---|---|---|
| *Aspergillus kawachii* egA | C-terminal CBM1 | pRDH145 | 55034.58 |
| *Heterodera schachtii* eng1 | C-terminal CBM2 | pRDH146 | 43739.46 |
| *Hypocrea jecorina* (anamorph: *Trichoderma reesei*) eg2 | N-terminal CBM1 | pRDH147 | 44226.91 |
| *Orpinomyces* sp. PC-2 celB CBM10 | 2x C-terminal | pRDH148 | 53103.40 |
| *Irpex lacteus* en1 | N-terminal CBM1 | pRDH149 | 42357.15 |

Figure 28:
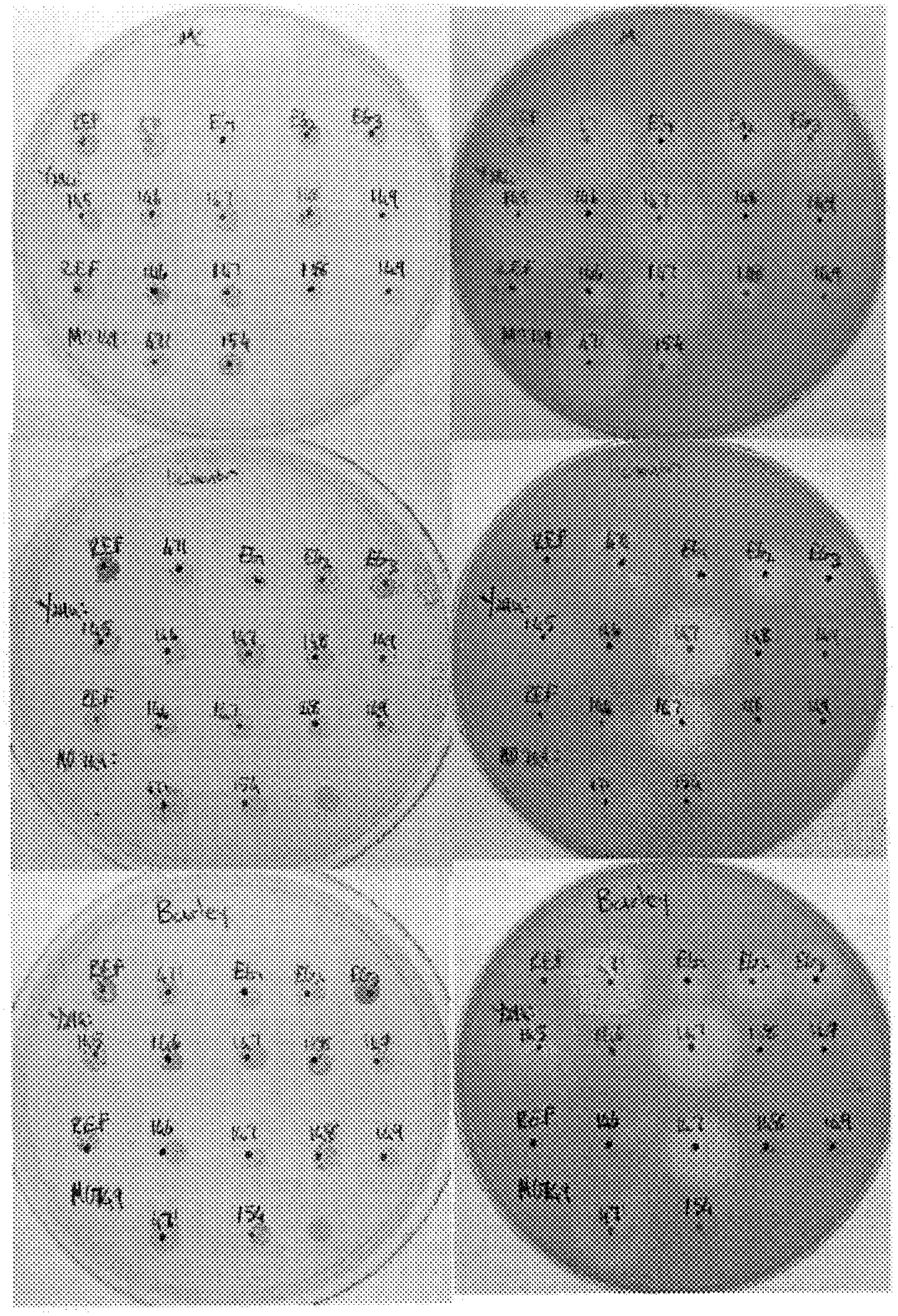
FIG. 28 depicts cultures spotted on $SC^{-URA}$ plates containing 0.2% of either CMC or lichenin or barley-β-glucan. The top two rows of each plate were Y294 based cultures, and the bottom two rows contained M0749 based strains. Numbers indicate the plasmid contained by each strain. pMU471 contains the C.f.EG and served as positive control. Plates were incubated for 24 hours at 30° C. (pictured on the left), after which colonies were washed of and the plates were stained with 0.1% congo red and destained with 1% NaCl (pictured on the right).

All plasmids expressing the 5 new EG2-type cellulases were transformed to Y294 (a lab strain) and M0749 (robust xylose utilizing strain; described above) and transformants were confirmed via PCR. FIG. 28 shows several of the M0749 strains that were spotted on SC$^{-URA}$ plates containing 0.2% of either CMC or lichenin or barley-β-glucan. As can be seen in FIG. 28, the M0749 reference strain yielded small zones on the CMC containing plates. Both pMU471 (*Coptotermes formosanus* EG) and pRDH147 based strains yielded very good clearing zones on all the tested substrates.

Figure 29:
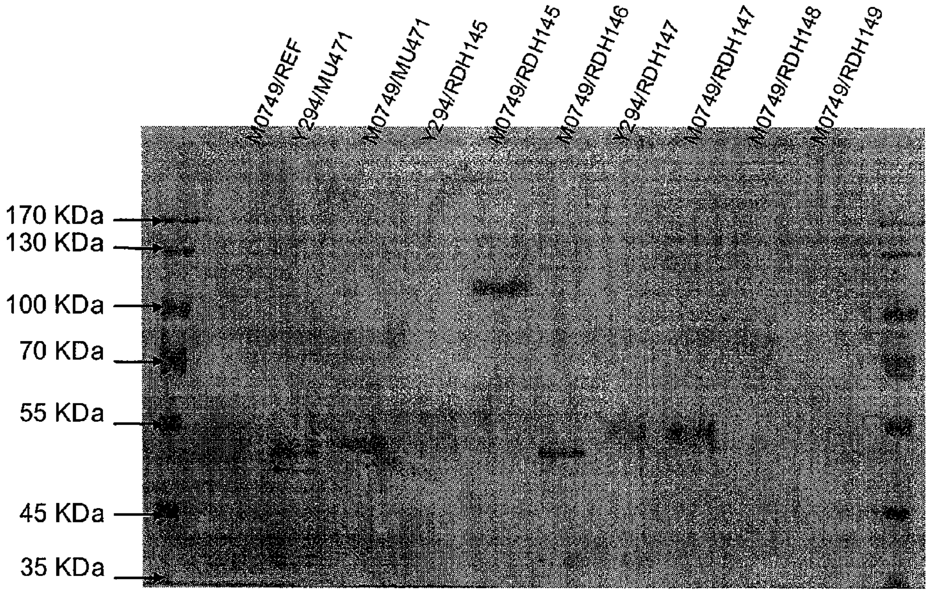
FIG. 29 depicts SDS-PAGE analysis of the supernatants of Cel5 cellulase producing strains. A strain containing a plasmid with no foreign gene was used as reference strain (REF). The strain containing the plasmid pMU471 expressing C.f.EG, the most successful EG previously found was also included.

Along with the reference strain and a strain expressing the *Coptotermes formosanus* EG (pMU471), the five eg2 expressing strains were tested for avicel and PASC hydrolysis while the cbh2 expressing strains were tested for activity on avicel. The strains were grown in double strength SC$^{-URA}$ medium (3.4 g/L YNB; 3 g/L amino acid dropout pool without uracil; 10 g/L ammonium sulfate; 20 g/L glucose) that was buffered to pH 6 (20 g/L succinic acid; 12 g/L NaOH, set pH to 6 with NaOH). 10 mL Cultures in 125 mL Erlenmeyer flasks were grown at 30° C. for three days. Three flasks were inoculated for each strain. After incubation, samples were taken for gel analysis and activity measurement. After centrifugation of the samples, 120 of each was taken, added to 5 μl of protein loading buffer and boiled for 5 minutes. The samples were subsequently loaded on a 10% SDS-PAGE and separated, followed by silver staining. The results are shown in FIG. 29. Not all strains produced visible bands in the expected size range. The C.f.EG appeared as a band of about 55 kDa as previously seen but the band produced by M0749 seems to be slightly larger than the one produced by Y294. No bands were visible for the *H. schachtii* eng1, *Orpinomyces* celB, or *I. lacteus* en1 products. The *H. jecorina* EG2 produced by Y294 and M0749 was visible as ~57 kDa bands. The increased weight compared to the predicted 44 kDA size may represent hyperglycosylation. The *A. kawachii* EGA produced by Y294 was visible as a ~42 kDa band. However, the *A. kawachii* EGA produced by M0749 was clearly visible as a ~120 kDa band. The extra weight may signify hyperglycosylation.

Figure 30:
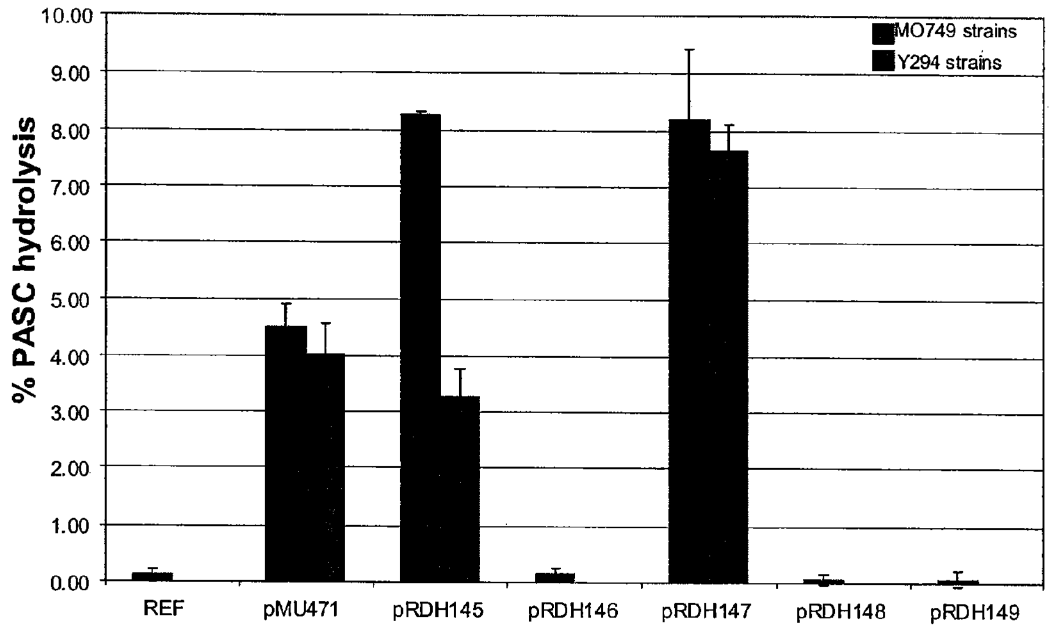
FIG. 30 depicts the activity of strains expressing EGs on (A) PASC (2 hours) and (B) avicel (24 hours). A strain containing a plasmid with no foreign gene was used as reference strain (REF) and the strain expressing C.f.EG (pMU471) was included as positive control.
Figure 30:
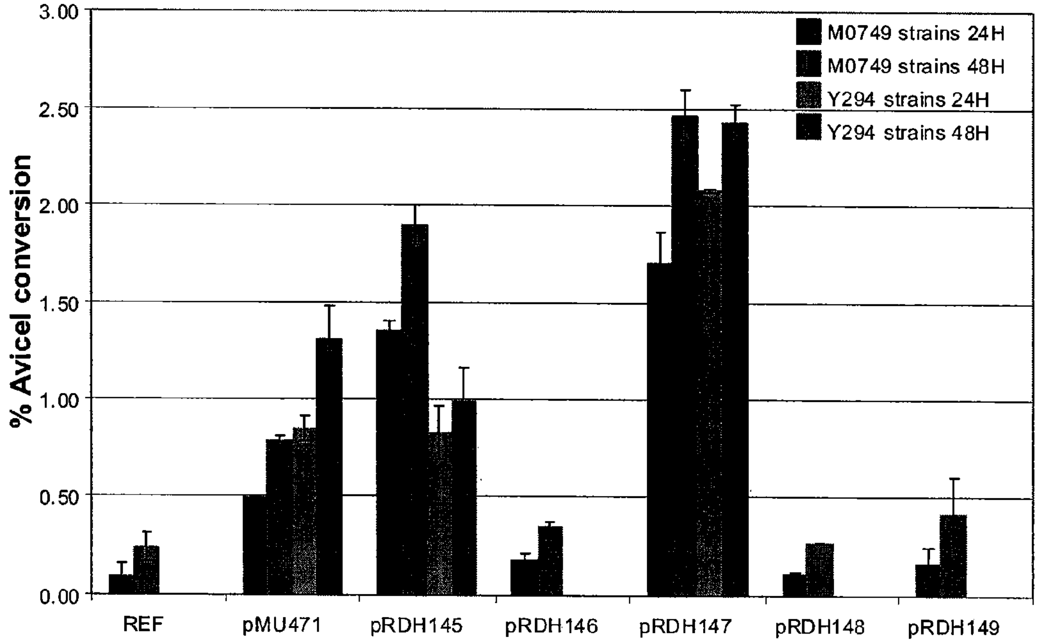

All strains were tested for activity using the high-throughput avicel conversion method as prescribed. Strains expressing endoglucanases were also tested for activity on PASC. The DNS used for the assay procedure contained phenol which, according to literature, renders greater sensitivity. Activity data can be seen in FIG. 30.

The M0749 strain expressing H.j.eg2 (pRDH147) produced the highest levels of secreted activity as measured on PASC or avicel of the EG2s tested. The activity of this enzyme was higher on PASC and avicel than C.f.EG (pMU471). The synthetic A.k.EGA (pRDH145) also gave appreciable activity on both substrates. This product seems to have been produced at higher levels in M0749 than in Y294 and yielded greater activity than C.f.EG on avicel and PASC when produced in this strain.

Example 17

Expression of an Endogluconase in Robust Xylose-Utilizing Yeast

Figure 31:
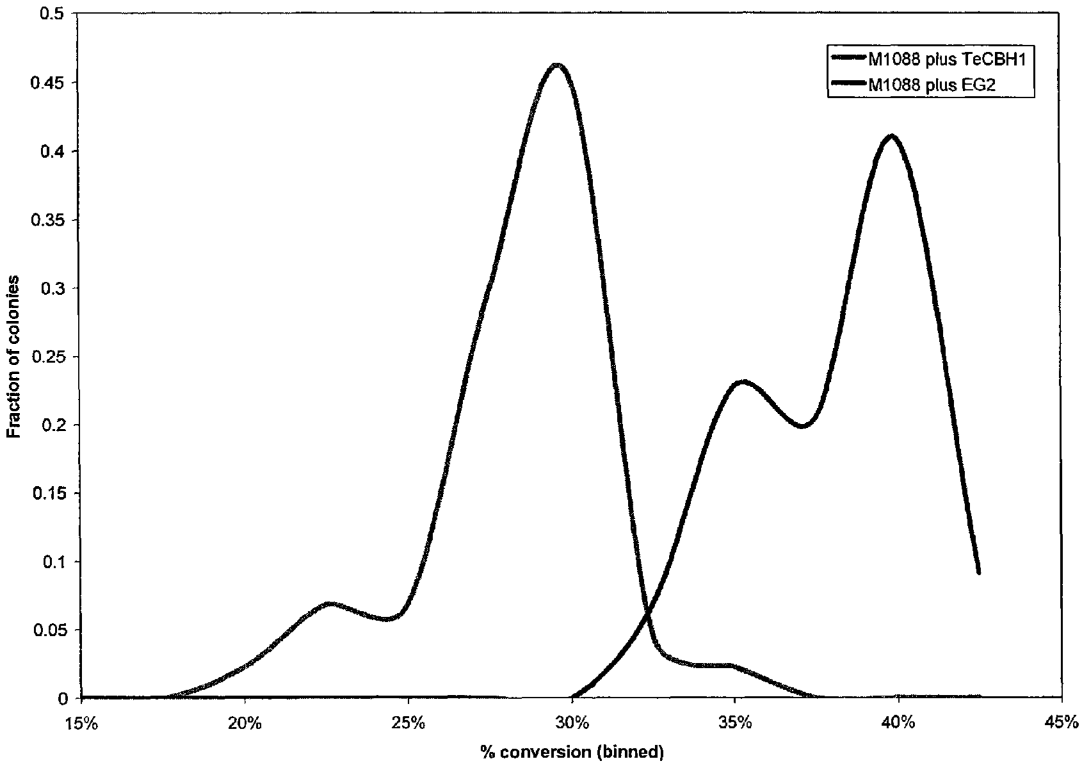
FIG. 31 depicts the distribution of avicel conversion ability of yeast supernatants from transformation with TrEG2 and additional TeCBH1w/TrCBD. M1088 conversion is presented as a dark vertical line, and the dotted lines flanking this line represent the standard deviation of the measurement.

Several strains were created to test the impact of co-expressing TrEG2 with CBHs in a robust xylose utilizing strain background. M1088 was transformed with a construct to integrate TrEG2 at the rDNA locus using the Sh-ble gene as a marker (pMU1409). A similar transformation was done, but integrating TeCBH1w/TrCBD to increase the copy number of that gene. 43 transformants from both transformations along with duplicate M1088 cultures were grown in 20 ug/mL zeocin containing YPD and the avicel assay was performed. FIG. 31 shows the results of those assays. The data show that a very large proportion of strains transformed with the TrEG2 construct had significantly increased avicel conversion ability, while transformants with additional TeCBH1w/TrCBD copies had only marginal improvements in avicel hydrolysis.

Figure 32:
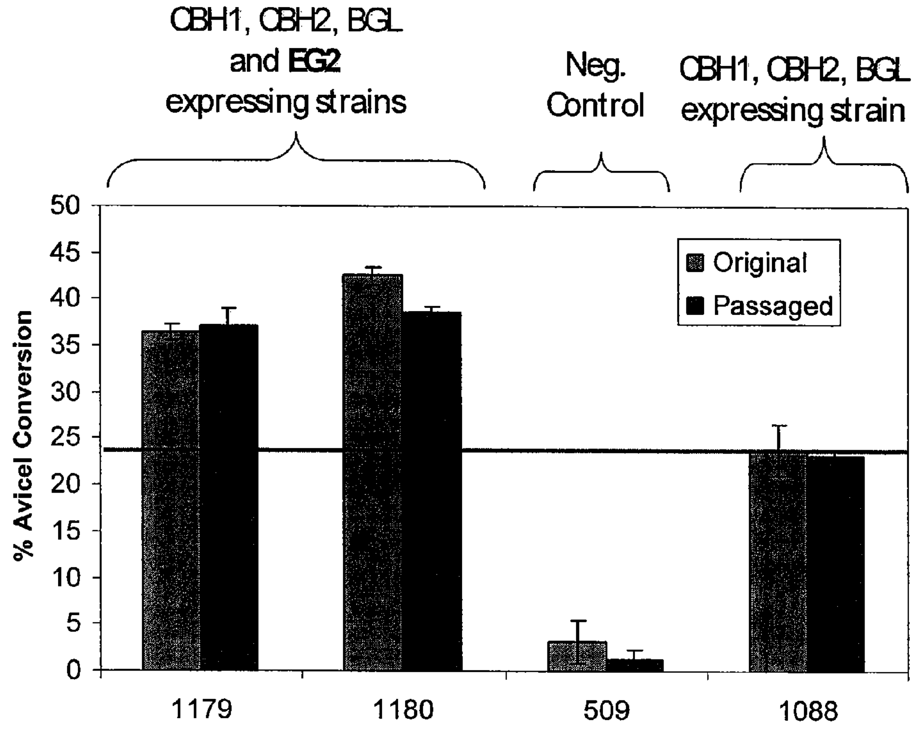
FIG. 32 depicts the conversion of Avicel in the HTP avicel assay (48 hour time point) by supernatants of cellulase expressing yeast strains. M0509 is the negative control expressing no cellulases. Strain 1088 is the parental strain expressing only CBH1, CBH2, and BGL, whereas 1179, 1180, and 1181 are transformants of 1088 also expressing TrEG2.

Of the strains assayed, the top 9 candidates were chosen and restreaked for single colonies. These single colonies were then grown in YPD with 2 transfers to equal a total of 18 generations. The final transfer (passaged data in FIG. 32) was compared to the first YPD culture (original data in FIG. 32). The data confirms that there is an ~50% increase in ability of the yeast supernatant to convert avicel when TrEG2 is overexpressed.

In addition, strain M1403, which contains heterologous genes encoding *S. fibuligera* (SfBGL), cellobiohydrolase 2b from *C. lucknowense* (C1CBH2b), cellobiohydrolase I from *T. emersonii* fused to the *T. reesei* cellobiohydrolase I cellulose binding domain (TeCBH1+CBDTrCBH1), and *Heterodera schachtii* eng1 was produced in the M1254 background. Strain M1284, which contains heterologous genes encoding those same four cellulases was produced in the M0509 background. Strains M1284 and M1403 are described in more detail in Table 15.

TABLE 15

Endogluconase Expressing Yeast Strains.

| Strain | Genotype | Parent | Description |
|---|---|---|---|
| M1403 | (pMU1339) delta::MET3prom-SfBGL-PGKterm, ENO1prom-TeCBH1 + TrCBD-ENO1term (pMU1260) delta::PGKprom-SfBGL-PGKterm, ENO1prom-TeCBH + TrCBD-ENO1term (pMU1169) delta::PGKprom-SfBGL-PGKterm, ENO1prom-C1CBH2-ENO1term (pMU1409) rDNA::ZeoMX, ENO1prom-HjEG2-ENO1term | M1254 | Linear DNA cassettes created by restriction digests of plasmids were integrated in multiple copies into the genome at the Ty1 delta sites and rDNA sites. |
| M0991 | gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PTPI-XKS LEU2/leu2D::hph | M0509 | A single copy of the genomic LEU-2 gene was deleted and replaced with a hygMX cassette. |
| M0992 | gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PTPI-XKS leu2D::hph/leu2D::nat | M0991 | The second copy of the genomic LEU-2 gene was deleted and replaced with a *Streptomyces noursei* nat1 cassette. |

TABLE 15-continued

| Endogluconase Expressing Yeast Strains. | | | |
|---|---|---|---|
| Strain | Genotype | Parent | Description |
| M1162 | gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PTPI-XKS leu2D::hph/leu2D::nat (pMU1379) delta::leu2-19, ENO1prom-TeCBH + TrCBD-ENO1term | M0992 | A linear DNA cassette created by restriction digests of plasmid pMU1379 was integrated in multiple copies into the genome at the Ty1 delta sites. |
| M1284 | gre3::loxP/gre3::loxP TAL1+/loxP-PTPI-TAL1 RKI1+/loxP-PTPI-RKI1 RPE1+/loxP-PTPI-RPE1 TKL+/loxP-PTPI-TKL delta::PTPI-xylA PTPI-XKS leu2D::hph/leu2D::nat (pMU1379) delta::leu2-19, ENO1prom-TeCBH + TrCBD-ENO1term (pMU1169) delta::PGKprom-SfBGL-PGKterm, ENO1prom-ClCBH2-ENO1term (pMU1409) rDNA::ZeoMX, ENO1prom-HjEG2-ENO1term | M1162 | Linear DNA cassettes created by restriction digests of plasmids pMU1169 and pMU1409 were integrated in multiple copies into the genome at the Ty1 delta sites and rDNA sites. |

Example 18

Conversion Of Lignocellulosic Substrates Via CBP Yeast Strains

Expression of cellulases in yeast, particularly CBH1 (*T. emersonii* CBH1 w/*T. reesei* CBD attached), CBH2 (*C. lucknowense* CBH2b), EG2 (*T. reesei* EG2), and BGL (*S. fibuligera* BGL) dramatically reduces the need for externally added enzymes during enzymatic conversion of lignocellulose to ethanol. To test the effect of overexpressing these enzymes, several strains were constructed and tested on a number of substrates.

Figure 33:
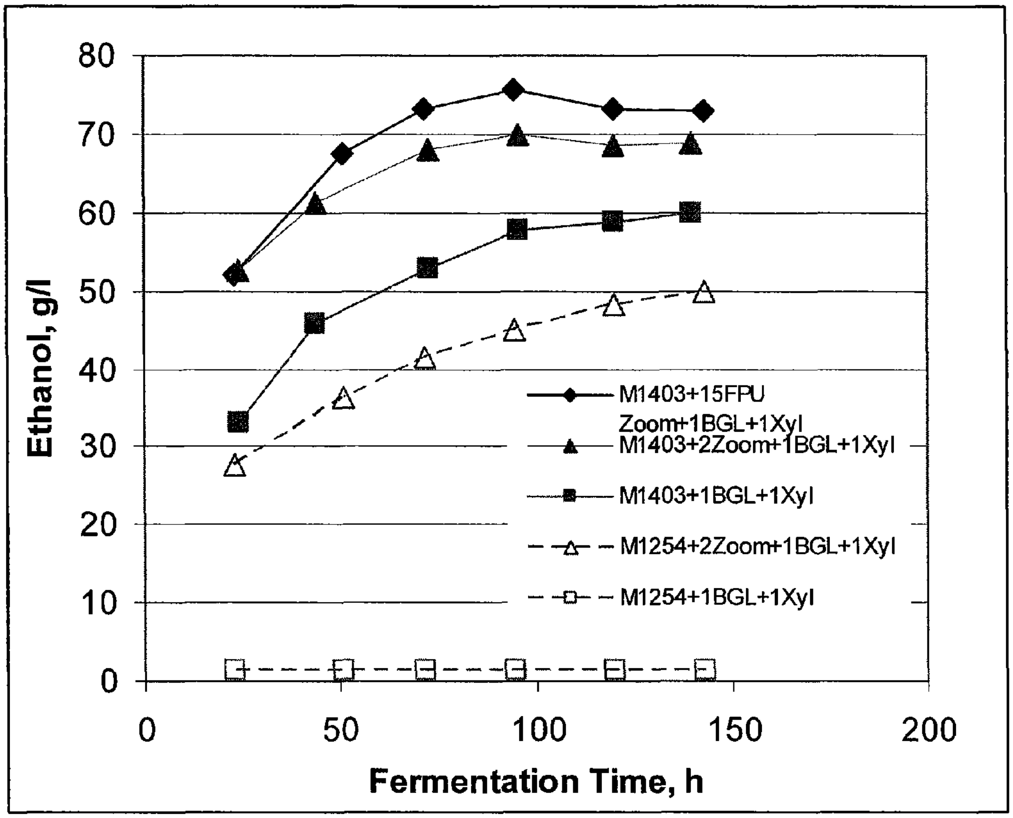
FIG. 33 depicts ethanol production in paper sludge CBP/SSF with cellulolytic strain M1403 and non-cellulolytic background strain M1254 with various amounts of commercial enzyme supplementation. Experimental conditions: 30% solids fed batch, 10 g/l cell inoculuation, pH 5.5 and temperature 40° C., Zoom=Novozymes 22C cellulase preparation, BGL=AB Enzymes EL2008044L BGL preparation, Xyl=AB Enzymes EL2007020L xylanase preparation.

FIG. 33 presents data from a CBP fermentation of paper sludge by an engineered thermotolerant *S. cerevisiae* host strain (parent strain M1254, cellulolytic derivative M1403). The data for M1254 alone demonstrates that the addition of cellulase (i.e. zoomerase) is required for ethanol production from paper sludge. The data for M1430 where no external cellulase is added (filled orange squares), demonstrates that this strain can convert a substantial fraction (~80%) of the "convertible" substrate by virtue of its expressed cellulases. Fermentations with additional external cellulase added to the M1403 strain demonstrate the ultimate potential of enzymatic conversion for the paper sludge substrate. Visual inspections demonstrated that the non-CBP strain was not able to liquefy the substrate, whereas the CBP strain was.

Figure 34:
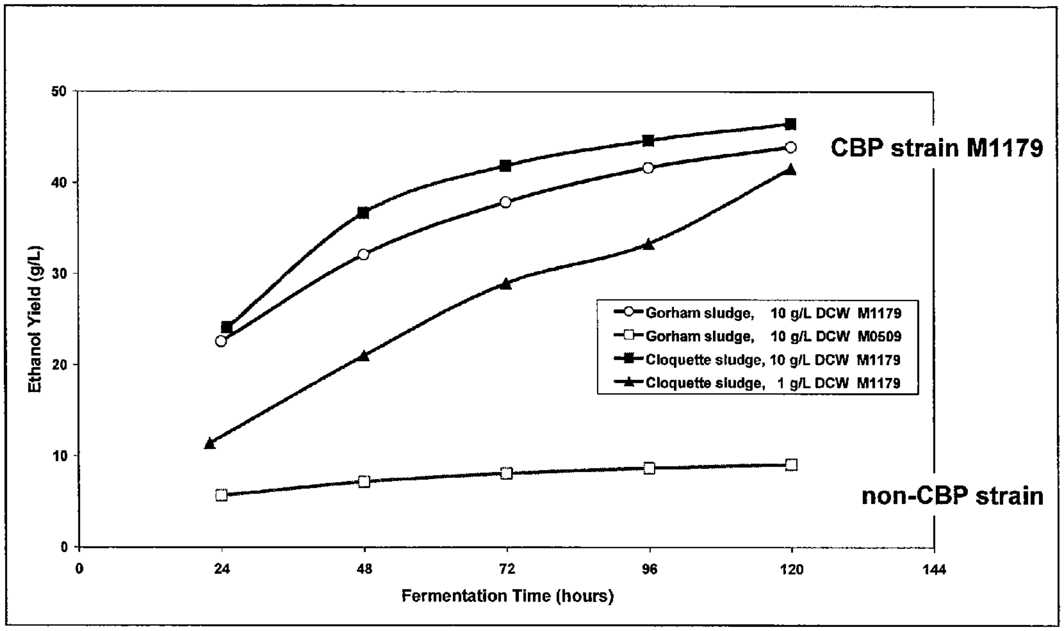
FIG. 34 depicts fermentation of two types of paper sludge by CBP yeast (M1179) and a control strain M0509, not expressing cellulases. Experimental conditions: 18% solids, cells loaded at 10 or 1 g/L, pH 5.5, Temp: 35 C, 1 mg/g BGL and 1 mg/g Xyl loaded. BGL=AB Enzymes EL2008044L BGL preparation, Xyl=AB Enzymes EL2007020L xylanase preparation.

Furthermore, the CBP strain M1179, which expresses CBH1, CBH2, EG2, and BGL can convert paper sludge to a large extent without added cellulase enzyme. FIG. 34. The control strain in this reaction, M0509, made only a small amount of ethanol during this reaction. The data also show that M1179 can convert this material when loaded at lower cell density (1 g/L) as opposed to the higher cell density (10 g/L) used in other reactions. This implies that the strain is able to grow and produce cellulase throughout the fermentation experiments.

Figure 35:
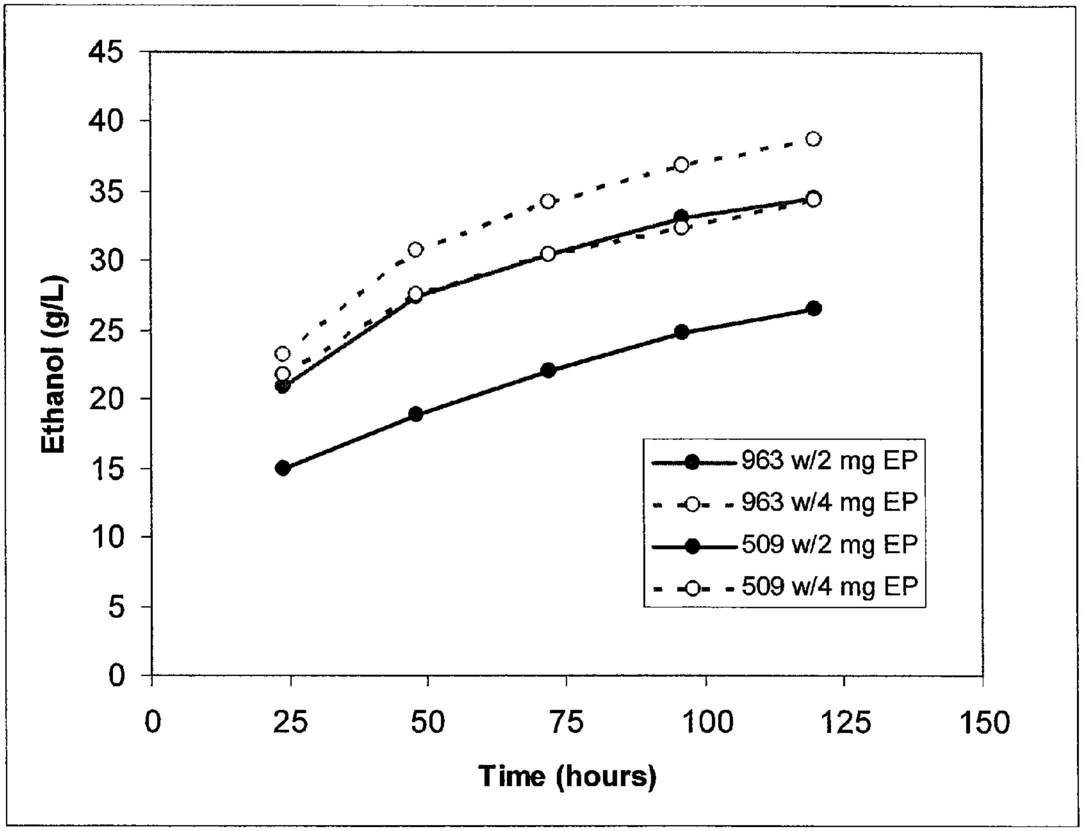
FIG. 35 depicts the performance of cellulolytic yeast strain M0963 and non-cellulolytic control strain (M0509) on 22% unwashed solids of pretreated hardwood (PHW) (MS149) at various external cellulase concentrations. Experimental conditions: 22% solids fed batch, pH 5.4, temperature 35° C., all enzyme protein (EP) was "zoomerase" (Novozymes 22C).

Pretreated hardwood (PHW) can also be converted by CBP strains. FIG. 35, shows the effect of using a cellulase expressing strain (M0963), compared to a control strain not expressing cellulases (M0509) during fermentation of PHW. The comparison demonstrates that the CBP strain can achieve the same yield of ethanol from PHW when only 2 mg/g of external enzyme are loaded compared to when 4 mg/g of M0509 are loaded in the process. This 2-fold reduction in external enzyme needed represents a large potential cost reduction in the process.

Figure 36:
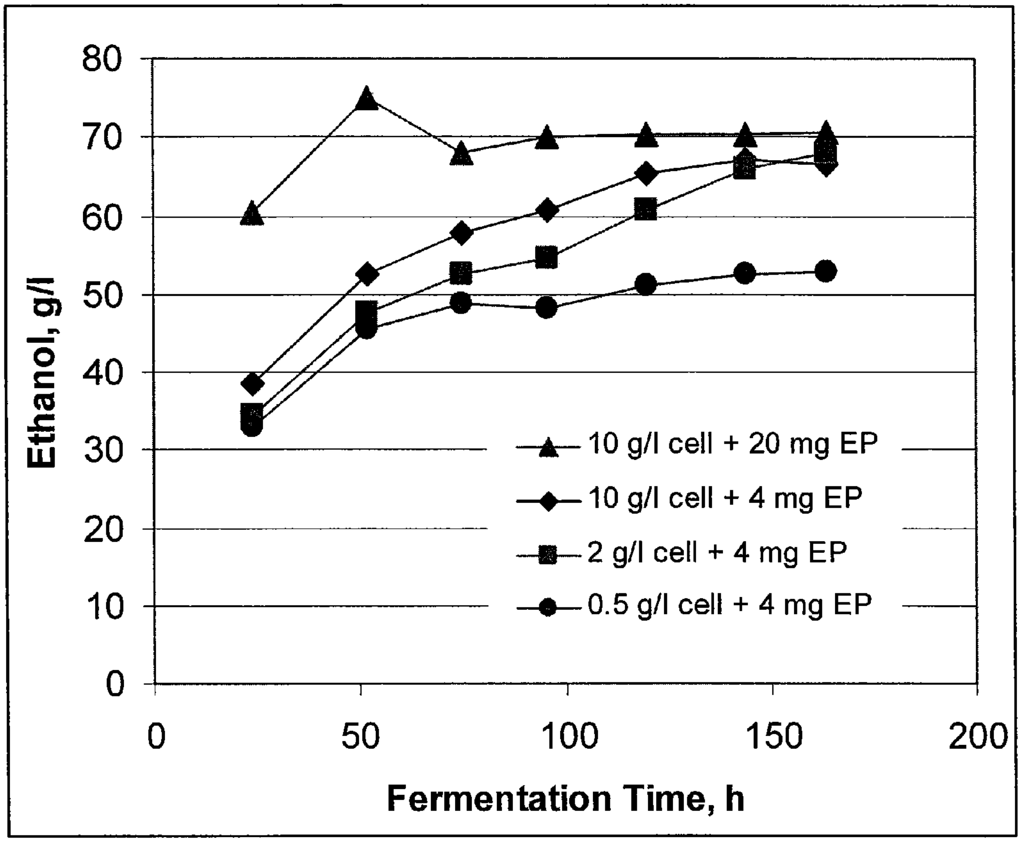
FIG. 36 depicts the performance of cellulolytic yeast strain M1284 on 30% solids of washed pretreated hardwood at various initial cell loadings. Experimental conditions: 30% solids fed batch, pH 5.0, temperature 35° C., 4 mg EP=0.25 mg BGL+0.25 mg Xylanase+0.25 mg Pectinase+3.25 mg Zoomerase, 20 mg EP=1 mg BGL+1 mg Xylanase+1 mg Pectinase+16.7 mg Zoomerase. Zoomerase=Novozymes 22C cellulase preparation, BGL=AB Enzymes EL2008044L BGL preparation, Xyl=AB Enzymes EL2007020L xylanase preparation, Pectinase=Genencor Multifect pectinase FE.

CBP strains are capable of producing high ethanol titers from PHW as well. FIG. 36 shows that a 30% washed solids fermentation can generate titers of ethanol up to about 70 g/L with minimal external enzyme loaded 4 mg/g and a relatively low cell inoculum (2 g/L). The ability of the low cell density cultivation to eventually catch up to and pass the high cell density culture indicates that the strain grows and continues to make enzyme throughout the fermentation.

Figure 37:
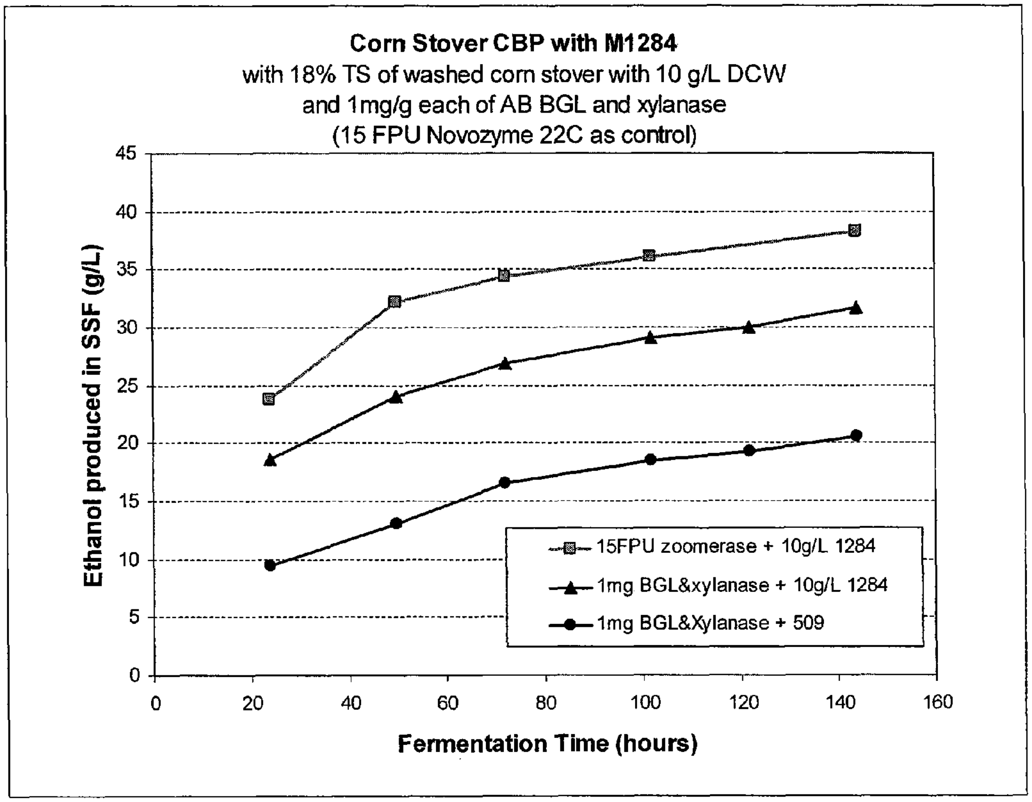
FIG. 37 depicts the ethanol production in washed corn stover CBP/SSF with cellulolytic strain M1284 and non-cellulolytic background strain M0509 with various amounts of commercial enzyme supplementation. Experimental conditions: 18% solids fed batch, 10 g/l cell inoculuation, pH 5.0 and temperature 35° C., 1 mg/g BGL and 1 mg/g xylanase loaded in each case. BGL=AB Enzymes EL2008044L BGL preparation, Xyl=AB Enzymes EL2007020L xylanase preparation.
Figure 38A:
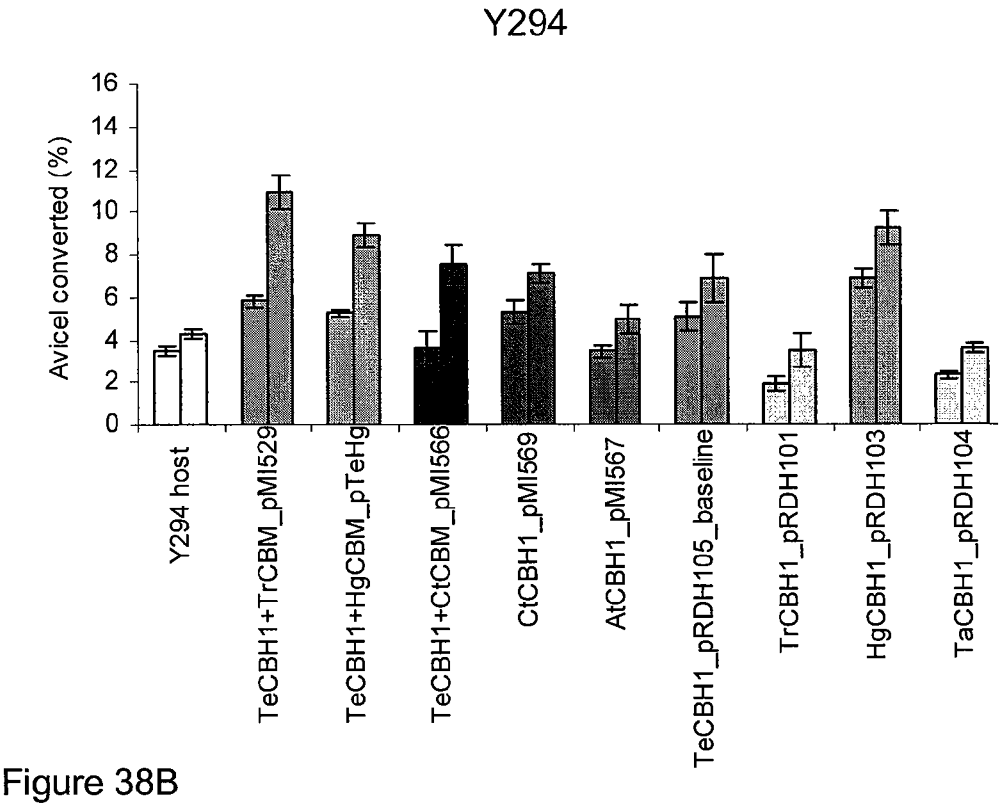
FIG. 38 depicts the activity on Avicel (A, B) or MULac (C, D) of yeast culture supernatants expressing different CBH1 genes, and estimated CBH1 concentration (mg/L, E, F) based on MULac. The host strain was either Y294 or M0749. The CBH1 genes are: Te, *Talaromyces emersonii*; Ct, *Chaetomium thermophilum*; At, *Acremonium thermophilum*; Tr, *Trichoderma reesei*; Hg, *Humicola grisea*; Ta, *Thermoascus aurantiacus*. The plasmid names are indicated. Yeast were cultivated in YPD in triplicate for 3 days. The data are means±standard deviation.
Figure 38B:
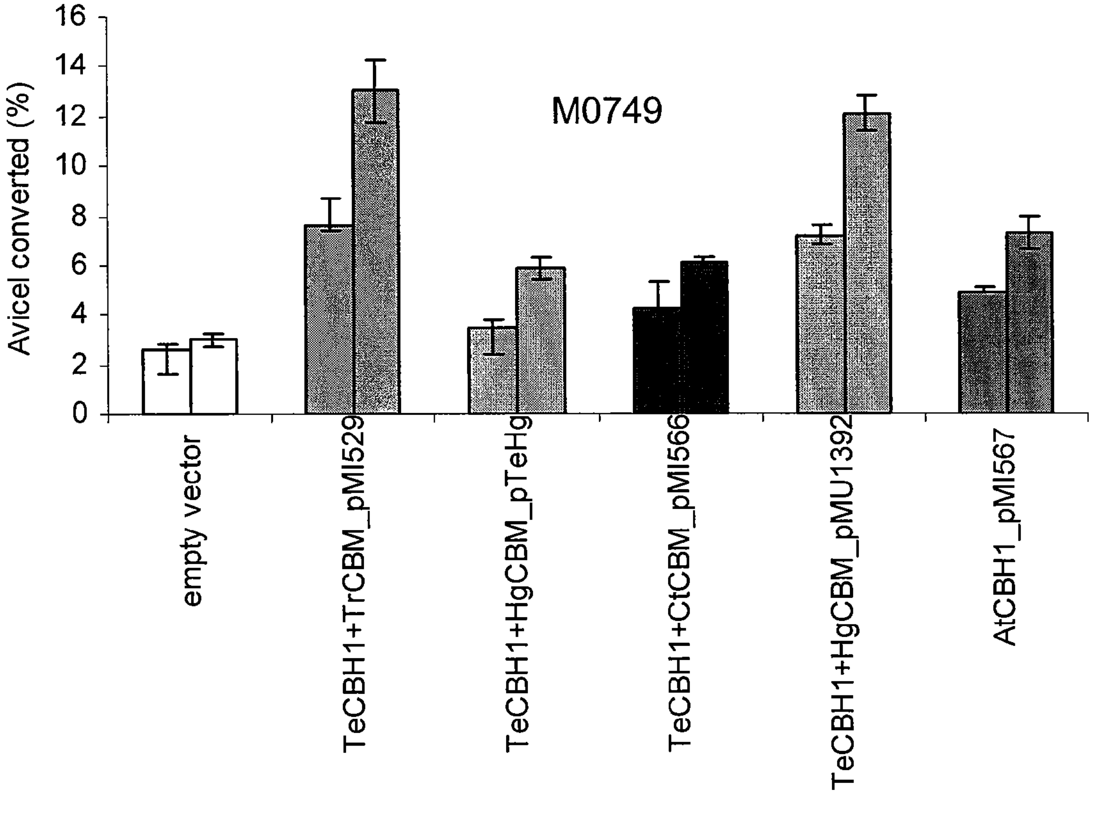
Figure 38C:
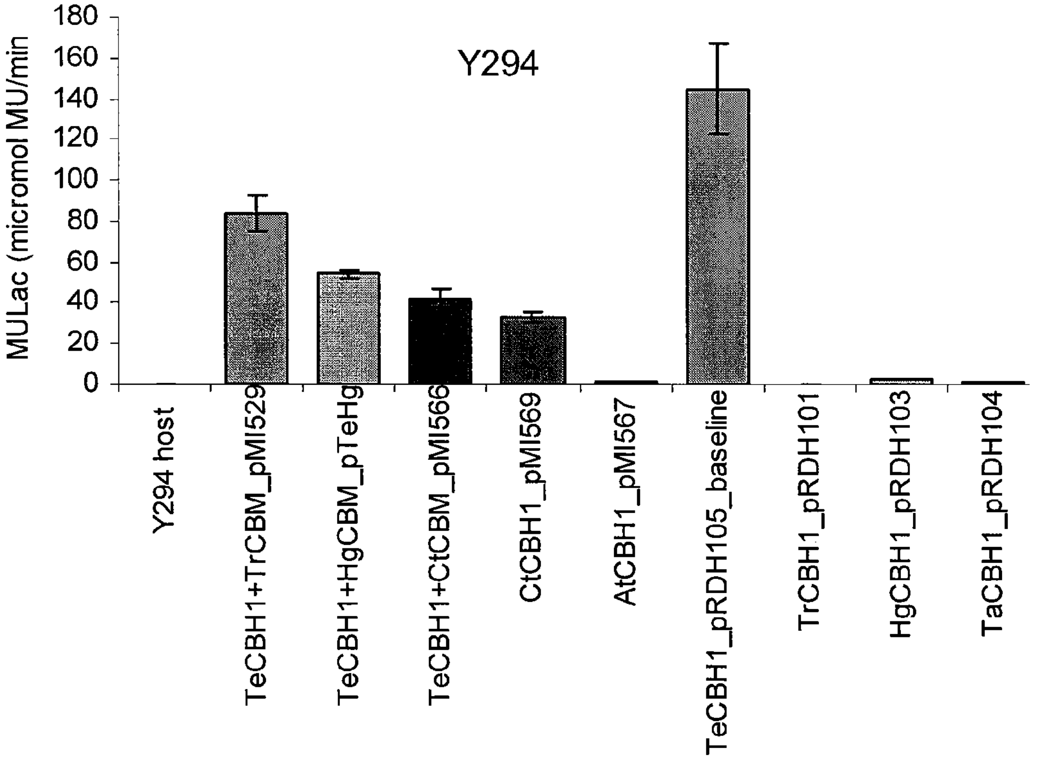
Figure 38D:
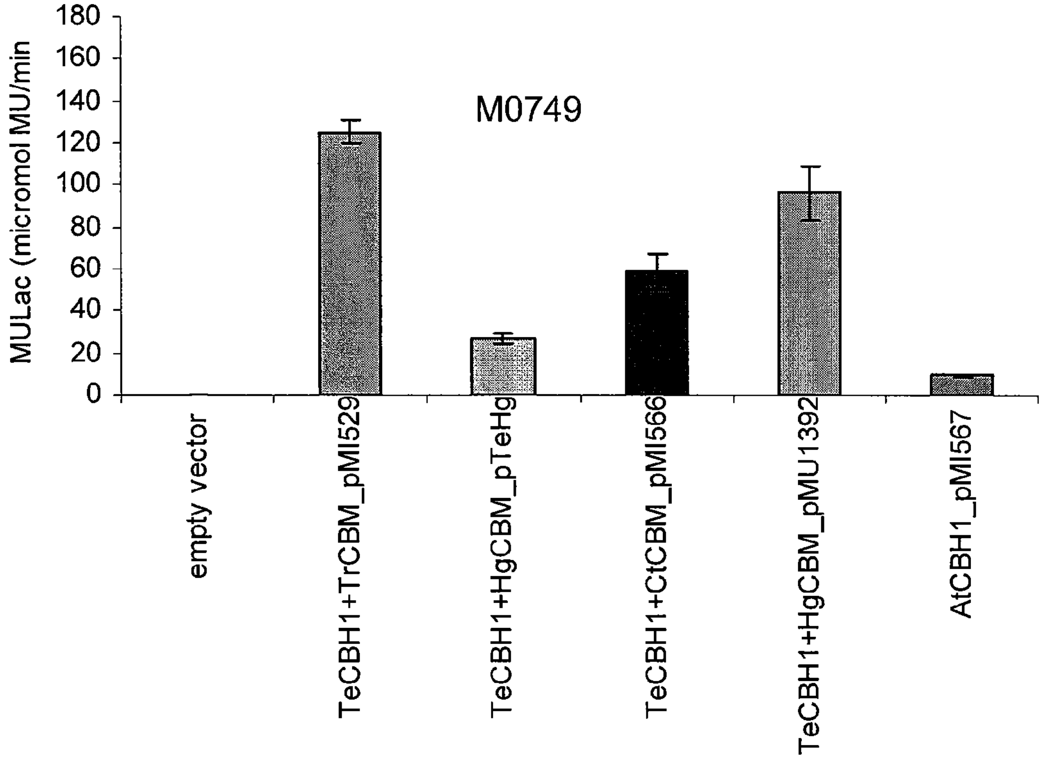
Figure 38E:
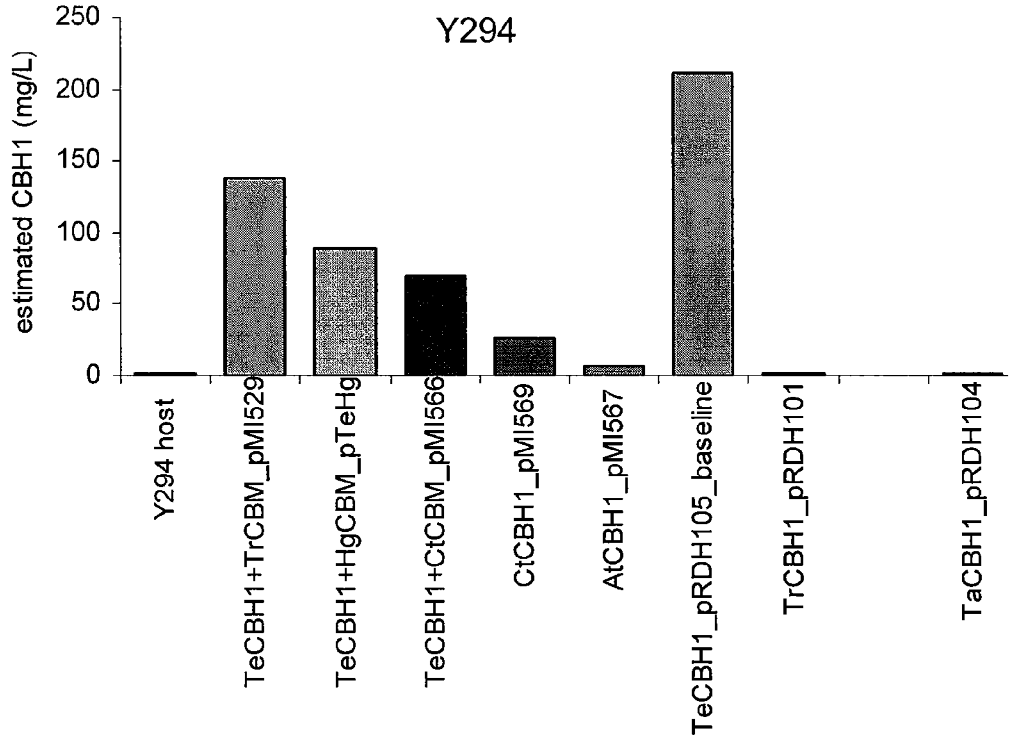
Figure 38F:
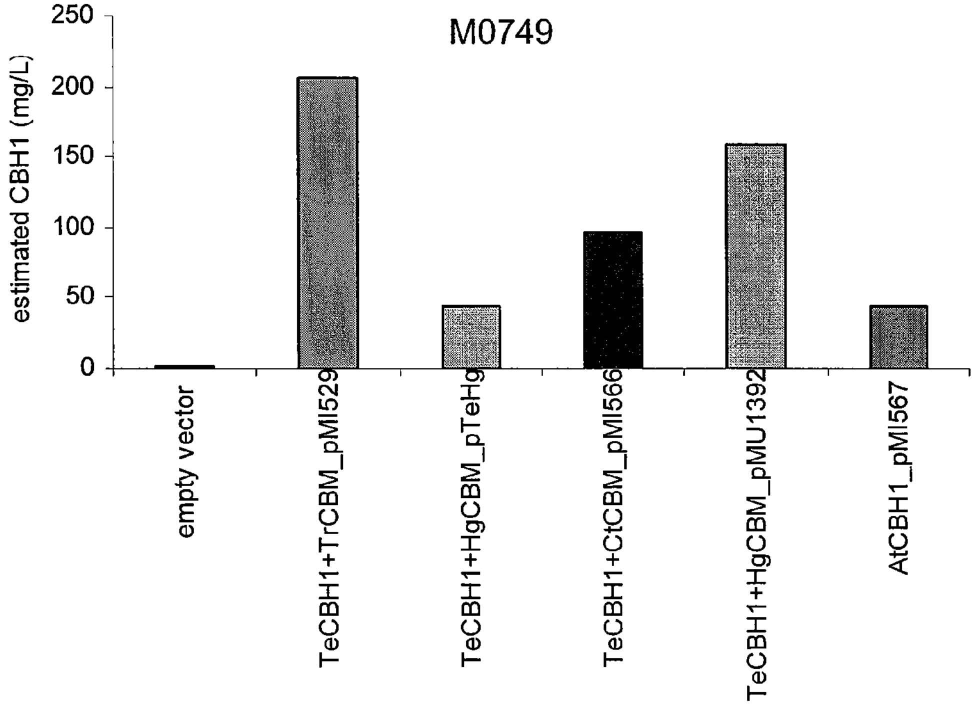

In addition to PHW, corn stover has been implicated as good substrate for conversion to ethanol via an enzymatic saccharification. FIG. 37 demonstrates that pretreated corn stover can be converted well by CBP yeast strains. The CBP strain in this experiment was able to convert about 82% of what was converted with a high enzyme loading (15 FPU, or about 20 mg/g) could achieve. The non-CBP strain made about 60% of the ethanol that the CBP strain was able to achieve.

Example 19

Comparison of CBH1 Cellulases

In order to provide additional data on the expression levels of different CBH1 enzymes, selected strains were grown in YPD-medium and activities on MULac and Avicel were assayed. Both Y294 and M0749 transformants were studied, and the results are shown in FIG. 38.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A thermotolerant yeast host cell comprising 1. at least one heterologous polynucleotide comprising a nucleic acid which encodes an endoglucanase;
2. at least one heterologous polynucleotide comprising a nucleic acid which encodes a β-glucosidase;
3. at least one heterologous polynucleotide comprising a nucleic acid which encodes a cellobiohydrolase I; and
4. at least one heterologous polynucleotide comprising a nucleic acid which encodes a cellobiohydrolase II;

wherein the thermotolerant yeast host cell can grow at a temperature of at least 35° C. or above, wherein the endoglucanase, β-glucosidase, cellobiohydrolase I, and cellobiohydrolase II are secreted; and wherein the host cell is capable of producing ethanol from Avicel.

2. The thermotolerant yeast host cell of claim 1, wherein the β-glucosidase is a *Saccharomycopsis fibuligera* β-glucosidase comprising the amino acids of SEQ ID NO-40.

3. The thermotolerant yeast host cell of claim 1, wherein the cellobiohydrolase I is a *Talaromyces emersonii* cellobiohydrolase I comprising the amino acids of SEQ ID NO:23.

4. The thermotolerant yeast host cell of claim 3, wherein the *Talaromyces emersonii* cellobiohydrolase I is fused to a cellulose binding module (CBM).

5. The thermotolerant yeast host cell of claim 4, wherein the CBM is the CBM of *Trichoderma reesei* Cbh1 comprising amino acids 503 to 535 of SEQ ID NO:27 or *Humicola grisea* Cbh1 comprising amino acids 492 to 525 of SEQ ID NO: 21.

6. The thermotolerant yeast host cell of claim 1, wherein the cellobiohydrolase 11 is a *Chrysoporium lucknowense* cellobiohydrolase 11 comprising the amino acids of SEQ ID NO:25.

7. The thermotolerant yeast host cell of claim 1, wherein the endoglucanase is an *Humicola grisea, Thermoascus aurantiacus, Taalaromyces emersonii, Trichoderma reesei, Coptotermes lacteus, Coptotermes formosanus, Nasutitermes takasagoensis, Coptotermes acinaciformis, Mastotermes darwinensis, Nasutitermes walkeri, Saccharomycopsis fibuligera, Chrysosporium lucknowense, Reticulitermes speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Chaetomium thermophilum, Aspergillus terreus, Neurospora Crassa, Reticulitermes flavipes*, or *Arabidopsis thaliana* endoglucanase.

8. The thermotolerant yeast host cell of claim 1, further comprising a heterologous polynucleotide comprising a nucleic acid which encodes a second endoglucanase.

9. The thermotolerant yeast host cell of claim 1, wherein the β-glucosidase is a *Saccharomycopsis fibuligera* β-glucosidase comprising the amino acids of SEQ ID NO:40, the cellobiohydrolase I is a *Taalaromyces emersonii* cellobiohydrolase I comprising the amino acids of SEQ ID NO:23, and the cellobiohydrolase II is a *Chrysosporium lucknowense* cellobiohydrolase II comprising the amino acids of SEQ ID NO 25.

10. The thermotolerant yeast host cell of claim 9, further comprising a second heterologous polynucleotide comprising a nucleic acid which encodes a second endoglucanase, and wherein the endoglucanase and the second endoglucanase are selected from the group consisting of *Humicola grisea, Thermoascus aurantiacus, Taalaromyces emersonii, Trichoderma reesei, Coptotermes lacteus, Coptotermes formosanus, Nasutitermes takasagoensis, Coptotermes acinaciformis, Mastotermes darwinensis, Nasutitermes walkeri, Saccharomycopsis fibuligera, Chrysosporium lucknowense, Reticulitermes speratus, Thermobfida fusca, Clostridum thermocellum, Clostridium cellulolyticum, Clostridum josui, Bacillus pumilis, Cellulomonas fimi, Saccharophagus degradans, Piromyces equii, Neocallimastix patricarum, Neosartorya fischeri, Chaetomium thermophilum, Aspergillus terreus, Neurospora Crassa, Reticulitermes flavipes*, or *Arabidopsis thaliana* endoglucanases.

11. The thermotolerant yeast host cell of claim 1, wherein the host cell is a *Kluveromyces* host cell.

12. The thermotolerant yeast host cell of claim 1, wherein the host cell is a *Saccharomyces cerevisiae* host cell.

13. The thermotolerant yeast host cell of claim 1, wherein the host cell is capable of fermenting pentose sugars.

14. The thermotolerant yeast host cell of claim 13, wherein the host cell is capable of fermenting xylose.

15. The thermotolerant yeast host cell of claim 14, wherein the host cell expresses xylose isomerase, xylulokinase, ribulose 5-phosphate isomerase, ribulose 5-phosphate epimerase, transketolase, transaldolase or a combination thereof.

16. The thermotolerant yeast host cell of claim 15, wherein the host cell expresses xylose isomerase, xylulokinase, ribulose 5-phosphate isomerase, ribulose 5-phosphate epimerase, transketolase and transaldolase.

17. The thermotolerant yeast host cell of claim 13, wherein the host cell does not express the GRE3 gene encoding aldose reductase.

18. A method of fermenting cellulose comprising culturing the host cell of claim 1 in medium that contains cellulose under suitable conditions for a period sufficient to allow saccharification and fermentation of the cellulose.

19. A culture comprising the host cell of claim 1 and cellulose.

20. The thermotolerant yeast host cell of claim 1, wherein the endoglucanase is an *Aspergillus kawachii, Heterodera schachtii, Hypocrea jecorina, Orpinomyces* sp., *Irpex lacteus, Acremonium thermophilum, Chaetomium globosum*, or *Aspergillus fumigatus* endoglucanase.

21. The thermotolerant yeast host cell of claim 9, further comprising a second heterologous polynucleotide comprising a nucleic acid which encodes a second endoglucanase, and wherein the endoglucanase and the second endoglucanase are selected from the group consisting of *Aspergillus kawachii, Heterodera schachtii, Hypocrea jecorina, Orpinomyces* sp., *Irpex lacteus, Acremonium thermophilum, Chaetomium globosum*, and *Aspergillus fumigatus* endoglucanase.

22. The thermotolerant yeast host cell of claim 1, wherein the endoglucanase is a *Neosartorya fischeri* endoglucanase comprising the amino acids of SEQ ID NO:37.

23. The thermotolerant yeast host cell of claim 1, wherein the thermotolerant yeast host cell can grow at temperatures of at least 38° C. or above.

24. The thermotolerant yeast host cell of claim 1, wherein the thermotolerant yeast host cell can grow at temperatures of at least 40° C. or above.

25. The thermotolerant yeast host cell of claim 1, wherein the thermotolerant yeast host cell can grow at temperature from 40° C. to 50° C.

26. The thermotolerant yeast host cell of claim 9, wherein the *Talaromyces emersonii* cellobiohydrolase I is fused to a cellulose binding module (CBM).

27. A thermotolerant yeast host cell comprising (a) at least one heterologous polynucleotide comprising a nucleic acid which encodes an endoglucanase;

(b) at least one heterologous polynucleotide comprising a nucleic acid which encodes a β-glucosidase;

(c) at least one heterologous polynucleotide comprising a nucleic acid which encodes a cellobiohydrolase I; and (d) at least one heterologous polynucleotide comprising a nucleic acid which encodes a cellobiohydrolase II;

wherein the thermotolerant yeast host cell can crow at a temperature of at least 35° C. or above, wherein the cellobiohydrolase I, the cellobiohydrolase I, or both is fused to a cellulose binding module (CBM); and wherein the host cell is capable of producing ethanol from Avicel.

* * * * *